United States Patent
Yoo et al.

(10) Patent No.: US 11,542,331 B2
(45) Date of Patent: Jan. 3, 2023

(54) METHODS OF TREATING CANCER USING ANTIBODIES AND MOLECULES THAT BIND TO BTN1A1 OR BTN1A1-LIGANDS

(71) Applicant: STCUBE & CO., INC., Seoul (KR)

(72) Inventors: Stephen Sunghan Yoo, Centreville, VA (US); Ezra Myung Chul Chung, North Potomac, MD (US); Yong-Sik Bong, Frederick, MD (US); Yong-Soo Kim, Rockville, MD (US)

(73) Assignee: STCUBE & CO., INC., Seoul (KR)

( * ) Notice: Subject to any disclaimer, the term of this patent is extended or adjusted under 35 U.S.C. 154(b) by 89 days.

(21) Appl. No.: 16/618,764

(22) PCT Filed: Jun. 5, 2018

(86) PCT No.: PCT/US2018/036026
§ 371 (c)(1),
(2) Date: Dec. 2, 2019

(87) PCT Pub. No.: WO2018/226671
PCT Pub. Date: Dec. 13, 2018

(65) Prior Publication Data
US 2020/0131269 A1    Apr. 30, 2020

Related U.S. Application Data

(60) Provisional application No. 62/516,071, filed on Jun. 6, 2017.

(51) Int. Cl.
*A61K 39/00* (2006.01)
*C07K 16/28* (2006.01)

(52) U.S. Cl.
CPC ...... *C07K 16/2815* (2013.01); *C07K 2317/54* (2013.01); *C07K 2317/55* (2013.01); *C07K 2317/76* (2013.01)

(58) Field of Classification Search
CPC ............ C07K 16/2815; C07K 2317/54; C07K 2317/55; C07K 2317/76; C07K 16/2803
See application file for complete search history.

(56) References Cited

U.S. PATENT DOCUMENTS

| | | |
|---|---|---|
| 3,817,837 A | 6/1974 | Rubenstein et al. |
| 3,850,752 A | 11/1974 | Schuurs et al. |
| 3,939,350 A | 2/1976 | Kronick et al. |
| 3,996,345 A | 12/1976 | Ullman et al. |
| 4,016,043 A | 4/1977 | Schuurs et al. |
| 4,018,653 A | 4/1977 | Mennen |
| 4,179,337 A | 12/1979 | Davis et al. |
| 4,196,265 A | 4/1980 | Koprowski et al. |
| 4,275,149 A | 6/1981 | Litman et al. |
| 4,277,437 A | 7/1981 | Maggio |
| 4,366,241 A | 12/1982 | Tom et al. |
| 4,424,279 A | 1/1984 | Bohn et al. |
| 4,444,887 A | 4/1984 | Hoffmann |
| 4,469,797 A | 9/1984 | Albarella |
| 4,472,509 A | 9/1984 | Gansow et al. |
| 4,485,045 A | 11/1984 | Regen |
| 4,526,938 A | 7/1985 | Churchill et al. |
| 4,544,545 A | 10/1985 | Ryan et al. |
| 4,606,855 A | 8/1986 | Deutsch et al. |
| 4,676,980 A | 6/1987 | Segal et al. |
| 4,703,003 A | 10/1987 | Struck |
| 4,716,111 A | 12/1987 | Osband et al. |
| 4,741,900 A | 5/1988 | Alvarez et al. |
| 4,742,159 A | 5/1988 | Batz et al. |
| 4,767,720 A | 8/1988 | Lingwood |
| 4,816,397 A | 3/1989 | Boss et al. |
| 4,816,567 A | 3/1989 | Cabilly et al. |
| 4,867,973 A | 9/1989 | Goers et al. |
| 4,870,287 A | 9/1989 | Cole et al. |
| 4,880,078 A | 11/1989 | Inoue et al. |
| 4,938,948 A | 7/1990 | Ring et al. |
| 4,946,778 A | 8/1990 | Ladner et al. |
| 4,980,286 A | 12/1990 | Morgan et al. |
| 5,013,556 A | 5/1991 | Woodle et al. |
| 5,021,236 A | 6/1991 | Gries et al. |
| 5,091,513 A | 2/1992 | Huston et al. |
| 5,128,326 A | 7/1992 | Balazs et al. |
| 5,164,296 A | 11/1992 | Blaustein et al. |
| 5,196,066 A | 3/1993 | Kusuda et al. |
| 5,223,409 A | 6/1993 | Ladner et al. |
| 5,225,539 A | 7/1993 | Winter |
| 5,258,498 A | 11/1993 | Huston et al. |

(Continued)

FOREIGN PATENT DOCUMENTS

| | | |
|---|---|---|
| EP | 0 592 106 B1 | 4/1994 |
| EP | 0 239 400 B1 | 8/1994 |

(Continued)

OTHER PUBLICATIONS

Cedeno-Laurent (Clin Immunol 142:107-116 2012 (Year: 2012).*
The Human Protein Atlas, BTN1A1 expression in blood cell (website 2021) (Year: 2021).*
Paliard et al, J Immunol 141:849-855 1988 (Year: 1988).*
Abra et al., "The next generation of liposome delivery systems: recent experience with tumor-targeted, sterically-stabilized immunoliposomes and active-loading gradients," *J. Liposome Res.*, 12(1-2):1-3 (2002).
Al-Lazikani et al., "Standard conformations for the canonical structures of immunoglobulins," *J. Mol. Biol.*, 273:927-948 (1997).

(Continued)

*Primary Examiner* — Lei Yao
(74) *Attorney, Agent, or Firm* — Jones Day

(57) ABSTRACT

Provided herein are methods for treating cancer using molecules having an antigen binding fragment that immunospecifically binds to BTN1A1 or a BTN1A1 ligand, such as anti-BTN1A1 antibodies or anti-BTN1A1 ligand antibodies. Also provided herein are BTN1A1 ligands, such as Galectin-1, Galectin-9, Neuropilin-2, and B- and T-Lymphocyte Attenuator.

Figure 1:
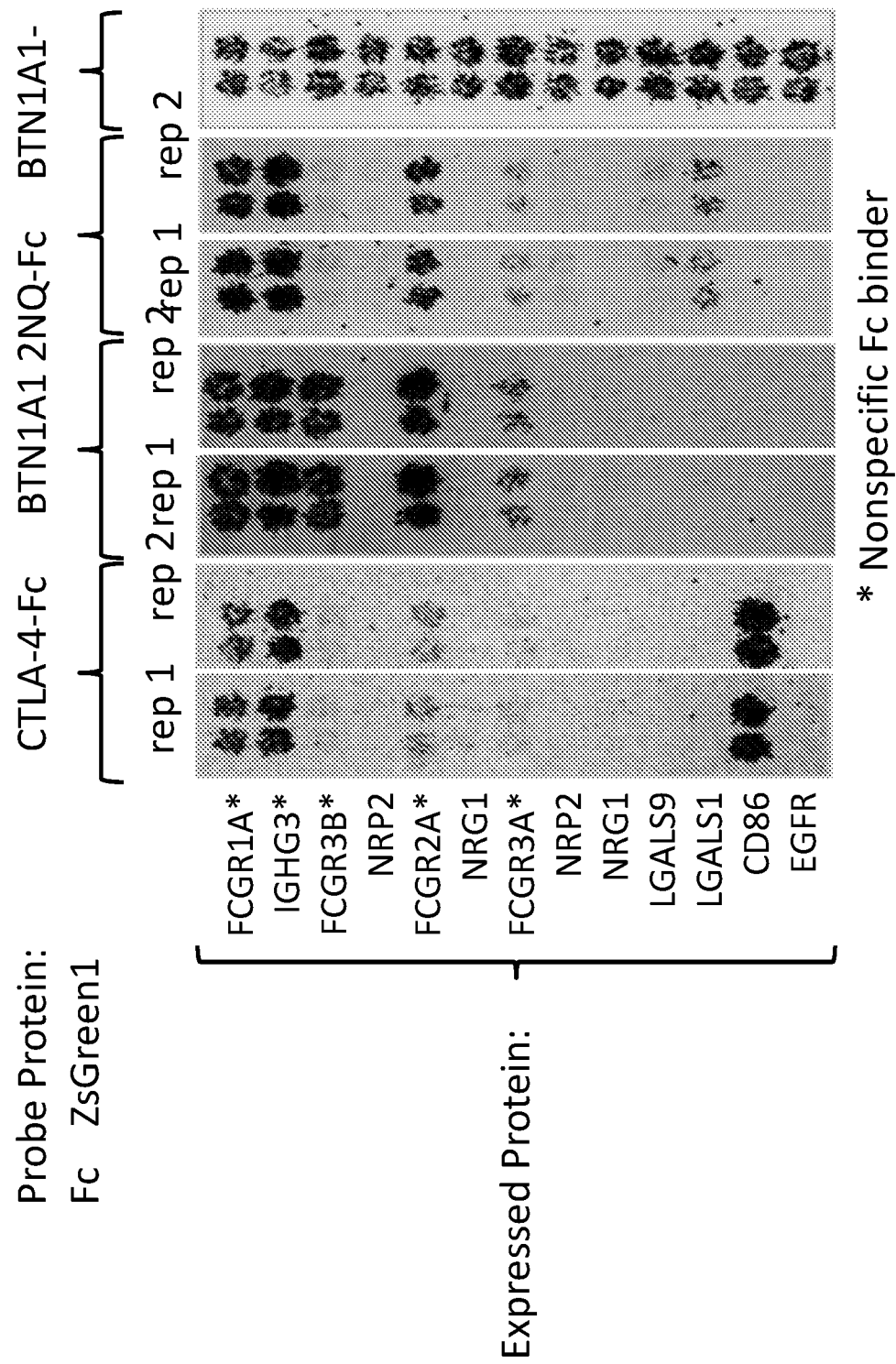

18 Claims, 8 Drawing Sheets
Specification includes a Sequence Listing.

(56) References Cited

U.S. PATENT DOCUMENTS

| | | |
|---|---|---|
| 5,290,540 A | 3/1994 | Prince et al. |
| 5,403,484 A | 4/1995 | Ladner et al. |
| 5,413,923 A | 5/1995 | Kucherlapati et al. |
| 5,420,253 A | 5/1995 | Emery et al. |
| 5,427,908 A | 6/1995 | Dower et al. |
| 5,516,637 A | 5/1996 | Huang et al. |
| 5,530,101 A | 6/1996 | Queen et al. |
| 5,545,806 A | 8/1996 | Lonberg et al. |
| 5,565,332 A | 10/1996 | Hoogenboom et al. |
| 5,569,825 A | 10/1996 | Lonberg et al. |
| 5,571,698 A | 11/1996 | Ladner et al. |
| 5,580,717 A | 12/1996 | Dower et al. |
| 5,585,089 A | 12/1996 | Queen et al. |
| 5,587,459 A | 12/1996 | Uckun |
| 5,618,709 A | 4/1997 | Gewirtz et al. |
| 5,624,821 A | 4/1997 | Winter et al. |
| 5,625,126 A | 4/1997 | Lonberg et al. |
| 5,627,052 A | 5/1997 | Schrader |
| 5,633,425 A | 5/1997 | Lonberg et al. |
| 5,648,239 A | 7/1997 | Hawkins et al. |
| 5,656,434 A | 8/1997 | Terano et al. |
| 5,658,727 A | 8/1997 | Barbas et al. |
| 5,661,016 A | 8/1997 | Lonberg et al. |
| 5,679,377 A | 10/1997 | Bernstein et al. |
| 5,698,426 A | 12/1997 | Huse |
| 5,728,868 A | 3/1998 | Springer et al. |
| 5,733,743 A | 3/1998 | Johnson et al. |
| 5,734,033 A | 3/1998 | Reed |
| 5,739,169 A | 4/1998 | Ocain et al. |
| 5,750,753 A | 5/1998 | Kimae et al. |
| 5,760,395 A | 6/1998 | Johnstone |
| 5,770,376 A | 6/1998 | Bagrov |
| 5,780,225 A | 7/1998 | Wigler et al. |
| 5,789,208 A | 8/1998 | Sharon |
| 5,801,005 A | 9/1998 | Cheever et al. |
| 5,807,715 A | 9/1998 | Morrison et al. |
| 5,814,318 A | 9/1998 | Lonberg et al. |
| 5,821,047 A | 10/1998 | Garrard et al. |
| 5,821,337 A | 10/1998 | Carter et al. |
| 5,824,311 A | 10/1998 | Greene et al. |
| 5,830,880 A | 11/1998 | Sedlacek et al. |
| 5,840,745 A | 11/1998 | Buzzetti et al. |
| 5,843,597 A | 12/1998 | Getz |
| 5,844,091 A | 12/1998 | Blaustein et al. |
| 5,846,945 A | 12/1998 | McCormick |
| 5,855,913 A | 1/1999 | Hanes et al. |
| 5,858,657 A | 1/1999 | Winter et al. |
| 5,861,155 A | 1/1999 | Lin |
| 5,863,904 A | 1/1999 | Nabel et al. |
| 5,871,907 A | 2/1999 | Winter et al. |
| 5,872,223 A | 2/1999 | Uckun |
| 5,874,064 A | 2/1999 | Edwards et al. |
| 5,885,834 A | 3/1999 | Epstein |
| 5,888,533 A | 3/1999 | Dunn |
| 5,911,995 A | 6/1999 | Uckun |
| 5,912,015 A | 6/1999 | Bernstein et al. |
| 5,916,597 A | 6/1999 | Lee et al. |
| 5,916,771 A | 6/1999 | Hori et al. |
| 5,922,844 A | 7/1999 | Hawkins et al. |
| 5,925,376 A | 7/1999 | Heng |
| 5,934,272 A | 8/1999 | Lloyd et al. |
| 5,939,598 A | 8/1999 | Kucherlapati et al. |
| 5,945,155 A | 8/1999 | Grill et al. |
| 5,958,769 A | 9/1999 | Roberts et al. |
| 5,969,108 A | 10/1999 | McCafferty et al. |
| 5,985,309 A | 11/1999 | Edwards et al. |
| 5,985,877 A | 11/1999 | Dionne et al. |
| 5,989,463 A | 11/1999 | Tracy et al. |
| 5,998,596 A | 12/1999 | Bergan et al. |
| 6,019,968 A | 2/2000 | Platz et al. |
| 6,034,053 A | 3/2000 | Uckun et al. |
| 6,040,305 A | 3/2000 | Taveras et al. |
| 6,051,574 A | 4/2000 | Anthony |
| 6,051,582 A | 4/2000 | Taveras |
| 6,054,297 A | 4/2000 | Carter et al. |
| 6,054,466 A | 4/2000 | Ciccarone et al. |
| 6,057,300 A | 5/2000 | Nabel et al. |
| 6,063,930 A | 5/2000 | Dinsmore et al. |
| 6,066,738 A | 5/2000 | Dinsmore et al. |
| 6,071,935 A | 6/2000 | Lyssikatos |
| 6,077,853 A | 6/2000 | Graham et al. |
| 6,080,870 A | 6/2000 | Anthony et al. |
| 6,090,948 A | 7/2000 | Dinsmore et al. |
| 6,093,737 A | 7/2000 | Anthony et al. |
| 6,103,723 A | 8/2000 | Bergman et al. |
| 6,124,295 A | 9/2000 | Taveras et al. |
| 6,124,465 A | 9/2000 | Bourzat et al. |
| 6,127,366 A | 10/2000 | Kim et al. |
| 6,133,303 A | 10/2000 | Bikker et al. |
| 6,143,766 A | 11/2000 | Kaltenbronn et al. |
| 6,159,984 A | 12/2000 | Guzi et al. |
| 6,165,464 A | 12/2000 | Hudziak et al. |
| 6,169,096 B1 | 1/2001 | Venet et al. |
| 6,187,786 B1 | 2/2001 | Venet et al. |
| 6,194,551 B1 | 2/2001 | Idusogie et al. |
| 6,211,193 B1 | 4/2001 | Remiszewski et al. |
| 6,218,372 B1 | 4/2001 | Nabel et al. |
| 6,218,406 B1 | 4/2001 | Bourzat et al. |
| 6,218,410 B1 | 4/2001 | Uehata et al. |
| 6,225,322 B1 | 5/2001 | Cooper et al. |
| 6,228,856 B1 | 5/2001 | Njoroge et al. |
| 6,228,865 B1 | 5/2001 | Doll et al. |
| 6,232,338 B1 | 5/2001 | Davies et al. |
| 6,239,140 B1 | 5/2001 | Cooper et al. |
| 6,242,196 B1 | 6/2001 | Spiegelman et al. |
| 6,245,759 B1 | 6/2001 | Bilodeau et al. |
| 6,248,756 B1 | 6/2001 | Anthony et al. |
| 6,265,422 B1 | 7/2001 | Bikker et al. |
| 6,268,363 B1 | 7/2001 | Lee et al. |
| 6,271,242 B1 | 8/2001 | Barbacid |
| 6,277,375 B1 | 8/2001 | Ward |
| 6,277,832 B1 | 8/2001 | Sugiyama et al. |
| 6,300,501 B1 | 10/2001 | Dobrusin et al. |
| 6,331,415 B1 | 12/2001 | Cabilly et al. |
| 6,335,156 B1 | 1/2002 | Hermeking et al. |
| 6,342,487 B1 | 1/2002 | Riou et al. |
| 6,342,765 B1 | 1/2002 | Arnould |
| 6,362,188 B1 | 3/2002 | Guzi et al. |
| 6,365,157 B2 | 4/2002 | Rockwell et al. |
| 6,369,034 B1 | 4/2002 | Doherty et al. |
| 6,372,747 B1 | 4/2002 | Taveras et al. |
| 6,383,790 B1 | 5/2002 | Shokat |
| 6,387,905 B2 | 5/2002 | Njoroge et al. |
| 6,399,615 B1 | 6/2002 | Guzi et al. |
| 6,399,633 B1 | 6/2002 | Dumont et al. |
| 6,403,581 B1 | 6/2002 | Ayral-Kaloustian et al. |
| 6,406,867 B1 | 6/2002 | Yu et al. |
| 6,407,213 B1 | 6/2002 | Carter et al. |
| 6,410,539 B1 | 6/2002 | Arnould |
| 6,410,541 B2 | 6/2002 | Remiszewski et al. |
| 6,414,145 B1 | 7/2002 | Boyle et al. |
| 6,420,387 B1 | 7/2002 | Venet et al. |
| 6,432,959 B1 | 8/2002 | Cooper et al. |
| 6,436,960 B1 | 8/2002 | Shin et al. |
| 6,440,974 B2 | 8/2002 | Doll et al. |
| 6,451,812 B1 | 9/2002 | End et al. |
| 6,458,935 B1 | 10/2002 | Burns et al. |
| 6,639,055 B1 | 10/2003 | Carter et al. |
| 6,709,659 B1 | 3/2004 | Lok et al. |
| 6,709,873 B1 | 3/2004 | Yatscoff et al. |
| 6,719,971 B1 | 4/2004 | Carter et al. |
| 6,753,407 B2 | 6/2004 | Noga et al. |
| 6,787,153 B1 | 9/2004 | Hosokawa et al. |
| 6,800,738 B1 | 10/2004 | Carter et al. |
| 6,814,965 B2 | 11/2004 | Gao et al. |
| 6,849,259 B2 | 2/2005 | Haurum et al. |
| 6,861,242 B1 | 3/2005 | Canfield |
| 6,861,572 B1 | 3/2005 | Etches et al. |
| 6,875,434 B1 | 4/2005 | Schenk |
| 6,891,024 B2 | 5/2005 | Marsh |
| 6,946,546 B2 | 9/2005 | Vaughan et al. |
| 6,982,323 B1 | 1/2006 | Wang et al. |
| 7,138,262 B1 | 11/2006 | Daniel |
| 7,407,659 B2 | 8/2008 | Karumanchi et al. |

(56) References Cited

U.S. PATENT DOCUMENTS

| | | |
|---|---|---|
| 7,943,743 B2 | 5/2011 | Korman et al. |
| 8,008,449 B2 | 8/2011 | Korman et al. |
| 8,178,098 B2 | 5/2012 | Lahn et al. |
| 8,354,509 B2 | 1/2013 | Carven et al. |
| 8,609,089 B2 | 12/2013 | Langermann et al. |
| 2003/0044407 A1 | 3/2003 | Chang et al. |
| 2003/0124652 A1 | 7/2003 | Canfield |
| 2005/0074403 A1 | 4/2005 | Kayyem et al. |
| 2005/0214860 A1 | 9/2005 | Zhu et al. |
| 2010/0028330 A1 | 2/2010 | Collins et al. |
| 2012/0039906 A1 | 2/2012 | Olive |
| 2012/0114649 A1 | 5/2012 | Langermann et al. |
| 2014/0242077 A1 | 8/2014 | Choi et al. |
| 2018/0355035 A1* | 12/2018 | Yoo .......................... A61P 1/00 |

FOREIGN PATENT DOCUMENTS

| | | |
|---|---|---|
| EP | 0 519 596 B1 | 2/2005 |
| GB | 2 188 638 B | 5/1990 |
| GB | 2 209 757 B | 10/1990 |
| WO | WO 1988/07089 A1 | 9/1988 |
| WO | WO 1989/07142 A1 | 8/1989 |
| WO | WO 1990/02809 A1 | 3/1990 |
| WO | WO 1991/05548 A1 | 5/1991 |
| WO | WO 1991/09967 A1 | 7/1991 |
| WO | WO 1991/10737 A1 | 7/1991 |
| WO | WO 1991/10741 A1 | 7/1991 |
| WO | WO 1992/01047 A1 | 1/1992 |
| WO | WO 1992/18619 A1 | 10/1992 |
| WO | WO 1992/19244 A2 | 11/1992 |
| WO | WO 1992/22324 A1 | 12/1992 |
| WO | WO 1993/11236 A1 | 6/1993 |
| WO | WO 1995/15982 A2 | 6/1995 |
| WO | WO 1995/20401 A1 | 8/1995 |
| WO | WO 1996/20698 A2 | 7/1996 |
| WO | WO 1996/33735 A1 | 10/1996 |
| WO | WO 1996/34096 A1 | 10/1996 |
| WO | WO 1997/32572 A2 | 9/1997 |
| WO | WO 1997/33899 A1 | 9/1997 |
| WO | WO 1997/34911 A1 | 9/1997 |
| WO | WO 1997/38731 A1 | 10/1997 |
| WO | WO 1997/44013 A1 | 11/1997 |
| WO | WO 1998/16654 A1 | 4/1998 |
| WO | WO 1998/23289 A1 | 6/1998 |
| WO | WO 1998/24893 A2 | 6/1998 |
| WO | WO 1998/31346 A1 | 7/1998 |
| WO | WO 1998/46645 A2 | 10/1998 |
| WO | WO 1998/50433 A2 | 11/1998 |
| WO | WO 1999/15154 A1 | 4/1999 |
| WO | WO 1999/20253 A1 | 4/1999 |
| WO | WO 1999/23105 A1 | 5/1999 |
| WO | WO 1999/51642 A1 | 10/1999 |
| WO | WO 1999/58572 A1 | 11/1999 |
| WO | WO 1999/66903 A2 | 12/1999 |
| WO | WO 2000/42072 A2 | 7/2000 |
| WO | WO 2003/026494 A2 | 4/2003 |
| WO | WO 2004/028564 A2 | 4/2004 |
| WO | WO 2004/029092 A2 | 4/2004 |
| WO | WO 2004/029207 A2 | 4/2004 |
| WO | WO 2006/121168 | 11/2006 |
| WO | WO 2007/005874 | 1/2007 |
| WO | WO 2008/076560 A2 | 6/2008 |
| WO | WO 2008/143665 A1 | 11/2008 |
| WO | WO 2008/143666 A2 | 11/2008 |
| WO | WO 2009/030884 A2 | 3/2009 |
| WO | WO 2009/101611 A1 | 8/2009 |
| WO | WO 2009/114335 A2 | 9/2009 |
| WO | WO 2010/027827 A2 | 3/2010 |
| WO | WO 2010/077634 A1 | 7/2010 |
| WO | WO 2010/106051 A1 | 9/2010 |
| WO | WO 2011/014438 A1 | 2/2011 |
| WO | WO 2011/066342 A2 | 6/2011 |
| WO | WO 2011/156520 A2 | 12/2011 |
| WO | WO 2015/013388 A2 | 1/2015 |
| WO | WO 2015/013389 A2 | 1/2015 |
| WO | WO 2015/100219 A1 | 7/2015 |
| WO | WO 2015/185875 A2 | 12/2015 |
| WO | WO 2016/160792 A1 | 10/2016 |
| WO | WO 2017/096026 A1 | 6/2017 |
| WO | WO 2017/096051 A1 | 6/2017 |
| WO | WO2017/096052 * | 6/2017 |
| WO | WO 2017/172518 A1 | 10/2017 |
| WO | WO 2018/222685 A1 | 12/2018 |
| WO | WO 2018/222689 A1 | 12/2018 |

OTHER PUBLICATIONS

Allen et al., "Large unilamellar liposomes with low uptake into the reticuloendothelial system," *FEBS Lett.*, 223:42-46 (1987).

Allen et al., "The use of glycolipids and hydrophilic polymoers in avoiding rapid uptake of liposomes by the mononuclear phagocyte system," *Adv. Drug Deliv. Rev*, 13:285-309 (1994).

Allen et al., "Anti-body targeted stealth liposomes," *Stealth Liposomes*, 233-244 (1994).

Alley et al., "Antibody-drug conjugates: targeted drug delivery for cancer," *Curr. Opin. Chem. Biol.*, 14(4):529-537 (2010).

Ames et al., "Conversion of murine Fabs isolated from a combinatorial phage display library to full length immunoglobulins," *J. Immunol. Methods*, 184:177-186 (1995).

Arnon et al., "Monoclonal Antibodies For Immunotargeting Of Drugs In Cancer Therapy," *Monoclonal Antibodies And Cancer Therapy*, 243-256 (1985).

Order, "Analysis, Results, And Future Prospective Of The Therapeutic Use Of Radiolabeled Antibody In Cancer Therapy," *Monoclonal Antibodies For Cancer Detection And Therapy*, 303-316 (1985).

Angal et al., "A single amino acid substitution abolishes the heterogeneity of chimeric mouse/human (IgG4) antibody," *Mol. Immunol.*, 30:105-108 (1993).

Arnett et al., "Immune modulation by butyrophilins," *Nat. Rev. Immunol.*, 14:559-569 (2014).

Aurrand-Lions et al., "Vanin-1, a novel GPI-linked perivascular molecule involved in thymus homing," *Immunity*, 5(5):391-405(1996).

Austin-Ward and Villaseca, "Gene therapy and its applications," *Rev. Med. Chil.*, 126(7):838-845 (1998). English Abstract.

Ausubel et al., "Preparation and Analysis of DNA," *Current Protocols in Moleuclar Biology*, 1:2.10.2-2.10.3, 6.3.1-6.3.6 (1989).

Banghart et al., "Butyrophilin is expressed in mammary epithelial cells from a single-sized messenger RNA as a Type I membrane glycoprotein," *J. Biol. Chem.*, 273(7):4171-4179 (1998).

Barderas et al., "Affinity maturation of antibodies assisted by in silico modeling," *Proc. Natl. Acad. Sci. USA*, 105:9029-9034 (2008).

Bendas, "Immunoliposomes A Promising Approach to Targeting Cancer Therapy," *BioDrugs*, 15(4):215-224 (2001).

Bendig, "Humanization of Rodent Monoclonal Antibodies by CDR Grafting," *Methods: A Companion to Methods in Enzymology*, 8:83-93 (1995).

Better et al., "*Escherichia coli* secretion of an active chimeric antibody fragment," *Science*, 240:1041-1043 (1988).

Blume et al., "Liposomes for the sustained drug release in vivo," *Biochim. Biophys. Acta.*, 1029: 91-97 (1990).

Bollenbach et al., "Evolution and multilevel optimization of the genetic code," *Genome Res.*, 17:401-404 (2007).

Bostrom et al., "Improving antibody binding affinity and ificity for therapeutic development," *Methods Mol. Biol.*, 525:353-376 (2009).

Brahmer et al., "Safety and activity of anti-PD-L1 antibody in patients with advanced cancer," *N. Engl. J. Med.*, 66:2455-2465 (2012).

Brinkman et al., "Phage display of disulfide-stabilized Fv fragments," J. Immunol. Methods, 182:41-50 (1995).

Buchwald et al., "Long-term, continuous intravenous heparin administration by an implantable infusion pump in ambulatory patients with recurrent venous thrombosis," *Surgery*, 88(4):507-516 (1980).

Bukowski et al., "Signal transduction abnormalities in T lymphocytes from patients with advanced renal carcinoma: clinical relevance and effects of cytokine therapy," *Clin. Cancer Res.*, 4(10):2337-2347 (1998).

(56) References Cited

OTHER PUBLICATIONS

Burton et al., "Human antibodies from combinatorial libraries," *Adv. Immunol.*, 57:191-280 (1994).
Caron et al., "Engineered humanized dimeric forms of IgC are more effective antibodies," *J. Exp Med.*, 176:1191-95 (1992).
Carter et al., "Antibody-drug conjugates for cancer therapy," *Cancer J.*, 14(3):154-169 (2008).
Carter et al., "Humanization of an anti-p185HER2 antibody for human cancer therapy," *Proc. Natl. Acad. Sci. USA*, 89:4285-4289 (1992).
Carter et al., "Designer antibody-based therapeutics for oncology," *Amer. Assoc. Cancer Res. Educ. Book*, 1:147-154 (2005).
Chari, "Targeted cancer therapy: conferring ificity to cytotoxic drugs," *Acc. Chem. Res.*, 41(1):98-107 (2008).
Chen et al., "13II-labeled monoclonal antibody targeting neuropilin receptor type-2 for tumor SPECT imaging," *Int. J. Oncol.*, 50(2):649-659 (2016).
Chen et al., "Selection and analysis of an optimized anti-VEGF antibody: crystal structure of an affinity-matured Fab in complex with antigen," *J. Mol. Biol.*, 293:865-881 (1999).
Cheung et al., "Scanning N-glycosylation mutagenesis of membrane proteins," *Methods*, 41(4):451-459 (2007).
Chothia et al., "Canonical structures for the hypervariable regions of immunoglobulins," *J. Mol. Biol.*, 196:901-917 (1987).
Chothia et al., "Structural determinants in the sequences of immunoglobulin variable domain," *J. Mol. Biol.*, 278:457-479 (1998).
Christodoulides et al., "Immunization with recombinant class 1 outer-membrane protein from *Neisseria meningitidis*: influence of liposomes and adjuvants on antibody avidity, recognition of native protein and the induction of a bactericidal immune response against meningococci," *Microbiology*, 144:3027-3037 (1998).
Cleek et al., "Biodegradable Polymeric Carriers for a bFGF Antibody for Cardiovascular Application," *Pro. Int'l. Symp. Control. Rel. Bioact. Mater.*, 24:853-854 (1997).
Colman, "Effects of amino acid sequence changes on antibody-antigen interactions," *Research in Immunology*, 145:33-36 (1994).
Davidson et al., "Intralesional cytokine therapy in cancer: a pilot study of GM-CSF infusion in mesothelioma," *J Immunother.*, 21(5):389-398(1998).
Davies et al., "Expression of GnTIII in a recombinant anti-CD20 CHO production cell line: Expression of antibodies with altered glycoforms leads to an increase in ADCC through higher affinity for FC gamma RIII," *Biotechnol. Bioeng.*, 74:288-294 (2001).
Dernardo et al., "Comparison of 1,4,7,10-tetraazacyclododecane-N,N',N'',N'''-tetraacetic acid (DOTA)-peptide-ChL6, a novel immunoconjugate with catabolizable linker, to 2-iminothiolane-2-[p-(bromoacetamido)benzyl]-DOTA-ChL6 in breast cancer xenografts.," *Clin Cancer Res.*, 4(10):2483-2490 (1998).
Desmyter et al., "Crystal structure of a camel single-domain VH antibody fragment in complex with lysozyme," *Nat. Struct. Biol.*, 3:803-811 (1996).
Dietrich et al., "Functional immobilization of a DNA-binding protein at a membrane interface via histidine tag and synthetic chelator lipids," *Biochemistry*, 35:1100-1105 (1996).
Dolcetti et al., "Measurement of myeloid cell immune suppressive activity," *Curr. Protoc. Immunol.*, 14.17.1-14.17.25 (2010).
Doronina et al., "Development of potent monoclonal antibody aurtistatin conjugates for cancer therapy," *Nat. Biotechnol.*, 21(7):778-784 (2003).
Ducry et al., "Antibody-drug conjugates: linking cytotoxic payloads to monoclonal antibodies," *Bioconjug. Chem.*, 21(1):5-13(2010).
During et al., "Controlled release of dopamine from a polymeric brain implant: in vivo characterization," *Ann. Neurol.*, 25(4):351-356 (1989).
Elbein et al., "Kifunensine, a potent inhibitor of the glycoprotein processing mannosidase I," *J. Biol. Chem.*, 265(26):15599-15605 (1990).
Elliott et al., "Enhancement of therapeutic protein in vivo activities through glycoengineering," *Nat. Biotechnol.*, 21:414-421 (2003).
Eppstein et al., "Biological activity of liposome-encapsulated murine interferon gamma is mediated by a cell membrane receptor," *Proc. Natl. Acad. Sci. USA*, 82(11):3688-3692 (1985).
Finlay et al., "Affinity maturation of a humanized rat antibody for anti-RAGE therapy: comprehensive mutagenesis reveals a high level of mutational plasticity both inside and outside the complementarity-determining regions," *J. Mol. Biol.*, 388:541-558 (2009).
Foote et al., "Antibody framework residues affecting the conformation of the hypervariable loops," *J. Mol. Biol.*, 224(2):487-499 (1992).
Huse, "Combinatorial anitbody expression libraris in filamentous phage," *Antibody Engineering: A Practical Guide*, 103-120 (1991).
Fujihara et al., "Galectin-9 in cancer therapy," *Recent Patents on Endocrine, Metabolic and Immune Drug Discovery*, 7(2):130-137 (2013).
Gillies et al., "High-level expression of chimeric antibodies using adapted cDNA variable region cassettes," *J. Immunol. Methods*, 125:191-202 (1989).
Glaser et al., "Antibody engineering by codon-based mutagenesis in a filamentous phage vector system," *J. Immunol.*, 149:3903-3913 (1992).
Goodson, "Dental Applications," Medical Applications of Controlled Release, 2:115-138 (1984).
Grosjean et al., "Preferential codon usage in prokaryotic genes: the optimal codon-anticodon interaction energy and the selective codon usage in efficiently expressed genes," *Gene*, 18:199-209 (1982).
Gustchina et al., "Affinity maturation by targeted diversification of the CDR-H2 loop of a monoclonal Fab derived from a synthetic naïve human antibody library and directed against the internal trimeric coiled-coil of gp41 yields a set of Fabs with improved HIV-1 neutralization potency and breadth," *Virology*, 393:112-119 (2009).
Hackel et al., "Stability and CDR composition biases enrich binder functionality landscapes," *J. Mol. Biol.*, 401:84-96 (2010).
Hamers-Casterman et al., "Naturally occurring antibodies devoid of light chains," *Nature*, 363:446-448 (1993).
Hamid et al., "Safety and tumor responses with lambrolizumab (anti-PD-1) in melanoma," *N. Eng. J. Med.*, 369(2):134-144 (2013).
Hanibuchi et al., "Therapeutic efficacy of mouse-human chimeric anti-ganglioside GM2 monoclonal antibody against multiple organ micrometastases of human lung cancer in NK cell-depleted SCID mice," *Int. J. Cancer*, 78(4):480-485 (1998).
Hansen et al., "Attachment of antibodies to sterically stabilized liposomes: evaluation, comparison and optimization of coupling procedures," *Biochim. Biophys. Acta.*, 1239(2):133-144 (1995).
Helenius et al., "Intracellular functions of N-linked glycans," *Science*, 291(5512):2364-2369 (2001).
Hellstrand et al., "Histamine and cytokine therapy," *Acta Oncol.*, 37(4):347-353(1998).
Hellstrom et al., "Antibodies For Drug Delivery", *Controlled Drug Delivery*, 623-653 (1987).
Hollander, "Immunotherapy for B-Cell lymphoma: current status and prospective advances," *Front. Immunol.*, 3:3. doi: 10.3389/fimmu.2012.00003 (2012).
Honegger et al., "Yet another numbering scheme for immunoglobulin variable domains: an automatic modeling and analysis tool," *J. Mol. Biol.*, 309(3):657-670 (2001).
Howard et al., "Intracerebral drug delivery in rats with lesion-induced memory deficits," *J. Neurosurg.*, 71(1):105-112 (1989).
Hu et al., "Minibody: A novel engineered anti-carcinoembryonic antigen antibody fragment (single-chain Fv-CH3) which exhibits rapid, high-level targeting of xenografts," *Cancer Res.*, 56:3055-3061 (1996).
Hui et al., "Pathways for potentiation of immunogenicity during adjuvant-assisted immunizations with Plasmodium falciparum major merozoite surface protein 1," *Infect. Immun.*, 66(11):5329-5336(1998).
Huston et al., "Antigen recognition and targeted delivery by the single-chain Fv," *Cell Biophys.*, 22:189-224 (1993).
Huston et al., "Protein engineering of single-chain Fv analogs and fusion proteins," *Methods Enzymol.*, 203:46-88 (1991).

(56) References Cited

OTHER PUBLICATIONS

Hwang et al., "Hepatic uptake and degradation of unilamellar sphingomyelin/cholesterol liposomes: a kinetic study," *Proc. Natl. Acad. Sci. USA*, 77:4030-4034 (1980).
Jeong et al., "The PRY/SPRY/B30.2 domain of butyrophilin 1A1 (BTN1A1) binds to xanthine oxidoreductase: implicaitons for the function of BTN1A1 in the mammary gland and other tissues," *J. Biol. Chem.*, 284(33):22444-22456 (2009).
Jestin et al., "Optimization models and the structure of the genetic code," *J. Mol. Evol.*, 69:452-457 (2009).
Joliot et al., "Antennapedia homeobox peptide regulates neural morphogenesis," *Proc. Natl. Acad. Sci. USA*, 88(5):1864-1868 (1991).
Jones et al., "Replacing the complementarity-determining regions in a human antibody with those from a mouse," *Nature*, 321(6069):522-525 (1986).
Kabat et al., "Unusual distributions of amino acids in complementarity-determining (hypervariable) segments of heavy and light chains of immunoglobulins and their possible roles in specificity of antibody-combining sites," *J. Biol. Chem.*, 252:6609-6616 (1977).
Kabat, "The structural basis of antibody complementarity," *Adv. Protein Chem.*, 32:1-75 (1978).
Kantarjian et al., "Treatment of philadelphia chromosome-positive, accelerated-phase chronic myelogenous leukemia with imatinib mesylate," *Clin. Cancer Res.*, 8:2167-2176 (2002).
Katoh et al., "MAFFT: a novel method for rapid multiple sequence alignment based on fast Fourier transform," *Nucleic Acids Res.*, 30(14):3059-3066 (2002).
Kettleborough et al., "Isolation of tumor cell-specific single-chain Fv from immunized mice using phage-antibody libraries and the re-construction of whole antibodies from these antibody fragments," *Eur. J. Immunol.*, 24:952-958 (1994).
Khantasup et al., "Design and generation of humanized single-chain Fv derived from mouse hybridoma for potential targeting application," *Monoclonal Antibodies in Immunodiganosi and Immunotherapy*, 34(6):404-417 (2015).
Klibanov et al., "Activity of amphipathic poly(ethylene glycol) 5000 to prolong the circulation time of liposomes depends on the liposome size and is unfavorable for immunoliposome binding to target," *Biochim Biophys Acta*, 1062(2):142-148 (1991).
Klibanov et al., "Amphipathic polyethyleneglycols effectively prolong the circulation time of liposomes," *FEBS Letts.*, 268(1):235-237 (1990).
Knappik et al., "An improved affinity tag based on the FLAG peptide for the detection and purification of recombinant antibody fragments," *Biotechniques*, 17(4):754-761 (1994).
Krause et al., "An insertion mutation that distorts antibody binding site architecture enhances function of a human antibody," *MBio*, 2:e000345-10, 1-8 (2011).
Kuan et al., "Affinity-matured anti-glycoprotein NMB recombinant immunotoxins targeting malignant gliomas and melanomas," *Int. J. Cancer*, 129:111-121 (2011).
Kurland et al., "Optimization of translation accuracy," *Prog. Nucleic Acid Res. Mol. Biol.*, 31:191-219 (1984).
Lam et al., "Microencapsulation of recombinant humanized monoclonal antibody for local delivery," *Proc. Int'l. Symp. Control Rel. Bioact. Mater.*, 24:759-760 (1997).
Langer et al., "New methods of drug delivery," *Science*, 249(4976):1527-1533 (1990).
Larocca et al., "Akt1 is essential for postnatal mammary gland development, function, and the expression of Btn 1 a 1," *PLoS ONE*, 6(9):e24432 (2011).
Lebrero-Fernandez et al., "Altered expression of butyrophilin (BTN) and BTN-like (BTNL) genes in intestinal inflammation and colon cancer: BTN and BTNL genes in inflammation and cancer," *Immunity Inflammation Dis.*, 4(2):191-200 (2016).
Lefranc et al., "IMGT, the international ImMunoGeneTics database," *Nucleic Acids Res.*, 27(1):209-212 (1999).

Levy et al., "Inhibition of calcification of bioprosthetic heart valves by local controlled-release diphosphonate," *Science*, 228(4696):190-192 (1985).
Litzinger et al., "Effect of liposome size on the circulation time and intraorgan distribution of amphipathic poly(ethylene glycol)-containing liposomes," *Biochim. Biophys. Acta*, 1190:99-107 (1994).
Lonberg et al., "Human antibodies from transgenic mice," *Int. Rev. Immunol.*, 13:65-93 (1995).
Loughrey et al., "A non-covalent method of attaching antibodies to liposomes," *Biochim. Biophys. Acta*, 901:157-160 (1987).
Lowry et al., "Protein measurement with the folin phenol reagent," *J. Biol. Chem.*, 193:265-275 (1951).
Marchler-Bauer et al., "CDD: a conserved domain database for the functional annotation of proteins," *Nucleic Acids Res.*, 39:D225-D229 (2011).
Martin et al., "Structural families in loops of homologous proteins: automatic classification, modelling and application to antibodies," *J. Mol. Biol.*, 263(5):800-815 (1996).
Martin et al., "Irreversible coupling of immunoglobulin fragments to preformed vesicles. An improved method for liposome targeting," *J. Biol. Chem.*, 257(1):286-288 (1982).
La Mar et al., "Proton nuclear magnetic resonance investigation of the nature of solution conformational equilibria of monomeric insect deoxyhemoglobins," *Biochemistry*, 20(15):4429-4438 (1981).
Maruyama et al., "Effect of molecular weight in amphipathic polyethyleneglycol on prolonging the circulation time of large unilamellar liposomes," *Chem. Pharm. Bull.*, 39: 1620-1622 (1991).
Maruyama, "In vivo targeting by liposomes," *Biol. Pharm. Bull.*, 23(7): 791-799 (2000).
Mohammad et al., "A new tubulin polymerization inhibitor, auristatin PE, induces tumor regression in a human Waldenstrom's macroglobulinemia xenograft model," *Int. J. Oncol.*, 15:367-372(1999).
Mohammad et al., "Bryostatin 1 induces differentiation and potentiates the antitumor effect of Auristatin PE in a human pancreatic tumor (PANC-1) xenograft model," *Anticancer Drugs*, 12:735-740 (2001).
Montgomery et al., "Affinity maturation and characterization of a human monoclonal antibody against HIV-1 gp41," *MAbs*, 1:462-474 (2009).
Morea et al., "Antibody modeling: implications for engineering and design," *Methods*, 20:267-279 (2000).
Morrison et al., "Chimeric human antibody molecules: mouse antigen-binding domains with human constant region domains," *Proc. Natl. Acad. Sci. USA*, 81(21):6851-6855 (1984).
Morrison, "Transfectomas provide novel chimeric antibodies," *Science*, 229:1202-1207 (1985).
Mueller et al., "Humanized porcine VCAM-specific monoclonal antibodies with chimeric IgG2/G4 constant regions block human leukocyte binding to porcine endothelial cells," *Mol. Immunol.*, 34:441-452 (1997).
Mullinax et al., "Expression of a heterodimeric Fab antibody protein in one cloning step," *Biotechniques*, 12:864-869 (1992).
Murali et al., "Antibody like peptidomimetics as large scale immunodetection probes," *Cell Mol. Biol.* (*Noisy-le grand*), 49:209-216 (2003).
Mustapha et al., "Evaluation of galectin-9 blocking monclonal antibodies as novel immune-chckpoint inhibitors via the targeting of regulatory T cells in cancer," *Eur. J. Immunol.*, 26(Suppl 1):16 (2016).
Ning et al., "Intratumoral radioimmunotherapy of a human colon cancer xenograft using a sustained-release gel," *Radiother. Oncol.*, 39:179-189 (1996).
Niwa et al., "Defucosylated Chimeric Anti-CC Chemokine Receptor 4 IgG1 with Enhanced Antibody-Dependent Cellular Cytotoxicity Shows Potent Therapeutic Activity to T-Cell Leukemia and Lympoma," *Cancer Res.*, 64:2127-33 (2004).
Ogg et al., "Expression of butyrophilin (Btn 1 a 1) in lactating mammary gland essential for the regulated secretion of milk-lipid droplets," *Proc. Natl. Acad. Sci. USA*, 101(27):10084-10089 (2004).
Oi et al., "Chimeric Antibodies," *BioTechniques*, 4:214-221 (1986).

(56) References Cited

OTHER PUBLICATIONS

Okazaki et al., "Fucose depletion from human IgG1 oligosaccharide enhances binding enthalpy and association rate between IgG1 andFcγRIIIa," *J. Mol. Biol.*, 336:1239-1249 (2004).
Olive D, "B7/ butyrophilin family members are leading the race for immune intervention," *Exp. Opin. Ther. Patents*, 17(3):357-359 (2007).
Padlan, "A possible procedure for reducing the immunogenicity of antibody variable domains while preserving their ligand-binding properties," *Mol. Immunol.*, 28:489-498 (1991).
Park et al., "Immunoliposomes for cancer treatment," *Adv. Pharmacol.*, 40:399-435 (1997).
Park, "Tumor-directed targeting of liposomes," *Bioscience Rep.*, 22(2): 267-281 (2002).
Paul, "Structure and function of immunoglobulins," *Fundamental Immunology*, 292-295 (1993).
Persic et al., "An integrated vector system for the eukaryotic expression of antibodies or their fragments after selection from phage display libraries," *Gene*, 187:9-19 (1997).
Peterson et al., "Enzymatic cleavage of peptide-linked radiolabels from immunoconjugates," *Bioconjug. Chem.*, 10(4):553-557 (1999).
Pluckthun et al., "Expression of functional antibody Fv and Fab fragments in *Escherichia coli*," *Methods Enzymol.*, 178:497-515 (1989).
Presta, "Antibody engineering," *Curr. Opin. Struct. Biol.*, 2:593-596 (1992).
Presta, "Molecular engineering and design of therapeutic antibodies," *Curr. Opin. Immunol.*, 20:460-470 (2008).
Qin et al., "Interferon-β gene therapy inhibits tumor formation and causes regression of established tumors in immune-deficient mice," *Proc Natl Acad Sci USA*, 95(24):14411-14416 (1998).
Langer et al., "Chemical and physical structure of polymers as carriers for controlled release of bioactive agents: a review," *J. Macromol. Sci. Rev. Macromol. Chem.*, 23:61-126 (1983).
Ravetch et al., "Fc receptors," *Annu. Rev. Immunol.*, 9:457-492 (1991).
Riechmann et al., "Reshaping human antibodies for therapy," *Nature*, 332(6162):323-327 (1988).
Robenek et al., "Butyrophilin controls milk fat globule secretion," *Proc. Natl. Acad. Sci. USA*, 103(27):10385-10390 (2006).
Roguska et al., "Humanization of murine monoclonal antibodies through variable domain resurfacing," *Proc. Natl. Acad. Sci. USA*, 91:969-973 (1994).
Rothman et al., "Antibody-dependent cytotoxicity mediated by natural killer cells is enhanced by castanospermine-induced alterations of IgG glycosylation," *Molecular Immunology* 26:1113-1123 (1989).
Routledge et al., "The effect of aglycosylation on the immunogenicity of a humanized therapeutic CD3 monoclonal antibody," *Transplantation*, 60:847-853 (1995).
Rudikoff et al., "Single amino acid substitution altering antigen-binding specificity," *Proc. Natl. Acad. Sci. USA*, 79(6):1979-1983 (1982).
Sali et al., "Comparative protein modelling by satisfaction of spatial restraints," *J. Molec. Biol.*, 234:779-815(1993).
Sarter et al., "Btn2a2, a T cell immunomodulatory molecule coregulated with MHC class II genes," *J. Exp. Med.*, 213(2):177-187 (2016).
Saudek et al., "A preliminary trial of the programmable implantable medication system for insulin delivery," *N.Engl. J. Med.* 321(9):574-579 (1989).
Sawai et al., "Direct production of the Fab fragment derived from the sperm immobilizing antibody using polymerase chain reaction and cDNA expression vectors," *Am. J. Reprod. Immunol.*, 34:26-34 (1995).
Schier et al., "Isolation of picomolar affinity anti-c-erbB-2 single-chain Fv by molecular evolution of the complementarity determining regions in the center of the antibody binding site," *J. Mol. Biol.*, 263:551-567 (1996).
Schwarz et al., "Mechanisms and principles of N-linked protein glycosylation," *Curr. Opin. Struct. Biol.*, 21:576-582 (2011).

Sefton, "Inplantable pumps," *CRC Crit. Ref Biomed. Eng.* 14:201-240 (1987).
Senter, "Potent antibody drug conjugates for cancer therapy," *Curr. Opin. Chem. Biol.*, 13(3):235-244 (2009).
Shields et al., "Lack of fucose on human IgG1 N-linked oligosaccharide improves binding to human Fcgamma RIII and antibody-dependent cellular toxicity," *J. Biol. Chem.*, 277:26733-26740 (2002).
Shinkawa et al., "The absence of fucose but not the presence of galactose or bisecting N-acetylglucosamine of human IgG1 complex-type oligosaccharides shows the critical role of enhancing antibody-dependent cellular cytotoxicity," *J Biol. Chem.*, 278:3466-73 (2003).
Shopes, "A genetically engineered human IgG mutant with enhanced cytolytic activity," *Immunol.*, 148:2918-2922 (1992).
Shu et al., "Secretion of a single-gene-encoded immunoglobulin from myeloma cells," *Proc. Natl. Acad. Sci. USA*, 90:7995-7999 (1993).
Skerra et al., "Assembly of a functional immunoglobulin Fv fragment in *Escherichia coli*," *Science*, 240:1038-1041 (1988).
Smith et al., "BTN1A1, the mammary gland butyrophilin, and BTN2A2 are both inhibitors of T cell activation," *J. Immunol.*, 184(7):3514-3525 (2010).
Song et al., "Antibody mediated lung targeting of long-circulating emulsions," *PDA J. Pharm. Sci. Tech.*, 50:372-377 (1996).
Søreide, "Receiver-operating characteristic curve analysis in diagnostic, prognostic and predictive biomarker research," *J. Clin. Pathol.*, 62(1):1-5 (2009).
Steffer et al., "Butyrophilin, a milk protein, modulates the encephalitogenic T cell response to myelin oligodendrocyte glycoprotein in experimental autoimmune encephalomyelitis," *J. Immunol.*, 165(5):2859-2865 (2000).
Steidl et al., "In vitro affinity maturation of human GM-CSF antibodies by targeted CDR-diversification," *Mol. Immunol.*, 46:135-144 (2008).
Stevenson et al., "A chimeric antibody with dual Fc regions (bisFabFc) prepared by mannipulations at the IgG hinge," *Anticancer Drug Design*, 3:219-30 (1989).
Studnicka et al., "Human-engineered monoclonal antibodies retain full specific binding activity by preserving non-CDR complementarity-modulating residues," *Protein Eng.*, 7:805-814 (1994).
Swann et al., "Considerations for the development of therapeutic monoclonal antibodies," *Curr. Opin. Immunol.*, 20:493-499 (2008).
Takahashi et al., "Human Fas ligand: gene structure, chromosomal location and species specificity," *Int. Immunol.*, 6:1567-1574 (1994).
Tao et al., "Studies of aglycosylated chimeric mouse-human IgG. Role of carbohydrate in the structure and effector functions mediated by the human IgG constant region," *J. Immunol.*, 143:2595-2601 (1989).
Taylor et al., "A transgenic mouse that expresses a diversity of human sequence heavy and light chain immunoglobulins," *Nucleic Acids Res.*, 20:6287-6295 (1992).
Taylor et al., "Cloning and sequence analysis of human butyrophilin reveals a potential receptor function," *Biochim. Biophys. Acta.*, 1306(1):1-4 (1996).
Teicher, "Antibody-drug conjugate targets," *Curr. Cancer Drug Targets*, 9(8):982-1004 (2009).
Thorpe et al., "The preparation and cytotoxic properties of antibody-toxin conjugates," *Immunol. Rev.*, 62:119-158 (1982).
Thorpe, "Antibody Carriers Of Cytotoxic Agents In Cancer Therapy: A Review", *Monoclonal Antibodies '84: Biological and Clinical Applications*, 475-506 (1985).
Topalian et al., "Safety, activity, and immune correlates of anti-PD-1 antibody in cancer," *N. Engl. J. Med.*, 366(26):2443-2454 (2012).
Torchilin et al., "How do polymers prolong circulation time of liposomes," *J. Liposome Res.*, 6: 99-116 (1996).
Umana et al., "Engineered glycoforms of an antineuroblastoma IgG1 with optimized antibody-dependent cellular cytotoxic activity," *Nature Biotechnology*, 17:176-180 (1999).
Vingerhoeds et al., "Immunoliposomes in vivo," *Immunomethods*, 4(3):259-272 (1994).
Wall et al., "Modulation of cIAP-1 by novel antitubulin agents when combined with bryostatin 1 results in increased apoptosis in the human early pre-B acute lymphoblastic leukemia cell line Reh," *Biochem. Biophys. Res. Commun.*, 266:76-80 (1999).

(56) References Cited

OTHER PUBLICATIONS

Wallick et al., "Glycosylation of a VH residue of a monoclonal antibody against alpha (1—6) dextran increases its affinity for antigen," *J. Exp. Med.*, 168:1099-1109 (1988).

Wilson et al., "The structure of an antigenic determinant in a protein," *Cell*, 37:767-778 (1984).

Wohlgemuth et al., Evolutionary optimization of speed and accuracy of decoding on the ribosome, *Philos. Trans. R. Soc. Lond. B. Biol. Sci.*, 366:2979-2986 (2011).

Wolff et al., "Monoclonal Antibody Homodimers: Enhanced Antitumor Activity in Nude Mice," *Cancer Research*, 53:2560-2565 (1993).

Woyke et al., "Effect of auristatin PHE on microtubule integrity and nuclear localization in Cryptococcus neoformans," *Antimicrob. Agents Chemother.*, 46:3802-3808 (2002).

Woyke et al., "In vitro activities and postantifungal effects of the potent dolastatin 10 derivative auristatin PHE," *Antimcrob. Agents Chemother.*, 45:3580-3584 (2001).

Wu et al., "Receptor-mediated in vitro gene transformation by a soluble DNA carrier system," *J. Biol. Chem.*, 262(10):4429-4432 (1987).

Wu et al., "Stepwise in vitro affinity maturation of Vitaxin, an alphav beta3-specific humanized mAb," *Proc. Natl. Acad. Sci. USA*, 95:6037-6042 (1998).

Yelton et al., "Affinity maturation of the BR96 anti-carcinoma antibody by codon-based mutagenesis," *J. Immunol.*, 155:1994-2004 (1995).

Zimmerman et al., "A triglycine linker improves tumor uptake and biodistributions of 67-Cu-labeled anti-neuroblastoma MAb chCE7 F(ab')2 fragments," *Nucl. Med. Biol.*, 26(8):943-950 (1999).

\* cited by examiner

SEQUENCE LISTING

```
<160> NUMBER OF SEQ ID NOS: 14

<210> SEQ ID NO 1
<211> LENGTH: 526
<212> TYPE: PRT
<213> ORGANISM: Homo sapiens

<400> SEQUENCE: 1

Met Ala Val Phe Pro Ser Ser Gly Leu Pro Arg Cys Leu Leu Thr Leu
1               5                   10                  15

Ile Leu Leu Gln Leu Pro Lys Leu Asp Ser Ala Pro Phe Asp Val Ile
            20                  25                  30

Gly Pro Pro Glu Pro Ile Leu Ala Val Val Gly Glu Asp Ala Lys Leu
        35                  40                  45

Pro Cys Arg Leu Ser Pro Asn Ala Ser Ala Glu His Leu Glu Leu Arg
    50                  55                  60

Trp Phe Arg Lys Lys Val Ser Pro Ala Val Leu Val His Arg Asp Gly
65                  70                  75                  80

Arg Glu Gln Glu Ala Glu Gln Met Pro Glu Tyr Arg Gly Arg Ala Thr
                85                  90                  95

Leu Val Gln Asp Gly Ile Ala Lys Gly Arg Val Ala Leu Arg Ile Arg
            100                 105                 110

Gly Val Arg Val Ser Asp Asp Gly Glu Tyr Thr Cys Phe Phe Arg Glu
        115                 120                 125

Asp Gly Ser Tyr Glu Glu Ala Leu Val His Leu Lys Val Ala Ala Leu
130                 135                 140

Gly Ser Asp Pro His Ile Ser Met Gln Val Gln Glu Asn Gly Glu Ile
145                 150                 155                 160

Cys Leu Glu Cys Thr Ser Val Gly Trp Tyr Pro Glu Pro Gln Val Gln
                165                 170                 175

Trp Arg Thr Ser Lys Gly Glu Lys Phe Pro Ser Thr Ser Glu Ser Arg
            180                 185                 190

Asn Pro Asp Glu Glu Gly Leu Phe Thr Val Ala Ala Ser Val Ile Ile
        195                 200                 205

Arg Asp Thr Ser Ala Lys Asn Val Ser Cys Tyr Ile Gln Asn Leu Leu
    210                 215                 220

Leu Gly Gln Glu Lys Lys Val Glu Ile Ser Ile Pro Ala Ser Ser Leu
225                 230                 235                 240

Pro Arg Leu Thr Pro Trp Ile Val Ala Val Ala Val Ile Leu Met Val
                245                 250                 255

Leu Gly Leu Leu Thr Ile Gly Ser Ile Phe Phe Thr Trp Arg Leu Tyr
            260                 265                 270

Asn Glu Arg Pro Arg Glu Arg Arg Asn Glu Phe Ser Ser Lys Glu Arg
        275                 280                 285

Leu Leu Glu Glu Leu Lys Trp Lys Lys Ala Thr Leu His Ala Val Asp
    290                 295                 300

Val Thr Leu Asp Pro Asp Thr Ala His Pro His Leu Phe Leu Tyr Glu
305                 310                 315                 320

Asp Ser Lys Ser Val Arg Leu Glu Asp Ser Arg Gln Lys Leu Pro Glu
                325                 330                 335
```

Lys Thr Glu Arg Phe Asp Ser Trp Pro Cys Val Leu Gly Arg Glu Thr
            340                 345                 350

Phe Thr Ser Gly Arg His Tyr Trp Glu Val Glu Val Gly Asp Arg Thr
        355                 360                 365

Asp Trp Ala Ile Gly Val Cys Arg Glu Asn Val Met Lys Lys Gly Phe
    370                 375                 380

Asp Pro Met Thr Pro Glu Asn Gly Phe Trp Ala Val Glu Leu Tyr Gly
385                 390                 395                 400

Asn Gly Tyr Trp Ala Leu Thr Pro Leu Arg Thr Pro Leu Pro Leu Ala
                405                 410                 415

Gly Pro Pro Arg Arg Val Gly Ile Phe Leu Asp Tyr Glu Ser Gly Asp
            420                 425                 430

Ile Ser Phe Tyr Asn Met Asn Asp Gly Ser Asp Ile Tyr Thr Phe Ser
        435                 440                 445

Asn Val Thr Phe Ser Gly Pro Leu Arg Pro Phe Phe Cys Leu Trp Ser
    450                 455                 460

Ser Gly Lys Lys Pro Leu Thr Ile Cys Pro Ile Ala Asp Gly Pro Glu
465                 470                 475                 480

Arg Val Thr Val Ile Ala Asn Ala Gln Asp Leu Ser Lys Glu Ile Pro
                485                 490                 495

Leu Ser Pro Met Gly Glu Asp Ser Ala Pro Arg Asp Ala Asp Thr Leu
            500                 505                 510

His Ser Lys Leu Ile Pro Thr Gln Pro Ser Gln Gly Ala Pro
        515                 520                 525

```
<210> SEQ ID NO 2
<211> LENGTH: 1581
<212> TYPE: DNA
<213> ORGANISM: Homo sapiens

<400> SEQUENCE: 2
atggcagttt tcccaagctc cggtctcccc agatgtctgc tcaccctcat tctcctccag      60
ctgcccaaac tggattcagc tccctttgac gtgattggac ccccggagcc catcctggcc     120
gttgtgggtg aggacgccaa gctgccctgt cgcctgtctc cgaacgcgag cgccgagcac     180
ttggagctac gctggttccg aaagaaggtt tcgccggccg tgctggtgca tagggacggg     240
cgcgagcagg aagccgagca gatgcccgag taccgcgggc gggcgacgct ggtccaggac     300
ggcatcgcca aggggcgcgt ggccttgagg atccgtggcg tcagagtctc tgacgacggg     360
gagtacacgt gcttttttcag ggaggatgga agctacgaag aagccctggt gcatctgaag     420
gtggctgctc tgggctctga ccctcacatc agtatgcaag ttcaagagaa tggagaaatc     480
tgtctggagt gcacctcagt gggatggtac ccagagcccc aggtgcagtg agaacttcc      540 aagggagaga agtttccatc tacatcagag tccaggaatc ctgatgaaga aggtttgttc     600
actgtggctg cttcagtgat catcagagac acttctgcga aaaatgtgtc ctgctacatc     660
cagaatctcc ttcttggcca ggagaagaaa gtagaaatat ccataccagc ttcctccctc     720
ccaaggctga ctccctggat agtggctgtg ctgtcatcc tgatggttct aggacttctc      780
accattgggt ccatattttt cacttggaga ctatacaacg aaagaccag agagaggagg      840 aatgaattca gctctaaaga gagactcctg aagaactca atggaaaaa ggctaccttg      900 catgcagttg atgtgactct ggacccagac acagctcatc cccacctctt tctttatgag     960
gattcaaaat ctgttcgact ggaagattca cgtcagaaac tgcctgagaa aacagagaga    1020
```

```
tttgactcct ggccctgtgt gttgggccgt gagaccttca cctcaggaag gcattactgg    1080
gaggtggagg tgggagacag gactgactgg gcaatcggcg tgtgtaggga gaatgtgatg    1140
aagaaaggat ttgaccccat gactcctgag aatgggttct gggctgtaga gttgtatgga    1200
aatgggtact gggccctcac tcctctccgg acccctctcc cattggcagg gcccccacgc    1260
cgggttggga ttttcctaga ctatgaatca ggagacatct ccttctacaa catgaatgat    1320
ggatctgata tctatacttt ctccaatgtc actttctctg ccccctccg gcccttcttt     1380 tgcctatggt ctagcggtaa aaagcccctg accatctgcc caattgctga tgggcctgag    1440
agggtcacag tcattgctaa tgcccaggac ctttctaagg agatcccatt gtcccccatg    1500
ggggaggact ctgcccctag ggatgcagac actctccatt ctaagctaat ccctacccaa    1560
cccagccaag gggcacctta a                                              1581
```

<210> SEQ ID NO 3
<211> LENGTH: 443
<212> TYPE: PRT
<213> ORGANISM: Artificial Sequence
<220> FEATURE:
<223> OTHER INFORMATION: Synthetic polypeptide

<400> SEQUENCE: 3

```
Ala Pro Phe Asp Val Ile Gly Pro Pro Glu Pro Ile Leu Ala Val Val
1               5                   10                  15

Gly Glu Asp Ala Glu Leu Pro Cys Arg Leu Ser Pro Asn Ala Ser Ala
            20                  25                  30

Glu His Leu Glu Leu Arg Trp Phe Arg Lys Lys Val Ser Pro Ala Val
        35                  40                  45

Leu Val His Arg Asp Gly Arg Glu Gln Glu Ala Glu Gln Met Pro Glu
    50                  55                  60

Tyr Arg Gly Arg Ala Thr Leu Val Gln Asp Gly Ile Ala Lys Gly Arg
65                  70                  75                  80

Val Ala Leu Arg Ile Arg Gly Val Arg Val Ser Asp Asp Gly Glu Tyr
                85                  90                  95

Thr Cys Phe Phe Arg Glu Asp Gly Ser Tyr Glu Glu Ala Leu Val His
            100                 105                 110

Leu Lys Val Ala Ala Leu Gly Ser Asp Pro His Ile Ser Met Gln Val
        115                 120                 125

Gln Glu Asn Gly Glu Ile Cys Leu Glu Cys Thr Ser Val Gly Trp Tyr
    130                 135                 140

Pro Glu Pro Gln Val Gln Trp Arg Thr Ser Lys Gly Glu Lys Phe Pro
145                 150                 155                 160

Ser Thr Ser Glu Ser Arg Asn Pro Asp Glu Glu Gly Leu Phe Thr Val
                165                 170                 175

Ala Ala Ser Val Ile Ile Arg Asp Thr Ser Ala Lys Asn Val Ser Cys
            180                 185                 190

Tyr Ile Gln Asn Leu Leu Leu Gly Gln Glu Lys Lys Val Glu Ile Ser
        195                 200                 205

Ile Pro Ala Ser Ser Leu Pro Arg Asp Lys Thr His Thr Cys Pro Pro
    210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
```

```
                260                 265                 270
Trp Tyr Val Asp Gly Val Glu Val His Asn Ala Lys Thr Lys Pro Arg
            275                 280                 285

Glu Glu Gln Tyr Asn Ser Thr Tyr Arg Val Val Ser Val Leu Thr Val
        290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440

<210> SEQ ID NO 4
<211> LENGTH: 222
<212> TYPE: PRT
<213> ORGANISM: Artificial Sequence
<220> FEATURE:
<223> OTHER INFORMATION: Synthetic polypeptide

<400> SEQUENCE: 4

Ala Pro Phe Asp Val Ile Gly Pro Pro Glu Pro Ile Leu Ala Val Val
1               5                   10                  15

Gly Glu Asp Ala Glu Leu Pro Cys Arg Leu Ser Pro Asn Ala Ser Ala
            20                  25                  30

Glu His Leu Glu Leu Arg Trp Phe Arg Lys Lys Val Ser Pro Ala Val
        35                  40                  45

Leu Val His Arg Asp Gly Arg Glu Gln Glu Ala Glu Gln Met Pro Glu
    50                  55                  60

Tyr Arg Gly Arg Ala Thr Leu Val Gln Asp Gly Ile Ala Lys Gly Arg
65                  70                  75                  80

Val Ala Leu Arg Ile Arg Gly Val Arg Val Ser Asp Asp Gly Glu Tyr
                85                  90                  95

Thr Cys Phe Phe Arg Glu Asp Gly Ser Tyr Glu Glu Ala Leu Val His
            100                 105                 110

Leu Lys Val Ala Ala Leu Gly Ser Asp Pro His Ile Ser Met Gln Val
        115                 120                 125

Gln Glu Asn Gly Glu Ile Cys Leu Glu Cys Thr Ser Val Gly Trp Tyr
    130                 135                 140

Pro Glu Pro Gln Val Gln Trp Arg Thr Ser Lys Gly Glu Lys Phe Pro
145                 150                 155                 160

Ser Thr Ser Glu Ser Arg Asn Pro Asp Glu Glu Gly Leu Phe Thr Val
                165                 170                 175

Ala Ala Ser Val Ile Ile Arg Asp Thr Ser Ala Lys Asn Val Ser Cys
```

```
                    180                 185                 190
Tyr Ile Gln Asn Leu Leu Gly Gln Glu Lys Lys Val Glu Ile Ser
                195                 200                 205
Ile Pro Ala Ser Ser Leu Pro Arg His His His His His
            210                 215                 220
```

<210> SEQ ID NO 5
<211> LENGTH: 524
<212> TYPE: PRT
<213> ORGANISM: Mouse

<400> SEQUENCE: 5

```
Met Ala Val Pro Thr Asn Ser Cys Leu Leu Val Cys Leu Leu Thr Leu
1               5                   10                  15
Thr Val Leu Gln Leu Pro Thr Leu Asp Ser Ala Ala Pro Phe Asp Val
                20                  25                  30
Thr Ala Pro Gln Glu Pro Val Leu Ala Leu Val Gly Ser Asp Ala Glu
            35                  40                  45
Leu Thr Cys Gly Phe Ser Pro Asn Ala Ser Ser Glu Tyr Met Glu Leu
        50                  55                  60
Leu Trp Phe Arg Gln Thr Arg Ser Lys Ala Val Leu Leu Tyr Arg Asp
65                  70                  75                  80
Gly Gln Glu Gln Glu Gly Gln Gln Met Thr Glu Tyr Arg Gly Arg Ala
                85                  90                  95
Thr Leu Ala Thr Ala Gly Leu Leu Asp Gly Arg Ala Thr Leu Leu Ile
            100                 105                 110
Arg Asp Val Arg Val Ser Asp Gln Gly Glu Tyr Arg Cys Leu Phe Lys
        115                 120                 125
Asp Asn Asp Asp Phe Glu Glu Ala Ala Val Tyr Leu Lys Val Ala Ala
130                 135                 140
Val Gly Ser Asp Pro Gln Ile Ser Met Thr Val Gln Glu Asn Gly Glu
145                 150                 155                 160
Met Glu Leu Glu Cys Thr Ser Ser Gly Trp Tyr Pro Glu Pro Gln Val
                165                 170                 175
Gln Trp Arg Thr Gly Asn Arg Glu Met Leu Pro Ser Thr Ser Glu Ser
            180                 185                 190
Lys Lys His Asn Glu Glu Gly Leu Phe Thr Val Ala Val Ser Met Met
        195                 200                 205
Ile Arg Asp Ser Ser Ile Lys Asn Met Ser Cys Cys Ile Gln Asn Ile
210                 215                 220
Leu Leu Gly Gln Gly Lys Glu Val Glu Ile Ser Leu Pro Ala Pro Phe
225                 230                 235                 240
Val Pro Arg Leu Thr Pro Trp Ile Val Ala Val Ala Ile Ile Leu Leu
                245                 250                 255
Ala Leu Gly Phe Leu Thr Ile Gly Ser Ile Phe Phe Thr Trp Lys Leu
            260                 265                 270
Tyr Lys Glu Arg Ser Ser Leu Arg Lys Lys Glu Phe Gly Ser Lys Glu
        275                 280                 285
Arg Leu Leu Glu Glu Leu Arg Cys Lys Lys Thr Val Leu His Glu Val
290                 295                 300
Asp Val Thr Leu Asp Pro Asp Thr Ala His Pro His Leu Phe Leu Tyr
305                 310                 315                 320
Glu Asp Ser Lys Ser Val Arg Leu Glu Asp Ser Arg Gln Ile Leu Pro
                325                 330                 335
```

Asp Arg Pro Glu Arg Phe Asp Ser Trp Pro Cys Val Leu Gly Arg Glu
            340                 345                 350

Thr Phe Thr Ser Gly Arg His Tyr Trp Glu Val Glu Val Gly Asp Arg
        355                 360                 365

Thr Asp Trp Ala Ile Gly Val Cys Arg Glu Asn Val Val Lys Lys Gly
    370                 375                 380

Phe Asp Pro Met Thr Pro Asp Asn Gly Phe Trp Ala Val Glu Leu Tyr
385                 390                 395                 400

Gly Asn Gly Tyr Trp Ala Leu Thr Pro Leu Arg Thr Ser Leu Arg Leu
                405                 410                 415

Ala Gly Pro Pro Arg Arg Val Gly Val Phe Leu Asp Tyr Asp Ala Gly
            420                 425                 430

Asp Ile Ser Phe Tyr Asn Met Ser Asn Gly Ser Leu Ile Tyr Thr Phe
            435                 440                 445

Pro Ser Ile Ser Phe Ser Gly Pro Leu Arg Pro Phe Phe Cys Leu Trp
        450                 455                 460

Ser Cys Gly Lys Lys Pro Leu Thr Ile Cys Ser Thr Ala Asn Gly Pro
465                 470                 475                 480

Glu Lys Val Thr Val Ile Ala Asn Val Gln Asp Ile Pro Leu Ser
                485                 490                 495

Pro Leu Gly Glu Gly Cys Thr Ser Gly Asp Lys Asp Thr Leu His Ser
            500                 505                 510

Lys Leu Ile Pro Phe Ser Pro Ser Gln Ala Ala Pro
            515                 520

<210> SEQ ID NO 6
<211> LENGTH: 1575
<212> TYPE: DNA
<213> ORGANISM: Mouse

<400> SEQUENCE: 6

```
atggcagttc ccaccaactc ctgcctcctg gtctgtctgc tcaccctcac tgtcctacag      60
ctgcccacgc tggattcggc agctcccttc gatgtgaccg cacctcagga gccagtgttg     120
gccctagtgg gctcagatgc cgagctgacc tgtggctttt ccccaaacgc gagctcagaa     180
tacatggagc tgctgtggtt tcgacagacg aggtcgaaag cggtacttct ataccgggat     240
ggccaggagc aggagggcca gcagatgacg gagtaccgcg ggagggcgac gctggcgaca     300
gccgggcttc tagacggccg cgctactctg ctgatccgag atgtcagggt ctcagaccag     360
ggggagtacc ggtgcctttt caaagacaac gacgacttcg aggaggccgc cgtatacctc     420
aaagtggctg ctgtgggttc agatcctcaa atcagtatga cggttcaaga gaatggagaa     480
atggagctgg agtgcacctc ctctggatgg tacccagagc tcaggtgca gtggagaaca      540
ggcaacagag agatgctacc atccacgtca gagtccaaga agcataatga ggaaggcctg     600
ttcactgtgg cagtttcaat gatgatcaga gacagctcca taagaacat gtcctgctgc      660
atccagaata tcctccttgg ccaggggaag gaagtagaga tctccttacc agctcccttc     720
gtgccaaggc tgactccctg gatagtagct gtggctatca tcttactggc cttaggattt     780
ctcaccattg gtccatatt tttcacttgg aaactataca ggaaagatc cagtctgcgg      840
aagaaggaat ttggctctaa agagagactt ctggaagaac tcagatgcaa aaagactgta     900
ctgcatgaag ttgacgtgac tctggatcca gacacagccc accccacct cttcctgtat     960
gaagattcaa agtcagttcg attggaagat tcacgtcaga cctgcctga tagaccagag    1020
agatttgact cctggcctg tgtgttgggc cgtgagacct ttacttcagg agacattac     1080
```

```
tgggaggtgg aggtgggaga tagaactgac tgggccattg gtgtgtgtag ggagaatgtg    1140
gtgaagaaag ggtttgaccc catgactcct gataatgggt tctgggctgt ggagttgtat    1200
ggaaatgggt actgggccct caccccactc aggacctctc tccgattagc agggccccct    1260
cgcagagttg gggttttcct ggactatgac gcaggagaca tttccttcta caacatgagt    1320
aacggatctc ttatctatac tttccctagc atctctttct ctggccccct ccgtcccttc    1380
ttttgtctgt ggtcctgtgg taaaaagccc ctgaccatct gttcaactgc aatgggcct    1440 gagaaagtca cagtcattgc taatgtccag gacgacattc ccttgtcccc gctgggggaa    1500
ggctgtactt ctggagacaa agacactctc cattctaaac tgatcccgtt ctcacctagc    1560
caagcggcac cataa                                                      1575
```

<210> SEQ ID NO 7
<211> LENGTH: 135
<212> TYPE: PRT
<213> ORGANISM: Homo sapiens

<400> SEQUENCE: 7

```
Met Ala Cys Gly Leu Val Ala Ser Asn Leu Asn Leu Lys Pro Gly Glu
1               5                   10                  15

Cys Leu Arg Val Arg Gly Glu Val Ala Pro Asp Ala Lys Ser Phe Val
            20                  25                  30

Leu Asn Leu Gly Lys Asp Ser Asn Asn Leu Cys Leu His Phe Asn Pro
        35                  40                  45

Arg Phe Asn Ala His Gly Asp Ala Asn Thr Ile Val Cys Asn Ser Lys
    50                  55                  60

Asp Gly Gly Ala Trp Gly Thr Glu Gln Arg Glu Ala Val Phe Pro Phe
65                  70                  75                  80

Gln Pro Gly Ser Val Ala Glu Val Cys Ile Thr Phe Asp Gln Ala Asn
                85                  90                  95

Leu Thr Val Lys Leu Pro Asp Gly Tyr Glu Phe Lys Phe Pro Asn Arg
            100                 105                 110

Leu Asn Leu Glu Ala Ile Asn Tyr Met Ala Ala Asp Gly Asp Phe Lys
        115                 120                 125

Ile Lys Cys Val Ala Phe Asp
    130                 135
```

<210> SEQ ID NO 8
<211> LENGTH: 408
<212> TYPE: DNA
<213> ORGANISM: Homo sapiens

<400> SEQUENCE: 8

```
atggcttgtg gtctggtcgc cagcaacctg aatctcaaac ctggagagtg ccttcgagtg     60
cgaggcgagg tggctcctga cgctaagagc ttcgtgctga acctgggcaa agacagcaac    120
aacctgtgcc tgcacttcaa ccctcgcttc aacgcccacg gcgacgccaa caccatcgtg    180
tgcaacagca aggacggcgg ggcctggggg accgagcagc gggaggctgt ctttcccttc    240
cagcctggaa gtgttgcaga ggtgtgcatc accttcgacc aggccaacct gaccgtcaag    300
ctgccagatg gatacgaatt caagttcccc aaccgcctca acctggaggc catcaactac    360
atggcagctg acggtgactt caagatcaaa tgtgtggcct ttgactga                 408
```

<210> SEQ ID NO 9
<211> LENGTH: 246

<212> TYPE: PRT
<213> ORGANISM: Homo sapiens

<400> SEQUENCE: 9

```
Met Ala Phe Ser Gly Ser Gln Ala Pro Tyr Leu Ser Pro Ala Val Pro
1               5                   10                  15

Phe Ser Gly Thr Ile Gln Gly Leu Gln Asp Gly Leu Gln Ile Thr
            20                  25                  30

Val Asn Gly Thr Val Leu Ser Ser Ser Gly Thr Arg Phe Ala Val Asn
        35                  40                  45

Phe Gln Thr Gly Phe Ser Gly Asn Asp Ile Ala Phe His Phe Asn Pro
    50                  55                  60

Arg Phe Glu Asp Gly Gly Tyr Val Val Cys Asn Thr Arg Gln Asn Gly
65                  70                  75                  80

Ser Trp Gly Pro Glu Glu Arg Lys Thr His Met Pro Phe Gln Lys Gly
                85                  90                  95

Met Pro Phe Asp Leu Cys Phe Leu Val Gln Ser Ser Asp Phe Lys Val
            100                 105                 110

Met Val Asn Gly Ile Leu Phe Val Gln Tyr Phe His Arg Val Pro Phe
        115                 120                 125

His Arg Val Asp Thr Ile Ser Val Asn Gly Ser Val Gln Leu Ser Tyr
130                 135                 140

Ile Ser Phe Gln Pro Pro Gly Val Trp Pro Ala Asn Pro Ala Pro Ile
145                 150                 155                 160

Thr Gln Thr Val Ile His Thr Val Gln Ser Ala Pro Gly Gln Met Phe
                165                 170                 175

Ser Thr Pro Ala Ile Pro Pro Met Met Tyr Pro His Pro Ala Tyr Pro
            180                 185                 190

Met Pro Phe Ile Thr Thr Ile Leu Gly Gly Leu Tyr Pro Ser Lys Ser
        195                 200                 205

Ile Leu Leu Ser Gly Thr Val Leu Pro Ser Ala Gln Arg Cys Gly Ser
    210                 215                 220

Cys Val Lys Leu Thr Ala Ser Arg Trp Pro Trp Met Val Ser Thr Cys
225                 230                 235                 240

Leu Asn Thr Thr Ile Ala
                245
```

<210> SEQ ID NO 10
<211> LENGTH: 971
<212> TYPE: DNA
<213> ORGANISM: Homo sapiens

<400> SEQUENCE: 10

```
atggccttca gcggttccca ggctccctac ctgagtccag ctgtcccctt ttctgggact    60
attcaaggag gtctccagga cggacttcag atcactgtca atgggaccgt tctcagctcc   120
agtggaacca ggtttgctgt gaactttcag actggcttca gtggaaatga cattgccttc   180
cacttcaacc ctcggtttga agatggaggg tacgtggtgt gcaacacgag gcagaacgga   240
agctggggc ccgaggagag gaagacacac atgcctttcc agaaggggat gccctttgac   300
ctctgcttcc tggtgcagag ctcagatttc aaggtgatgg tgaacgggat cctcttcgtg   360
cagtacttcc accgcgtgcc cttccaccgt gtggacacca tctccgtcaa tggctctgtg   420
cagctgtcct acatcagctt ccagcctccc ggcgtgtggc ctgccaaccc ggctcccatt   480
acccagacag tcatccacac agtgcagagc gccctggac agatgttctc tactcccgcc   540
```

```
atcccactat gatgtacccc cacccgcct atccgatgcc tttcatcacc accattctgg      600
gagggctgta cccatccaag tccatcctcc tgtcaggcac tgtcctgccc agtgctcaga      660
ggttccacat caacctgtgc tctgggaacc acatcgcctt ccacctgaac cccgttttg       720 atgagaatgc tgtggtccgc aacacccaga tcgacaactc tgggggtct gaggagcgaa       780 gtctgccccg aaaaatgccc ttcgtccgtg ccagagctt ctcagtgtgg atcttgtgtg       840
aagctcactg cctcaaggtg gccgtggatg tcagcaccct gtttgaatac taccatcgcc       900
tgaggaacct gcccaccatc aacagactgg aagtgggggg cgacatccag ctgacccatg      960
tgcagacata g                                                            971
```

```
<210> SEQ ID NO 11
<211> LENGTH: 926
<212> TYPE: PRT
<213> ORGANISM: Homo sapiens

<400> SEQUENCE: 11

Met Asp Met Phe Pro Leu Thr Trp Val Phe Leu Ala Leu Tyr Phe Ser
1               5                   10                  15

Arg His Gln Val Arg Gly Gln Pro Asp Pro Cys Gly Gly Arg Leu
            20                  25                  30

Asn Ser Lys Asp Ala Gly Tyr Ile Thr Ser Pro Gly Tyr Pro Gln Asp
        35                  40                  45

Tyr Pro Ser His Gln Asn Cys Glu Trp Ile Val Tyr Ala Pro Glu Pro
    50                  55                  60

Asn Gln Lys Ile Val Leu Asn Phe Asn Pro His Phe Glu Ile Glu Lys
65                  70                  75                  80

His Asp Cys Lys Tyr Asp Phe Ile Glu Ile Arg Asp Gly Asp Ser Glu
                85                  90                  95

Ser Ala Asp Leu Leu Gly Lys His Cys Gly Asn Ile Ala Pro Pro Thr
            100                 105                 110

Ile Ile Ser Ser Gly Ser Met Leu Tyr Ile Lys Phe Thr Ser Asp Tyr
        115                 120                 125

Ala Arg Gln Gly Ala Gly Phe Ser Leu Arg Tyr Glu Ile Phe Lys Thr
    130                 135                 140

Gly Ser Glu Asp Cys Ser Lys Asn Phe Thr Ser Pro Asn Gly Thr Ile
145                 150                 155                 160

Glu Ser Pro Gly Phe Pro Glu Lys Tyr Pro His Asn Leu Asp Cys Thr
                165                 170                 175

Phe Thr Ile Leu Ala Lys Pro Lys Met Glu Ile Ile Leu Gln Phe Leu
            180                 185                 190

Ile Phe Asp Leu Glu His Asp Pro Leu Gln Val Gly Glu Gly Asp Cys
        195                 200                 205

Lys Tyr Asp Trp Leu Asp Ile Trp Asp Gly Ile Pro His Val Gly Pro
    210                 215                 220

Leu Ile Gly Lys Tyr Cys Gly Thr Lys Thr Pro Ser Glu Leu Arg Ser
225                 230                 235                 240

Ser Thr Gly Ile Leu Ser Leu Thr Phe His Thr Asp Met Ala Val Ala
                245                 250                 255

Lys Asp Gly Phe Ser Ala Arg Tyr Tyr Leu Val His Gln Glu Pro Leu
            260                 265                 270

Glu Asn Phe Gln Cys Asn Val Pro Leu Gly Met Glu Ser Gly Arg Ile
        275                 280                 285

Ala Asn Glu Gln Ile Ser Ala Ser Ser Thr Tyr Ser Asp Gly Arg Trp
```

-continued

```
              290                 295                 300
Thr Pro Gln Gln Ser Arg Leu His Gly Asp Asp Asn Gly Trp Thr Pro
305                 310                 315                 320

Asn Leu Asp Ser Asn Lys Glu Tyr Leu Gln Val Asp Leu Arg Phe Leu
                325                 330                 335

Thr Met Leu Thr Ala Ile Ala Thr Gln Gly Ala Ile Ser Arg Glu Thr
                340                 345                 350

Gln Asn Gly Tyr Tyr Val Lys Ser Tyr Lys Leu Glu Val Ser Thr Asn
                355                 360                 365

Gly Glu Asp Trp Met Val Tyr Arg His Gly Lys Asn His Lys Val Phe
370                 375                 380

Gln Ala Asn Asn Asp Ala Thr Glu Val Val Leu Asn Lys Leu His Ala
385                 390                 395                 400

Pro Leu Leu Thr Arg Phe Val Arg Ile Arg Pro Gln Thr Trp His Ser
                405                 410                 415

Gly Ile Ala Leu Arg Leu Glu Leu Phe Gly Cys Arg Val Thr Asp Ala
                420                 425                 430

Pro Cys Ser Asn Met Leu Gly Met Leu Ser Gly Leu Ile Ala Asp Ser
                435                 440                 445

Gln Ile Ser Ala Ser Ser Thr Gln Glu Tyr Leu Trp Ser Pro Ser Ala
                450                 455                 460

Ala Arg Leu Val Ser Ser Arg Ser Gly Trp Phe Pro Arg Ile Pro Gln
465                 470                 475                 480

Ala Gln Pro Gly Glu Glu Trp Leu Gln Val Asp Leu Gly Thr Pro Lys
                485                 490                 495

Thr Val Lys Gly Val Ile Ile Gln Gly Ala Arg Gly Gly Asp Ser Ile
                500                 505                 510

Thr Ala Val Glu Ala Arg Ala Phe Val Arg Lys Phe Lys Val Ser Tyr
                515                 520                 525

Ser Leu Asn Gly Lys Asp Trp Glu Tyr Ile Gln Asp Pro Arg Thr Gln
                530                 535                 540

Gln Pro Lys Leu Phe Glu Gly Asn Met His Tyr Asp Thr Pro Asp Ile
545                 550                 555                 560

Arg Arg Phe Asp Pro Ile Pro Ala Gln Tyr Val Arg Val Tyr Pro Glu
                565                 570                 575

Arg Trp Ser Pro Ala Gly Ile Gly Met Arg Leu Glu Val Leu Gly Cys
                580                 585                 590

Asp Trp Thr Asp Ser Lys Pro Thr Val Glu Thr Leu Gly Pro Thr Val
                595                 600                 605

Lys Ser Glu Glu Thr Thr Thr Pro Tyr Pro Thr Glu Glu Ala Thr
610                 615                 620

Glu Cys Gly Glu Asn Cys Ser Phe Glu Asp Asp Lys Asp Leu Gln Leu
625                 630                 635                 640

Pro Ser Gly Phe Asn Cys Asn Phe Asp Phe Leu Glu Glu Pro Cys Gly
                645                 650                 655

Trp Met Tyr Asp His Ala Lys Trp Leu Arg Thr Thr Trp Ala Ser Ser
                660                 665                 670

Ser Ser Pro Asn Asp Arg Thr Phe Pro Asp Asp Arg Asn Phe Leu Arg
                675                 680                 685

Leu Gln Ser Asp Ser Gln Arg Glu Gly Gln Tyr Ala Arg Leu Ile Ser
                690                 695                 700

Pro Pro Val His Leu Pro Arg Ser Pro Val Cys Met Glu Phe Gln Tyr
705                 710                 715                 720
```

```
Gln Ala Thr Gly Gly Arg Gly Val Ala Leu Gln Val Arg Glu Ala
            725                 730                 735

Ser Gln Glu Ser Lys Leu Leu Trp Val Ile Arg Glu Asp Gln Gly Gly
            740                 745                 750

Glu Trp Lys His Gly Arg Ile Ile Leu Pro Ser Tyr Asp Met Glu Tyr
            755                 760                 765

Gln Ile Val Phe Glu Gly Val Ile Gly Lys Gly Arg Ser Gly Glu Ile
            770                 775                 780

Ala Ile Asp Asp Ile Arg Ile Ser Thr Asp Val Pro Leu Glu Asn Cys
785                 790                 795                 800

Met Glu Pro Ile Ser Ala Phe Ala Val Asp Ile Pro Glu Ile His Glu
            805                 810                 815

Arg Glu Gly Tyr Glu Asp Glu Ile Asp Asp Glu Tyr Glu Val Asp Trp
            820                 825                 830

Ser Asn Ser Ser Ser Ala Thr Ser Gly Ser Gly Ala Pro Ser Thr Asp
            835                 840                 845

Lys Glu Lys Ser Trp Leu Tyr Thr Leu Asp Pro Ile Leu Ile Thr Ile
            850                 855                 860

Ile Ala Met Ser Ser Leu Gly Val Leu Leu Gly Ala Thr Cys Ala Gly
865                 870                 875                 880

Leu Leu Leu Tyr Cys Thr Cys Ser Tyr Ser Gly Leu Ser Ser Arg Ser
            885                 890                 895

Cys Thr Thr Leu Glu Asn Tyr Asn Phe Glu Leu Tyr Asp Gly Leu Lys
            900                 905                 910

His Lys Val Lys Met Asn His Gln Lys Cys Cys Ser Glu Ala
            915                 920                 925

<210> SEQ ID NO 12
<211> LENGTH: 2775
<212> TYPE: DNA
<213> ORGANISM: Homo sapiens

<400> SEQUENCE: 12
atgtttcctc tcacctgggt tttcttagcc ctctacttt caagacacca agtgagaggc      60
caaccagacc caccgtgcgg aggtcgtttg aattccaaag atgctggcta tatcacctct     120
cccggttacc cccaggacta cccctcccac cagaactgcg agtggattgt ttacgccccc     180
gaacccaacc agaagattgt cctcaacttc aaccctcact ttgaaatcga aagcacgac      240 tgcaagtatg actttatcga gattcgggat ggggacagtg aatccgcaga cctcctgggc     300
aaacactgtg gaacatcgc cccgcccacc atcatctcct cgggctccat gctctacatc      360
aagttcacct ccgactacgc ccggcagggg gcaggcttct ctctgcgcta cgagatcttc     420
aagacaggct ctgaagattg ctcaaaaaac ttcacaagcc caacgggac catcgaatct     480 cctgggtttc ctgagaagta tccacacaac ttggactgca cctttaccat cctggccaaa     540
cccaagatgg agatcatcct gcagttcctg atctttgacc tggagcatga cccttttgcag    600 gtgggagagg gggactgcaa gtacgattgg ctggacatct gggatggcat tccacatgtt     660 ggcccctga ttgcaagta ctgtgggacc aaaacaccct tgaacttcg ttcatcgacg       720 gggatcctct ccctgacctt tcacacggac atggcggtgg ccaaggatgg cttctctgcg    780
cgttactacc tggtccacca agagccacta gagaactttc agtgcaatgt tcctctgggc    840
atggagtctg gccggattgc taatgaacag atcagtgcct catctaccta ctctgatggg    900
aggtggaccc ctcaacaaag ccggctccat ggtgatgaca atgctggac ccccaacttg    960
```

-continued

```
gattccaaca aggagtatct ccaggtggac ctgcgctttt taaccatgct cacggccatc   1020
gcaacacagg gagcgatttc cagggaaaca cagaatggct actatgtcaa atcctacaag   1080
ctggaagtca gcactaatgg agaggactgg atggtgtacc ggcatggcaa aaaccacaag   1140
gtatttcaag ccaacaacga tgcaactgag gtggttctga acaagctcca cgctccactg   1200
ctgacaaggt ttgttagaat ccgccctcag acctggcact caggtatcgc cctccggctg   1260
gagctcttcg gctgccgggt cacagatgct ccctgctcca acatgctggg gatgctctca   1320
ggcctcattg cagactccca gatctccgcc tcttccaccc aggaatacct ctggagcccc   1380
agtgcagccc gcctggtcag cagccgctcg ggctggttcc ctcgaatccc tcaggcccag   1440
cccggtgagg agtggcttca ggtagatctg ggaacaccca agacagtgaa aggtgtcatc   1500
atccagggag cccgcggagg agacagtatc actgctgtgg aagccagagc atttgtgcgc   1560
aagttcaaag tctcctacag cctaaacggc aaggactggg aatacattca ggaccccagg   1620
acccagcagc caaagctgtt cgaagggaac atgcactatg acacccctga catccgaagg   1680
tttgacccca ttccggcaca gtatgtgcgg gtatacccgg agaggtggtc gccggcgggg   1740
attgggatgc ggctggaggt gctgggctgt gactggacag actccaagcc cacggtagag   1800
acgctgggac ccactgtgaa gagcgaagag acaaccaccc cctaccccac cgaagaggag   1860
gccacagagt gtggggagaa ctgcagcttt gaggatgaca agatttgca gctcccttcg   1920 ggattcaatt gcaacttcga tttcctcgag gagccctgtg gttggatgta tgaccatgcc   1980
aagtggctcc ggaccacctg gccagcagca tccagcccaa cgaccggac gtttccagat   2040 gacaggaatt tcttgcggct gcagagtgac agccagagag agggccagta tgcccggctc   2100
atcagccccc ctgtccacct gccccgaagc ccggtgtgca tggagttcca gtaccaggcc   2160
acgggcggcc gcggggtggc gctgcaggtg gtgcgggaag ccagccagga gagcaagttg   2220
ctgtgggtca tccgtgagga ccagggcggc gagtggaagc acgggcggat catcctgccc   2280
agctacgaca tggagtacca gattgtgttc gagggagtga tagggaaagg acgttccgga   2340
gagattgcca ttgatgacat tcggataagc actgatgtcc cactggagaa ctgcatggaa   2400
cccatctcgg cttttgcagt ggacatccca gaaatacatg agagagaagg atatgaagat   2460
gaaattgatg atgaatacga ggtggactgg agcaattctt cttctgcaac ctcagggtct   2520
ggcgccccct cgaccgacaa agaaaagagc tggctgtaca ccctggatcc catcctcatc   2580
accatcatcg ccatgagctc actgggcgtc ctcctggggg ccacctgtgc aggcctcctg   2640
ctctactgca cctgttccta ctcgggcctg agctcccgaa gctgcaccac actggagaac   2700
tacaacttcg agctctacga tggccttaag cacaaggtca agatgaacca ccaaaagtgc   2760
tgctccgagg catga                                                    2775
```

<210> SEQ ID NO 13
<211> LENGTH: 289
<212> TYPE: PRT
<213> ORGANISM: Homo sapiens

<400> SEQUENCE: 13

```
Met Lys Thr Leu Pro Ala Met Leu Gly Thr Gly Lys Leu Phe Trp Val
1               5                   10                  15

Phe Phe Leu Ile Pro Tyr Leu Asp Ile Trp Asn Ile His Gly Lys Glu
            20                  25                  30

Ser Cys Asp Val Gln Leu Tyr Ile Lys Arg Gln Ser Glu His Ser Ile
        35                  40                  45
```

Leu Ala Gly Asp Pro Phe Glu Leu Glu Cys Pro Val Lys Tyr Cys Ala
    50                  55                  60

Asn Arg Pro His Val Thr Trp Cys Lys Leu Asn Gly Thr Thr Cys Val
 65                  70                  75                  80

Lys Leu Glu Asp Arg Gln Thr Ser Trp Lys Glu Lys Asn Ile Ser
                    85                  90                  95

Phe Phe Ile Leu His Phe Glu Pro Val Leu Pro Asn Asp Asn Gly Ser
                100                 105                 110

Tyr Arg Cys Ser Ala Asn Phe Gln Ser Asn Leu Ile Glu Ser His Ser
            115                 120                 125

Thr Thr Leu Tyr Val Thr Asp Val Lys Ser Ala Ser Glu Arg Pro Ser
    130                 135                 140

Lys Asp Glu Met Ala Ser Arg Pro Trp Leu Leu Tyr Arg Leu Leu Pro
145                 150                 155                 160

Leu Gly Gly Leu Pro Leu Leu Ile Thr Thr Cys Phe Cys Leu Phe Cys
                165                 170                 175

Cys Leu Arg Arg His Gln Gly Lys Gln Asn Glu Leu Ser Asp Thr Ala
            180                 185                 190

Gly Arg Glu Ile Asn Leu Val Asp Ala His Leu Lys Ser Glu Gln Thr
        195                 200                 205

Glu Ala Ser Thr Arg Gln Asn Ser Gln Val Leu Leu Ser Glu Thr Gly
    210                 215                 220

Ile Tyr Asp Asn Asp Pro Asp Leu Cys Phe Arg Met Gln Glu Gly Ser
225                 230                 235                 240

Glu Val Tyr Ser Asn Pro Cys Leu Glu Glu Asn Lys Pro Gly Ile Val
                245                 250                 255

Tyr Ala Ser Leu Asn His Ser Val Ile Gly Pro Asn Ser Arg Leu Ala
            260                 265                 270

Arg Asn Val Lys Glu Ala Pro Thr Glu Tyr Ala Ser Ile Cys Val Arg
        275                 280                 285

Ser

<210> SEQ ID NO 14
<211> LENGTH: 726
<212> TYPE: DNA
<213> ORGANISM: Homo sapiens

<400> SEQUENCE: 14
atgaagacat tgcctgccat gcttggaact gggaaattat tttgggtctt cttcttaatc      60
ccatatctgg acatctggaa catccatggg aaagaatcat gtgatgtaca gctttatata     120
aagagacaat ctgaacactc catcttagca ggagatccct ttgaactaga atgccctgtg     180
aaatactgtg ctaacaggcc tcatgtgact tggtgcaagc tcaatggaac aacatgtgta     240
aaacttgaag atagacaaac aagttggaag gaagagaaga catttcatt tttcattcta     300 cattttgaac cagtgcttcc taatgacaat gggtcatacc gctgttctgc aaattttcag     360
tctaatctca ttgaaagcca ctcaacaact ctttatgtga caggaaagca aaatgaactc     420
tctgacacag caggaaggga aattaacctg gttgatgctc accttaagag tgagcaaaca     480
gaagcaagca ccaggcaaaa ttcccaagta ctgctatcag aaactggaat ttatgataat     540
gaccctgacc tttgtttcag gatgcaggaa gggtctgaag tttattctaa tccatgcctg     600
gaagaaaaca aaccaggcat tgtttatgct tccctgaacc attctgtcat tggaccgaac     660

```
tcaagactgg caagaaatgt aaaagaagca ccaacagaat atgcatccat atgtgtgagg    720
agttaa                                                              726
```

METHODS OF TREATING CANCER USING ANTIBODIES AND MOLECULES THAT BIND TO BTN1A1 OR BTN1A1-LIGANDS

CROSS REFERENCE TO RELATED APPLICATIONS

This application is the U.S. national stage application of PCT/US2018/036026, filed Jun. 5, 2018, which claims the benefit of U.S. Provisional Application No. 62/516,071, filed Jun. 6, 2017; the disclosures of each of which are incorporated herein by reference in their entirety.

REFERENCE TO A SEQUENCE LISTING

This application is being filed with a computer readable form (CRF) copy of a Sequence Listing named 13532-020-999 ST25.txt, created on Dec. 2, 2019, and being 40,362 bytes in size; which is incorporated herein by reference in its entirety.

1. FIELD

The present invention relates in general to the field of cancer immunology and molecular biology. Provided herein are methods for treating cancer using anti-BTN1A1 antibodies or anti-BTN1A1-ligand antibodies or other molecules having an antigen binding fragment that immunospecifically bind to BTN1A1 or a BTN1A1 ligand. In some embodiments, the anti-BTN1A1 antibodies or anti-BTN1A1 ligand antibodies can disrupt the BTN1A1-BTN1A1 ligand interaction. In some embodiments, the anti-BTN1A1 ligand antibodies include anti-Galectin 1 (GAL-1) antibodies, anti-Galectin 9 (GAL-9) antibodies, anti-Neuropilin-2 (NRP-2) antibodies or anti-B- and T-Lymphocyte Attenuator (BTLA) antibodies.

2. BACKGROUND

The immune system of humans and other mammals protects them against infections and diseases. A number of stimulatory and inhibitory ligands and receptors provide a tight control system to maximize immune response against infection while limiting self-immunity. Recently, therapeutics that modulate immune response, such as anti-PD1 or anti-PDL1 antibodies, were found to be effective in some cancer treatments. However, development of new therapeutics that safely and effectively treat diseases by modulating the immune system remain an urgent need, especially for anti-PD1 therapy or anti-PD-L1 therapy resistant or refractory cancers. The methods described herein meet these needs and provide other related advantages.

3. SUMMARY

In one aspect, provided herein is a molecule including an antigen binding fragment that immunospecifically binds to BTN1A1, whereby the molecule inhibits binding of a BTN1A1 ligand, such as Galectin-1 (GAL-1), Galectin-9 (GAL-9), NRP-2 (Nrp-2), or B- and T-Lymphocyte Attenuator (BTLA), to BTN1A1.

In some embodiments, the antigen binding fragment immunospecifically binds to BTN1A1 and the molecule inhibits binding of BTN1A1 to GAL-1.

In some embodiments, the antigen binding fragment immunospecifically binds to BTN1A1 and the molecule inhibits binding of BTN1A1 to GAL-9.

In some embodiments, the antigen binding fragment immunospecifically binds to BTN1A1 and the molecule inhibits binding of BTN11A1 to NRP-2.

In some embodiments, the antigen-binding fragment immunospecifically binds to BTN1A1 and the molecule inhibits binding of BTN1A1 to BTLA.

In some embodiments, the antigen binding fragment immunospecifically binds to BTN1A1 and the molecule inhibits two or more BN1A1 ligands, such as GAL-1, GAL-9, NRP-2, or BTLA, to BTN1A1.

In some embodiments, the antigen binding fragment immunospecifically binds to the extracellular domain (ECD) of BTN1A1.

In another aspect, provided herein is a molecule including an antigen binding fragment that immunospecifically binds to a BTN1A1 ligand, such as GAL-1, GAL-9, NRP-2 or BTLA, whereby the molecule inhibits binding of the BTN1A1 ligand to BTN1A1.

In some embodiments, the antigen binding fragment immunospecifically binds to GAL-1 and the molecule inhibits binding of GAL-1 to BTN1A1.

In some embodiments, the antigen binding fragment immunospecifically binds to GAL-9 and the molecule inhibits binding of GAL-9 to BTN1A1.

In some embodiments, the antigen binding fragment immunospecifically binds to NRP-2 and the molecule inhibits binding of NRP-2 to BTN1A1.

In some embodiments, the antigen binding fragment immunospecifically binds to BTLA and the molecule inhibits binding of BTLA to BTN1A1.

In some embodiments, the molecule modulates an activity or signaling of BTN1A1 or an activity or signaling of a complex of BTN1A1 and a BTN1A1 ligand, such as GAL-1, GAL-9, NRP-2, or BTLA.

In some embodiments, the molecule inhibits the binding of the BTN1A1 ligand to BTN1A1 with an IC50 of no more than 1 µM.

In some embodiments, the molecule inhibits the binding of the BTN1A1 ligand to BTN1A1 with an IC50 of no more than 500 nM, no more than 400 nM, no more than 300 nM, no more than 200 nM, no more than 100 nM, no more than 50 nM, no more than 10 nM, or no more than 5 nM.

In some embodiments, the molecule can modulate T-cell activity.

In some embodiment, the T-cell is a CD8+ cell.

In some embodiments, the molecule can increase T-cell activation or T-cell proliferation.

In some embodiments, the molecule can inhibit T-cell apoptosis.

In some embodiments, the antigen binding fragment preferentially binds glycosylated BTN1A1 over non-glycosylated BTN1A1.

In some embodiments, the antigen binding fragment preferentially binds dimeric BTN1A1 over monomeric BTN1A1.

In some embodiments, the antigen-binding fragment immunospecifically binds BTN1A1 or the BTN1A1 ligand with a dissociation constant ($K_D$) of no more than 1 µM.

In some embodiments, the antigen-binding fragment immunospecifically binds BTN1A1 or the BTN1A1 ligand with a dissociation constant ($K_D$) of no more than 500 nM, no more than 400 nM, no more than 300 nM, no more than 200 nM, no more than 100 nM, no more than 50 nM, no more than 10 nM, or no more than 5 nM.

In some embodiments, the antigen binding fragment immunospecifically binds BTN1A1 or the BTN1A1 ligand with a $K_D$ of lower than or equal to the $K_D$ of a BTN1A1-

GAL-1 interaction, a BTN1A1-GAL-9 interaction, a BTN1A1-NRP2 interaction or a BTN1A1-BTLA interaction.

In some embodiments, the antigen binding fragment immunospecifically binds BTN1A1 or the BTN1A1 ligand with a $K_D$ at least 2 times lower, at least 5 times lower, at least 10 times lower, at least 15 times lower, at least 20 times lower, at least 25 times lower, at least 30 times lower, at least 40 times lower, or at last 50 times lower than the $K_D$ of a BTN1A1-GAL-1-1 interaction, a BTN1A1-GAL-9 interaction, a BTN1A1-NRP2 interaction or a BTN1A1-BTLA interaction.

In some embodiments, the molecule inhibits the binding of the BTN1A1 ligand to BTN1A1 with an IC50 of no more than 1 µM.

In some embodiments, the molecule inhibits the binding of the BTN1A1 ligand to BTN1A1 with an IC50 of no more than 500 nM, no more than 400 nM, no more than 300 nM, no more than 200 nM, no more than 100 nM, no more than 50 nM, no more than 10 nM, or no more than 5 nM.

In some embodiments, BTN1A1 binding, BTN1A1 ligand binding, or inhibition of BTN1A1 ligand binding to BTN1A1 is analyzed in by co-immunoprecipitation (co-IP), surface plasmon resonance (SPR) assay, β-galactosidase complementation, or bio-layer interferometry (BLI).

In some embodiments, the molecule is an antibody.

In some embodiments, the molecule is a monoclonal antibody.

In some embodiments, the antibody is a human antibody or a humanized antibody.

In some embodiments, the antibody is an IgG, IgM, or IgA.

In some embodiments, the molecule is a Fab', a F(ab')2, a F(ab')3, a monovalent scFv, a bivalent scFv, or a single domain antibody.

In some embodiments, the molecule is recombinantly produced.

In another aspect, provided herein is a pharmaceutical composition including a molecule provided herein, and a pharmaceutically acceptable carrier.

In some embodiments, the pharmaceutical composition is formulated for parenteral administration.

In another aspect, provided herein is a method of activating T-cells including contacting the T-cells with an effective amount of a molecule provided herein, whereby the T-cells are activated through inhibition of BTN1A1 ligand binding to BTN1A1.

In another aspect, provided herein is a method of inhibiting binding of a BTN1A1 ligand to a T-cell expressed BTN1A1, comprising contacting the T-cell with an effective amount of a molecule provided herein, thereby inhibiting binding of the BTN1A1 ligand to the T-cell.

In some embodiments, the T-cells are CD8+ cells.

In some embodiments, T-cell activation includes (i) increasing T-cell proliferation, (ii) decreasing T-cell apoptosis, or (iii) increasing cytokine production.

In some embodiments, the cytokine is IFNγ or IL-2.

In another aspect, provided herein is a method of treating cancer in a subject, including administering to the subject a therapeutically effective amount of a molecule provided herein or a pharmaceutical composition provided herein, wherein the molecule inhibits binding of a BTN1A1 ligand to BTN1A1 in the subject.

In another aspect, provided herein is a method of inhibiting BTN1A1 ligand binding to BTN1A1, administering to the subject a therapeutically effective amount of a molecule provided herein or a pharmaceutical composition provided herein, wherein the molecule inhibits binding of a BTN1A1 ligand to BTN1A1 in the subject.

In some embodiments, the method further includes administering a high-dose radiation therapy to the patient.

In some embodiments, the cancer can include lung cancer, prostate cancer, pancreas cancer, ovarian cancer, liver cancer, head & neck cancer, breast cancer, and stomach cancer.

In some embodiments, the cancer can include lung cancer.

In some embodiments, the lung cancer is a non small cell lung cancer (NSCLC).

In some embodiments, the NSCLC is squamous NSCLC.

In some embodiment, the cancer is an anti-PD-1 therapy or an anti-PD-L1 therapy resistant or refractory cancer.

In some embodiments, the cancer is a breast cancer or a lung cancer.

In some embodiments, the cancer is a mammary carcinoma or a Lewis lung carcinoma.

In some embodiments, the molecule is not STC810 or comprises a CDR or VH or VL amino acid sequence of STC810, as described in International Application No. PCT/US16/64436.

4. BRIEF DESCRIPTION OF THE DRAWINGS

The following drawings form part of the present specification and are included to further demonstrate certain embodiments of the present invention. The invention can be better understood by reference to one or more of these drawings in combination with the detailed description of specific embodiments presented herein.

FIG. 1—Identification of Galectin-1, Galectin-2, and Neuropilin-2 as BTN1A1 Binders. FIG. 1 shows an image illustrating results of an exemplary plasma membrane protein array experiment to reconfirm Galectin-1 (GAL-1, "LGALS1"), Galectin-2 (GAL-2, "LGALS9") and Neuropilin-2 (NRP-2) as BTN1A1 ligands. Expression vectors of indicated expressed proteins were spotted in duplicates on two slides each ("rep1," "rep2") and reverese transfected into HEK293T cells. The transfected cells were then fixed and probebed with CTLA-4-Fc, BTN1A1-2NQ-Fc (unglycosylated), BTN1A1-Fc (glycosylated), or secondary antibody alone (cells expressing CD86/ZsGreen1 positive control vector). Binding of probe protein to expressed proteins was detected following addition of a fluorescent labeled secondary antibody using fluorescence imaging.

Figure 2A:
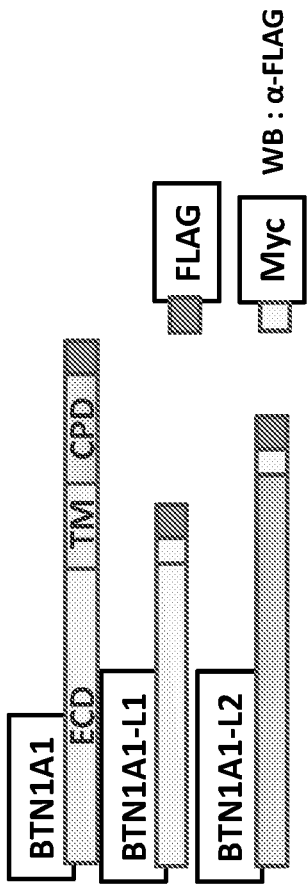
Figure 2B:
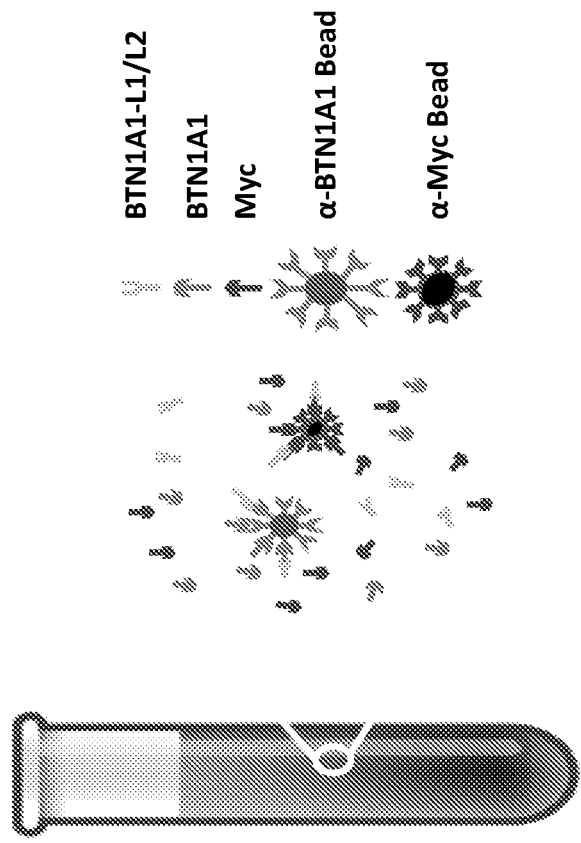
Figure 2C:
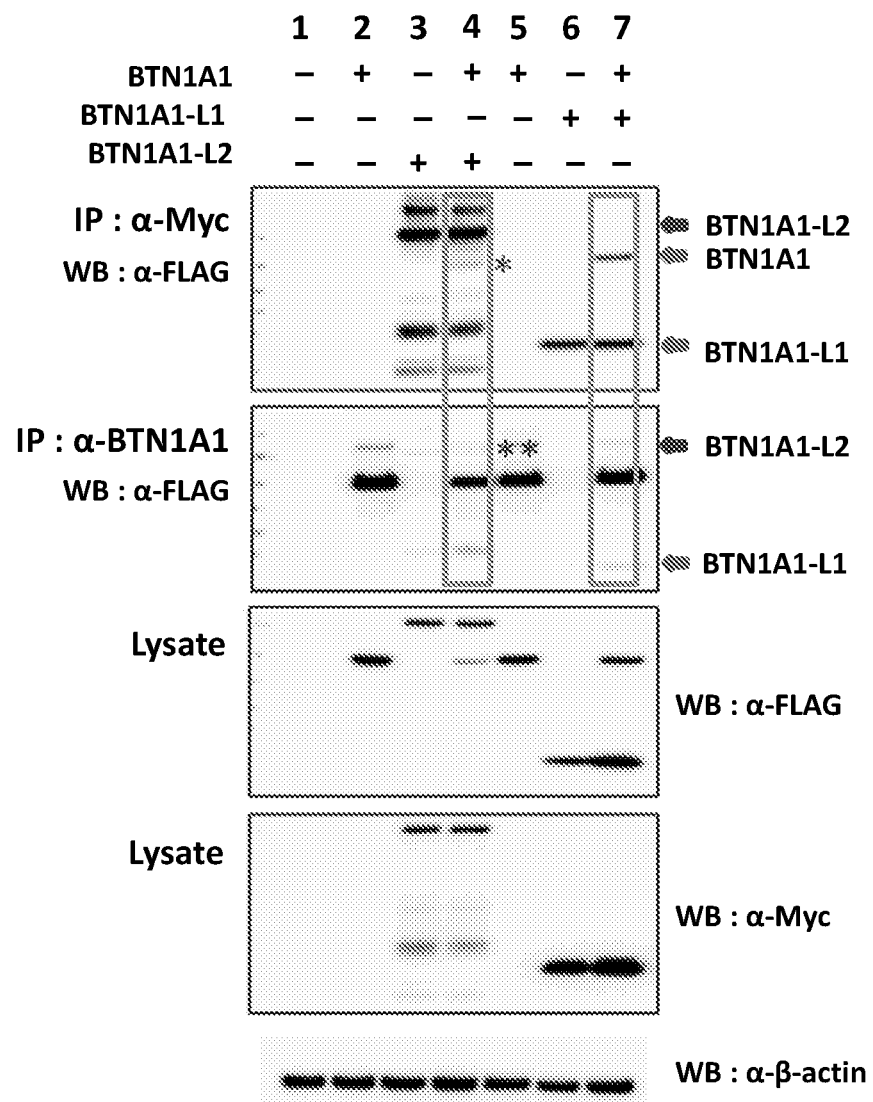

FIGS. 2A-C—Validation of GAL-1 and GAL-9 as BTN1A1 ligands by immunoprecipitation. FIG. 2A shows schematics of BTN1A1 and BTN1A1-ligand (GAL-1 or GAL-9) protein contructs used for immunoprecipitation. BTN1A1 included an extracellular domain (ECD), a transmembrane domain (TM), a cytosolic protein domain (CPD), and a Flag-tag. BTN1A1-ligands included Myc- and Flag-tags. FIG. 2B shows a graph illustrating an immunoprecipitation experiment. BTN1A1 or BTN1A1-ligands were pulled down from HEK293T cell lysates using beads coated with anti-BTN1A1 antibodies or anti-Myc antibodies. FIG. 2C shows images of western blots following immunoprecipitation. Asterixes indicate BTN1A1 bands (*) or BTN1A1-ligand bands (**).

Figure 3A:
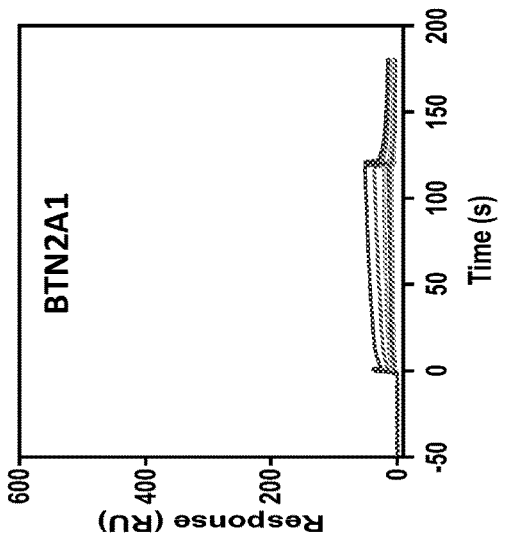
Figure 3C:
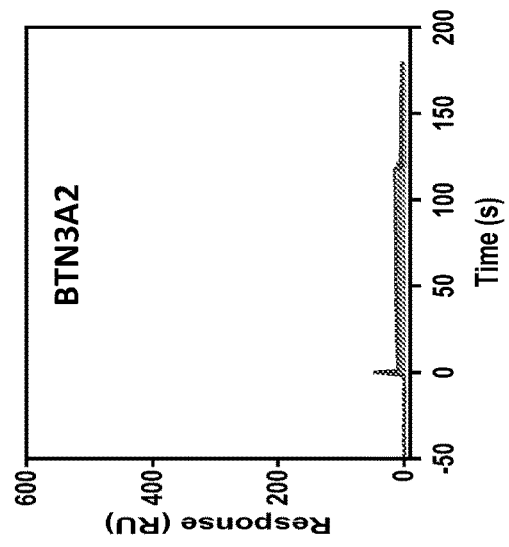
Figure 3B:
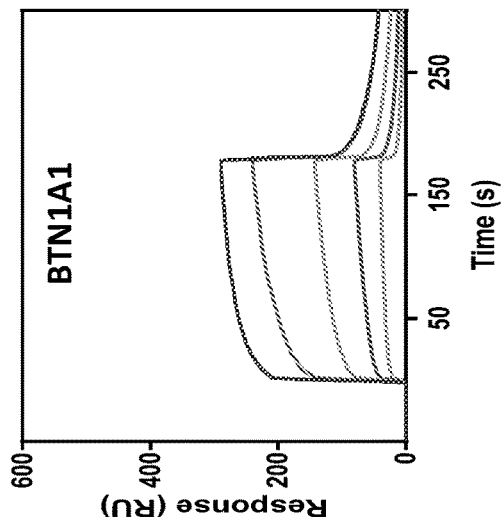
Figure 3D:
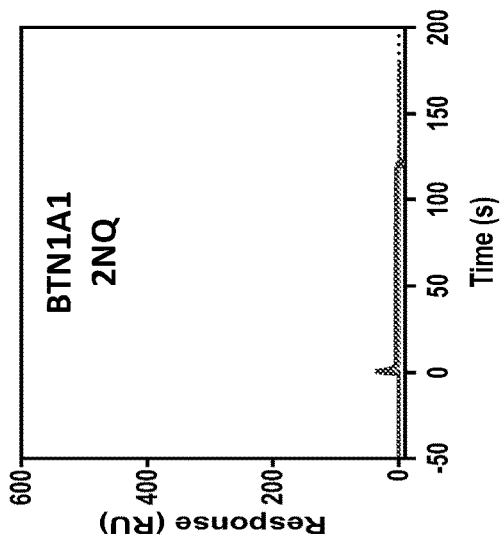

FIGS. 3A-D—Analysis of BTN1A1-GAL-1 interaction by surface plasmon resonance (SPR). FIGS. 3A-D show sensograms of exemplary SPR assays. GAL-1 protein was injected on a sensor chip with immobilized glycosylated wild-type BTN1A1-Fc (FIG. 3A), unglycosylated BTN1A1-2NQ-Fc (FIG. 3B), glycosylated wild-type BTN2A1 (FIG. 3C), or glycosylated wild-type BTN3A2 (FIG. 3D).

Figure 4B:
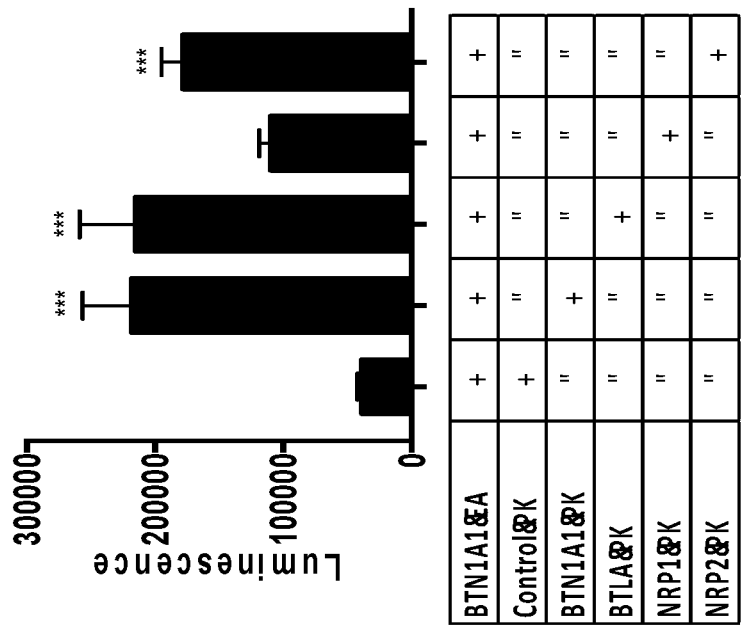
Figure 4A:
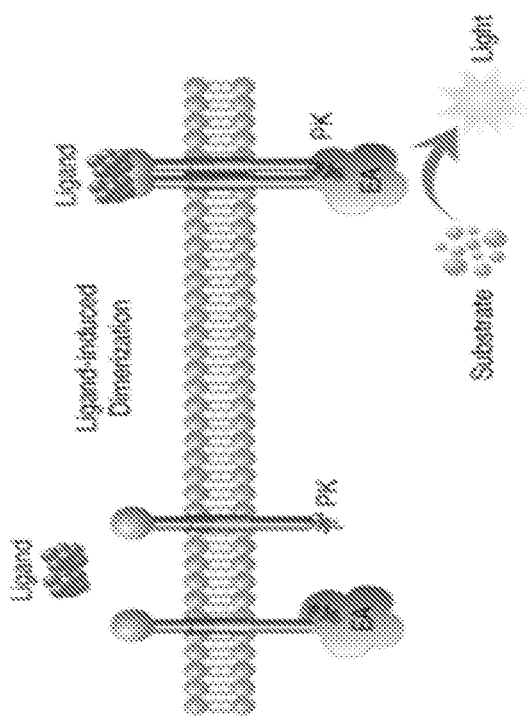

FIGS. 4A and 4B—Identification of BTLA as a BTN1A1 ligand. FIG. 4A shows a schematic illustrating a β-galactosidase (β-gal) complementation assay, in which β-gal is split into enzyme donor (ED) and the enzyme acceptor (EA). Interaction of an ED-fusion protein with an EA-fusion protein results in reconstitution of functional β-gal that is detectable using a luminescent β-gal substrate. FIG. 4B shows a bar diagram illustrating the results of an exemplary β-galactosidase (β-gal) complementation assay.

Figure 5:
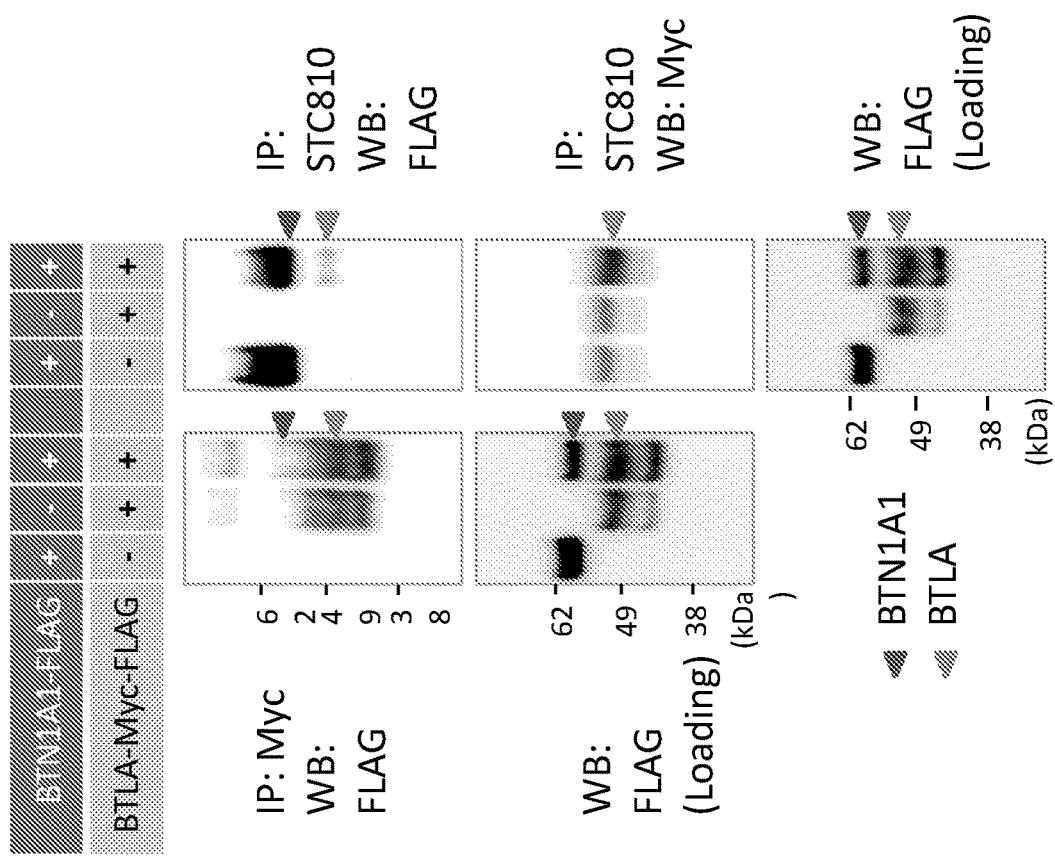

FIG. 5—Validation of BTLA as a BTN1A1 ligand by immunoprecipitation.

FIG. 5 shows results of exemplary western blots following immunoprecipitation of BTN1A1-Flag or BTLA-Myc-Flag with an anti-Myc antibody or an anti-BTN1A1 antibody (STC810).

Figure 6B:
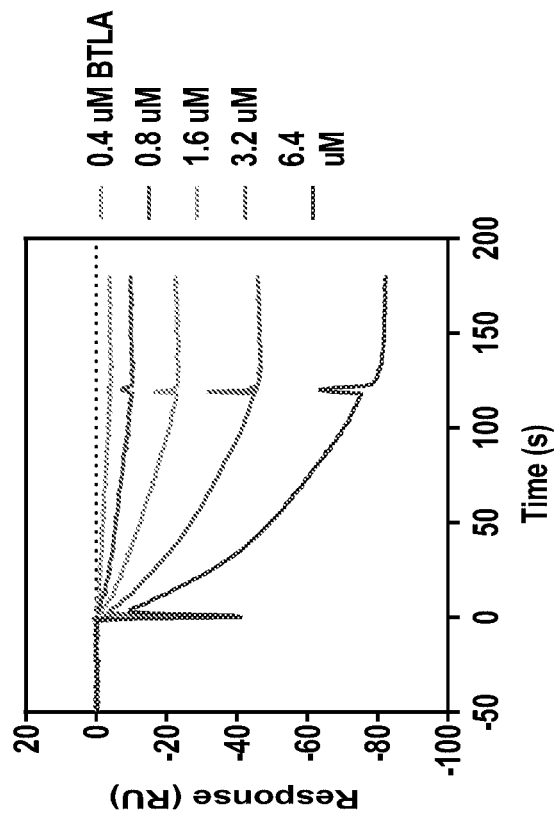
Figure 6A:
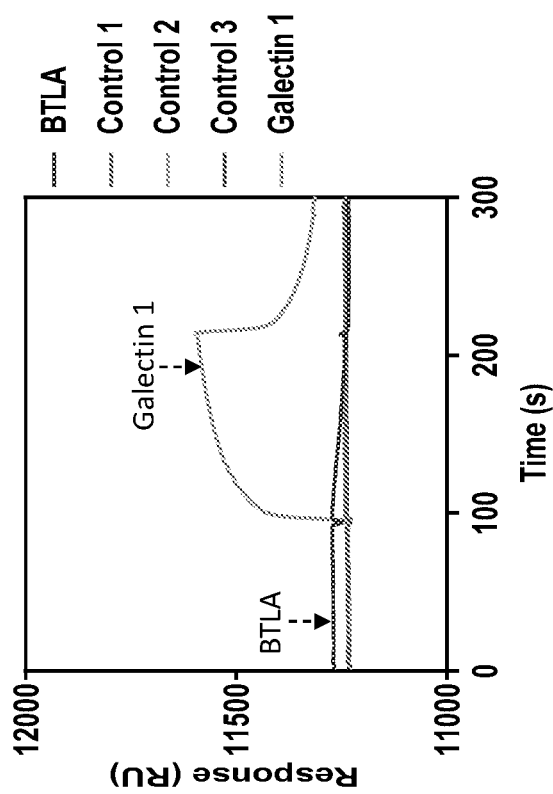

FIGS. 6A and 6B—Analysis of BTN1A1-BTLA interaction by surface plasmon resonance (SPR). FIG. 6A shows sensograms of SPR assays, in which GAL-1, BTLA or a control protein (Control 1, Control 2, or Control 3) was injected onto a sensor chip with immobilized glycosylated wild-type BTN1A1-Fc at a single concentration of 3.2 µM. FIG. 6B shows sensograms of SPR assays in which BTLA was injected onto a sensor chip with immobilized glycosylated wild-type BTN1A1-Fc at indicated concentration.

Figure 7:
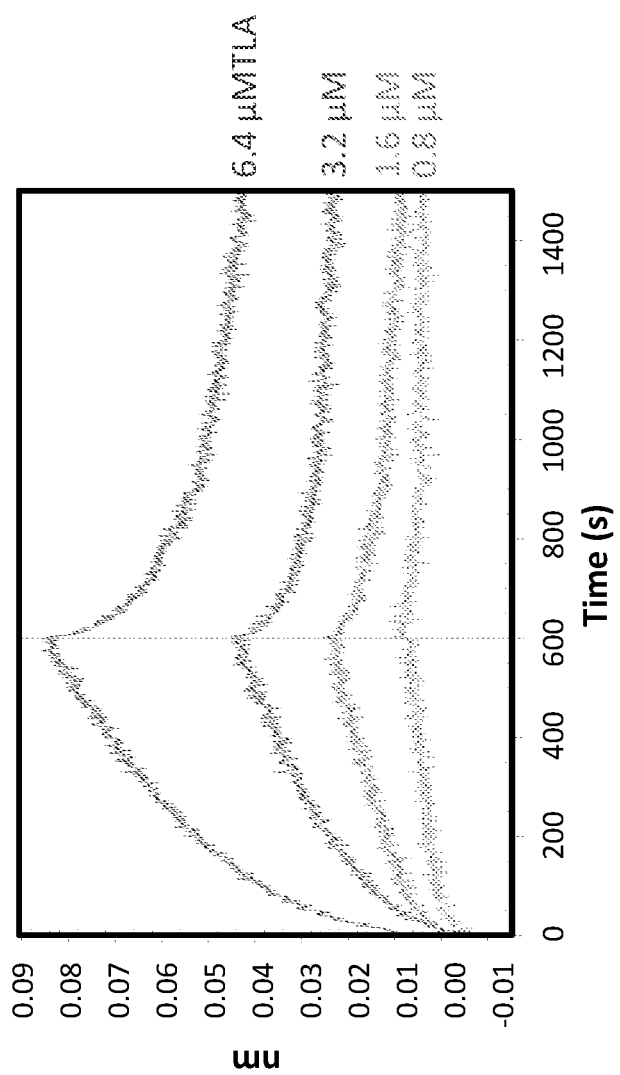

FIGS. 7—Analysis of BTN1A1-BTLA interaction by bio-layer interferometry (BLI). FIG. 7 shows sensograms of BLI experiments in which soluble BTLA was contacted at indicated concentrations with immobilized BTN1A1-Fc.

5. DETAILED DESCRIPTIONS

The B7 family of co-stimulatory molecules can drive the activation and inhibition of immune cells. A related family of molecules—the buryrophilins—also have immunomodulatory functions similar to B7 family members. Butyrophilin, subfamily 1, member A1 ("BTN1A1") is a type I membrane glycoprotein and a major component of milk fat globule membrane, and has structural similarities to the B7 family. BTN1A1 is known as a major protein regulating the formation of fat droplets in the milk. (Ogg et al. *PNAS*, 101(27):10084-10089 (2004)). BTN1A1 is expressed in immune cells, including T cells. Treatment with recombinant BTN1A1 was found to inhibit T cell activation and protect animal models of EAE. (Stefferl et al., *J. Immunol.* 165(5):2859-65 (2000)).

BTN1A1 is also specifically and highly expressed in cancer cells. The BTN1A1 expressed in cancer cells is generally glycosylated. The expression of BTN1A1 can be used to aid cancer diagnosis as well as to evaluate the efficacy of a cancer treatment.

This disclosure is based, at least in part, on the finding that GAL-1, GAL-9, NRP-2 and BTLA can act as BTN1A1 ligands. See, e.g., Examples 1 and 2. Without being limited by any specific theory, it is believed that inhibition of GAL-1, GAL-9, NRP-2, or BTLA complex formation with BTN1A1, including disruptions of already formed complexes of BTN1A1 with BTN1A1 ligands, such as GAL-1, GAL-9, NRP-2, or BTLA, can modulate a BTLA activity or signaling. It is further believed that this modulation of BTLA activity or signaling can activate T-cells, such as CD8+ T-cells, e.g., by promoting T-cell proliferation, inhibiting T-cell apoptosis, or inducing cytokine secretion (e.g., IFNγ or IL2). T-cell activation can result in an anti-cancer immune response that is useful for treating or preventing cancer.

Provided herein are methods for treating cancer using anti-BTN1A1 antibodies, anti-BTN1A1 ligand (e.g., GAL-1, GAL-9, NRP-2, or BTLA) antibodies and other molecules that can immunospecifically bind to BTN1A1 or a BTN1A1 ligand (e.g., GAL-1, GAL-9, NRP-2, or BTLA) and inhibit BTN1A-BTN1 ligand complexes. Also provided are methods for cancer diagnosis and for selecting patients using such anti-BTN1A1 antibodies or anti-BTN1A1-ligand antibodies and other molecules that can immunospecifically bind to BTN1A1 or a BTN1A1 ligand.

5.1. Definitions

As used herein, and unless otherwise specified, the articles "a," "an," and "the" refer to one or to more than one of the grammatical object of the article. By way of example, an antibody refers to one antibody or more than one antibodies.

As used herein, and unless otherwise specified, the term "Butyrophilin, subfamily 1, member A1" or "BTN1A1" refers to BTN1A1 from any vertebrate source, including mammals such as primates (e.g., humans, cynomolgus monkey (cyno)), dogs, and rodents (e.g., mice and rats). Unless otherwise specified, BTN1A1 also includes various BTN1A1 isoforms, related BTN1A1 polypeptides, including SNP variants thereof, as well as different modified forms of BTN1A1, including but not limited to phosphorylated BTN1A1, glycosylated BTN1A1, and ubiquitinated BTN1A1. As used herein, glycosylated BTN1A1 include BTN1A1 with N55, N215, and/or N449 glycosylation.

An exemplary amino acid sequence of human BTN1A1 (BC096314.1 GI: 64654887), is provided below with the potential glycosylation sites bolded and underlined:

```
                                                (SEQ ID NO: 1)
MAVFPSSGLPRCLLTLILLQLPKLDSAPFDVIGPPEPILAVVGEDAKLP

CRLSPNASAEHLELRWFRKKVSPAVLVHRDGREQEAEQMPEYRGRATLV

QDGIAKGRVALRIRGVRVSDDGEYTCFFREDGSYEEALVHLKVAALGSD

PHISMQVQENGEICLECTSVGWYPEPQVQWRTSKGEKFPSTSESRNPDE

EGLFTVAASVIIRDTSAKNVSCYIQNLLLGQEKKVEISIPASSLPRLTP

WIVAVAVILMVLGLLTIGSIFFTWRLYNERPRERRNEFSSKERLLEELK

WKKATLHAVDVTLDPDTAHPHLFLYEDSKSVRLEDSRQKLPEKTERFDS

WPCVLGRETFTSGRHYWEVEVGDRTDWAIGVCRENVMKKGFDPMTPENG

FWAVELYGNGYWALTPLRTPLPLAGPPRRVGIFLDYESGDISFYNIVIN

DGSDIYTFSNVTFSGPLRPFFCLWSSGKKPLTICPIADGPERVTVIANA

QDLSKEIPLSPMGEDSAPRDADTLHSKLIPTQPSQGAP
```

An exemplary encoding nucleic acid sequence of human BTN1A1 (BC096314.1 GI: 64654887), is provided below:

```
                                                (SEQ ID NO: 2)
ATGGCAGTTTTCCCAAGCTCCGGTCTCCCCAGATGTCTGCTCACCCTCA

TTCTCCTCCAGCTGCCCAAACTGGATTCAGCTCCCTTTGACGTGATTGG

ACCCCCGGAGCCCATCCTGGCCGTTGTGGGTGAGGACGCCAAGCTGCCC

TGTCGCCTGTCTCCGAACGCGAGCGCCGAGCACTTGGAGCTACGCTGGT

TCCGAAAGAAGGTTTCGCCGGCCGTGCTGGTGCATAGGGACGGGCGCGA

GCAGGAAGCCGAGCAGATGCCCGAGTACCGCGGGCGGGCGACGCTGGTC
```

-continued
```
CAGGACGGCATCGCCAAGGGGCGCGTGGCCTTGAGGATCCGTGGCGTCA

GAGTCTCTGACGACGGGGAGTACACGTGCTTTTTCAGGGAGGATGGAAG

CTACGAAGAAGCCCTGGTGCATCTGAAGGTGGCTGCTCTGGGCTCTGAC

CCTCACATCAGTATGCAAGTTCAAGAGAATGGAGAAATCTGTCTGGAGT

GCACCTCAGTGGGATGGTACCCAGAGCCCCAGGTGCAGTGGAGAACTTC

CAAGGGAGAGAAGTTTCCATCTACATCAGAGTCCAGGAATCCTGATGAA

GAAGGTTTGTTCACTGTGGCTGCTTCAGTGATCATCAGAGACACTTCTG

CGAAAAATGTGTCCTGCTACATCCAGAATCTCCTTCTTGGCCAGGAGAA

GAAAGTAGAAATATCCATACCAGCTTCCTCCCTCCCAAGGCTGACTCCC

TGGATAGTGGCTGTGGCTGTCATCCTGATGGTTCTAGGACTTCTCACCA

TTGGGTCCATATTTTTCACTTGGAGACTATACAACGAAAGACCCAGAGA

GAGGAGGAATGAATTCAGCTCTAAAGAGAGACTCCTGGAAGAACTCAAA

TGGAAAAAGGCTACCTTGCATGCAGTTGATGTGACTCTGGACCCAGACA

CAGCTCATCCCCACCTCTTTCTTTATGAGGATTCAAAATCTGTTCGACT

GGAAGATTCACGTCAGAAACTGCCTGAGAAAACAGAGAGATTTGACTCC

TGGCCCTGTGTGTTGGGCCGTGAGACCTTCACCTCAGGAAGGCATTACT

GGGAGGTGGAGGTGGGAGACAGGACTGACTGGGCAATCGGCGTGTGTAG

GGAGAATGTGATGAAGAAGGATTTGACCCCATGACTCCTGAGAATGGG

TTCTGGGCTGTAGAGTTGTATGGAAATGGGTACTGGGCCCTCACTCCTC

TCCGGACCCCTCTCCCATTGGCAGGGCCCCACGCCGGGTTGGGATTTT

CCTAGACTATGAATCAGGAGACATCTCCTTCTACAACATGAATGATGGA

TCTGATATCTATACTTTCTCCAATGTCACTTTCTCTGGCCCCCTCCGGC

CCTTCTTTTGCCTATGGTCTAGCGGTAAAAAGCCCCTGACCATCTGCCC

AATTGCTGATGGGCCTGAGAGGGTCACAGTCATTGCTAATGCCCAGGAC

CTTTCTAAGGAGATCCCATTGTCCCCCATGGGGAGGACTCTGCCCCTA

GGGATGCAGACACTCTCCATTCTAAGCTAATCCCTACCCAACCCAGCCA

AGGGGCACCTTAA
```

An exemplary amino acid sequence of an exemplary dimeric BTN1A1 extracellular domain construct (BTN1A1-ECD-Fc) is provided below.

```
                                        (SEQ ID NO: 3)
APFDVIGPPEPILAVVGEDAELPCRLSPNASAEHLELRWFRKKVSPAVL

VHRDGREQEAEQMPEYRGRATLVQDGIAKGRVALRIRGVRVSDDGEYTC

FFREDGSYEEALVHLKVAALGSDPHISMQVQENGEICLECTSVGWYPEP

QVQWRTSKGEKFPSTSESRNPDEEGLFTVAASVIIRDTSAKNVSCYIQN

LLLGQEKKVEISIPASSLPRDKTHTCPPCPAPELLGGPSVFLFPPKPKD

TLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQ

VYTLPPSREEMTKNQVSLTCLVKGFYPSDIAVEWESNGQPENNYKTTPP

VLDSDGSFFLYSKLTVDKSRWQQGNVFSCSVMHEALHNHYTQKSLSLSP

GK
```

An exemplary amino acid sequence of an exemplary monomeric BTN1A1 extracellular domain construct (BTN1A1-His6) is provided below.

```
                                        (SEQ ID NO: 4)
APFDVIGPPEPILAVVGEDAELPCRLSPNASAEHLELRWFRKKVSPAVL

VHRDGREQEAEQMPEYRGRATLVQDGIAKGRVALRIRGVRVSDDGEYTC

FFREDGSYEEALVHLKVAALGSDPHISMQVQENGEICLECTSVGWYPEP

QVQWRTSKGEKFPSTSESRNPDEEGLFTVAASVIIRDTSAKNVSCYIQN

LLLGQEKKVEISIPASSLPRHHHHHH
```

An exemplary amino acid sequence of mouse BTN1A1 (GenBank: AAH11497.1), is provided below with the potential glycosylation sites bolded and underlined:

```
                                        (SEQ ID NO: 5)
MAVPTNSCLLVCLLTLTVLQLPTLDSAAPFDVTAPQEPVLALVGSDAEL

TCGFSPNASSEYMELLWFRQTRSKAVLLYRDGQEQEGQQMTEYRGRATL

ATAGLLDGRATLLIRDVRVSDQGEYRCLFKDNDDFEEAAVYLKVAAVGS

DPQISMTVQENGEMELECTSSGWYPEPQVQWRTGNREMLPSTSESKKHN

EEGLFTVAVSMMIRDSSIKNMSCCIQNILLGQGKEVEISLPAPFVPRLT

PWIVAVAIILLALGFLTIGSIFFTWKLYKERSSLRKKEFGSKERLLEEL

RCKKTVLHEVDVTLDPDTAHPHLFLYEDSKSVRLEDSRQILPDRPERFD

SWPCVLGRETFTSGRHYWEVEVGDRTDWAIGVCRENVVKKGFDPMTPDN

GFWAVELYGNGYWALTPLRTSLRLAGPPRRVGVFLDYDAGDISFYNMSN

GSLIYTFPSISFSGPLRPFFCLWSCGKKPLTICSTANGPEKVTVIANVQ

DDIPLSPLGEGCTSGDKDTLHSKLIPFSPSQAAP
```

An exemplary encoding nucleic acid sequence of mouse BTN1A1 (GenBank: BC011497.1), is provided below:

```
                                        (SEQ ID NO: 6)
ATGGCAGTTCCCACCAACTCCTGCCTCCTGGTCTGTCTGCTCACCCTCA

CTGTCCTACAGCTGCCCACGCTGGATTCGGCAGCTCCCTTCGATGTGAC

CGCACCTCAGGAGCCAGTGTTGGCCCTAGTGGGCTCAGATGCCGAGCTG

ACCTGTGGCTTTTCCCCAAACGCGAGCTCAGAATACATGGAGCTGCTGT

GGTTTCGACAGACGAGGTCGAAAGCGGTACTTCTATACCGGGATGGCCA

GGAGCAGGAGGGCCAGCAGATGACGGAGTACCGCGGGAGGGCGACGCTG

GCGACAGCCGGGCTTCTAGACGGCCGCGCTACTCTGCTGATCCGAGATG

TCAGGGTCTCAGACCAGGGGAGTACCGGTGCCTTTTCAAAGACAACGA

CGACTTCGAGGAGGCCGCCGTATACCTCAAAGTGGCTGCTGTGGGTTCA

GATCCTCAAATCAGTATGACGGTTCAAGAGAATGGAGAAATGGAGCTGG

AGTGCACCTCCTCTGGATGGTACCCAGAGCCTCAGGTGCAGTGGAGAAC

AGGCAACGAGAGATGCTACCATCCACGTCAGAGTCCAAGAAGCATAAT

GAGGAAGGCCTGTTCACTGTGGCAGTTTCAATGATGATCAGAGACAGCT

CCATAAAGAACATGTCCTGCTGCATCCAGAATATCCTCCTTGGCCAGGG

GAAGGAAGTAGAGATCTCCTTACCAGCTCCCTTCGTGCCAAGGCTGACT
```

```
CCCTGGATAGTAGCTGTGGCTATCATCTTACTGGCCTTAGGATTTCTCA

CCATTGGGTCCATATTTTTCACTTGGAAACTATACAAGGAAAGATCCAG

TCTGCGGAAGAAGGAATTTGGCTCTAAAGAGAGACTTCTGGAAGAACTC

AGATGCAAAAAGACTGTACTGCATGAAGTTGACGTGACTCTGGATCCAG

ACACAGCCCACCCCCACCTCTTCCTGTATGAAGATTCAAAGTCAGTTCG

ATTGGAAGATTCACGTCAGATCCTGCCTGATAGACCAGAGAGATTTGAC

TCCTGGCCCTGTGTGTTGGGCCGTGAGACCTTTACTTCAGGGAGACATT

ACTGGGAGGTGGAGGTGGGAGATAGAACTGACTGGGCCATTGGTGTGTG

TAGGGAGAATGTGGTGAAGAAAGGGTTTGACCCCATGACTCCTGATAAT

GGGTTCTGGGCTGTGGAGTTGTATGGAAATGGGTACTGGGCCCTCACCC

CACTCAGGACCTCTCTCCGATTAGCAGGGCCCCCTCGCAGAGTTGGGGT

TTTTCTGGACTATGACGCAGGAGACATTTCCTTCTACAACATGAGTAAC

GGATCTCTTATCTATACTTTCCCTAGCATCTCTTTCTCTGGCCCCCTCC

GTCCCTTCTTTTGTCTGTGGTCCTGTGGTAAAAAGCCCCTGACCATCTG

TTCAACTGCCAATGGGCCTGAGAAAGTCACAGTCATTGCTAATGTCCAG

GACGACATTCCCTTGTCCCCGCTGGGGGAAGGCTGTACTTCTGGAGACA

AAGACACTCTCCATTCTAAACTGATCCCGTTCTCACCTAGCCAAGCGGC

ACCATAA
```

As used herein, and unless otherwise specified, the terms "Galectin-1," "GAL-1," "GAL1," "GBP," or "LGALS1" encompass a polypeptide ("polypeptide" and "protein" are used interchangeably herein), including any native polypeptide, from any vertebrate source, including mammals such as primates (e.g., humans and cynomolgus monkeys (cynomolgus)), dogs, and rodents (e.g., mice and rats), unless otherwise indicated. In certain embodiments, the terms include "related GAL-1 polypeptides," including SNP variants thereof. The term "GAL-1" also encompasses "full-length," unprocessed GAL-1 as well as any form of GAL-1 that results from processing in the cell. NCBI Reference Sequence NP 002296 provides an exemplary human GAL-1 amino acid sequence. NCBI Reference Sequence NM_002305 provides an exemplary human GAL-1 nucleic acid sequence (mRNA).

An exemplary amino acid sequence of human GAL-1 (NCBI Reference Sequence NP_002296), is provided below.

```
                                              (SEQ ID NO: 7)
MACGLVASNLNLKPGECLRVRGEVAPDAKSFVLNLGKDSNNLCLHFNPR

FNAHGDANTIVCNSKDGGAWGTEQREAVFPFQPGSVAEVCITFDQANLT

VKLPDGYEFKFPNRLNLEAINYMAADGDFKIKCVAFD
```

An exemplary nucleic acid sequence of human GAL-1 (NCBI Reference Sequence NM_002305 (coding sequence)), is provided below.

```
                                              (SEQ ID NO: 8)
ATG GCTTGTGGTC TGGTCGCCAG CAACCTGAAT CTCAAACCTGGA

GAGTGCCTTCGAGTGCGAGGCGAGGTGGCTCCTGACGCTAAGAGCTTCG

TGCTGAACCTGGGCAAAGACAGCAACAACCTGTGCCTGCACTTCAACCC

TCGCTTCAACGCCCACGGCGACGCCAACACCATCGTGTGCAACAGCAAG

GACGGCGGGGCCTGGGGGACCGAGCAGCGGGAGGCTGTCTTTCCCTTCC

AGCCTGGAAGTGTTGCAGAGGTGTGCATCACCTTCGACCAGGCCAACCT

GACCGTCAAGCTGCCAGATGGATACGAATTCAAGTTCCCCAACCGCCTC

AACCTGGAGGCCATCAACTACATGGCAGCTGACGGTGACTTCAAGATCA

AATGT GTGGCCTTTGACTGA
```

As used herein, and unless otherwise specified, the terms "Galectin-9," "HUAT," "GAL-9," "GALS," "LGALS9," or "LGALS9A" encompass a polypeptide ("polypeptide" and "protein" are used interchangeably herein), including any native polypeptide, from any vertebrate source, including mammals such as primates (e.g., humans and cynomolgus monkeys (cynomolgus)), dogs, and rodents (e.g., mice and rats), unless otherwise indicated. In certain embodiments, the terms include "related GAL-9 polypeptides," including SNP variants thereof. The term "GAL-9" also encompasses "full-length," unprocessed GAL-9 as well as any form of GAL-9 that results from processing in the cell. NCBI Reference Sequence NP_001317092 provides an exemplary human GAL-9 amino acid sequence. NCBI Reference Sequence NM_002308 provides an exemplary human GAL-9 nucleic acid sequence (mRNA).

An exemplary amino acid sequence of human GAL-9 (NCBI Reference Sequence NP_001317092), is provided below.

```
                                              (SEQ ID NO: 9)
MAFSGSQAPYLSPAVPFSGTIQGGLQDGLQITVNGTVLSSSGTRFAVNF

QTGFSGNDIAFHFNPRFEDGGYVVCNTRQNGSWGPEERKTHMPFQKGMP

FDLCFLVQSSDFKVMVNGILFVQYFHRVPFHRVDTISVNGSVQLSYISF

QPPGVWPANPAPITQTVIHTVQSAPGQMFSTPAIPPMMYPHPAYPMPFI

TTILGGLYPSKSILLSGTVLPSAQRCGSCVKLTASRWPWMVSTCLNTTI

A
```

An exemplary nucleic acid sequence of human GAL-9 (NCBI Reference Sequence NM_002308 (coding sequence)), is provided below.

```
                                              (SEQ ID NO: 10)
ATGGCCTTCAGCGGTTCCCAGGCTCCCTACCTGAGTCCAGCTGTCCCCT

TTTCTGGGACTATTCAAGGAGGTCTCCAGGACGGACTTCAGATCACTGT

CAATGGGACCGTTCTCAGCTCCAGTGGAACCAGGTTTGCTGTGAACTTT

CAGACTGGCTTCAGTGGAAATGACATTGCCTTCCACTTCAACCCTCGGT

TTGAAGATGGAGGGTACGTGGTGTGCAACACGAGGCAGAACGGAAGCTG

GGGGCCCGAGGAGAGGAAGACACACATGCCTTTCCAGAAGGGGATGCCC

TTTGACCTCTGCTTCCTGGTGCAGAGCTCAGATTTCAAGGTGATGGTGA

ACGGGATCCTCTTCGTGCAGTACTTCCACCGCGTGCCCTTCCACCGTGT

GGACACCATCTCCGTCAATGGCTCTGTGCAGCTGTCCTACATCAGCTTC

CAGCCTCCCGGCGTGTGGCCTGCCAACCCGGCTCCCATTACCCAGACAG

TCATCCACACAGTGCAGAGCGCCCCTGGACAGATGTTCTCTACTCCCGC
```

```
CATCCCACTATGATGTACCCCCACCCCGCCTATCCGATGCCTTTCATCA

CCACCATTCTGGGAGGGCTGTACCCATCCAAGTCCATCCTCCTGTCAGG

CACTGTCCTGCCCAGTGCTCAGAGGTTCCACATCAACCTGTGCTCTGGG

AACCACATCGCCTTCCACCTGAACCCCCGTTTTGATGAGAATGCTGTGG

TCCGCAACACCCAGATCGACAACTCCTGGGGGTCTGAGGAGCGAAGTCT

GCCCCGAAAAATGCCCTTCGTCCGTGGCCAGAGCTTCTCAGTGTGGATC

TTGTGTGAAGCTCACTGCCTCAAGGTGGCCGTGGATGGTCAGCACCTGT

TTGAATACTACCATCGCCTGAGGAACCTGCCCACCATCAACAGACTGGA

AGTGGGGGGCGACATCCAGCTGACCCATGTGCAGACATAG
```

As used herein, and unless otherwise specified, the terms "Neuropilin-2," "NRP-2," "NRP2," "NP2," "PRO2714," or "VEGF165R2" encompass a polypeptide ("polypeptide" and "protein" are used interchangeably herein), including any native polypeptide, from any vertebrate source, including mammals such as primates (e.g., humans and cynomolgus monkeys (cynomolgus)), dogs, and rodents (e.g., mice and rats), unless otherwise indicated. In certain embodiments, the terms include "related NRP-2 polypeptides," including SNP variants thereof. The term "NRP-2" also encompasses "full-length," unprocessed NRP-2 as well as any form of NRP-2 that results from processing in the cell. NCBI Reference Sequence NP_003863 provides an exemplary human NRP-2 amino acid sequence. NCBI Reference Sequence NM_003872 provides an exemplary human NRP-2 nucleic acid sequence (mRNA).

An exemplary amino acid sequence of human NRP-2 (NCBI Reference Sequence NP_003863), is provided below.

```
                                          (SEQ ID NO: 11)
MDMFPLTWVFLALYFSRHQVRGQPDPPCGGRLNSKDAGYITSPGYPQDY

PSHQNCEWIVYAPEPNQKIVLNFNPHFEIEKHDCKYDFIEIRDGDSESA

DLLGKHCGNIAPPTIISSGSMLYIKFTSDYARQGAGFSLRYEIFKTGSE

DCSKNFTSPNGTIESPGFPEKYPHNLDCTFTILAKPKMEIILQFLIFDL

EHDPLQVGEGDCKYDWLDIWDGIPHVGPLIGKYCGTKTPSELRSSTGIL

SLTFHTDMAVAKDGFSARYYLVHQEPLENFQCNVPLGMESGRIANEQIS

ASSTYSDGRWTPQQSRLHGDDNGWTPNLDSNKEYLQVDLRFLTMLTAIA

TQGAISRETQNGYYVKSYKLEVSTNGEDWMVYRHGKNHKVFQANNDATE

VVLNKLHAPLLTRFVRIRPQTWHSGIALRLELFGCRVTDAPCSNMLGML

SGLIADSQISASSTQEYLWSPSAARLVSSRSGWFPRIPQAQPGEEWLQV

DLGTPKTVKGVIIQGARGGDSITAVEARAFVRKFKVSYSLNGKDWEYIQ

DPRTQQPKLFEGNMHYDTPDIRRFDPIPAQYVRVYPERWSPAGIGMRLE

VLGCDWTDSKPTVETLGPTVKSEETTTPYPTEEEATECGENCSFEDDKD

LQLPSGFNCNFDFLEEPCGWMYDHAKWLRTTWASSSSPNDRTFPDDRNF

LRLQSDSQREGQYARLISPPVHLPRSPVCMEFQYQATGGRGVALQVVRE

ASQESKLLWVIREDQGGEWKHGRIILPSYDMEYQIVFEGVIGKGRSGEI

AIDDIRISTDVPLENCMEPISAFAVDIPEIHEREGYEDEIDDEYEVDWS
```

NSSSATSGSGAPSTDKEKSWLYTLDPILITIIAMSSLGVLLGATCAGLL

LYCTCSYSGLSSRSCTTLENYNFELYDGLKHKVKMNHQKCCSEA

An exemplary nucleic acid sequence of human GAL-1 (NCBI Reference Sequence NM_003872 (coding sequence)), is provided below.

```
                                          (SEQ ID NO: 12)
ATGTTTCCTCTCACCTGGGTTTTCTTAGCCCTCTACTTTTCAAGACACC

AAGTGAGAGGCCAACCAGACCCACCGTGCGGAGGTCGTTTGAATTCCAA

AGATGCTGGCTATATCACCTCTCCCGGTTACCCCCAGGACTACCCCTCC

CACCAGAACTGCGAGTGGATTGTTTACGCCCCCGAACCCAACCAGAAGA

TTGTCCTCAACTTCAACCCTCACTTTGAAATCGAGAAGCACGACTGCAA

GTATGACTTTATCGAGATTCGGGATGGGGACAGTGAATCCGCAGACCTC

CTGGGCAAACACTGTGGGAACATCGCCCCGCCCACCATCATCTCCTCGG

GCTCCATGCTCTACATCAAGTTCACCTCCGACTACGCCCGGCAGGGGGC

AGGCTTCTCTCTGCGCTACGAGATCTTCAAGACAGGCTCTGAAGATTGC

TCAAAAAACTTCACAAGCCCCAACGGGACCATCGAATCTCCTGGGTTTC

CTGAGAAGTATCCACACAACTTGGACTGCACCTTTACCATCCTGGCCAA

ACCCAAGATGGAGATCATCCTGCAGTTCCTGATCTTTGACCTGGAGCAT

GACCCTTTGCAGGTGGGAGAGGGGACTGCAAGTACGATTGGCTGGACA

TCTGGGATGGCATTCCACATGTTGGCCCCCTGATTGGCAAGTACTGTGG

GACCAAAACACCCTCTGAACTTCGTTCATCGACGGGGATCCTCTCCCTG

ACCTTTCACACGGACATGGCGGTGGCCAAGGATGGCTTCTCTGCGCGTT

ACTACCTGGTCCACCAAGAGCCACTAGAGAACTTTCAGTGCAATGTTCC

TCTGGGCATGGAGTCTGGCCGGATTGCTAATGAACAGATCAGTGCCTCA

TCTACCTACTCTGATGGGAGGTGGACCCCTCAACAAAGCCGGCTCCATG

GTGATGACAATGGCTGGACCCCCAACTTGGATTCCAACAAGGAGTATCT

CCAGGTGGACCTGCGCTTTTTAACCATGCTCACGGCCATCGCAACACAG

GGAGCGATTTCCAGGGAAACACAGAATGGCTACTATGTCAAATCCTACA

AGCTGGAAGTCAGCACTAATGGAGAGGACTGGATGGTGTACCGGCATGG

CAAAAACCACAAGGTATTTCAAGCCAACAACGATGCAACTGAGGTGGTT

CTGAACAAGCTCCACGCTCCACTGCTGACAAGGTTTGTTAGAATCCGCC

CTCAGACCTGGCACTCAGGTATCGCCCTCCGGCTGGAGCTCTTCGGCTG

CCGGGTCACAGATGCTCCCTGCTCCAACATGCTGGGGATGCTCTCAGGC

CTCATTGCAGACTCCCAGATCTCCGCCTCTTCCACCCAGGAATACCTCT

GGAGCCCCAGTGCAGCCCGCCTGGTCAGCAGCCGCTCGGGCTGGTTCCC

TCGAATCCCTCAGGCCCAGCCCGGTGAGGAGTGGCTTCAGGTAGATCTG

GGAACACCCAAGACAGTGAAAGGTGTCATCATCCAGGGAGCCCGCGGAG

GAGACAGTATCACTGCTGTGGAAGCCAGAGCATTTGTGCGCAAGTTCAA

AGTCTCCTACAGCCTAAACGGCAAGGACTGGGAATACATTCAGGACCCC

AGGACCCAGCAGCCAAAGCTGTTCGAAGGGAACATGCACTATGACACCC

CTGACATCCGAAGGTTTGACCCCATTCCGGCACAGTATGTGCGGGTATA
```

```
CCCGGAGAGGTGGTCGCCGGCGGGGATTGGGATGCGGCTGGAGGTGCTG

GGCTGTGACTGGACAGACTCCAAGCCCACGGTAGAGACGCTGGGACCCA

CTGTGAAGAGCGAAGAGACAACCACCCCCTACCCCACCGAAGAGGAGGC

CACAGAGTGTGGGGAGAACTGCAGCTTTGAGGATGACAAAGATTTGCAG

CTCCCTTCGGGATTCAATTGCAACTTCGATTTCCTCGAGGAGCCCTGTG

GTTGGATGTATGACCATGCCAAGTGGCTCCGGACCACCTGGGCCAGCAG

CTCCAGCCCAAACGACCGGACGTTTCCAGATGACAGGAATTTCTTGCGG

CTGCAGAGTGACAGCCAGAGAGAGGGCCAGTATGCCCGGCTCATCAGCC

CCCCTGTCCACCTGCCCCGAAGCCCGGTGTGCATGGAGTTCCAGTACCA

GGCCACGGGCGGCCGCGGGGTGGCGCTGCAGGTGGTGCGGGAAGCCAGC

CAGGAGAGCAAGTTGCTGTGGGTCATCCGTGAGGACCAGGGCGGCGAGT

GGAAGCACGGGCGGATCATCCTGCCCAGCTACGACATGGAGTACCAGAT

TGTGTTCGAGGGAGTGATAGGGAAAGGACGTTCCGGAGAGATTGCCATT

GATGACATTCGGATAAGCACTGATGTCCCACTGGAGAACTGCATGGAAC

CCATCTCGGCTTTTGCAGTGGACATCCCAGAAATACATGAGAGAGAAGG

ATATGAAGATGAAATTGATGATGAATACGAGGTGGACTGGAGCAATTCT

TCTTCTGCAACCTCAGGGTCTGGCGCCCCTCGACCGACAAAGAAAAGA

GCTGGCTGTACACCCTGGATCCCATCCTCATCACCATCATCGCCATGAG

CTCACTGGGCGTCCTCCTGGGGGCCACCTGTGCAGGCCTCCTGCTCTAC

TGCACCTGTTCCTACTCGGGCCTGAGCTCCCGAAGCTGCACCACACTGG

AGAACTACAACTTCGAGCTCTACGATGGCCTTAAGCACAAGGTCAAGAT

GAACCACCAAAAGTGCTGCTCCGAGGCATGA
```

As used herein, and unless otherwise specified, the term "B- and T-lymphocyte attenuator" or "BTLA" refers to BTLA from any vertebrate source, including mammals such as primates (e.g., humans, cynomolgus monkey (cyno)), dogs, and rodents (e.g., mice and rats). Unless otherwise specified, BTLA also includes various BTLA isoforms, related BTLA polypeptides, including SNP variants thereof, as well as different modified forms of BTLA, including but not limited to phosphorylated BTLA, glycosylated BTLA, and ubiquitinated BTLA.

An exemplary amino acid sequence of human BTLA is provided below, in which the sites for N-linked glycosylation are bolded underlined (N75, N94, and N110):

```
                                            (SEQ ID NO: 13)
MKTLPAMLGTGKLFWVFFLIPYLDIWNIHGKESCDVQLYIKRQSEHSIL

AGDPFELECPVKYCANRPHVTWCKLNGTTCVKLEDRQTSWKEEKNISFF

ILHFEPVLPNDNGSYRCSANFQSNLIESHSTTLYVTDVKSASERPSKDE

MASRPWLLYRLLPLGGLPLLITTCFCLFCCLRRHQGKQNELSDTAGREI

NLVDAHLKSEQTEASTRQNSQVLLSETGIYDNDPDLCFRMQEGSEVYSN

PCLEENKPGIVYASLNHSVIGPNSRLARNVKEAPTEYASICVRS
```

An exemplary nucleic acid sequence of human BTLA is provided below (NCBI Reference Sequence NM_001085357.1 (coding sequence)):

```
                                            (SEQ ID NO: 14)
ATGAAGACATTGCCTGCCATGCTTGGAACTGGGAAATTATTTTGGGTCT

TCTTCTTAATCCCATATCTGGACATCTGGAACATCCATGGGAAAGAATC

ATGTGATGTACAGCTTTATATAAAGAGACAATCTGAACACTCCATCTTA

GCAGGAGATCCCTTTGAACTAGAATGCCCTGTGAAATACTGTGCTAACA

GGCCTCATGTGACTTGGTGCAAGCTCAATGGAACAACATGTGTAAAACT

TGAAGATAGACAAACAAGTTGGAAGGAAGAGAAGAACATTTCATTTTTC

ATTCTACATTTTGAACCAGTGCTTCCTAATGACAATGGGTCATACCGCT

GTTCTGCAAATTTTCAGTCTAATCTCATTGAAAGCCACTCAACAACTCT

TTATGTGACAGGAAAGCAAAATGAACTCTCTGACACAGCAGGAAGGGAA

ATTAACCTGGTTGATGCTCACCTTAAGAGTGAGCAAACAGAAGCAAGCA

CCAGGCAAAATTCCCAAGTACTGCTATCAGAAACTGGAATTTATGATAA

TGACCCTGACCTTTGTTTCAGGATGCAGGAAGGGTCTGAAGTTTATTCT

AATCCATGCCTGGAAGAAAACAAACCAGGCATTGTTTATGCTTCCCTGA

ACCATTCTGTCATTGGACCGAACTCAAGACTGGCAAGAAATGTAAAAGA

AGCACCAACAGAATATGCATCCATATGTGTGAGGAGTTAAG
```

As used herein, and unless otherwise specified, the terms "Programmed Death 1," "Programmed Cell Death 1," "Protein PD-1," "PD-1," "PD-1 polypeptide," or "PD1" encompass a polypeptide ("polypeptide" and "protein" are used interchangeably herein), including any native polypeptide, from any vertebrate source, including mammals such as primates (e.g., humans and cynomolgus monkeys (cynomolgus)), dogs, and rodents (e.g., mice and rats), unless otherwise indicated. In certain embodiments, the terms include "related PD-1 polypeptides," including SNP variants thereof. The term "PD-1" also encompasses "full-length," unprocessed PD-1 as well as any form of PD-1 that results from processing in the cell. NCBI Reference Sequence NP_005009.2 provides and exemplary human PD-L1 amino acid sequence. GenBank™ accession number L27440.1 provides an exemplary human PD-1 nucleic acid sequence.

As used herein, and unless otherwise specified, the term "anti-PD-1 therapy" encompasses any inhibitor of PD-1. In some embodiments, an anti-PD-1 therapy can include an anti-PD-1 antibody or antigen binding fragment thereof, an inhibitory nucleic acid, or a soluble PD-1 ligand (e.g., a soluble PD-L1), or a fusion-protein thereof (e.g., an Fc-fusion protein). In some embodiments, the anti-PD-1 therapy includes nivolumab (Opdivo), pembrolizumab (Keytruda), pidilizumab, AMP-514, or AMP-224.

In some embodiments, the anti-PD-1 therapy includes Nivolumab (CAS Registry Number: 946414-94-4). Nivolumab is also known as MDX-1 106, MDX-1 106-04, ONO-4538, or BMS-936558. Nivolumab is a fully human IgG4 monoclonal antibody that specifically blocks PD-1. Nivolumab (clone 5C4) and other human monoclonal antibodies that specifically bind to PD-1 are disclosed in U.S. Pat. No. 8,008,449 and WO2006/121 168.

In some embodiments, the anti-PD-1 therapy includes Pembrolizumab. Pembrolizumab is also known as KEYTRUDA®, lambrolizumab, Merck 3745, MK-3475 or SCH-900475. Pembrolizumab is a humanized IgG4 monoclonal antibody that binds to PD-1. Pembrolizumab is disclosed, e.g., in Hamid, O. et al. (2013) New England Journal of Medicine 369 (2): 134-44, WO2009/1 14335, and U.S. Pat. No. 8,354,509.

In some embodiments, the anti-PD-1 therapy is Pidilizumab. Pidilizumab, also known as CT-011 (CureTech), is a humanized IgG1 monoclonal antibody that binds to PD-1. Pidilizumab and other humanized anti-PD-1 monoclonal antibodies are disclosed in WO2009/101611.

In some embodiments, the anti-PD-1 therapy includes an anti-PD-1 antibody provided in International Application No. PCT/US2016/64394.

Additional anti-PD 1 antibodies that can be useful as anti-PD1 therapies are disclosed in U.S. Pat. No. 8,609,089, US 2010028330, and/or US 201201 14649.

In some embodiments, the anti-PD-1 therapy includes the fusion protein AMP 514 (Amplimmune). AMP-224, also known as B7-DCIg is, e.g., disclosed in WO2010/027827 and WO201 1/066342. AMP-224 is a PD-L2 Fc fusion soluble receptor that blocks the interaction between PD1 and B7-H1.

In some embodiments, the anti-PD-1 therapy includes an immunoadhesin (e.g., an immunoadhesin including an extracellular or PD-1 binding portion of PD-L1 or PD-L2 fused to a constant region (e.g., an Fc region of an immunoglobulin sequence)). In some embodiments, the anti-PD-1 therapy includes the fusion protein AMP-224 (Fc-fusion of PD-L2).

As used herein, and unless otherwise specified, the terms "Programmed Death 1 Ligand 1," "Programmed Cell Death 1 Ligand 1," "Protein PD-L1," "PD-L1," "PD-L1 polypeptide," or "PD1-L1" encompass a polypeptide ("polypeptide" and "protein" are used interchangeably herein), including any native polypeptide, from any vertebrate source, including mammals such as primates (e.g., humans and cynomolgus monkeys (cynomolgus)), dogs, and rodents (e.g., mice and rats), unless otherwise indicated. In certain embodiments, the terms include "related PD-L1 polypeptides," including SNP variants thereof. The term "PD-L1" also encompasses "full-length," unprocessed PD-L1 as well as any form of PD-L1 that results from processing in the cell. NCBI Reference Sequence NP_054862.1 provides and exemplary human PD-L1 amino acid sequence. GenBank™ accession number NM_014143 provides an exemplary human PD-1 nucleic acid sequence.

As used herein, and unless otherwise specified, the term "anti-PD-L1 therapy" encompasses any inhibitor of PD-L1. In some embodiments, an anti-PD-1 therapy can include an anti-PD-L1 antibody or antigen binding fragment thereof, an inhibitory nucleic acid, or a soluble PD-L1 ligand (e.g., a soluble PD-1), or a fusion-protein thereof (e.g., an Fc-fusion protein). In some embodiments, the anti-PD-L1 therapy includes YW243.55.S70, MPDL3280A, MEDI-4736, MSB-0010718C, or MDX-1105.

In some embodiments, the anti-PD-L1 therapy includes MDX-1105. MDX-1105, is also known as BMS-936559. See, e.g., WO2007/005874.

In some embodiments, the PD-L1 therapy includes the antibody YW243.55.S70, as described, e.g., in WO 2010/077634 (heavy and light chain variable region sequences shown in SEQ ID NOS: 20 and 21, respectively).

In some embodiments, the PD-L1 therapy includes MDPL3280A (Genentech/Roche). MDPL3280A is a human Fc optimized IgG1 monoclonal antibody that binds to PD-L1. MDPL3280A and other human monoclonal antibodies to PD-L1 are disclosed, e.g., in U.S. Pat. No. 7,943,743 and U.S. Publication No.: 20120039906.

In some embodiments, the anti-PD-L1 therapy includes the antibody MSB0010718C (Merck Serono). MSB0010718C is also known as A09-246-2.

In some embodiments, the anti-PD-L1 therapy includes MDPL3280A (Genentech/Roche), a human Fc optimized IgG1 monoclonal antibody that binds to PD-L1. MDPL3280A and other human monoclonal antibodies to PD-L1 are disclosed in U.S. Pat. No. 7,943,743 and U.S. Publication No.: 20120039906.

In some embodiments, the anti-PD-L1 therapy includes an antibody provided in International Application No. PCT/US2016/024691, published as WO 2016/160792 A1, and International Application No. PCT/US2017/024027.

As used herein, and unless otherwise specified, the term "antibody" refers to a polypeptide product of B cells within the immunoglobulin (or "Ig") class of polypeptides that is able to bind to a specific molecular antigen and is composed of two identical pairs of polypeptide chains, whereby each pair has one heavy chain (about 50-70 kDa) and one light chain (about 25 kDa) and each amino-terminal portion of each chain includes a variable region of about 100 to about 130 or more amino acids and each carboxy-terminal portion of each chain includes a constant region (See Borrebaeck (ed.) (1995) *Antibody Engineering*, Second Edition, Oxford University Press.; Kuby (1997) *Immunology*, Third Edition, W.H. Freeman and Company, New York). Here, the specific molecular antigen includes the targets BTN1A1, GAL-1, GAL-9, NRP-2 and BTLA which can be a BTN1A1 polypeptide, GAL-1 polypeptide, GAL-9 polypeptide, NRP-2 polypeptide or BTLA polypeptide, a BTN1A1 fragment, a GAL-1 fragment, a GAL-9 fragment, a NRP-2 fragment or a BTLA fragment, or BTN1A1 epitope, GAL-1 epitope, GAL-9 epitope, NRP-2 epitope, or BTLA epitope. Antibodies provided herein include, but are not limited to, monoclonal antibodies, synthetic antibodies, recombinantly produced antibodies, bi-specific antibodies, multispecific antibodies, human antibodies, humanized antibodies, camelized antibodies, chimeric antibodies, intrabodies, anti-idiotypic (anti-Id) antibodies.

As used herein, and unless otherwise specified, the term "monoclonal antibody" refers to an antibody that is the product of a single cell clone or hybridoma or a population of cells derived from a single cell. A monoclonal antibody also is intended to refer to an antibody produced by recombinant methods from heavy and light chain encoding immunoglobulin genes to produce a single molecular immunoglobulin species. Amino acid sequences for antibodies within a monoclonal antibody preparation are substantially homogeneous and the binding activity of antibodies within such a preparation exhibit substantially the same antigen binding activity. In contrast, polyclonal antibodies are obtained from different B cells within a population, which are a combination of immunoglobulin molecules that bind a specific antigen. Each immunoglobulin of the polyclonal antibodies can bind a different epitope of the same antigen. Methods for producing both monoclonal antibodies and polyclonal antibodies are well known in the art (Harlow and Lane., *Antibodies: A Laboratory Manual*, Cold Spring Harbor Laboratory Press (1989) and Borrebaeck (ed.), *Antibody Engineering: A Practical Guide*, W.H. Freeman and Co., Publishers, New York, pp. 103-120 (1991)).

As used herein, and unless otherwise specified, the term "human antibody" refers to an antibody that has a human variable region and/or a human constant region or a portion thereof corresponding to human germline immunoglobulin sequences. Such human germline immunoglobulin sequences are described by Kabat et al. (1991) *Sequences of Proteins of Immunological Interest*, Fifth Edition, U.S. Department of Health and Human Services, NIH Publication No. 91-3242. Here, a human antibody can include an antibody that binds to BTN1A1 and is encoded by a nucleic acid sequence that is a naturally occurring somatic variant of the human germline immunoglobulin nucleic acid sequence.

As used herein, and unless otherwise specified, the term "chimeric antibody" refers to an antibody that a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., *Proc. Natl. Acad. Sci. USA,* 81:6851-6855 (1984)).

As used herein, and unless otherwise specified, the term "humanized antibody" refers to chimeric antibodies that include human immunoglobulins (e.g., recipient antibody) in which the native Complementarity Determining Region ("CDR") residues are replaced by residues from the corresponding CDR of a nonhuman species (e.g., donor antibody) such as mouse, rat, rabbit or nonhuman primate having the desired specificity, affinity, and capacity. In some instances, one or more FR region residues of the human immunoglobulin are replaced by corresponding nonhuman residues. Furthermore, humanized antibodies can have residues that are not found in the recipient antibody or in the donor antibody. These modifications are made to further refine antibody performance. A humanized antibody heavy or light chain can have substantially all of at least one or more variable regions, in which all or substantially all of the CDRs correspond to those of a nonhuman immunoglobulin and all or substantially all of the FRs are those of a human immunoglobulin sequence. The humanized antibody can have at least a portion of an immunoglobulin constant region (Fc), typically that of a human immunoglobulin. For further details, see, Jones et al., *Nature,* 321:522-525 (1986); Riechmann et al., *Nature,* 332:323-329 (1988); and Presta, *Curr. Op. Struct. Biol.,* 2:593-596 (1992); Carter et al., *Proc. Natl. Acad. Sci. USA* 89:4285-4289 (1992); and U.S. Pat. Nos. 6,800,738, 6,719,971, 6,639,055, 6,407,213, and 6,054,297.

As used herein, and unless otherwise specified, the term "recombinant antibody" refers to an antibody that is prepared, expressed, created or isolated by recombinant means. Recombinant antibodies can be antibodies expressed using a recombinant expression vector transfected into a host cell, antibodies isolated from a recombinant, combinatorial antibody library, antibodies isolated from an animal (e.g., a mouse or cow) that is transgenic and/or transchromosomal for human immunoglobulin genes (see, e.g., Taylor, L. D. et al., *Nucl. Acids Res.* 20:6287-6295(1992)) or antibodies prepared, expressed, created or isolated by any other means that involves splicing of immunoglobulin gene sequences to other DNA sequences. Such recombinant antibodies can have variable and constant regions, including those derived from human germline immunoglobulin sequences (see Kabat, E. A. et al. (1991) *Sequences of Proteins of Immunological Interest,* Fifth Edition, U.S. Department of Health and Human Services, NIH Publication No. 91-3242). The recombinant antibodies can also be subjected to in vitro mutagenesis (or, when an animal transgenic for human Ig sequences is used, in vivo somatic mutagenesis) and thus the amino acid sequences of the VH and VL regions of the recombinant antibodies can be sequences that, while derived from and related to human germline VH and VL sequences, do not naturally exist within the human antibody germline repertoire in vivo.

As used herein, and unless otherwise specified, a "neutralizing molecule" refers to an that blocks the binding the BTN1A1 with its natural ligands, such as GAL-1, GAL-9, NRP-2 or BTLA, and inhibits the signaling pathways mediated by BTN1A1 and/or its other physiological activities. In some embodiments, the neutralizing molecule is a neutralizing antibody. In some embodiments, the neutralizing molecule comprises an antigen binding fragment that immunospecifically binds BTN1A1 or a BTN1A1 ligand, such as GAL-1, GAL-9, NRP-2 or BTLA. The IC50 of a neutralizing molecule or neutralizing antibody refers to the concentration of the molecule or antibody that is required to neutralize 50% of BTN1A1 in a neutralization assay. The IC50 of the neutralizing molecule or neutralizing antibody can range between 0.01-10 μg/ml in the neutralization assay. In some embodiments a neutralizing molecule or neutralizing antibody can immunospecifically bind to BTN1A1. In some embodiments, a neutralizing molecule or neutralizing antibody can bind to a BTN1A1 ligand, such as GAL-1, GAL-9, NRP-2 or BTLA.

As used herein, and unless otherwise specified, the term "antigen binding fragment" and similar terms refer to a portion of an antibody which includes the amino acid residues that immunospecifically bind to an antigen and confer on the antibody its specificity and affinity for the antigen. An antigen binding fragment can be referred to as a functional fragment of an antibody. An antigen binding fragment can be monovalent, bivalent, or multivalent.

Molecules having an antigen binding fragment include, for example, an Fd, Fv, Fab, F(ab'), F(ab)$_2$, F(ab')$_2$, single chain Fv (scFv), diabody, triabody, tetrabody, minibody, or a single domain antibody. A scFv can be monovalent scFv or bivalent scFv. Other molecules having an antigen binding fragment can include, for example, heavy or light chain polypeptides, variable region polypeptides or CDR polypeptides or portions thereof so long as such antigen binding fragments retain binding activity. Such antigen binding fragments can be found described in, for example, Harlow and Lane, *Antibodies: A Laboratory Manual,* Cold Spring Harbor Laboratory, New York (1989); Myers (ed.), *Molec. Biology and Biotechnology: A Comprehensive Desk Reference,* New York: VCH Publisher, Inc.; Huston et al., *Cell Biophysics,* 22:189-224 (1993); Plückthun and Skerra, *Meth. Enzymol.,* 178:497-515 (1989) and in Day, E. D., *Advanced Immunochemistry,* Second Ed., Wiley-Liss, Inc., New York, N.Y. (1990). An antigen binding fragment can be a polypeptide having an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, or at least 250 contiguous amino acid residues.

The heavy chain of an antibody refers to a polypeptide chain of about 50-70 kDa, whereby the amino-terminal portion includes a variable region of about 120 to 130 or more amino acids and a carboxy-terminal portion that includes a constant region. The constant region can be one of five distinct types, referred to as alpha (α), delta (δ), epsilon (ε), gamma (γ) and mu (μ), based on the amino acid sequence of the heavy chain constant region. The distinct heavy chains differ in size: α, δ and γ contain approximately 450 amino acids, while μ and ε contain approximately 550 amino acids. When combined with a light chain, these distinct types of heavy chains give rise to five well known classes of antibodies, IgA, IgD, IgE, IgG and IgM, respectively, including four subclasses of IgG, namely IgG1, IgG2, IgG3 and IgG4. A heavy chain can be a human heavy chain.

The light chain of an antibody refers to a polypeptide chain of about 25 kDa, whereby the amino-terminal portion includes a variable region of about 100 to about 110 or more amino acids and a carboxy-terminal portion that includes a constant region. The approximate length of a light chain is 211 to 217 amino acids. There are two distinct types, referred to as kappa (κ) of lambda (λ) based on the amino acid sequence of the constant domains. Light chain amino acid sequences are well known in the art. A light chain can be a human light chain.

The variable domain or variable region of an antibody refers to a portion of the light or heavy chains of an antibody that is generally located at the amino-terminal of the light or heavy chain and has a length of about 120 to 130 amino acids in the heavy chain and about 100 to 110 amino acids in the light chain, and are used in the binding and specificity of each particular antibody for its particular antigen. The variable domains differ extensively in sequence between different antibodies. The variability in sequence is concentrated in the CDRs while the less variable portions in the variable domain are referred to as framework regions (FR). The CDRs of the light and heavy chains are primarily responsible for the interaction of the antibody with antigen. Numbering of amino acid positions used herein is according to the EU Index, as in Kabat et al. (1991) *Sequences of proteins of immunological interest*. (U.S. Department of Health and Human Services, Washington, D.C.) $5^{th}$ ed. A variable region can be a human variable region.

A CDR refers to one of three hypervariable regions (H1, H2 or H3) within the non-framework region of the immunoglobulin (Ig or antibody) VH β-sheet framework, or one of three hypervariable regions (L1, L2 or L3) within the non-framework region of the antibody VL β-sheet framework. Accordingly, CDRs are variable region sequences interspersed within the framework region sequences. CDR regions are well known to those skilled in the art and have been defined by, for example, Kabat as the regions of most hypervariability within the antibody variable (V) domains (Kabat et al., *J. Biol. Chem.* 252:6609-6616 (1977); Kabat, *Adv. Prot. Chem.* 32:1-75 (1978)). CDR region sequences also have been defined structurally by Chothia as those residues that are not part of the conserved β-sheet framework, and thus are able to adapt different conformations (Chothia and Lesk, *J. Mol. Biol.* 196:901-917 (1987)). Both terminologies are well recognized in the art. The positions of CDRs within a canonical antibody variable domain have been determined by comparison of numerous structures (Al-Lazikani et al., *J. Mol. Biol.* 273:927-948 (1997); Morea et al., *Methods* 20:267-279 (2000)). Because the number of residues within a hypervariable region varies in different antibodies, additional residues relative to the canonical positions are conventionally numbered with a, b, c and so forth next to the residue number in the canonical variable domain numbering scheme (Al-Lazikani et al., supra (1997)). Such nomenclature is similarly well known to those skilled in the art.

For example, CDRs defined according to standard designations are set forth in the Table 1 below.

TABLE 1

CDR Definitions

| | Exemplary (Kabat + Chothia) | IMGT | Kabat | AbM | Chothia | Contact |
|---|---|---|---|---|---|---|
| $V_H$ CDR1 | 26-35 | 27-38 | 31-35 | 26-35 | 26-32 | 30-35 |
| $V_H$ CDR2 | 50-65 | 56-65 | 50-65 | 50-58 | 53-55 | 47-58 |
| $V_H$ CDR3 | 95-102 | 105-117 | 95-102 | 95-102 | 96-101 | 93-101 |
| $V_L$ CDR1 | 24-34 | 27-38 | 24-34 | 24-34 | 26-32 | 30-36 |
| $V_L$ CDR2 | 50-56 | 56-65 | 50-56 | 50-56 | 50-52 | 46-55 |
| $V_L$ CDR3 | 89-97 | 105-117 | 89-97 | 89-97 | 91-96 | 89-96 |

One or more CDRs also can be incorporated into a molecule either covalently or noncovalently to make it an immunoadhesin. An immunoadhesin can incorporate the CDR(s) as part of a larger polypeptide chain, can covalently link the CDR(s) to another polypeptide chain, or can incorporate the CDR(s) noncovalently. The CDRs permit the immunoadhesin to bind to a particular antigen of interest.

The "framework" or "FR" residues refer to those variable domain residues flanking the CDRs. FR residues are present, e.g., in chimeric, humanized, human, domain antibodies, diabodies, linear antibodies, and bispecific antibodies. FR residues are those variable domain residues other than the hypervariable region residues herein defined.

As used herein, and unless otherwise specified, the term "isolated" as used in reference to an antibody means the antibody is substantially free of cellular material or other contaminating proteins from the cell or tissue source and/or other contaminant components from which the antibody is derived, or substantially free of chemical precursors or other chemicals when chemically synthesized. The language "substantially free of cellular material" includes preparations of an antibody in which the antibody is separated from cellular components of the cells from which it is isolated or recombinantly produced. Thus, an antibody that is substantially free of cellular material includes preparations of antibody having less than about 30%, 20%, 10%, or 5% (by dry weight) of heterologous protein (also referred to herein as a "contaminating protein"). In certain embodiments, when the antibody is recombinantly produced, it is substantially free of culture medium, e.g., culture medium represents less than about 20%, 10%, or 5% of the volume of the protein preparation. In certain embodiments, when the antibody is produced by chemical synthesis, it is substantially free of chemical precursors or other chemicals, e.g., it is separated from chemical precursors or other chemicals which are involved in the synthesis of the protein. Accordingly such preparations of the antibody have less than about 30%, 20%, 10%, 5% (by dry weight) of chemical precursors or compounds other than the antibody of interest. Contaminant components can also include, but are not limited to, materials that would interfere with therapeutic uses for the antibody, and may include enzymes, hormones, and other proteinaceous or nonproteinaceous solutes. In certain embodiments, the antibody will be purified (1) to greater than 95% by weight of antibody as determined by the Lowry method (Lowry et al. J. Bio. Chem. 193: 265-275, 1951), such as 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step. In a specific embodiment, antibodies provided herein are isolated As used herein, and unless otherwise specified, the term "polynucleotide," "nucleotide," nucleic acid" "nucleic acid molecule" and other similar terms are used interchangeable and include DNA, RNA, mRNA and the like.

As used herein, and unless otherwise specified, the term "isolated" as used in reference to a nucleic acid molecule means the nucleic acid molecule is one which is separated from other nucleic acid molecules which are present in the natural source of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. In a specific embodiment, a nucleic acid molecule(s) encoding an antibody provided herein is isolated or purified.

As used herein and unless otherwise specified, the term "bind" or "binding" refers to an interaction between molecules. Interactions can be, for example, non-covalent interactions including hydrogen bonds, ionic bonds, hydrophobic interactions, and/or van der Waals interactions. The strength of the total non-covalent interactions between an antibody and a single epitope of a target molecule, such as BTN1A1, GAL-1, GAL-9, NRP-2, or BTLA is the affinity of the antibody for that epitope. "Binding affinity" generally refers to the strength of the sum total of noncovalent interactions between a single binding site of a molecule (e.g., a binding protein such as an antibody) and its binding partner (e.g., an antigen).

The affinity of a binding molecule X, such as an antibody, for its binding partner Y, such as the antibody's cognate antigen can generally be represented by the dissociation constant ($K_D$). Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present disclosure. The "$K_D$" or "$K_D$ value" can be measured by assays known in the art, for example by a binding assay. The $K_D$ can be measured in a radiolabeled antigen binding assay (MA), for example, performed with the Fab version of an antibody of interest and its antigen (Chen, et al., (1999) *J. Mol. Biol.* 293:865-881). The $K_D$ or $K_D$ value can also be measured by using surface plasmon resonance assays by Biacore, using, for example, a BIAcore™-2000 or a BIAcore™-3000 BIAcore, Inc., Piscataway, N.J.), or by biolayer interferometry using, for example, the OctetQK384 system (ForteBio, Menlo Park, Calif.).

As used herein, and unless otherwise specified, a molecule is said to be able to "immunospecifically bind" a second molecule if such binding exhibits the specificity and affinity of an antibody to its cognate antigen. An antibody immunospecifically binds to a target region or conformation ("epitope") of an antigen if such binding involves the antigen recognition site of the antibody. An antibody that immunospecifically binds to a particular antigen can bind to other antigens with lower affinity if the other antigen has some sequence or conformational similarity that is recognized by the antigen recognition site as determined by, e.g., immunoassays, BIACORE® assays, or other assays known in the art. An antibody in general do not bind to a totally unrelated antigen. Some antibodies (and their antigen binding fragments) does not cross-react with other antigens.

Antibodies can also bind to other molecules in a way that is not immunospecific, such as to FcR receptors, by virtue of binding domains in other regions/domains of the antibody that do not involve the antigen recognition site, such as the Fc region.

An antibody or antigen binding fragment that immunospecifically binds to an antigen or an epitope of an antigen that includes a glycosylation site can bind to the antigen or the epitope in both glycosylated form or unglycosylated form. In some embodiments, the antibody or antigen binding fragment preferentially binds the glycosylated antigen or epitope over the unglycosylated antigen or epitope. The preferential binding can be determined by binding affinity. For example, an antibody or antigen binding fragment that preferentially binds glycosylated BTN1A1 over unglycosylated BTN1A1 can bind to glycosylated BTN1A1 with a $K_D$ less than the $K_D$ exhibited relative to unglycosylated BTN1A1. In some embodiments, the antibody or antigen binding fragment binds to glycosylated BTN1A1 with a $K_D$ less than half of the $K_D$ exhibited relative to unglycosylated BTN1A1. In some embodiments, the antibody or antigen binding fragment binds to glycosylated BTN1A1 with Ku at least 10 times less than the $K_D$ exhibited relative to unglycosylated BTN1A1. In some embodiments, the antibody or antigen binding fragment binds to glycosylated BTN1A1 with $K_D$ that is about 75%, about 50%, about 25%, about 10%, about 5%, about 2.5%, or about 1% of the $K_D$ exhibited relative to unglycosylated BTN1A1.

An antibody or antigen binding fragment that immunospecifically binds to BTN1A1 can bind to a BTN1A1 monomer or a BTN1A1 dimer. In some embodiments, the antibody or antigen binding fragment preferentially binds a BTN1A1 dimer over a BTN1A1 monomers. BTN1A1 binding can occur, e.g., to a cell surface expressed BTN1A1 or to a soluble BTN1A1 domain construct, such as a BTN1A1 extracellular domain (ECD) construct (e.g., flag-tagged BTN1A1-ECD or a BTN1A1-CED-Fc fusion construct). In some embodiments, the BTN1A1 monomer or dimer is glycosylated at one or more positions. In some embodiments, the antibody or antigen binding fragment binds to BTN1A1 dimer with a Ku less than half of the $K_D$ exhibited relative to a BTN1A1 monomer. In some embodiments, the antibody or antigen binding fragment binds to aBTN1A1 dimer with a $K_D$ at least 10 times less than the $K_D$ exhibited relative to a BTN1A1 monomer. In some embodiments, the antibody or antigen binding fragment binds to a BTN1A1 dimer with a $K_D$ that is about 75%, about 50%, about 25%, about 10%, about 5%, about 2.5%, or about 1% of the $K_D$ exhibited relative to aBTN1A1 monomer.

The preferential binding can also be determined by binding assays and be indicated by, for example, mean fluorescence intensity ("MFI"). For example, an antibody or antigen binding fragment that preferentially binds the glycosylated BTN1A1 can bind to glycosylated BTN1A1 with an MFI that is higher than the MFI as exhibited relative to unglycosylated BTN1A1. In some embodiments, the antibody or antigen binding fragment binds to glycosylated BTN1A1 with an MFI that is at least twice as high as the MFI as exhibited relative to unglycosylated BTN1A1. In some embodiments, antibody or the antigen binding fragment binds to glycosylated BTN1A1 with an MFI that is at least three times as high as the MFI as exhibited relative to unglycosylated BTN1A1. In some embodiments, antibody or the antigen binding fragment binds to glycosylated BTN1A1 with an MFI that is at least five times, at least ten times, at least fifteen times, or at least twenty times as high as the MFI as exhibited relative to unglycosylated BTN1A1.

As used herein, and unless otherwise specified, a molecule is said to "immunospecifically mask" glycosylation of an antigen or epitope, or a specified glycosylation site thereof, refers to its ability to either (1) block the glycosylation site of an unglycosylated antigen or epitope so that the antigen or epitope cannot be glycosylated, or (2) bind to the glycosylated antigen or epitope or at the specified glycosylation site of the glycosylated antigen or epitope and prevent the physiological effect of the glycosylation, such as the downstream signaling mediated by the glycosylation. For example, an antibody or antigen binding fragment that immunospecifically masks BTN1A1 glycosylation refers to the antibody or antigen binding fragment that (1) either blocks the glycosylation site of an unglycosylated BTN1A1 and prevents its glycosylation or (2) binds to glycosylated BTN1A1 and prevents the physiological effects of the glycosylation, such as the immunosuppressive effect mediated by the glycosylation. For another example, an antibody or antigen binding fragment that immunospecifically masks BTN1A1 glycosylation at N55 and N215 refers to the antibody or antigen binding fragment that either (1) blocks N55 and N215 of an unglycosylated BTN1A1 and prevents the glycosylation of N55 and N215 or (2) binds to BTN1A1 glycosylated at N55 and N215 and prevent the physiological effect of the glycosylation, such as the immunosuppressive effect mediated by the glycosylation.

As used herein, and unless otherwise specified, the term "carrier" refers to a diluent, adjuvant (e.g., Freund's adjuvant (complete or incomplete)), excipient, stabilizers or vehicle with which a therapeutic agent is administered. A "pharmaceutically acceptable carrier" is a carrier that is nontoxic to the cell or mammal being exposed thereto at the dosages and concentrations employed, which can be sterile liquids, such as water and oils, including those of petroleum, animal, vegetable or synthetic origin, such as peanut oil, soybean oil, mineral oil, sesame oil and the like.

As used herein, and unless otherwise specified, the term "vector" refers to a substance that is used to introduce a nucleic acid molecule into a host cell. Vectors applicable for use include, for example, expression vectors, plasmids, phage vectors, viral vectors, episomes and artificial chromosomes, which can include selection sequences or markers operable for stable integration into a host cell's chromosome. Additionally, the vectors can include one or more selectable marker genes and appropriate expression control sequences. Selectable marker genes that can be included, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more nucleic acid molecules are to be co-expressed (e.g. both an antibody heavy and light chain), both nucleic acid molecules can be inserted, for example, into a single expression vector or in separate expression vectors. For single vector expression, the encoding nucleic acids can be operationally linked to one common expression control sequence or linked to different expression control sequences, such as one inducible promoter and one constitutive promoter. The introduction of nucleic acid molecules into a host cell can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of an introduced nucleic acid sequence or its corresponding gene product. It is understood by those skilled in the art that the nucleic acid molecule is expressed in a sufficient amount to produce the desired product (e.g. an anti-BTN1A1 antibody provided herein), and it is further understood that expression levels can be optimized to obtain sufficient expression using methods well known in the art.

As used herein, and unless otherwise specified, the term "host cell" refers to the particular subject cell transfected with a nucleic acid molecule and the progeny or potential progeny of such a cell. Progeny of such a cell may not be identical to the parent cell transfected with the nucleic acid molecule due to mutations or environmental influences that may occur in succeeding generations or integration of the nucleic acid molecule into the host cell genome.

As used herein, and unless otherwise specified, the term "subject" refers to an animal that is the object of treatment, observation and/or experiment. "Animal" includes vertebrates and invertebrates, such as fish, shellfish, reptiles, birds, and, in particular, mammals. "Mammal" includes, but not limited to, mice, rats, rabbits, guinea pigs, dogs, cats, sheep, goats, cows, horses, primates, such as monkeys, chimpanzees, apes, and humans.

As used herein, and unless otherwise specified, the term "cancer" or "cancerous" refers to the physiological condition in mammals that is typically characterized by unregulated cell growth. Examples of cancer include, but are not limited to, hematological cancers and solid tumors.

As used herein, and unless otherwise specified, the term "treat," "treating," "treatment," when used in reference to a cancer patient, refer to an action that reduces the severity of the cancer, or retards or slows the progression of the cancer, including (a) inhibiting the cancer growth, or arresting development of the cancer, and (b) causing regression of the cancer, or delaying or minimizing one or more symptoms associated with the presence of the cancer.

As used herein, and unless otherwise specified, the term "resistant" or "refractory" refers to a circumstance where patients, even after intensive treatment, have residual cancer cells (e.g., lung cancer or breast cancer cells) in a tissue or an organ (e.g., lung or breast).

The term "responsiveness" or "responsive" when used in reference to a treatment refers to the degree of effectiveness of the treatment in lessening or decreasing the symptoms of a disease, e.g., an anti-PD1 therapy or an anti-PD-L1 therapy resistant or refractory cancer, being treated. For example, the term "increased responsiveness" when used in reference to a treatment of a cell or a subject refers to an increase in the effectiveness in lessening or decreasing the symptoms of the disease compared to a reference treatment (e.g., of the same cell or subject, or of a different cell or subject) when measured using any methods known in the art. In certain embodiments, the increase in the effectiveness is at least about 5%, at least about 10%, at least about 20%, at least about 30%, at least about 40%, or at least about 50%.

As used herein, the terms "effective subject response," "effective patient response," and "effective patient tumor response" refer to any increase in the therapeutic benefit to the patient. An "effective patient tumor response" can be, for example, about 5%, about 10%, about 25%, about 50%, or about 100% decrease in the rate of progress of the tumor. An "effective patient tumor response" can be, for example, about 5%, about 10%, about 25%, about 50%, or about 100% decrease in the physical symptoms of a cancer. An "effective patient tumor response" can also be, for example, about 5%, about 10%, about 25%, about 50%, about 100%, about 200%, or more increase in the response of the patient, as measured by any suitable means, such as gene expression, cell counts, assay results, tumor size, etc.

An improvement in the cancer or cancer-related disease can be characterized as a complete or partial response. "Complete response" refers to an absence of clinically detectable disease with normalization of any previously abnormal radiographic studies, bone marrow, and cerebrospinal fluid (CSF) or abnormal monoclonal protein measurements. "Partial response" refers to at least about 10%, about 20%, about 30%, about 40%, about 50%, about 60%, about 70%, about 80%, or about 90% decrease in all measurable tumor burden (i.e., the number of malignant cells present in the subject, or the measured bulk of tumor masses or the quantity of abnormal monoclonal protein) in the absence of new lesions. The term "treatment" contemplates both a complete and a partial response.

The term "likelihood" generally refers to an increase in the probability of an event. The term "likelihood" when used in reference to the effectiveness of a patient tumor response generally contemplates an increased probability that the rate of tumor progress or tumor cell growth will decrease. The term "likelihood" when used in reference to the effectiveness of a patient tumor response can also generally mean the increase of indicators, such as mRNA or protein expression, that may evidence an increase in the progress in treating the tumor.

The term "predict" generally means to determine or tell in advance. When used to "predict" the effectiveness of a cancer treatment, for example, the term "predict" can mean that the likelihood of the outcome of the cancer treatment can be determined at the outset, before the treatment has begun, or before the treatment period has progressed substantially.

The term "monitor," as used herein, generally refers to the overseeing, supervision, regulation, watching, tracking, or surveillance of an activity. For example, the term "monitoring the effectiveness of a compound" refers to tracking the effectiveness in treating cancer in a patient or in a tumor cell culture. Similarly, the term "monitoring," when used in connection with patient compliance, either individually, or in a clinical trial, refers to the tracking or confirming that the patient is actually taking a drug being tested as prescribed. The monitoring can be performed, for example, by following the expression of mRNA or protein biomarkers.

"Tumor," as used herein, refers to all neoplastic cell growth and proliferation, whether malignant or benign, and all pre-cancerous and cancerous cells and tissues. "Neoplastic," as used herein, refers to any form of dysregulated or unregulated cell growth, whether malignant or benign, resulting in abnormal tissue growth. Thus, "neoplastic cells" include malignant and benign cells having dysregulated or unregulated cell growth.

As used herein, and unless otherwise specified, the term "therapeutically effective amount" refers to the amount of an agent (e.g., an antibody described herein or any other agent described herein) that is sufficient to reduce and/or ameliorate the severity and/or duration of a given disease, disorder or condition, and/or a symptom related thereto. A therapeutically effective amount of an agent, including a therapeutic agent, can be an amount necessary for (i) reduction or amelioration of the advancement or progression of a given disease, disorder, or condition, (ii) reduction or amelioration of the recurrence, development or onset of a given disease, disorder or conditions, and/or (iii) to improve or enhance the prophylactic or therapeutic effect of another therapy (e.g., a therapy other than the administration of an antibody provided herein). A therapeutically effective amount of a substance/molecule/agent of the present disclosure (e.g., an anti-BTN1A1 antibody) can vary according to factors such as the disease state, age, sex, and weight of the individual, and the ability of the substance/molecule/agent, to elicit a desired response in the individual. A therapeutically effective amount encompasses an amount in which any toxic or detrimental effects of the substance/molecule/agent are outweighed by the therapeutically beneficial effects.

As used herein, and unless otherwise specified, the term "administer" or "administration" refers to the act of injecting or otherwise physically delivering a substance as it exists outside the body into a patient, such as by mucosal, intradermal, intravenous, intramuscular delivery and/or any other method of physical delivery described herein or known in the art. When a disease, disorder or condition, or a symptom thereof, is being treated, administration of the substance typically occurs after the onset of disease, disorder or condition or symptoms thereof. When a disease, disorder or condition, or symptoms thereof, are being prevented, administration of the substance typically occurs before the onset of the disease, disorder or condition or symptoms thereof.

A "biological marker" or "biomarker" is a substance whose detection indicates a particular biological state, such as, for example, the presence of cancer. In some embodiments, biomarkers can be determined individually. In other embodiments, several biomarkers can be measured simultaneously. In some embodiments of the methods provided herein, BTN1A1 is a biomarker indicating the presence of cancer. In some embodiments PD-L1 is a biomarker indicating the presence of cancer. In some embodiments, BTN1A1 and PD-L1 can be used in combination to indicate the presence of a cancer (e.g., an anti-PD1 or anti-PD-L1 therapy resistant or refractory cancer that is responsive to treatment with, e.g., an anti-BTN1A1 antibody).

In some embodiments, a "biomarker" indicates a change in the level of mRNA expression that may correlate with the risk or progression of a disease, or with the susceptibility of the disease to a given treatment. In some embodiments, the biomarker is a nucleic acid, such as mRNA or cDNA (e.g., BTN1A1 or PD-L1 mRNA or cDNA).

In additional embodiments, a "biomarker" indicates a change in the level of polypeptide or protein expression that may correlate with the risk or progression of a disease, or patient's susceptibility to treatment. In some embodiments, the biomarker can be a polypeptide or protein, or a fragment thereof (e.g., BTN1A1 or PD-L1 protein). The relative level of specific proteins can be determined by methods known in the art. For example, antibody based methods, such as an immunoblot, enzyme-linked immunosorbent assay (ELISA), or other methods can be used.

The term "expressed" or "expression" as used herein refers to the transcription from a gene to give an RNA nucleic acid molecule at least complementary in part to a region of one of the two nucleic acid strands of the gene. The term "expressed" or "expression" as used herein also refers to the translation from the RNA molecule to give a protein, a polypeptide, or a portion thereof.

The term "level" refers to the amount, accumulation, or rate of a biomarker molecule (e.g., BTN1A1 or PD-L1). A level can be represented, for example, by the amount or the rate of synthesis of a messenger RNA (mRNA) encoded by a gene, the amount or the rate of synthesis of a polypeptide or protein encoded by a gene, or the amount or the rate of synthesis of a biological molecule accumulated in a cell or biological fluid. The term "level" refers to an absolute amount of a molecule in a sample or a relative amount of the molecule, determined under steady-state or non-steady-state conditions.

The terms "determining," "measuring," "evaluating," "assessing," and "assaying" as used herein generally refer to any form of measurement, and include determining whether an element is present or not. These terms include quantitative and/or qualitative determinations. Assessing may be relative or absolute. "Assessing the presence of" can include determining the amount of something present, as well as determining whether it is present or absent.

The term "sample" as used herein relates to a material or mixture of materials, typically, although not necessarily, in fluid form, containing one or more components of interest.

"Biological sample" as used herein refers to a sample obtained from a biological subject, including a sample of biological tissue or fluid origin, obtained, reached, or collected in vivo or in situ. A biological sample also includes samples from a region of a biological subject containing precancerous or cancer cells or tissues. Such samples can be, but are not limited to, organs, tissues, and cells isolated from a mammal. Exemplary biological samples include but are not limited to cell lysate, a cell culture, a cell line, a tissue, oral tissue, gastrointestinal tissue, an organ, an organelle, a biological fluid, a blood sample, a urine sample, a skin sample, and the like. Preferred biological samples include, but are not limited to, whole blood, partially purified blood, PBMC, tissue biopsies, and the like.

5.2 Molecules Having an Antigen Binding Fragment that Immunospecifically Bind to BTN1A1 or a BTN1A1 Ligand Provided herein are molecules having an antigen binding fragment that immunospecifically bind to BTN1A1 or a BTN1A1 ligand, such GAL-1, GAL-9, NRP-2, or BTLA, whereby the molecules can inhibit the binding of the BTN1A1 ligand to BTN1A1. In some embodiments, the molecule can inhibit formation of a BTN1A1-BTN1A1 ligand complex (e.g., a complex including GAL-1, GAL-9, NRP-2, or BTLA, and BTN1A1). In some embodiments, the molecule can disrupt a formed BTN1A1-BTN1A1 ligand complex (e.g., a complex including GAL-1, GAL-9, NRP-2, or BTLA, and BTN1A1). In some embodiments, the molecules are antibodies, including anti-BTN1A1 antibodies, anti-GAL-1 antibodies, anti-GAL-9 antibodies, anti-NRP-2 antibodies, or anti-BTLA antibodies. In some embodiments, the antigen binding fragment that immunospecifically binds BTN1A1 or a BTN1A1 ligand (e.g., GAL-1, GAL-9, NRP-2, or BTLA) binds to a fragment, or an epitope of BTN1A1 or the BTN1A1 ligand. In some embodiments, the antigen binding fragment immunospecifically binds to a BTN1A1 dimer. In some embodiments, the BTN1A1, GAL-1, GAL-9, NRP-2, or BTLA epitope can be a linear epitope. In some embodiments, the BTN1A1, GAL-1, GAL-9, NRP-2, or BTLA epitope can be a conformation epitope. In some embodiments, the BTN1A1 epitope is found in a BTN1A1 dimer and not found in a BTN1A1 monomer. In some embodiments, the molecules provided herein that have an antigen binding fragment that immunospecifically binds to BTN1A1, GAL-1, GAL-9, NRP-2, or BTLA inhibit the immune suppressive function of BTN1A1 or a BTN1A1-BTN1A1 ligand complex.

In some embodiments, the molecule is an anti-glycosylated BTN1A1 antibody or includes an antigen binding fragment of an anti-glycosylated BTN1A1 antibody. In some embodiments, the molecule is an anti-BTN1A1 dimer antibody, or includes an antigen binding fragment of an anti-BTN1A1 dimer antibody. In some embodiments, the molecule is a molecule having an antigen binding fragment that immunospecifically binds to BTN1A1, as described, e.g., in International Patent Application No. PCT/US2016/064436 (filed Dec. 1, 2016), in U.S. Provisional Application No. 62/513,389 (filed May 31, 2017) or U.S. Provisional Application No. 62/513,393 (filed May 31, 2017), which are incorporated herein by reference in their entireties. In some embodiments, the molecule includes an antigen binding fragment, or a VH, VL, or CDR sequence of anti-BTN1A1 antibodies STC703, STC810, STC820, STC1011, STC1012, or STC1029, or a humanized variant thereof, as described, e.g., in International Patent Application No. PCT/US2016/064436, in U.S. Provisional Application No. 62/513,389 or U.S. Provisional Application No. 62/513,393.

In some embodiments, the molecule is not STC810 or comprises an antigen-binding fragment or a VH, VL, or CDR amino acid sequence of STC810, as described in International Application No. PCT/US2016/64436.

In some embodiments, the molecule is an anti-GAL-1 antibody or includes an antigen binding fragment of an anti-GAL-1 antibody. In some embodiments, the molecule is an anti-GAL-1 antibody or includes an antigen binding fragment of an anti-GAL-1 antibody as described, e.g., in International Patent Application No. PCT/US2014/047783 (published, e.g., as WO 2015/013388 A3), which is incorporated herein by reference in its entirety.

In some embodiments, the molecule is an anti-GAL-9 antibody or includes an antigen binding fragment of an anti-GAL-9 antibody. In some embodiments, the molecule is an anti-GAL-9 antibody or includes an antigen binding fragment of an anti-GAL-9 antibody as described, e.g., in International Patent Application No. PCT/FR2015/051498 (published, e.g., as WO 2015/185875 A2), which is incorporated herein by reference in its entirety.

In some embodiments, the molecule is an anti-NRP-2 antibody or includes an antigen binding fragment of an anti-NRP-2 antibody. In some embodiments, the molecule is an anti-NRP-2 antibody or includes an antigen binding fragment of an anti-NRP-2 antibody as described, e.g., in International Patent Application No. PCT/US2007/069179 (published, e.g., as WO 2008/143665 A1), which is incorporated herein by reference in its entirety.

In some embodiments, the molecule is an anti-NRP-2 antibody or includes an antigen binding fragment of an anti-NRP-2 antibody. In some embodiments, the molecule is an anti-NRP-2 antibody or includes an antigen binding fragment of an anti-NRP-2 antibody as described, e.g., in International Patent Application No. PCT/US2007/069179 (published, e.g., as WO 2008/143665 A1) or PCT/US2007069185 (published, e.g., as WO 2008/143666 A2), which are incorporated herein by reference in their entirety.

In some embodiments, the molecule is an anti-BTLA antibody or includes an antigen binding fragment of an anti-BTLA antibody. In some embodiments, the molecule is an anti-BTLA antibody or includes an antigen binding fragment of an anti-BTLA antibody as described, e.g., in International Patent Application No. PCT/US2016/64385 (filed Dec. 1, 2016), PCT/US2010/043182 (published, e.g., as WO 2011/014438 A1), PCT/EP2010/053356 (published, e.g., as WO 2010/106051 A1), PCT/US2007/084792 (published, e.g., as WO 2008/076560 A2), which are incorporated herein by reference in their entirety.

In some embodiments, the molecule is an anti-BTN1A1 antibody or includes an antigen binding fragment of an anti-BTN1A1 antibody. In some embodiments, the molecule is an anti-BTN1A1 antibody or includes an antigen binding fragment of an anti-BTN1A1 antibody as described, e.g., in International Patent Application No. PCT/US2016/064436 (filed Dec. 1, 2016), which is incorporated herein by reference in its entirety.

In one aspect, provided herein is a molecule that includes an antigen binding fragment that immunospecifically binds to BTN1A1, whereby the molecule can inhibit binding of a BTN1A1 ligand, such as Galectin-1 (GAL-1), Galectin-9 (GAL-9), NRP-2 (Nrp-2), or B- and T-Lymphocyte Attenuator (BTLA), to BTN1A1. In some embodiments, the molecule can inhibit binding of BTN1A1 to GAL-1. In some embodiments, the molecule can inhibit binding of BTN1A1 to GAL-9. In some embodiments, the molecule can inhibit binding of BTN11A1 to NRP-2. In some embodiments, the molecule can inhibit binding of BTN1A1 to BTLA. In some embodiments, the molecule can inhibit binding of a BTN1A1 ligand, such as GAL-1, GAL-9, NRP-2, or BTLA to BTN1A1 completely. In some embodiments, the molecule can inhibit binding of a BTN1A1 ligand, such as GAL-1, GAL-9, NRP-2, or BTLA, to BTN1A1 at least partially. In some embodiments, the molecule can inhibit at least 1%, at least 3%, at least 5%, at least 10%, at least 15%, at least 20%, at least 25%, at least 30%, at least 40%, at least 50%, at least 60%, at least 70%, at least 80%, at least 90%, at least 95%, or at least 99% of binding of a BTN1A1 ligand, such as GAL-1, GAL-9, NPR-2, or BTLA to BTN1A1. In some embodiments, binding of BTN1A1 to a BTN1A1 ligand, such as GAL-1, GAL-9, NRP-2, or BTLA, or inhibition thereof, is determined using surface plasmon resonance, biolayer interferometry, or co-immunoprecipitation. In some embodiments, the molecule can inhibit binding of a BTN1A1 ligand, such as GAL-1, GAL-9, NRP-2, or BTLA, to BTN1A1 with an IC50 value of less than 1 µM, less than 900 nM, less than 800 nM, less than 700 nM, less than 600 nM, less than 500 nM, less than 400 nM, less than 300 nM, less than 200 nM, less than 100 nM, less than 90 nM, less than 80 nM, less than 70 nM, less than 60 nM, less than 50 nM, less than 40 nM, less than 30 nM, less than 20 nM, less than 10 nM, less than 9 nM, less than 8 nM, less than 8 nM, less than 7 nM, less than 6 nM, less than 5 nM, less than 4 nM, less than 3 nM, less than 2 nM, or less than 1 nM. In some embodiments, the neutralization assay is a surface plasmon resonance, biolayer interferometry, co-immunoprecipitation, FRET, or TR-FRET assay, or an ELISA.

In some embodiments, the molecule includes an antigen binding fragment that immunospecifically binds to BTN1A1, whereby the molecule can inhibit binding of two or more BN1A1 ligands, such as GAL-1, GAL-9, NRP-2, or BTLA, to BTN1A1. In some embodiments, the molecule can inhibit binding of GAL-1 and GAL-9 to BTN1A1. In some embodiments, the molecule can inhibit binding of GAL-1 and NRP-2 to BTN1A1. In some embodiments, the molecule can inhibits binding of GAL-1 and BTLA to BTN1A1. In some embodiments, the molecule can inhibit binding of GAL-9 and NRP-2 to BTN1A1. In some embodiments, the molecule can inhibit binding of GAL-9 and BTLA to BTN1A1. In some embodiments, the molecule can inhibit binding of NRP-2 and BTLA to BTN1A1. In some embodiment, the molecule can inhibit binding of GAL-1, GAL-9, and NRP-2 to BTN1A1. In some embodiments, the molecule can inhibit binding of GAL-1, GAL-9, and BTLA to BTN1A1. In some embodiments, the molecule can inhibit binding of GAL-1, NRP-2, and BTLA to BTN1A1. In some embodiments, the molecule can inhibit binding of GAL-9, NRP-2 and BTLA to BTN1A1. In some embodiments, the molecule can inhibit binding of GAL-1, GAL-9, NRP-2, and BTLA to BTN1A1.

In some embodiments, the molecule includes an antigen-binding domain that binds to the extracellular domain (ECD) of BTN1A1.

In another aspect, provided herein is a molecule including an antigen binding fragment that immunospecifically binds to a BTN1A1 ligand, such as GAL-1, GAL-9, NRP-2 or BTLA, whereby the molecule can inhibit binding of the BTN1A1 ligand to BTN1A1. In some embodiments, the antigen binding fragment immunospecifically binds to GAL-1 and the molecule can inhibit binding of GAL-1 to BTN1A1. In some embodiments, the antigen binding fragment immunospecifically binds to GAL-9 and the molecule can inhibit binding of GAL-9 to BTN1A1. In some embodiments, the antigen binding fragment immunospecifically binds NRP-2 and the molecule can inhibit binding of NRP-2 to BTN1A1. In some embodiments, the antigen binding fragment immunospecifically binds to BTLA and the molecule can inhibit binding of BTLA to BTN1A1. In some embodiments, the molecule can inhibit binding of a BTN1A1 ligand, such as GAL-1, GAL-9, NRP-2, or BTLA to BTN1A1 completely. In some embodiments, the molecule can inhibit binding of a BTN1A1 ligand, such as GAL-1, GAL-9, NRP-2, or BTLA, to BTN1A1 at least partially. In some embodiments, the molecule can inhibit at least 1%, at least 3%, at least 5%, at least 10%, at least 15%, at least 20%, at least 25%, at least 30%, at least 40%, at least 50%, at least 60%, at least 70%, at least 80%, at least 90%, at least 95%, or at least 99% of binding of a BTN1A1 ligand, such as GAL-1, GAL-9, NPR-2, or BTLA to BTN1A1. In some embodiments, binding of BTN1A1 to a BTN1A1 ligand, such as GAL-1, GAL-9, NRP-2, or BTLA, or inhibition thereof, is determined using surface plasmon resonance, biolayer interferometry, or co-immunoprecipitation. In some embodiments, the molecule can inhibit binding of a BTN1A1 ligand, such as GAL-1, GAL-9, NRP-2, or BTLA, to BTN1A1 with an IC50 value of less than 1 µM, less than 900 nM, less than 800 nM, less than 700 nM, less than 600 nM, less than 500 nM, less than 400 nM, less than 300 nM, less than 200 nM, less than 100 nM, less than 90 nM, less than 80 nM, less than 70 nM, less than 60 nM, less than 50 nM, less than 40 nM, less than 30 nM, less than 20 nM, less than 10 nM, less than 9 nM, less than 8 nM, less than 8 nM, less than 7 nM, less than 6 nM, less than 5 nM, less than 4 nM, less than 3 nM, less than 2 nM, or less than 1 nM. In some embodiments, the neutralization assay is a surface plasmon resonance, biolayer interferometry, co-immunoprecipitation, FRET, or TR-FRET assay, or an ELISA.

In some embodiments the antigen binding fragment of a molecule provided herein can bind a BTN1A1 ligand, such as GAL-1, GAL-9, NRP-2, or BTLA, with a dissociation constant of 1 µM or less, 900 nM or less, 800 nM or less, 700 nM or less, 600 nM or less, 500 nM or less, 400 nM or less, 300 nM or less, 200 nM or less, 100 nM or less, 90 nM or less, 80 nM or less, 70 nM or less, 60 nM or less, 50 nM or less, 40 nM or less, 30 nM or less, 20 nM or less, 10 nM or less, 5 nM or less, 3 nM or less, or 1 nM or less. In some embodiments, the antigen binding fragment can bind to GAL-1 with a dissociation constant of 1 µM or less, 900 nM or less, 800 nM or less, 700 nM or less, 600 nM or less, 500 nM or less, 400 nM or less, 300 nM or less, 200 nM or less, 100 nM or less, 90 nM or less, 80 nM or less, 70 nM or less, 60 nM or less, 50 nM or less, 40 nM or less, 30 nM or less, 20 nM or less, 10 nM or less, 5 nM or less, 3 nM or less, or 1 nM or less. In some embodiments, the antigen binding fragment can bind to GAL-9 with a dissociation constant of 1 μM or less, 900 nM or less, 800 nM or less, 700 nM or less, 600 nM or less, 500 nM or less, 400 nM or less, 300 nM or less, 200 nM or less, 100 nM or less, 90 nM or less, 80 nM or less, 70 nM or less, 60 nM or less, 50 nM or less, 40 nM or less, 30 nM or less, 20 nM or less, 10 nM or less, 5 nM or less, 3 nM or less, or 1 nM or less. In some embodiments, the antigen binding fragment can bind NRP-2 with a dissociation constant of 1 μM or less, 900 nM or less, 800 nM or less, 700 nM or less, 600 nM or less, 500 nM or less, 400 nM or less, 300 nM or less, 200 nM or less, 100 nM or less, 90 nM or less, 80 nM or less, 70 nM or less, 60 nM or less, 50 nM or less, 40 nM or less, 30 nM or less, 20 nM or less, 10 nM or less, 5 nM or less, 3 nM or less, or 1 nM or less. In some embodiments, the antigen binding fragment can bind BTLA with a dissociation constant of 1 μM or less, 900 nM or less, 800 nM or less, 700 nM or less, 600 nM or less, 500 nM or less, 400 nM or less, 300 nM or less, 200 nM or less, 100 nM or less, 90 nM or less, 80 nM or less, 70 nM or less, 60 nM or less, 50 nM or less, 40 nM or less, 30 nM or less, 20 nM or less, 10 nM or less, 5 nM or less, 3 nM or less, or 1 nM or less.

In some embodiments, the molecule can modulate an activity or signaling of BTN1A1 or an activity or signaling of a complex of BTN1A1 and a BTN1A1 ligand, such as GAL-1, GAL-9, NRP-2, or BTLA.

In some embodiments, the molecule can modulate T-cell activity. In some embodiment, the T-cell is a CD8+ cell. In some embodiments, the molecule can increase T-cell activation or T-cell proliferation. In some embodiments, the molecule can inhibit T-cell apoptosis.

N-glycosylation is a posttranslational modification that is initiated in the endoplasmic reticulum (ER) and subsequently processed in the Golgi (Schwarz and Aebi, *Curr. Opin. Struc. Bio.*, 21(5):576-582 (2011). This type of modification is first catalyzed by a membrane-associated oligosaccharyl transferase (OST) complex that transfers a preformed glycan composed of oligosaccharides to an asparagine (Asn) side-chain acceptor located within the NXT motif (-Asn-X-Ser/Thr-) (Cheung and Reithmeier, *Methods*, 41:451-459 2007); Helenius and Aebi, Science, 291 (5512):2364-9 (2001). The addition or removal of saccharides from the preformed glycan is mediated by a group of glycotransferases and glycosidases, respectively, which tightly regulate the N-glycosylation cascade in a cell- and location-dependent manner.

In some embodiments, the molecules have an antigen binding fragment that selectively binds to one or more glycosylation motifs of BTN1A1. In some embodiments, the antigen binding fragment immunospecifically binds to a glycopeptide having a glycosylation motif and the adjacent peptide. In some embodiments, the antigen binding fragment immunospecifically binds to a peptide sequence that is located near one or more of the glycosylation motifs in three dimensions. In some embodiments, the antigen binding fragment selectively binds one or more glycosylation motifs of a BTN1A1 dimer over the one or more glycosylations motifs of a BTN1A1 monomer.

In some embodiments, the antigen binding fragment binds to glycosylated BTN1A1 (e.g., a glycosylated BTN1A1 dimer) with $K_D$ less than at least 30%, 40%, 50%, 60%, 70%, 80%, or 90% of the $K_D$ exhibited relative to unglycosylated BTN1A1. In certain embodiments, the antigen binding fragment binds to glycosylated BTN1A1 with $K_D$ less than 50% of the $K_D$ exhibited relative to unglycosylated BTN1A1. In some embodiments, the antigen binding fragment binds to glycosylated BTN1A1 with $K_D$ that is less than 1%, 2%, 3%, 4%, 5%, 6%, 7%, 8%, 9%, 10%, 15%, 20%, 30%, 40%, 50% of the $K_D$ exhibited relative to unglycosylated BTN1A1. In some embodiments, the antigen binding fragment binds to glycosylated BTN1A1 with $K_D$ at least 10 times less than the $K_D$ exhibited relative to unglycosylated BTN1A1.

The specific glycosylation sites of a particular BTN1A1 isoform or variant can vary from amino acids at position 55, 215, or 449 of that particular BTN1A1 isoform or variant. In those circumstances, a person of ordinary skill in the art would be able to determine the glycosylation sites of any particular BTN1A1 isoform or variant that correspond to N55, N215, and N449 of the human BTN1A1 exemplified above based on sequence alignment and other common knowledge in the art. As such, provided herein are also molecules having an antigen binding fragment that immunospecifically binds to a glycosylated form of a BTN1A1 isoform or variant relative to the unglycosylated BTN1A1 isoform or variant. The glycosylated sites of a BTN1A1 isoform or variant can be the corresponding sites of N55, N215, and N449 of human BTN1A1 sequence as provided above.

In some embodiments, the molecules have an antigen binding fragment that immunospecifically binds to glycosylated BTN1A1 (e.g., a glycosylated BTN1A1 dimer). In some embodiments, the antigen binding fragment immunospecifically binds to BTN1A1 glycosylated at positions N55, N215, and/or N449. In some embodiments, the antigen binding fragment immunospecifically binds to BTN1A1 glycosylated at position N55. In some embodiments, the antigen binding fragment immunospecifically binds to BTN1A1 glycosylated at position N215. In some embodiments, the antigen binding fragment immunospecifically binds to BTN1A1 glycosylated at position N449. In some embodiments, the antigen binding fragment immunospecifically binds to one or more glycosylation motifs. In some embodiments, the antigen binding fragment immunospecifically binds to BTN1A1 glycosylated at positions N55 and N215. In some embodiments, the antigen binding fragments immunospecifically binds to BTN1A1 glycosylated at positions N215 and N449. In some embodiments, the antigen binding fragments immunospecifically binds to BTN1A1 glycosylated at positions N55 and N449. In some embodiments, the antigen binding fragments immunospecifically binds to BTN1A1 glycosylated at positions N55, N215 and N449.

In some embodiments, the molecules have an antigen binding fragment that immunospecifically binds to glycosylated BTN1A1, whereby the antigen binding fragment preferentially binds glycosylated BTN1A1 (e.g., a glycosylated BTN1A1 dimer) over non-glycosylated BTN1A1. In some embodiments, the antigen binding fragments preferentially bind to BTN1A1 glycosylated at positions N55, N215, and/or N449 over non-glycosylated BTN1A1. In some embodiments, the antigen binding fragments preferentially bind to BTN1A1 glycosylated at position N55 over non-glycosylated BTN1A1. In some embodiments, the antigen binding fragments preferentially bind to BTN1A1 glycosylated at position N215 over non-glycosylated BTN1A1. In some embodiments, the antigen binding fragments preferentially bind to BTN1A1 glycosylated at position N449 over non-glycosylated BTN1A1. In some embodiments, the antigen binding fragments preferentially bind to one or more glycosylation motifs. In some embodiments, the antigen binding fragments preferentially binds BTN1A1 glycosylated at positions N55 and N215 over non-glycosylated BTN1A1. In some embodiments, the antigen binding fragments preferentially bind to BTN1A1 glycosylated at positions N215 and N449 over non-glycosylated BTN1A1. In some embodiments, the antigen binding fragments preferentially bind to BTN1A1 glycosylated at positions N55 and N449 over non-glycosylated BTN1A1. In some embodiments, the antigen binding fragments preferentially binds BTN1A1 glycosylated at positions N55, N215 and N449 over non-glycosylated BTN1A1.

The preferential binding can be determined by binding affinity. For example, an antibody or antigen binding fragment that preferentially binds to the glycosylated BTN1A1 (e.g., a glycosylated BTN1A1 dimer) can bind to glycosylated BTN1A1 with a $K_D$ less than the $K_D$ exhibited relative to unglycosylated BTN1A1. In some embodiments, the antibody or antigen binding fragment binds to glycosylated BTN1A1 with $K_D$ less than half of the $K_D$ exhibited relative to unglycosylated BTN1A1. In some embodiments, the antibody or antigen binding fragment binds to glycosylated BTN1A1 with $K_D$ at least 2 times less than the $K_D$ exhibited relative to unglycosylated BTN1A1. In some embodiments, the antibody or antigen binding fragment binds to glycosylated BTN1A1 with $K_D$ at least 5 times less than the $K_D$ exhibited relative to unglycosylated BTN1A1. In some embodiments, the antibody or antigen binding fragment binds to glycosylated BTN1A1 with $K_D$ at least 10 times less than the $K_D$ exhibited relative to unglycosylated BTN1A1. In some embodiments, the antibody or antigen binding fragment binds to glycosylated BTN1A1 with $K_D$ at least 15 times less than the $K_D$ exhibited relative to unglycosylated BTN1A1. In some embodiments, the antibody or antigen binding fragment binds to glycosylated BTN1A1 with $K_D$ at least 20 times less than the $K_D$ exhibited relative to unglycosylated BTN1A1. In some embodiments, the antibody or antigen binding fragment binds to glycosylated BTN1A1 with $K_D$ at least 25 times less than the $K_D$ exhibited relative to unglycosylated BTN1A1. In some embodiments, the antibody or antigen binding fragment binds to glycosylated BTN1A1 with $K_D$ at least 30 times less than the $K_D$ exhibited relative to unglycosylated BTN1A1. In some embodiments, the antibody or antigen binding fragment binds to glycosylated BTN1A1 with $K_D$ at least 40 times less than the $K_D$ exhibited relative to unglycosylated BTN1A1. In some embodiments, the antibody or antigen binding fragment binds to glycosylated BTN1A1 with $K_D$ at least 50 times less than the $K_D$ exhibited relative to unglycosylated BTN1A1. In some embodiments, the antibody or antigen binding fragment binds to glycosylated BTN1A1 with $K_D$ that is about 75% of the $K_D$ exhibited relative to unglycosylated BTN1A1. In some embodiments, the antibody or antigen binding fragment binds to glycosylated BTN1A1 with $K_D$ that is about 50% of the $K_D$ exhibited relative to unglycosylated BTN1A1. In some embodiments, the antibody or antigen binding fragment binds to glycosylated BTN1A1 with $K_D$ that is about 25% of the $K_D$ exhibited relative to unglycosylated BTN1A1. In some embodiments, the antibody or antigen binding fragment binds to glycosylated BTN1A1 with $K_D$ that is about 10% of the $K_D$ exhibited relative to unglycosylated BTN1A1. In some embodiments, the antibody or antigen binding fragment binds to glycosylated BTN1A1 with $K_D$ that is about 5% of the $K_D$ exhibited relative to unglycosylated BTN1A1. In some embodiments, the antibody or antigen binding fragment binds to glycosylated BTN1A1 with $K_D$ that is about 2.5% of the $K_D$ exhibited relative to unglycosylated BTN1A1. In some embodiments, the antibody or antigen binding fragment binds to glycosylated BTN1A1 with $K_D$ that is about 1% of the $K_D$ exhibited relative to unglycosylated BTN1A1.

The preferential binding can also be determined by in a binding assay as indicated by, for example, fluorescence intensity ("MFI"). For example, an antibody or antigen binding fragment that preferentially binds to the glycosylated BTN1A1 (e.g., a glycosylated BTN1A1 dimer) can bind to glycosylated BTN1A1 with an MFI that is higher than the MFI as exhibited relative to unglycosylated BTN1A1. In some embodiments, the antibody or antigen binding fragment binds to glycosylated BTN1A1 with an MFI that is at least twice as high as the MFI as exhibited relative to unglycosylated BTN1A1. In some embodiments, antibody or the antigen binding fragment binds to glycosylated BTN1A1 with an MFI that is at least two times as high as the MFI as exhibited relative to unglycosylated BTN1A1. In some embodiments, antibody or the antigen binding fragment binds to glycosylated BTN1A1 with an MFI that is at least three times as high as the MFI as exhibited relative to unglycosylated BTN1A1. In some embodiments, antibody or the antigen binding fragment binds to glycosylated BTN1A1 with an MFI that is at least five times as high as the MFI as exhibited relative to unglycosylated BTN1A1. In some embodiments, antibody or the antigen binding fragment binds to glycosylated BTN1A1 with an MFI that is at least ten times as high as the MFI as exhibited relative to unglycosylated BTN1A1. In some embodiments, antibody or the antigen binding fragment binds to glycosylated BTN1A1 with an MFI that is at least fifteen times as high as the MFI as exhibited relative to unglycosylated BTN1A1. In some embodiments, antibody or the antigen binding fragment binds to glycosylated BTN1A1 with an MFI that is at least twenty times as high as the MFI as exhibited relative to unglycosylated BTN1A1. In some embodiments, antibody or the antigen binding fragment binds to glycosylated BTN1A1 with an MFI that is at least twenty-five times as high as the MFI as exhibited relative to unglycosylated BTN1A1. In some embodiments, antibody or the antigen binding fragment binds to glycosylated BTN1A1 with an MFI that is at least thirty times as high as the MFI as exhibited relative to unglycosylated BTN1A1. In some embodiments, antibody or the antigen binding fragment binds to glycosylated BTN1A1 with an MFI that is at least forty times as high as the MFI as exhibited relative to unglycosylated BTN1A1. In some embodiments, antibody or the antigen binding fragment binds to glycosylated BTN1A1 with an MFI that is at least fifty times as high as the MFI as exhibited relative to unglycosylated BTN1A1.

In some embodiments, the antigen binding fragments immunospecifically mask BTN1A1 glycosylation (e.g., in a glycosylated BTN1A1 dimer) at positions N55, N215, and/or N449. In some embodiments, the antigen binding fragments immunospecifically mask BTN1A1 glycosylation at position N55. In some embodiments, the antigen binding fragments immunospecifically mask BTN1A1 glycosylation at position N215. In some embodiments, the antigen binding fragments immunospecifically mask BTN1A1 glycosylation at position N449. In some embodiments, the antigen binding fragments immunospecifically mask one or more glycosylation motifs of BTN1A1. In some embodiments, the antigen binding fragments immunospecifically mask BTN1A1 glycosylation at positions N55 and N215. In some embodiments, the antigen binding fragments immunospecifically mask BTN1A1 glycosylation at positions N215 and N449. In some embodiments, the antigen binding fragments immunospecifically mask BTN1A1 glycosylation at positions N55 and N449. In some embodiments, the antigen binding fragments immunospecifically mask BTN1A1 glycosylation at positions N55, N215 and N449

In some embodiments, the molecules have an antigen binding fragment that selectively binds to a BTN1A1 dimer over a BTN1A1 monomer. In some embodiments, the BTN1A1 dimer is expressed at the surface of a cell. In some embodiments, the BTN1A1 dimer is a soluble protein fragment of BTN1A1, e.g., an extracellular domain construct of BTN1A1, such as an Fc-fusion protein construct (e.g., BTN1A1-ECD-Fc). In some embodiments, the BTN1A1 monomer is an extracellular domain construct of BTN1A1, such as a Flag-tagged or a His6-tagged BTN1A1-ECD construct. In some embodiments, the molecules selectively binding to a BTN1A1 dimer are molecules provided herein that selectively bind to glycosylated BTN1A1. In some embodiments, preferential binding to a BTN1A1 dimer over a BTN1A1 monomer is determined by determining preferential binding to a BTN1A1-ECD-Fc construct over a BTN1A1-ECD-His6 or a BTN1A1-ECD-Flag construct, e.g., using a surface plasmon resonance assay (e.g., BIAcore).

In some embodiments, the antigen binding fragment binds to a BTN1A1 dimer (e.g., a glycosylated BTN1A1 dimer) with $K_D$ less than at least 30%, 40%, 50%, 60%, 70%, 80%, or 90% of the $K_D$ exhibited relative to a BTN1A1 monomer (e.g., a glycosylated BTN1A1 monomer). In certain embodiments, the antigen binding fragment binds to a BTN1A1 dimer (e.g., a glycosylated BTN1A1 dimer) with $K_D$ less than 50% of the $K_D$ exhibited relative to a BTN1A1 monomer (e.g., a glycosylated BTN1A1 monomer). In some embodiments, the antigen binding fragment binds to a BTN1A1 dimer (e.g., a glycosylated BTN1A1 dimer) with $K_D$ that is less than 1%, 2%, 3%, 4%, 5%, 6%, 7%, 8%, 9%, 10%, 15%, 20%, 30%, 40%, 50% of the $K_D$ exhibited relative to a BTN1A1 monomer (e.g., a glycosylated BTN1A1 monomer). In some embodiments, the antigen binding fragment binds to a BTN1A1 dimer (e.g., a glycosylated BTN1A1 dimer) with $K_D$ at least 10 times less than the $K_D$ exhibited relative to a BTN1A1 monomer (e.g., a glycosylated BTN1A1 monomer).

The preferential binding can be determined by binding affinity. For example, an antibody or antigen binding fragment that preferentially binds to the BTN1A1 dimer (e.g., a glycosylated BTN1A1 dimer) can bind to a BTN1A1 dimer (e.g., a glycosylated BTN1A1 dimer) with a $K_D$ less than the $K_D$ exhibited relative to a BTN1A1 monomer (e.g., a glycosylated BTN1A1 monomer). In some embodiments, the antibody or antigen binding fragment binds to a BTN1A1 dimer (e.g., a glycosylated BTN1A1 dimer) with $K_D$ less than half of the $K_D$ exhibited relative to a BTN1A1 monomer (e.g., a glycosylated BTN1A1 monomer). In some embodiments, the antibody or antigen binding fragment binds to a BTN1A1 dimer (e.g., a glycosylated BTN1A1 dimer) with $K_D$ at least 2 times less than the Ku exhibited relative to a BTN1A1 monomer (e.g., a glycosylated BTN1A1 monomer). In some embodiments, the antibody or antigen binding fragment binds to a BTN1A1 dimer (e.g., a glycosylated BTN1A1 dimer) with $K_D$ at least 5 times less than the $K_D$ exhibited relative to a BTN1A1 monomer (e.g., a glycosylated BTN1A1 monomer). In some embodiments, the antibody or antigen binding fragment binds to a BTN1A1 dimer (e.g., a glycosylated BTN1A1 dimer) with Ku at least 10 times less than the $K_D$ exhibited relative to a BTN1A1 monomer (e.g., a glycosylated BTN1A1 monomer). In some embodiments, the antibody or antigen binding fragment binds to a BTN1A1 dimer (e.g., a glycosylated BTN1A1 dimer) with $K_D$ at least 15 times less than the $K_D$ exhibited relative to a BTN1A1 monomer (e.g., a glycosylated BTN1A1 monomer). In some embodiments, the antibody or antigen binding fragment binds to a BTN1A1 dimer (e.g., a glycosylated BTN1A1 dimer) with $K_D$ at least 20 times less than the $K_D$ exhibited relative to a BTN1A1 monomer (e.g., a glycosylated BTN1A1 monomer). In some embodiments, the antibody or antigen binding fragment binds to a BTN1A1 dimer (e.g., a glycosylated BTN1A1 dimer) with $K_D$ at least 25 times less than the $K_D$ exhibited relative to a BTN1A1 monomer (e.g., a glycosylated BTN1A1 monomer). In some embodiments, the antibody or antigen binding fragment binds to a BTN1A1 dimer (e.g., a glycosylated BTN1A1 dimer) with $K_D$ at least 30 times less than the $K_D$ exhibited relative to a BTN1A1 monomer (e.g., a glycosylated BTN1A1 monomer). In some embodiments, the antibody or antigen binding fragment binds to a BTN1A1 dimer (e.g., a glycosylated BTN1A1 dimer) with $K_D$ at least 40 times less than the $K_D$ exhibited relative to a BTN1A1 monomer (e.g., a glycosylated BTN1A1 monomer). In some embodiments, the antibody or antigen binding fragment binds to a BTN1A1 dimer (e.g., a glycosylated BTN1A1 dimer) with Ku at least 50 times less than the $K_D$ exhibited relative to a BTN1A1 monomer (e.g., a glycosylated BTN1A1 monomer). In some embodiments, the antibody or antigen binding fragment binds to a BTN1A1 dimer (e.g., a glycosylated BTN1A1 dimer) with a $K_D$ that is about 75% of the $K_D$ exhibited relative to a BTN1A1 monomer (e.g., a glycosylated BTN1A1 monomer). In some embodiments, the antibody or antigen binding fragment binds to a BTN1A1 dimer (e.g., a glycosylated BTN1A1 dimer) with a $K_D$ that is about 50% of the $K_D$ exhibited relative to a BTN1A1 monomer (e.g., a glycosylated BTN1A1 monomer). In some embodiments, the antibody or antigen binding fragment binds to a BTN1A1 dimer (e.g., a glycosylated BTN1A1 dimer) with a $K_D$ that is about 25% of the $K_D$ exhibited relative to a BTN1A1 monomer (e.g., a glycosylated BTN1A1 monomer). In some embodiments, the antibody or antigen binding fragment binds to a BTN1A1 dimer (e.g., a glycosylated BTN1A1 dimer) with a $K_D$ that is about 10% of the $K_D$ exhibited relative to a BTN1A1 monomer (e.g., a glycosylated BTN1A1 monomer). In some embodiments, the antibody or antigen binding fragment binds to a BTN1A1 dimer (e.g., a glycosylated BTN1A1 dimer) with Ku that is about 5% of the $K_D$ exhibited relative to a BTN1A1 monomer (e.g., a glycosylated BTN1A1 monomer). In some embodiments, the antibody or antigen binding fragment binds to a BTN1A1 dimer (e.g., a glycosylated BTN1A1 dimer) with $K_D$ that is about 2.5% of the $K_D$ exhibited relative to a BTN1A1 monomer (e.g., a glycosylated BTN1A1 monomer). In some embodiments, the antibody or antigen binding fragment binds to a BTN1A1 dimer with a $K_D$ that is about 1% of the $K_D$ exhibited relative to a BTN1A1 monomer (e.g., a glycosylated BTN1A1 monomer).

The preferential binding can also be determined by in a binding assay as indicated by, for example, fluorescence intensity ("MFI"). For example, an antibody or antigen binding fragment that preferentially binds to the BTN1A1 dimer (e.g., a glycosylated BTN1A1 dimer) can bind to a BTN1A1 monomer (e.g., a glycosylated BTN1A1 monomer) with an MFI that is higher than the MFI as exhibited relative to the BTN1A1 monomer. In some embodiments, the antibody or antigen binding fragment binds to a BTN1A1 dimer (e.g., a glycosylated BTN1A1 dimer) with an MFI that is at least twice as high as the MFI as exhibited relative to a BTN1A1 monomer (e.g., a glycosylated BTN1A1 monomer). In some embodiments, antibody or the antigen binding fragment binds to a BTN1A1 dimer (e.g., a glycosylated BTN1A1 dimer) with an MFI that is at least three times as high as the MFI as exhibited relative to a BTN1A1 monomer (e.g., a glycosylated BTN1A1 monomer). In some embodiments, the antibody or antigen binding fragment binds to a BTN1A1 dimer (e.g., a glycosylated BTN1A1 dimer) with an MFI that is at least five times as high as the MFI as exhibited relative to a BTN1A1 monomer (e.g., a glycosylated BTN1A1 monomer). In some embodiments, the antibody or the antigen binding fragment binds to a BTN1A1 dimer (e.g., a glycosylated BTN1A1 dimer) with an MFI that is at least ten times as high as the MFI as exhibited relative to a BTN1A1 monomer (e.g., a glycosylated BTN1A1 monomer). In some embodiments, the antibody or the antigen binding fragment binds to a BTN1A1 dimer (e.g., a glycosylated BTN1A1 dimer) with an MFI that is at least fifteen times as high as the MFI as exhibited relative to a BTN1A1 monomer (e.g., a glycosylated BTN1A1 monomer). In some embodiments, the antibody or the antigen binding fragment binds to a BTN1A1 dimer (e.g., a glycosylated BTN1A1 dimer) with an MFI that is at least twenty times as high as the MFI as exhibited relative to a BTN1A1 monomer (e.g., a glycosylated BTN1A1 monomer). In some embodiments, the antibody or the antigen binding fragment binds to a BTN1A1 dimer (e.g., a glycosylated BTN1A1 dimer) with an MFI that is at least twenty-five times as high as the MFI as exhibited relative to a BTN1A1 monomer (e.g., a glycosylated BTN1A1 monomer). In some embodiments, the antibody or the antigen binding fragment binds to a BTN1A1 dimer (e.g., a glycosylated BTN1A1 dimer) with an MFI that is at least thirty times as high as the MFI as exhibited relative to a BTN1A1 monomer (e.g., a glycosylated BTN1A1 monomer). In some embodiments, the antibody or the antigen binding fragment binds to a BTN1A1 dimer (e.g., a glycosylated BTN1A1 dimer) with an MFI that is at least forty times as high as the MFI as exhibited relative to a BTN1A1 monomer (e.g., a glycosylated BTN1A1 monomer). In some embodiments, the antibody or the antigen binding fragment binds to a BTN1A1 dimer (e.g., a glycosylated BTN1A1 dimer) with an MFI that is at least fifty times as high as the MFI as exhibited relative to a BTN1A1 monomer (e.g., a glycosylated BTN1A1 monomer).

In some embodiments, the antibody or antigen binding fragment preferentially binds a glycosylated dimer BTN1A1 over a glycosylated monomer BTN1A1. The two BTN1A1 monomers in a glycosylated BTN1A1 dimer can be independently glycosylated at the same positions or at different positions. In some embodiments, one of the monomers in a BTN1A1 dimer is not glycosylated. A glycosylated BTN1A1 monomer in a glycosylated BTN1A1 dimer can be glycosylated at positions N55, N215, and/or N449. In some embodiments, a glycosylated BTN1A1 monomer is glycosylated at position N55. In some embodiments, a glycosylated BTN1A1 monomer is glycosylated at position N215. In some embodiments, a glycosylated BTN1A1 monomer is glycosylated at position N449. In some embodiments, a glycosylated BTN1A1 monomer is glycosylated at positions N55 and N215. In some embodiments, a glycosylated BTN1A1 monomer is glycosylated at positions N55 and N449. In some embodiments, a glycosylated BTN1A1 monomer is glycosylated at positions N215 and N449. In some embodiments, a glycosylated BTN1A1 monomer is glycosylated at positions N55 N215, and N449.

5.2.1. Antibodies and Other Molecules Having an Antigen Binding Fragment

In some embodiments, the anti-BTN1A1 antibody or anti-BTN1A1 ligand (e.g., GAL-1, GAL-9, NRP-2, or BTLA) antibody can be an IgG, IgM, IgA, IgD, or IgE. The anti-BTN1A1 antibody or anti-BTN1A1 ligand (e.g., GAL-1, GAL-9, NRP-2, or BTLA) antibody can also be a chimeric antibody, an affinity matured antibody, a humanized antibody, or a human antibody. The anti-BTN1A1 antibody or anti-BTN1A1 ligand (e.g., GAL-1, GAL-9, NRP-2, or BTLA) antibody can also be a camelized antibody, an intrabody, an anti-idiotypic (anti-Id) antibody. In some embodiments, the anti-BTN1A1 antibody or anti-BTN1A1 ligand (e.g., GAL-1, GAL-9, NRP-2, or BTLA) antibody can be a polyclonal antibody or monoclonal antibody.

Antibodies can be produced from any animal source, including birds and mammals. In some embodiments, the antibodies are ovine, murine (e.g., mouse and rat), rabbit, goat, guinea pig, camel, horse, or chicken. In addition, newer technology permits the development of and screening for human antibodies from human combinatorial antibody libraries. For example, bacteriophage antibody expression technology allows specific antibodies to be produced in the absence of animal immunization, as described in U.S. Pat. No. 6,946,546, which is hereby incorporated by reference in its entirety. These techniques are further described in Marks (1992); Stemmer (1994); Gram et al. (1992); Barbas et al. (1994); and Schier et al. (1996); which are hereby incorporated by reference in their entireties.

Methods for producing polyclonal antibodies in various animal species, as well as for producing monoclonal antibodies of various types, including humanized, chimeric, and fully human, are well known in the art. For example, the following U.S. patents provide enabling descriptions of such methods and are herein incorporated by reference: U.S. Pat. Nos. 3,817,837; 3,850,752; 3,939,350; 3,996,345; 4,196,265; 4,275,149; 4,277,437; 4,366,241; 4,469,797; 4,472,509; 4,606,855; 4,703,003; 4,742,159; 4,767,720; 4,816,567; 4,867,973; 4,938,948; 4,946,778; 5,021,236; 5,164,296; 5,196,066; 5,223,409; 5,403,484; 5,420,253; 5,565,332; 5,571,698; 5,627,052; 5,656,434; 5,770,376; 5,789,208; 5,821,337; 5,844,091; 5,858,657; 5,861,155; 5,871,907; 5,969,108; 6,054,297; 6,165,464; 6,365,157; 6,406,867; 6,709,659; 6,709,873; 6,753,407; 6,814,965; 6,849,259; 6,861,572; 6,875,434; 6,891,024; 7,407,659; and 8,178,098, which are hereby incorporated by reference in their entireties.

The molecules having an antigen binding fragment that immunospecifically binds BTN1A1 or specifically binds a BTN1A1 ligand, such as GAL-1, GAL-9, NRP-2, BTLA, including the anti-BTN1A1 antibodies or anti-BTN1A1 ligand (e.g., GAL-1, GAL-9, NRP-2, or BTLA) antibodies, can also be produced by any method known in the art useful for the production of polypeptides, e.g., in vitro synthesis, recombinant DNA production, and the like. The humanized antibodies can be produced by recombinant DNA technology. The antibodies described herein can also be produced using recombinant immunoglobulin expression technology. The recombinant production of immunoglobulin molecules, including humanized antibodies are described in U.S. Pat. No. 4,816,397 (Boss et al.), U U.S. Pat. Nos. 6,331,415 and 4,816,567 (both to Cabilly et al.), U.K. patent GB 2,188,638 (Winter et al.), and U.K. patent GB 2,209,757; which are hereby incorporated by reference in their entireties. Techniques for the recombinant expression of immunoglobulins, including humanized immunoglobulins, can also be found, in Goeddel et al., Gene Expression Technology Methods in Enzymology Vol. 185 Academic Press (1991), and Borreback, Antibody Engineering, W. H. Freeman (1992); which are hereby incorporated by reference in their entireties. Additional information concerning the generation, design and expression of recombinant antibodies can be found in Mayforth, Designing Antibodies, Academic Press, San Diego (1993).

In certain embodiments, the anti-BTN1A1 antibody or anti-BTN1A1 ligand (e.g., GAL-1, GAL-9, NRP-2, or BTLA) antibody is a human antibody. Human antibodies can be made by a variety of methods known in the art including phage display methods described above using antibody libraries derived from human immunoglobulin sequences (see U.S. Pat. Nos. 4,444,887 and 4,716,111; and International Publication Nos. WO 98/46645, WO 98/50433, WO 98/24893, WO 98/16654, WO 96/34096, WO 96/33735, and WO 91/10741). Human antibodies can be produced using transgenic mice which are incapable of expressing functional endogenous immunoglobulins, but which can express human immunoglobulin genes. For example, the human heavy and light chain immunoglobulin gene complexes can be introduced randomly or by homologous recombination into mouse embryonic stem cells. Alternatively, the human variable region, constant region, and diversity region can be introduced into mouse embryonic stem cells in addition to the human heavy and light chain genes. The mouse heavy and light chain immunoglobulin genes can be rendered nonfunctional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized using conventional methodologies with a selected antigen, e.g., all or a portion of a BTN1A1, GAL-1, GAL-9, NRP-2, or BTLA polypeptide, or a glycosylated BTN1A1, GAL-1, GAL-9, NRP-2 or BTLA polypeptide, or a BTN1A1, GAL-1, GAL-9, NRP-2, or BTLA polypeptide dimer. Monoclonal antibodies directed against the antigen can be obtained from the immunized, transgenic mice using conventional hybridoma technology (see, e.g., U.S. Pat. No. 5,916,771). The human immunoglobulin transgenes harbored by the transgenic mice rearrange during B cell differentiation, and subsequently undergo class switching and somatic mutation. Thus, using such a technique, therapeutically useful IgG, IgA, IgM and IgE antibodies can be produced. For an overview of this technology for producing human antibodies, see Lonberg and Huszar (1995, Int. Rev. Immunol. 13:65-93, which is incorporated herein by reference in its entirety). For a detailed discussion of this technology for producing human antibodies and human monoclonal antibodies and protocols for producing such antibodies, see, e.g., International Publication Nos. WO 98/24893, WO 96/34096, and WO 96/33735; and U.S. Pat. Nos. 5,413,923, 5,625,126, 5,633,425, 5,569,825, 5,661, 016, 5,545,806, 5,814,318, and 5,939,598, which are incorporated by reference herein in their entirety. In addition, companies such as Abgenix, Inc. (Freemont, Calif.) and Medarex (Princeton, N.J.) can be engaged to provide human antibodies directed against a selected antigen using technology similar to that described above.

In some embodiments, the anti-BTN1A1 antibody or anti-BTN1A1 ligand (e.g., GAL-1, GAL-9, NRP-2, or BTLA) antibody is a chimeric antibody, for example, an antibody having antigen binding sequences from a non-human donor grafted to a heterologous non-human, human or humanized sequence (e.g., framework and/or constant domain sequences). In one embodiment, the non-human donor is a rat. In one embodiment, an antigen binding sequence is synthetic, e.g., obtained by mutagenesis (e.g., phage display screening of a human phage library, etc.). In one embodiment, a chimeric antibody can have murine V regions and human C regions. In one embodiment, the murine light chain V region is fused to a human kappa light chain. In one embodiment, the murine heavy chain V region is fused to a human IgG1 C region.

Methods for producing chimeric antibodies are known in the art. See e.g., Morrison, 1985, Science 229:1202; Oi et al., 1986, BioTechniques 4:214; Gillies et al., 1989, J. Immunol. Methods 125:191-202; and U.S. Pat. Nos. 6,311,415, 5,807, 715, 4,816,567, and 4,816,397; all of which are hereby incorporated by references in their entireties. Chimeric antibodies including one or more CDRs from a non-human species and framework regions from a human immunoglobulin molecule can be produced using a variety of techniques known in the art including, for example, CDR-grafting (EP 239,400; International Publication No. WO 91/09967; and U.S. Pat. Nos. 5,225,539, 5,530,101, and 5,585,089), veneering or resurfacing (EP 592,106; EP 519, 596; Padlan, 1991, Molecular Immunology 28(4/5):489-498; Studnicka et al., 1994, Protein Engineering 7:805; and Roguska et al., 1994, Proc. Natl. Acad. Sci. USA 91:969), and chain shuffling (U.S. Pat. No. 5,565,332); all of which are hereby incorporated by references in their entireties.

An exemplary process for the production of the recombinant chimeric anti-BTN1A1 or anti-BTN1A1 ligand (e.g., GAL-1, GAL-9, NRP-2, or BTLA) antibodies can include the following: a) constructing, by conventional molecular biology methods, an expression vector that encodes and expresses an antibody heavy chain in which the CDRs and variable region of the murine anti-BTN1A1 or anti-BTN1A1 ligand (e.g., GAL-1, GAL-9, NRP-2, or BTLA) monoclonal antibody are fused to an Fc region derived from a human immunoglobulin, thereby producing a vector for the expression of a chimeric antibody heavy chain; b) constructing, by conventional molecular biology methods, an expression vector that encodes and expresses an antibody light chain of the murine anti-BTN1A1 or anti-BTN1A1 ligand (e.g., GAL-1, GAL-9, NRP-2, or BTLA) monoclonal antibody, thereby producing a vector for the expression of chimeric antibody light chain; c) transferring the expression vectors to a host cell by conventional molecular biology methods to produce a transfected host cell for the expression of chimeric antibodies; and d) culturing the transfected cell by conventional cell culture techniques so as to produce chimeric antibodies.

An exemplary process for the production of the recombinant humanized anti-BTN1A1 antibodies can include the following: a) constructing, by conventional molecular biology methods, an expression vector that encodes and expresses an antibody heavy chain in which the CDRs and a minimal portion of the variable region framework that are required to retain donor antibody binding specificity are derived from a non-human immunoglobulin, such as the murine anti-BTN1A1 or anti-BTN1A1 ligand (e.g., GAL-1, GAL-9, NRP-2, or BTLA) monoclonal antibody, and the remainder of the antibody is derived from a human immunoglobulin, thereby producing a vector for the expression of a humanized antibody heavy chain; b) constructing, by conventional molecular biology methods, an expression vector that encodes and expresses an antibody light chain in which the CDRs and a minimal portion of the variable region framework that are required to retain donor antibody binding specificity are derived from a non-human immunoglobulin, such as the murine anti-BTN1A1 or anti-BTN1A1 ligand (e.g., GAL-1, GAL-9, NPR-2, or BTLA) monoclonal antibody, and the remainder of the antibody is derived from a human immunoglobulin, thereby producing a vector for the expression of humanized antibody light chain; c) transferring the expression vectors to a host cell by conventional molecular biology methods to produce a transfected host cell for the expression of humanized antibodies; and d) culturing the transfected cell by conventional cell culture techniques so as to produce humanized antibodies.

With respect to either exemplary method, host cells can be co-transfected with such expression vectors, which can contain different selectable markers but, with the exception of the heavy and light chain coding sequences, are preferably identical. This procedure provides for equal expression of heavy and light chain polypeptides. Alternatively, a single vector may be used which encodes both heavy and light chain polypeptides. The coding sequences for the heavy and light chains can include cDNA or genomic DNA or both. The host cell used to express the recombinant antibody can be either a bacterial cell such as *Escherichia coli*, or more preferably a eukaryotic cell (e.g., a Chinese hamster ovary (CHO) cell or a HEK-293 cell). The choice of expression vector is dependent upon the choice of host cell, and can be selected so as to have the desired expression and regulatory characteristics in the selected host cell. Other cell lines that can be used include, but are not limited to, CHO-K1, NSO, and PER.C6 (Crucell, Leiden, Netherlands). Furthermore, codon usage can by optimized when host cell is selected to account for species specific codon usage bias and enhance protein expression. For example, for CHO cell expression the DNA encoding the antibodies can incorporate codons used preferentially by *Cricetulus griseus* (from where Chinese Hamster ovaries cells are derived. Methods of codon optimization may be employed to facilitate improved expression by a desired host cell (see, e.g., Wohlgemuth, I. et al., *Philos. Trans. R. Soc. Lond. B Biol. Sci.* 366(1580): 2979-2986 (2011); Jestin, J. L. et al., *J. Mol. Evol.* 69(5): 452-457 (2009); Bollenbach, T. et al., *Genome Res.* 17(4): 401-404(2007); Kurland, C. G. et al., *Prog. Nucleic Acid Res. Mol. Biol.* 31:191-219 (1984); Grosjean, H. et al., *Gene* 18(3): 199-209(1982)).

In some embodiments, the anti-BTN1A1 antibodies or anti-BTN1A1 ligand (e.g., GAL-1, GAL-9, NPR-2, or BTLA) antibodies can be monoclonal antibodies. In some embodiments, the anti-BTN1A1 antibodies or anti-BTN1A1 ligand (e.g., GAL-1, GAL-9, NPR-2, or BTLA) antibodies can be polyclonal antibodies. Animals can be inoculated with an antigen, such as a BTN1A1 polypeptide or glycosylated BTN1A1 polypeptide, BTN1A1 dimer polypeptide, a GAL-1 polypeptide, a GAL-9 polypeptide, an NRP-2 polypeptide, or a BTLA polypeptide in order to produce antibodies specific for a BTN1A1 polypeptide or a glycosylated BTN1A1 polypeptide, a BTN1A1 dimer, a GAL-1 polypeptide, a GAL-9 polypeptide, an NRP-2 polypeptide, or a BTLA polypeptide. Frequently an antigen is bound or conjugated to another molecule to enhance the immune response. A conjugate can be any peptide, polypeptide, protein, or non-proteinaceous substance bound to an antigen that is used to elicit an immune response in an animal. Antibodies produced in an animal in response to antigen inoculation have a variety of non-identical molecules (polyclonal antibodies) made from a variety of individual antibody producing B lymphocytes. Given the correct conditions for polyclonal antibody production in an animal, most of the antibodies in the animal's serum recognize the collective epitopes on the antigenic compound to which the animal has been immunized.

This specificity can be further enhanced by affinity purification to select only those antibodies that recognize the antigen or epitope of interest. The methods for generating monoclonal antibodies (MAbs) can begin along the same lines as those for preparing polyclonal antibodies. In some embodiments, rodents such as mice and rats are used in generating monoclonal antibodies. In some embodiments, rabbit, sheep, or frog cells are used in generating monoclonal antibodies. The use of rats is well known and can provide certain advantages. Mice (e.g., BALB/c mice) are routinely used and generally give a high percentage of stable fusions.

Hybridoma technology involves the fusion of a single B lymphocyte from a mouse previously immunized with a BTN1A1 polypeptide, a glycosylated BTN1A1 polypeptide, a BTN1A1 dimer polypeptide, a GAL-1 polypeptide, a GAL-9 polypeptide, an NRP-2 polypeptide, or a BTLA polypeptide with an immortal myeloma cell (usually mouse myeloma). This technology provides a method to propagate a single antibody-producing cell for an indefinite number of generations, such that unlimited quantities of structurally identical antibodies having the same antigen or epitope specificity (monoclonal antibodies) can be produced.

In one embodiment, the antibody is an immunoglobulin single variable domain derived from a camelid antibody, preferably from a heavy chain camelid antibody, devoid of light chains, which are known as $V_HH$ domain sequences or Nanobodies™. A Nanobody™ (Nb) is the smallest functional fragment or single variable domain ($V_HH$) of a naturally occurring single-chain antibody and is known to the person skilled in the art. They are derived from heavy chain only antibodies seen in camelids (Hamers-Casterman et al., *Nature*, 363(6428):446-8 (1993); Desmyter et al., *Nat Struct Biol.*, 3(9):803-11. (1996)). In the family of "camelids," immunoglobulins devoid of light polypeptide chains are found. "Camelids" include old world camelids (*Camelus bactrianus* and *Camelus dromedarius*) and new world camelids (for example, *Lama paccos, Lama glama, Lama guanicoe* and *Lama vicugna*). The single variable domain heavy chain antibody is herein designated as a Nanobody™ or a $V_HH$ antibody. The small size and unique biophysical properties of Nbs excel conventional antibody fragments for the recognition of uncommon or hidden epitopes and for binding into cavities or active sites of protein targets. Further, Nbs can be designed as multi-specific and multivalent antibodies, attached to reporter molecules, or humanzied. Nbs are stable, survive the gastro-intestinal system and can easily be manufactured.

Unifying two antigen binding sites of different specificity into a single construct, bispecific antibodies have the ability to bring together two discreet antigens with exquisite specificity and therefore have great potential as therapeutic agents. Bispecific antibodies can be made by fusing two hybridomas, each capable of producing a different immunoglobulin. Bispecific antibodies can also be produced by joining two scFv antibody fragments while omitting the Fc portion present in full immunoglobulins. Each scFv unit in such constructs can be made up of one variable domain from each of the heavy (VH) and light (VL) antibody chains, joined with one another via a synthetic polypeptide linker, the latter often being genetically engineered so as to be minimally immunogenic while remaining maximally resistant to proteolysis. Respective scFv units can be joined by a number of techniques including incorporation of a short (usually less than 10 amino acids) polypeptide spacer bridging the two scFv units, thereby creating a bispecific single chain antibody. The resulting bispecific single chain antibody is therefore a species containing two VH/VL pairs of different specificity on a single polypeptide chain, whereby the VH and VL domains in a respective scFv unit are separated by a polypeptide linker long enough to allow intramolecular association between these two domains, and whereby the thusly formed scFv units are contiguously tethered to one another through a polypeptide spacer kept short enough to prevent unwanted association between, for example, the VH domain of one scFv unit and the VL of the other scFv unit.

Examples of molecules having an antigen binding fragment that immunospecifically binds to BTN1A1, glycosylated BTN1A1, BTN1A1 dimer, GAL-1, GAL-9, NRP-2, or BTLA, include, without limitation: (i) the Fab fragment, consisting of VL, VH, CL, and CH1 domains; (ii) the "Fd" fragment consisting of the VH and CH1 domains; (iii) the "Fv" fragment consisting of the VL and VH domains of a single antibody; (iv) the "dAb" fragment, which consists of a VH domain; (v) isolated CDR regions; (vi) F(ab')2 fragments, a bivalent fragment including two linked Fab fragments; (vii) single chain Fv molecules ("scFv"), whereby a VH domain and a VL domain are linked by a peptide linker that allows the two domains to associate to form a binding domain; (viii) bi-specific single chain Fv dimers (see U.S. Pat. No. 5,091,513); and (ix) diabodies, multivalent, or multispecific fragments constructed by gene fusion (U.S. Patent Appln. Publn. No. 20050214860). Fv, scFv, or diabody molecules may be stabilized by the incorporation of disulfide bridges linking the VH and VL domains. Minibodies having a scFv joined to a CH3 domain can also be made (Hu et al., *Cancer Res.*, 56(13):3055-61(1996)).

Antibody-like binding peptidomimetics are also contemplated in embodiments. Murali et al., *Cell Mol. Biol.*, 49 (2):209-216 (2003) describe "antibody like binding peptidomimetics" (ABiPs), which are peptides that act as pared-down antibodies and have certain advantages of longer serum half-life as well as less cumbersome synthesis methods, which is hereby incorporated by reference in its entirety.

Standard techniques known to those of skill in the art can be used to introduce mutations in the nucleotide sequence encoding an antigen binding fragment, or an antibody, provided herein, including, for example, site-directed mutagenesis and PCR-mediated mutagenesis which results in amino acid substitutions. In certain embodiments, the derivatives include less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the original molecule. In a specific embodiment, the derivatives have conservative amino acid substitutions are made at one or more predicted non-essential amino acid residues. A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed and the activity of the protein can be determined.

In some embodiments, the molecules provided herein can be chemically modified, e.g., by the covalent attachment of any type of molecule to the antibody. For example, but not by way of limitation, the antibody derivatives include antibodies that have been chemically modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formulation, metabolic synthesis of tunicamycin, etc. Additionally, the antibody may contain one or more non-classical amino acids.

The molecules provided herein can have a framework region known to those of skill in the art (e.g., a human or non-human fragment). The framework region can, for example, be naturally occurring or consensus framework regions. In specific embodiments, the framework region of an antibody provided herein is human (see, e.g., Chothia et al., 1998, *J. Mol. Biol.* 278:457-479 for a listing of human framework regions, which is incorporated by reference herein in its entirety). See also Kabat et al. (1991) *Sequences of Proteins of Immunological Interest* (U.S. Department of Health and Human Services, Washington, D.C.) 5th ed.

In another aspect, provided herein are molecules having an antigen binding fragment that competitively blocks (e.g., in a dose-dependent manner) a BTN1A1 epitope of an anti-BTN1A1 antibody, a GAL-1 epitope of an anti-GAL-1 antibody, an anti-GAL-9 epitope of an anti-GAL-9 antibody, an anti-NRP-2 epitope of an anti-NRP-2 antibody, or an BTLA epitope of an anti-BTLA antibody described herein. The molecule can be an antibody. The antibody can be a monoclonal antibody. The antibody can be a humanized antibody.

In some embodiments, provided herein are anti-BTN1A1 antibodies that competitively block (e.g., in a dose-dependent manner) a BTN1A1 epitope, a GAL-1 epitope of an anti-GAL-1 antibody, an anti-GAL-9 epitope of an anti-GAL-9 antibody, an anti-NRP-2 epitope of an anti-NRP-2 antibody, or an BTLA epitope of an anti-BTLA antibody described herein.

In certain embodiments, the molecules provided herein have a high affinity for BTN1A1, glycosylated BTN1A1, a BTN1A1 dimer (e.g., a glycosylated BTN1A1 dimer), GAL-1, GAL-9, NRP-2, BTLA, or a polypeptide, or polypeptide fragment or epitope thereof. In one embodiment, the molecules provided herein can be anti-BTN1A1 antibodies or anti-BTN1A1 ligand (e.g., GAL-1, GAL-9, NRP-2, or BTLA) antibodies that have a higher affinity for BTN1A1 or the BTN1A1 ligand (e.g., GAL-1, GAL-9, NRP-2, or BTLA) than known antibodies (e.g., commercially available monoclonal antibodies discussed elsewhere herein). In a specific embodiment, the molecules provided herein can be anti-BTN1A1 antibodies or anti-BTN1A1 ligand (e.g., GAL-1, GAL-9, NRP-2, or BTLA) antibodies that have a 2- to 10-fold (or more) higher affinity for a BTN1A1, GAL-1, GAL-9, NRP-2, or BTLA antigen than a known anti-BTN1A1 antibody or a know anti-BTN1A1 ligand (e.g., GAL-1, GAL-9, NRP-2, or BTLA) antibody, as assessed by techniques described herein or known to one of skill in the art (e.g., a BIAcore™ assay). In accordance with these embodiments, the affinity of the antibodies are, in one embodiment, assessed by a BIAcore™ assay.

In certain embodiments, molecules provided herein can have an antigen binding fragment that binds to BTN1A1, glycosylated BTN1A1, a BTN1A1 dimer (e.g., a glycosylated BTN1A1 dimer), GAL-1, GAL-9, NRP-2, BTLA, or a polypeptide, or polypeptide fragment or epitope thereof with a dissociation constant ($K_D$) of no more than 1 µM, no more than 100 nM, no more than 10 nM, no more than 1 nM, or no more than 0.1 nM. In some embodiments, molecules provided herein can be anti-BTN1A1 antibodies or anti-BTN1A1 ligand (e.g., GAL-1, GAL-9, NRP-2, or BTLA) antibodies having a $K_D$ of no more than 500 nM. In some embodiments, molecules provided herein can be anti-BTN1A1 antibodies or anti-BTN1A1 ligand (e.g., GAL-1, GAL-9, NRP-2, or BTLA) antibodies having a $K_D$ of no more than 200 nM. In some embodiments, molecules provided herein can be anti-BTN1A1 antibodies or anti-BTN1A1 ligand (e.g., GAL-1, GAL-9, NRP-2, or BTLA) antibodies having a $K_D$ of no more than 100 nM. In some embodiments, molecules provided herein can be anti-BTN1A1 antibodies or anti-BTN1A1 ligand (e.g., GAL-1, GAL-9, NRP-2, or BTLA) antibodies having a $K_D$ of no more than 50 nM. In some embodiments, molecules provided herein can be anti-BTN1A1 antibodies or anti-BTN1A1 ligand (e.g., GAL-1, GAL-9, NRP-2, or BTLA) antibodies having a $K_D$ of no more than 20 nM. In some embodiments, molecules provided herein can be anti-BTN1A1 antibodies or anti-BTN1A1 ligand (e.g., GAL-1, GAL-9, NRP-2, or BTLA) antibodies having a $K_D$ of no more than 10 nM. In some embodiments, molecules provided herein can be anti-BTN1A1 antibodies or anti-BTN1A1 ligand (e.g., GAL-1, GAL-9, NRP-2, or BTLA) antibodies having a $K_D$ of no more than 5 nM. In some embodiments, molecules provided herein can be anti-BTN1A1 antibodies or anti-BTN1A1 ligand (e.g., GAL-1, GAL-9, NRP-2, or BTLA) antibodies having a $K_D$ of no more than 2 nM. In some embodiments, molecules provided herein can be anti-BTN1A1 antibodies or anti-BTN1A1 ligand (e.g., GAL-1, GAL-9, NRP-2, or BTLA) antibodies having a $K_D$ of no more than 1 nM. In some embodiments, molecules provided herein can be anti-BTN1A1 antibodies or anti-BTN1A1 ligand (e.g., GAL-1, GAL-9, NRP-2, or BTLA) antibodies having a $K_D$ of no more than 0.5 nM. In some embodiments, molecules provided herein can be anti-BTN1A1 antibodies or anti-BTN1A1 ligand (e.g., GAL-1, GAL-9, NRP-2, or BTLA) antibodies having a $K_D$ of no more than 0.1 nM.

In certain embodiments, molecules provided herein can block or neutralize the activities of BTN1A1 or a BTN1A1 ligand, such as GAL-1, GAL-9, NRP-2, or BTLA. The molecule can be a neutralizing antibody. The neutralizing antibody can block the binding of BTN1A1 with natural ligands, such as GAL-1, GAL-9, NRP-2, or BTLA, and inhibit the signaling pathways mediated by BTN1A1 or a BTN1A1-BTN1A1 ligand (e.g., GAL-1, GAL-9, NRP-2, or BTLA) complex and/or its other physiological activities. The IC50 of a neutralizing antibody can range between 0.01-10 µg/ml in the neutralization assay. The IC50 of a neutralizing antibody can be no more than 10 µg/ml. The IC50 of a neutralizing antibody can be no more than 8 µg/ml. The IC50 of a neutralizing antibody can be no more than 6 µg/ml. The IC50 of a neutralizing antibody can be no more than 4 µg/ml. The IC50 of a neutralizing antibody can be no more than 2 µg/ml. The IC50 of a neutralizing antibody can be no more than 1 µg/ml. The IC50 of a neutralizing antibody can be no more than 0.8 µg/ml. The IC50 of a neutralizing antibody can be no more than 0.6 µg/ml. The IC50 of a neutralizing antibody can be no more than 0.4 µg/ml. The IC50 of a neutralizing antibody can be no more than 0.2 µg/ml. The IC50 of a neutralizing antibody can be no more than 0.1 µg/ml. The IC50 of a neutralizing antibody can be no more than 0.08 µg/ml. The IC50 of a neutralizing antibody can be no more than 0.06 µg/ml. The IC50 of a neutralizing antibody can be no more than 0.04 µg/ml. The IC50 of a neutralizing antibody can be no more than 0.02 µg/ml. The IC50 of a neutralizing antibody can be no more than 0.01 µg/ml.

The molecules provided herein having an antigen binding fragment that immunospecifically binds to BTN1A1 (e.g., glycosylated BTN1A1 or a BTN1A1 dimer) or a BTN1A1 ligand (e.g., GAL-1, GAL-9, NRP-2, or BTLA) can be anti-BTN1A1 antibodies or anti-BTN1A1 ligand (e.g., GAL-1, GAL-9, NRP-2, or BTLA) antibodies. Antibodies provided herein include, but are not limited to, synthetic antibodies, monoclonal antibodies, recombinantly produced antibodies, multispecific antibodies (including bi-specific antibodies), human antibodies, humanized antibodies, camelized antibodies, chimeric antibodies, intrabodies, anti-idiotypic (anti-Id) antibodies, and functional fragments of any of the above. Non-limiting examples of functional fragments include single-chain Fvs (scFv) (e.g., including monospecific, bispecific, etc.), Fab fragments, F(ab') fragments, F(ab)$_2$ fragments, F(ab')$_2$ fragments, disulfide-linked Fvs (sdFv), Fd fragments, Fv fragments, diabody, triabody, tetrabody and minibody.

In particular, molecules provided herein include immunoglobulin molecules and immunologically active portions of immunoglobulin molecules, e.g., molecules that contain an antigen binding fragment that immunospecifically binds to BTN1A1 (e.g., glycosylated BTN1A1 or a BTN1A1 dimer) or a BTN1A1 ligand (e.g., GAL-1, GAL-9, NRP-2, or BTLA). The immunoglobulin molecules provided herein can be of any type (e.g., IgG, IgE, IgM, IgD, IgA and IgY), class (e.g., IgG1, IgG2, IgG3, IgG4, IgA1 and IgA2) or subclass of immunoglobulin molecule.

The molecules provided herein can be monospecific, bispecific, trispecific antibodies or antibodies of greater multispecificity. Multispecific antibodies may be specific for different epitopes of BTN1A1 or a BTN1A1 ligand (e.g., GAL-1, GAL-9, NRP-2, or BTLA) as described herein, or can be specific for both a BTN1A1 polypeptide or a BTN1A1 ligand (e.g., GAL-1, GAL-9, NRP-2, or BTLA) polypeptide as well as for a heterologous epitope, such as a heterologous polypeptide or solid support material. In specific embodiments, the antibodies provided herein are monospecific for a given epitope of a BTN1A1 polypeptide or a BTN1A1 ligand (e.g., GAL-1, GAL-9, NRP-2, or BTLA) polypeptide and do not bind to other epitopes.

5.2.2. Modifications and Derivatives

The binding properties of any of the above molecules having an antigen binding fragment that immunospecifically binds to BTN1A1 (e.g., glycosylated BTN1A1 or a BTN1A1 dimer) or to a BTN1A1 ligand (e.g., GAL-1, GAL-9, NRP-2, or BTLA) can be further improved by screening for variants that exhibit desired properties. For example, such improvement can be done using various phage display methods known in the art. In phage display methods, functional antibody domains are displayed on the surface of phage particles which carry the polynucleotide sequences encoding them. In a particular embodiment, such phage can be utilized to display antigen binding fragments, such as Fab and Fv or disulfide-bond stabilized Fv, expressed from a repertoire or combinatorial antibody library (e.g., human or murine). Phage expressing an antigen binding fragment that binds the antigen of interest can be selected or identified with antigen, e.g., using labeled antigen or antigen bound or captured to a solid surface or bead. Phage used in these methods are typically filamentous phage, including fd and M13. The antigen binding fragments are expressed as a recombinantly fused protein to either the phage gene III or gene VIII protein. Examples of phage display methods that can be used to make the antibodies or other molecules having an antigen binding fragment as described herein include those disclosed in Brinkman et al., *J Immunol Methods*, 182:41-50 (1995); Ames et al., *J. Immunol. Methods*, 184:177-186 (1995); Kettleborough et al., *Eur. J Immunol.*, 24:952-958(1994); Persic et al., *Gene*, 187:9-18 (1997); Burton et al., *Adv. Immunol.* 57:191-280 (1994); PCT Publications WO 92/001047; WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; all of which are hereby incorporated by references in their entireties.

As described in the above references, after phage selection, the antibody coding regions from the phage can be isolated and used to generate whole antibodies, including humanized antibodies, or any other desired fragments, and expressed in any desired host, including mammalian cells, insect cells, plant cells, yeast, and bacteria, e.g., as described in detail below. For example, techniques to recombinantly produce Fab, Fab' and F(ab')$_2$ fragments can also be employed using methods known in the art such as those disclosed in PCT Publication WO 92/22324; Mullinax, R. L. et al., *BioTechniques*, 12(6):864-869 (1992); and Sawai et al., *Am. J. Reprod. Immunol.* 34:26-34 (1995); and Better, M. et al. *Science* 240:1041-1043(1988); all of which are hereby incorporated by references in their entireties. Examples of techniques which can be used to produce single-chain Fvs and antibodies include those described in U.S. Pat. Nos. 4,946,778 and 5,258,498; Huston, J. S. et al., *Methods in Enzymology* 203:46-88(1991); Shu, L. et al., *Proc. Natl. Acad. Sci.* (USA) 90:7995-7999; and Skerra. A. et al., *Science* 240:1038-1040 (1988); all of which are hereby incorporated by references in their entireties.

Phage display technology can be used to increase the affinity of an anti-BTN1A1 antibody or a BTN1A1 ligand (e.g., GAL-1, GAL-9, NRP-2, or BTLA) antibody, or other molecules having an antigen binding fragment that immunospecifically binds BTN1A1 (e.g., glycosylated BTN1A1 or a BTN1A1 dimer) or a BTN1A1 ligand (e.g., GAL-1, GAL-9, NRP-2, or BTLA) as described herein. This technique can be used in obtaining high affinity antibodies that could be used in the combinatorial methods described herein. This technology, referred to as affinity maturation, employs mutagenesis or CDR walking and re-selection using such receptors or ligands (or their extracellular domains) or an antigenic fragment thereof to identify antibodies that bind with higher affinity to the antigen when compared with the initial or parental antibody (See, e.g., Glaser, S. M. et al., *J. Immunol.* 149:3903-3913(1992)). Mutagenizing entire codons rather than single nucleotides results in a semi-randomized repertoire of amino acid mutations. Libraries can be constructed consisting of a pool of variant clones each of which differs by a single amino acid alteration in a single CDR and which contain variants representing each possible amino acid substitution for each CDR residue. Mutants with increased binding affinity for the antigen can be screened by contacting the immobilized mutants with labeled antigen. Any screening method known in the art can be used to identify mutant antibodies with increased avidity to the antigen (e.g., ELISA) (see, e.g., Wu, H. et al., *Proc. Natl. Acad. Sci.* (USA) 95(11):6037-6042 (1998); Yelton, D. E. et al., *J. Immunol.* 155:1994-2004 (1995). CDR walking which randomizes the light chain can also be used. (see Schier et al., *J. Mol. Biol.* 263:551-567 (1996)).

Random mutagenesis can be used in concert with methods of phage display to identify improved CDRs and/or variable regions. Phage display technology can alternatively be used to increase (or decrease) CDR affinity by directed mutagenesis (e.g., affinity maturation or "CDR-walking"). This technique uses the target antigen or an antigenic fragment thereof to identify antibodies having CDRs that bind with higher (or lower) affinity to the antigen when compared with the initial or parental antibody (see, e.g., Glaser, S. M. et al., *J. Immunol.* 149:3903-3913(1992)).

Methods for accomplishing such affinity maturation are described for example in: Krause, J. C. et al., *MBio.* 2(1) pii: e00345-10. doi: 10.1128/mBio.00345-10(2011); Kuan, C. T. et al., *Int. J. Cancer* 10.1002/ijc.25645; Hackel, B. J. et al., *J. Mol. Biol.* 401(1):84-96(2010); Montgomery, D. L. et al., *MAbs* 1(5):462-474(2009); Gustchina, E. et al., *Virology* 393(1):112-119 (2009); Finlay, W. J. et al., *J. Mol. Biol.* 388(3):541-558 (2009); Bostrom, J. et al., Methods Mol. Biol. 525:353-376 (2009); Steidl, S. et al., *Mol. Immunol.* 46(1):135-144 (2008); and Barderas, R. et al., *Proc. Natl. Acad. Sci.* (USA) 105(26):9029-9034 (2008); all of which are hereby incorporated by references in their entireties.

Provided herein are also derivatives of any of the above-described molecules having an antigen binding fragment that immunospecifically binds to BTN1A1 (e.g., glycosylated BTN1A1 or a BTN1A1 dimer) or a BTN1A1 ligand (e.g., GAL-1, GAL-9, NRP-2, or BTLA), which can be an anti-BTN1A1 antibody or a BTN1A1 ligand (e.g., GAL-1, GAL-9, NRP-2, or BTLA) antibody, but which has one, two, three, four, five or more amino acid substitutions, additions, deletions or modifications relative to a "parental" (or wild-type) molecule. Such amino acid substitutions or additions can introduce naturally occurring (i.e., DNA-encoded) or non-naturally occurring amino acid residues. Such amino acids can be glycosylated (e.g., have altered mannose, 2-N-acetylglucosamine, galactose, fucose, glucose, sialic acid, 5-N-acetylneuraminic acid, 5-glycolneuraminic acid, etc. content), acetylated, pegylated, phosphorylated, amidated, derivatized by known protecting/blocking groups, proteolytic cleavage, linked to a cellular ligand or other protein, etc. In some embodiments, the altered carbohydrate modifications modulate one or more of the following: solubilization of the antibody, facilitation of subcellular transport and secretion of the antibody, promotion of antibody assembly, conformational integrity, and antibody-mediated effector function. In some embodiments, the altered carbohydrate modifications enhance antibody mediated effector function relative to the antibody lacking the carbohydrate modification. Carbohydrate modifications that lead to altered antibody mediated effector function are well known in the art (for example, see Shields, R. L. et al., *J. Biol. Chem.* 277(30): 26733-26740 (2002); Davies J. et al. *Biotechnology & Bioengineering* 74(4): 288-294(2001); all of which are hereby incorporated by references in their entireties). Methods of altering carbohydrate contents are known to those skilled in the art, see, e.g., Wallick, S. C. et al., *J. Exp. Med.* 168(3): 1099-1109(1988); Tao, M. H. et al., *J. Immunol.* 143(8): 2595-2601 (1989); Routledge, E. G. et al., *Transplantation* 60(8):847-53 (1995); Elliott, S. et al., *Nature Biotechnol.* 21:414-21(2003); Shields, R. L. et al., *J. Biol. Chem.* 277(30): 26733-26740 (2002); all of which are hereby incorporated by references in their entireties.

In some embodiments, a humanized antibody is a derivative antibody. Such a humanized antibody includes amino acid residue substitutions, deletions or additions in one or more non-human CDRs. The humanized antibody derivative can have substantially the same binding, better binding, or worse binding when compared to a non-derivative humanized antibody. In some embodiments, one, two, three, four, or five amino acid residues of the CDR have been mutated, such as substituted, deleted or added.

The molecules and antibodies as described herein can be modified by chemical modifications using techniques known to those of skill in the art, including, but not limited to, specific chemical cleavage, acetylation, formulation, metabolic synthesis of tunicamycin, etc. In one embodiment, a derivative molecule or a derivative antibody possesses a similar or identical function as the parental molecule or antibody. In another embodiment, a derivative molecule or a derivative antibody exhibits an altered activity relative to the parent molecule or parental antibody. For example, a derivative antibody (or fragment thereof) can bind to its epitope more tightly or be more resistant to proteolysis than the parental antibody.

Substitutions, additions or deletions in the derivatized antibodies can be in the Fc region of the antibody and can thereby serve to modify the binding affinity of the antibody to one or more FcγR. Methods for modifying antibodies with modified binding to one or more FcγR are known in the art, see, e.g., PCT Publication Nos. WO 04/029207, WO 04/029092, WO 04/028564, WO 99/58572, WO 99/51642, WO 98/23289, WO 89/07142, WO 88/07089, and U.S. Pat. Nos. 5,843,597 and 5,642,821; all of which are hereby incorporated by references in their entireties. In some embodiments, the antibodies or other molecules can have altered affinity for an activating FcγR, e.g., FcγRIIIA Preferably such modifications also have an altered Fc-mediated effector function. Modifications that affect Fc-mediated effector function are well known in the art (see U.S. Pat. No. 6,194,551, and WO 00/42072). In some embodiments, the modification of the Fc region results in an antibody with an altered antibody-mediated effector function, an altered binding to other Fc receptors (e.g., Fc activation receptors), an altered antibody-dependent cell-mediated cytotoxicity (ADCC) activity, an altered C1q binding activity, an altered complement-dependent cytotoxicity activity (CDC), a phagocytic activity, or any combination thereof.

ADCC is a cell-mediated reaction in which antigen-nonspecific cytotoxic cells that express FcRs (e.g., natural killer (NK) cells, neutrophils, and macrophages) recognize antibody bound to the surface of a target cell and subsequently cause lysis of (i.e., "kill") the target cell. The primary mediator cells are NK cells. NK cells express FcγRIII only, with FcγRIIIA being an activating receptor and FcγRIIIB an inhibiting one; monocytes express FcγRI, FcγRII and FcγRIII (Ravetch et al. (1991) *Annu. Rev. Immunol.,* 9:457-92). ADCC activity can be expressed as a concentration of antibody or Fc fusion protein at which the lysis of target cells is half-maximal. Accordingly, in some embodiments, the concentration of an antibody or Fc fusion protein of the invention, at which the lysis level is the same as the half-maximal lysis level by the wild-type control, is at least 2-, 3-, 5-, 10-, 20-, 50-, 100-fold lower than the concentration of the wild-type control itself. Additionally, in some embodiments, the antibody or Fc fusion protein of the invention can exhibit a higher maximal target cell lysis as compared to the wild-type control. For example, the maximal target cell lysis of an antibody or Fc fusion protein can be 10%, 15%, 20%, 25% or more higher than that of the wild-type control.

The molecules and antibodies as described herein can be modified to have enhanced potency. In some embodiments, the molecules and antibodies are modified with respect to effector function, e.g., so as to enhance ADCC and/or complement dependent cytotoxicity (CDC). In some embodiments, these therapeutic molecules or antibodies have enhanced interaction with killer cells bearing Fc receptors. Enhancement of effector functions, such as ADCC, can be achieved by various means, including introducing one or more amino acid substitutions in an Fc region. Also, cysteine residue(s) can be introduced in the Fc region, allowing interchain disulfide bond formation in this region. The homodimeric antibody can also have improved internalization capability and/or increased CDC and ADCC. Caron et al., *J. Exp Med.,* 176:1191-95 (1992) and Shopes, B. *J. Immunol.,* 148:2918-22 (1992). Homodimeric antibodies with enhanced anti-cancer activity can also be prepared using heterobifunctional cross-linkers. Wolff et al., *Cancer Research,* 53:2560-65 (1993). Additionally, an antibody or molecule can be engineered which has dual Fc regions and can thereby have enhanced CDC and ADCC capabilities. Stevenson et al., *Anti-Cancer Drug Design* 3:219-30 (1989).

The glycosylation pattern of the Fc region can also be engineered. A number of antibody glycosylation forms have been reported as having a positive impact on effector function, including ADCC. Thus, engineering of the carbohydrate component of the Fc region, particularly reducing core fucosylation, can also have enhanced therapeutic potency. Shinkawa T, et al., *J Biol. Chem.,* 278:3466-73 (2003); Niwa R, et al., *Cancer Res.,* 64:2127-33 (2004); Okazaki A, et al., *J Mol. Biol.* 336:1239^19 (2004); and Shields R L, et al., *J Biol. Chem.* 277:26733-40 (2002). Antibodies or molecules described herein with select glycoforms can be produced by a number of means, including the use of glycosylation pathway inhibitors, mutant cell lines that have absent or reduced activity of particular enzymes in the glycosylation pathway, engineered cells with gene expression in the glycosylation pathway either enhanced or knocked out, and in vitro remodeling with glycosidases and glycosyltransferases. Methods to modify the glycosylation of Fc region and enhance the therapeutic potency of antibodies or other molecules having an antigen binding fragment are known in the art. Rothman et al., Molecular Immunology 26: 1113-1123 (1989); Umana et al., *Nature Biotechnology* 17: 176-180 (1999); Shields et al., JBC 277:26733-26740 (2002); Shinkawa et al., JBC 278: 3466-3473 (2003); Bischoff et al., *J. Biol. Chem.* 265(26):15599-15605 (1990); U.S. Pat. Nos. 6,861,242 and 7,138,262, as well as US Publication No. 2003/0124652; all of which are hereby incorporated by reference in their entireties. A person of ordinary skill in the art would understand that the antibodies and molecules provided herein can be modified by any methods known in the art to have enhanced therapeutic potency.

Derivative molecules or antibodies can also have altered half-lives (e.g., serum half-lives) of parental molecules or antibodies in a mammal, preferably a human. In some embodiments, such alteration results in a half-life of greater than 15 days, preferably greater than 20 days, greater than 25 days, greater than 30 days, greater than 35 days, greater than 40 days, greater than 45 days, greater than 2 months, greater than 3 months, greater than 4 months, or greater than 5 months. The increased half-lives of humanized antibodies or other molecules in a mammal, preferably a human, results in a higher serum titer of said antibodies or other molecules in the mammal, and thus, reduces the frequency of the administration of said antibodies or other molecules and/or reduces the concentration of said antibodies or other molecules to be administered. Molecules or antibodies having increased in vivo half-lives can be generated by techniques known to those of skill in the art. For example, molecules or antibodies with increased in vivo half-lives can be generated by modifying (e.g., substituting, deleting or adding) amino acid residues identified as involved in the interaction between the Fc domain and the FcRn receptor. The humanized antibodies as described herein can be engineered to increase biological half-lives (see, e.g. U.S. Pat. No. 6,277,375). For example, humanized antibodies as described herein can be engineered in the Fc-hinge domain to have increased in vivo or serum half-lives.

Molecules or antibodies as described herein with increased in vivo half-lives can be generated by attaching to said antibodies or antibody fragments polymer molecules such as high molecular weight polyethyleneglycol (PEG). PEG can be attached to the molecules or antibodies with or without a multifunctional linker either through site-specific conjugation of the PEG to the N- or C-terminus of said molecules or antibodies or via epsilon-amino groups present on lysine residues. Linear or branched polymer derivatization that results in minimal loss of biological activity can be used. The degree of conjugation can be closely monitored by SDS-PAGE and mass spectrometry to ensure proper conjugation of PEG molecules to the antibodies. Unreacted PEG can be separated from antibody-PEG conjugates by, e.g., size exclusion or ion-exchange chromatography.

The molecules or antibodies as described herein can also be modified by the methods and coupling agents described by Davis et al. (See U.S. Pat. No. 4,179,337) in order to provide compositions that can be injected into the mammalian circulatory system with substantially no immunogenic response. Removal of the Fc portion can reduce the likelihood that the antibody fragment elicits an undesirable immunological response and, thus, antibodies without Fc can be used for prophylactic or therapeutic treatments. As described above, antibodies can also be constructed so as to be chimeric, partially or fully human, so as to reduce or eliminate the adverse immunological consequences resulting from administering to an animal an antibody that has been produced in, or has sequences from, other species.

5.2.3. Fusions and Conjugates

Provided herein are molecules having an antigen binding fragment that immunospecifically binds to BTN1A1 (e.g., glycosylated BTN1A1 or a BTN1A1 dimer) or a BTN1A1 ligand (e.g., GAL-1, GAL-9, NRP-2, or BTLA), including anti-BTN1A1 antibodies and BTN1A1 ligand (e.g., GAL-1, GAL-9, NRP-2, or BTLA) antibodies. In some embodiments, such molecules are expressed as a fusion protein with other proteins or chemically conjugated to another moiety.

In some embodiments, the molecule is a fusion protein having an Fc portion, whereby the Fc portion can be varied by isotype or subclass, can be a chimeric or hybrid, and/or can be modified, for example to improve effector functions, control of half-life, tissue accessibility, augment biophysical characteristics such as stability, and improve efficiency of production (and less costly). Many modifications useful in construction of disclosed fusion proteins and methods for making them are known in the art, see for example Mueller, J. P. et al., Mol. Immun. 34(6):441-452 (1997), Swann, P. G., Curr. Opin. Immun. 20:493-499 (2008), and Presta, L. G., Curr. Opin. Immun. 20:460-470 (2008). In some embodiments the Fc region is the native IgG1, IgG2, or IgG4 Fc region. In some embodiments the Fc region is a hybrid, for example a chimeric having of IgG2/IgG4 Fc constant regions. Modications to the Fc region include, but are not limited to, IgG4 modified to prevent binding to Fc gamma receptors and complement, IgG1 modified to improve binding to one or more Fc gamma receptors, IgG1 modified to minimize effector function (amino acid changes), IgG1 with altered/no glycan (typically by changing expression host), and IgG1 with altered pH-dependent binding to FcRn. The Fc region can include the entire hinge region, or less than the entire hinge region.

Another embodiment includes IgG2-4 hybrids and IgG4 mutants that have reduce binding to FcR which increase their half-life. Representative IG2-4 hybrids and IgG4 mutants are described in Angal et al., Molec. Immunol. 30(1):105-108 (1993); Mueller et al., Mol. Immun. 34(6): 441-452 (1997); and U.S. Pat. No. 6,982,323; all of which are hereby incorporated by references in their entireties. In some embodiments the IgG1 and/or IgG2 domain is deleted for example, Angal et al. describe IgG1 and IgG2 having serine 241 replaced with a proline.

In some embodiments, the molecules are polypeptides having at least 10, at least 20, at least 30, at least 40, at least 50, at least 60, at least 70, at least 80, at least 90 or at least 100 amino acids.

In some embodiments, provided herein are molecules that have an antigen binding fragment that immunospecifically binds to BTN1A1 (e.g., glycosylated BTN1A1 or a BTN1A1 dimer) or to a BTN1A1 ligand (e.g., GAL-1, GAL-9, NRP-2, or BTLA), which link to or covalently bind or form into a complex with at least one moiety. Such a moiety can be, but is not limited to, one that increases the efficacy of molecules as diagnostic or therapeutic agents. In some embodiments, the moiety can be image agents, toxins, therapeutic enzymes, antibiotics, radio-labeled nucleotides and the like.

Molecules provided herein can include a therapeutic moiety (or one or more therapeutic moieties). Molecules provided herein can be an antibody conjugated or recombinantly fused to a therapeutic moiety, such as a cytotoxin, e.g., a cytostatic or cytocidal agent, a therapeutic agent or a radioactive metal ion, e.g., alpha-emitters. A cytotoxin or cytotoxic agent includes any agent that is detrimental to cells. Therapeutic moieties include, but are not limited to, antimetabolites (e.g., methotrexate, 6-mercaptopurine, 6-thioguanine, cytarabine, 5-fluorouracil decarbazine); alkylating agents (e.g., mechlorethamine, thioepa chlorambucil, melphalan, carmustine (BCNU) and lomustine (CCNU), cyclothosphamide, busulfan, dibromomannitol, streptozotocin, mitomycin C, and cisdichlorodiamine platinum (II) (DDP), and cisplatin); anthracyclines (e.g., daunorubicin (formerly daunomycin) and doxorubicin); antibiotics (e.g., d actinomycin (formerly actinomycin), bleomycin, mithramycin, and anthramycin (AMC)); Auristatin molecules (e.g., auristatin PHE, auristatin F, monomethyl auristatin E, bryostatin 1, and solastatin 10; see Woyke et al., Antimicrob. Agents Chemother. 46:3802-8 (2002), Woyke et al., Antimicrob. Agents Chemother. 45:3580-4 (2001), Mohammad et al., Anticancer Drugs 12:735-40 (2001), Wall et al., Biochem. Biophys. Res. Commun. 266:76-80 (1999), Mohammad et al., Int. J. Oncol. 15:367-72 (1999), all of which are incorporated herein by reference); hormones (e.g., glucocorticoids, progestins, androgens, and estrogens), DNA-repair enzyme inhibitors (e.g., etoposide or topotecan), kinase inhibitors (e.g., compound ST1571, imatinib mesylate (Kantarjian et al., Clin Cancer Res. 8(7):2167-76 (2002)); cytotoxic agents (e.g., paclitaxel, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucorticoids, procaine, tetracaine, lidocaine, propranolol, and puromycin and analogs or homologs thereof and those compounds disclosed in U.S. Pat. Nos. 6,245,759, 6,399,633, 6,383,790, 6,335,156, 6,271,242, 6,242,196, 6,218,410, 6,218,372, 6,057,300, 6,034,053, 5,985,877, 5,958,769, 5,925,376, 5,922,844, 5,911,995, 5,872,223, 5,863,904, 5,840,745, 5,728,868, 5,648,239, 5,587,459); farnesyl transferase inhibitors (e.g., R115777, BMS-214662, and those disclosed by, for example, U.S. Pat. Nos. 6,458, 935, 6,451,812, 6,440,974, 6,436,960, 6,432,959, 6,420,387, 6,414,145, 6,410,541, 6,410,539, 6,403,581, 6,399,615, 6,387,905, 6,372,747, 6,369,034, 6,362,188, 6,342,765, 6,342,487, 6,300,501, 6,268,363, 6,265,422, 6,248,756, 6,239,140, 6,232,338, 6,228,865, 6,228,856, 6,225,322, 6,218,406, 6,211,193, 6,187,786, 6,169,096, 6,159,984, 6,143,766, 6,133,303, 6,127,366, 6,124,465, 6,124,295, 6,103,723, 6,093,737, 6,090,948, 6,080,870, 6,077,853, 6,071,935, 6,066,738, 6,063,930, 6,054,466, 6,051,582, 6,051,574, and 6,040,305); topoisomerase inhibitors (e.g., camptothecin; irinotecan; SN-38; topotecan; 9-aminocamptothecin; GG-211 (GI 147211); DX-8951f; IST-622; rubitecan; pyrazoloacridine; XR-5000; saintopin; UCE6; UCE1022; TAN-1518A; TAN 1518B; KT6006; KT6528; ED-110; NB-506; ED-110; NB-506; and rebeccamycin); bulgarein; DNA minor groove binders such as Hoescht dye 33342 and Hoechst dye 33258; nitidine; fagaronine; epiberberine; coralyne; beta-lapachone; BC-4-1; bisphosphonates (e.g., alendronate, cimadronte, clodronate, tiludronate, etidronate, ibandronate, neridronate, olpandronate, risedronate, piridronate, pamidronate, zolendronate) HMG-CoA reductase inhibitors, (e.g., lovastatin, simvastatin, atorvastatin, pravastatin, fluvastatin, statin, cerivastatin, lescol, lupitor, rosuvastatin and atorvastatin); antisense oligonucleotides (e.g., those disclosed in the U.S. Pat. Nos. 6,277,832, 5,998,596, 5,885,834, 5,734,033, and 5,618,709); adenosine deaminase inhibitors (e.g., Fludarabine phosphate and 2-Chlorodeoxyadenosine); ibritumomab tiuxetan (Zevalin®); tositumomab (Bexxar®)) and pharmaceutically acceptable salts, solvates, clathrates, and prodrugs thereof.

Further, molecules provided herein be antibodies conjugated or recombinantly fused to a therapeutic moiety or drug moiety that modifies a given biological response. Therapeutic moieties or drug moieties are not to be construed as limited to classical chemical therapeutic agents. For example, the drug moiety may be a protein, peptide, or polypeptide possessing a desired biological activity. Such proteins may include, for example, a toxin such as abrin, ricin A, *pseudomonas* exotoxin, cholera toxin, or diphtheria toxin; a protein such as tumor necrosis factor, γ-interferon, α-interferon, nerve growth factor, platelet derived growth factor, tissue plasminogen activator, an apoptotic agent, e.g., TNF-γ, TNF-γ, AIM I (see, International Publication No. WO 97/33899), AIM II (see, International Publication No. WO 97/34911), Fas Ligand (Takahashi et al., 1994, *J. Immunol.*, 6:1567-1574), and VEGF (see, International Publication No. WO 99/23105), an anti-angiogenic agent, e.g., angiostatin, endostatin or a component of the coagulation pathway (e.g., tissue factor); or, a biological response modifier such as, for example, a lymphokine (e.g., interferon gamma, interleukin-1 ("IL-1"), interleukin-2 ("IL-2"), interleukin-5 ("IL-5"), interleukin-6 ("IL-6"), interleukin-7 ("IL-7"), interleukin 9 ("IL-9"), interleukin-10 ("IL-10"), interleukin-12 ("IL-12"), interleukin-15 ("IL-15"), interleukin-23 ("IL-23"), granulocyte macrophage colony stimulating factor ("GM-CSF"), and granulocyte colony stimulating factor ("G-CSF")), or a growth factor (e.g., growth hormone ("GH")), or a coagulation agent (e.g., calcium, vitamin K, tissue factors, such as but not limited to, Hageman factor (factor XII), high-molecular-weight kininogen (HMWK), prekallikrein (PK), coagulation proteins-factors II (prothrombin), factor V, XIIa, VIII, XIIIa, XI, XIa, IX, IXa, X, phospholipid, and fibrin monomer).

In addition, an antibody provided herein can be conjugated to therapeutic moieties such as a radioactive metal ion, such as alpha-emitters such as $^{213}$Bi or macrocyclic chelators useful for conjugating radiometal ions, including but not limited to, $^{131}$In, $^{131}$Lu, $^{131}$Y, $^{131}$Ho, $^{131}$SM, to polypeptides. In certain embodiments, the macrocyclic chelator is 1,4,7, 10-tetraazacyclododecane-N,N',N",N'''-tetraacetic acid (DOTA) which can be attached to the antibody via a linker molecule. Such linker molecules are commonly known in the art and described in Denardo et al., 1998, *Clin Cancer Res.* 4(10):2483-90; Peterson et al., 1999, *Bioconjug. Chem.* 10(4):553-7; and Zimmerman et al., 1999, *Nucl. Med. Biol.* 26(8):943-50, each incorporated by reference in their entireties.

The therapeutic moiety or drug conjugated or recombinantly fused to an antibody provided herein that immunospecifically binds to BTN1A1 (e.g., glycosylated BTN1A1 or a BTN1A1 dimer) or to a BTN1A1 ligand (e.g., GAL-1, GAL-9, NRP-2, or BTLA) should be chosen to achieve the desired prophylactic or therapeutic effect(s). In certain embodiments, the antibody is a modified antibody. A clinician or other medical personnel should consider the following when deciding on which therapeutic moiety or drug to conjugate or recombinantly fuse to an antibody provided herein: the nature of the disease, the severity of the disease, and the condition of the subject.

In some embodiments, the moiety can be enzymes, hormones, cell surface receptors, toxins (such as abrin, ricin A, *Pseudomonas* exotoxin (i.e., PE-40), diphtheria toxin, ricin, gelonin, or pokeweed antiviral protein), proteins (such as tumor necrosis factor, interferon (e.g., α-interferon, β-interferon), nerve growth factor, platelet derived growth factor, tissue plasminogen activator, or an apoptotic agent (e.g., tumor necrosis factor-α, tumor necrosis factor-β)), biological response modifiers (such as, for example, a lymphokine (e.g., interleukin-1 ("IL-1"), interleukin-2 ("IL-2"), interleukin-6 ("IL-6")), granulocyte macrophage colony stimulating factor ("GM-CSF"), granulocyte colony stimulating factor ("G-CSF"), or macrophage colony stimulating factor, ("M-CSF")), or growth factors (e.g., growth hormone ("GH"))), cytotoxins (e.g., a cytostatic or cytocidal agent, such as paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, monomethyl auristatin F (MMAF), monomethyl auristatin E (MMAE; e.g., vedotin), and puromycin and analogs or homologs thereof), antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, BiCNU® (carmustine; BSNU) and lomustine (CCNU), cyclothosphamide, busulfan, dibromomannitol, streptozotocin, mitomycin C, and cisdichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), or anti-mitotic agents (e.g., vincristine and vinblastine).

Techniques for conjugating such therapeutic moieties to antibodies are well known; see, e.g., Amon et al., "*Monoclonal Antibodies For Immunotargeting Of Drugs In Cancer Therapy*", in MONOCLONAL ANTIBODIES AND CANCER THERAPY, Reisfeld et al. (eds.), 1985, pp. 243-56, Alan R. Liss, Inc.); Hellstrom et al., "*Antibodies For Drug Delivery*", in CONTROLLED DRUG DELIVERY (2nd Ed.), Robinson et al. (eds.), 1987, pp. 623-53, Marcel Dekker, Inc.); Thorpe, "*Antibody Carriers Of Cytotoxic Agents In Cancer Therapy: A Review*", in MONOCLONAL ANTIBODIES '84: BIOLOGICAL AND CLINICAL APPLICATIONS, Pinchera et al. (eds.), 1985, pp. 475-506); "*Analysis, Results, And Future Prospective Of The Therapeutic Use Of Radiolabeled Antibody In Cancer Therapy*", in MONOCLONAL ANTIBODIES FOR CANCER DETECTION AND THERAPY, Baldwin et al. (eds.), 1985, pp. 303-16, Academic Press; Thorpe et al., *Immunol. Rev.* 62:119-158 (1982); Carter et al., *Cancer J.* 14(3):154-169 (2008); Alley et al., *Curr. Opin. Chem. Biol.* 14(4):529-537 (2010); Carter et al., *Amer. Assoc. Cancer Res. Educ. Book.* 2005(1):147-154 (2005); Carter et al., *Cancer J.* 14(3):154-169(2008); Chari, *Acc. Chem Res.* 41(1):98-107 (2008); Doronina et al., *Nat. Biotechnol.* 21(7):778-784(2003); Ducry et al., *Bioconjug Chem.* 21(1):5-13(2010); Senter, *Curr. Opin. Chem. Biol.* 13(3):235-244 (2009); and Teicher, *Curr Cancer Drug Targets.* 9(8):982-1004 (2009).

In some embodiments, molecules as described herein can be conjugated to a marker, such as a peptide, to facilitate purification. In some embodiments, the marker is a hexahistidine peptide, the hemagglutinin "HA" tag, which corresponds to an epitope derived from the influenza hemagglutinin protein (Wilson, I. A. et al., *Cell,* 37:767-778 (1984)), or the "flag" tag (Knappik, A. et al., *Biotechniques* 17(4):754-761 (1994)).

In some embodiments, the moiety can be an image agent that can be detected in an assay. Such image agent can be enzymes, prosthetic groups, radiolabels, nonradioactive paramagnetic metal ions, haptens, fluorescent labels, phosphorescent molecules, chemiluminescent molecules, chromophores, luminescent molecules, bioluminescent molecules, photoaffinity molecules, colored particles or ligands, such as biotin.

In some embodiments, the enzymes include, but not limited to, horseradish peroxidase, alkaline phosphatase, beta-galactosidase, or acetylcholinesterase; the prosthetic group complexes include, but not limited to, streptavidin/biotin and avidin/biotin; the fluorescent materials include, but not limited to, umbelliferone, fluorescein, fluorescein isothiocyanate, rhodamine, dichlorotriazinylamine fluorescein, dansyl chloride or phycoerythrin; the luminescent material such as, but not limited to, luminol; the bioluminescent materials include, but not limited to, luciferase, luciferin, and aequorin; the radioactive material include, but not limited to, bismuth ($^{213}$Bi), carbon ($^{14}$C), chromium ($^{51}$Cr), cobalt ($^{57}$Co), fluorine ($^{18}$F), gadolinium ($^{153}$Gd, $^{159}$Gd), gallium ($^{68}$Ga, $^{67}$Ga), germanium ($^{68}$Ge), holmium ($^{166}$Ho), indium ($^{115}$In, $^{113}$In, $^{112}$In, $^{111}$In), iodine ($^{131}$I, $^{125}$I, $^{123}$I, $^{121}$I), lanthanum ($^{140}$La), lutetium ($^{177}$Lu), manganese ($^{54}$Mn), molybdenum ($^{99}$Mo), palladium ($^{103}$Pd), phosphorous ($^{32}$P), praseodymium ($^{142}$Pr), promethium ($^{149}$Pm), rhenium ($^{186}$Re, $^{188}$Re), rhodium ($^{105}$Rh), ruthemium ($^{97}$Ru), samarium ($^{153}$Sm), scandium ($^{47}$Sc), selenium ($^{75}$Se), strontium ($^{85}$Sr), sulfur ($^{35}$S), technetium ($^{99}$Tc), thallium ($^{201}$Ti), tin ($^{113}$Sn, $^{117}$Sn), tritium ($^{3}$H), xenon ($^{133}$Xe), ytterbium ($^{169}$Yb, $^{175}$Yb) yttrium ($^{90}$Y), zinc ($^{65}$Zn); positron emitting metals using various positron emission tomographies, and nonradioactive paramagnetic metal ions.

The image agent can be conjugated to the molecule having an antigen binding fragment either directly, or indirectly through an intermediate (such as, for example, a linker known in the art) using techniques known in the art. See, for example, U.S. Pat. No. 4,741,900 for metal ions which can be conjugated to antibodies and other molecules as described herein for use as diagnostics. Some conjugation methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3-6α-diphenylglycouril-3 attached to the antibody. Monoclonal antibodies can also be reacted with an enzyme in the presence of a coupling agent such as glutaraldehyde or periodate. Conjugates with fluorescein markers can be prepared in the presence of these coupling agents or by reaction with an isothiocyanate.

The molecules as described herein can be conjugated to a second antibody to form an antibody heteroconjugate as described by Segal in U.S. Pat. No. 4,676,980. Such heteroconjugate antibodies can additionally bind to haptens (e.g., fluorescein), or to cellular markers (e.g., 4-1-BB, B7-H4, CD4, CD8, CD14, CD25, CD27, CD40, CD68, CD163, CTLA4, GITR, LAG-3, OX40, TIM3, TIM4, TLR2, LIGHT, ICOS, B7-H3, B7-H7, B7-H7CR, CD70, CD47) or to cytokines (e.g., IL-7, IL-15, IL-12, IL-4 TGF-beta, IL-10, IL-17, IFNγ, Flt3, BLys) or chemokines (e.g., CCL21).

The molecules as described herein can be attached to solid supports, which can be useful for immunoassays or purification of the target antigen or of other molecules that are capable of binding to target antigen that has been immobilized to the support via binding to an antibody or antigen binding fragment as described herein. Such solid supports include, but are not limited to, glass, cellulose, polyacrylamide, nylon, polystyrene, polyvinyl chloride or polypropylene.

Provided herein are also nucleic acid molecules (DNA or RNA) that encode any such antibodies, antigen binding fragments, and molecules having the antigen binding fragment that immunospecifically binds to BTN1A1 (e.g., glycosylated BTN1A1 or a BTN1A1 dimer). Provided herein are also vector molecules (such as plasmids) that are capable of transmitting or of replication such nucleic acid molecules. The nucleic acids can be single-stranded, double-stranded, and can contain both single-stranded and double-stranded portions.

Antibody-Drug Conjugates (ADCS)

As the molecules provided herein can result in internalization of BTN1A1 into the cells, provided herein are also Antibody-Drug Conjugates (ADCs) that include any anti-BTN1A1 antibody described herein.

In some embodiments, provided herein are antibody-drug conjugates, including an antibody-drug conjugate of the following formulas (Ia) and (Ib):

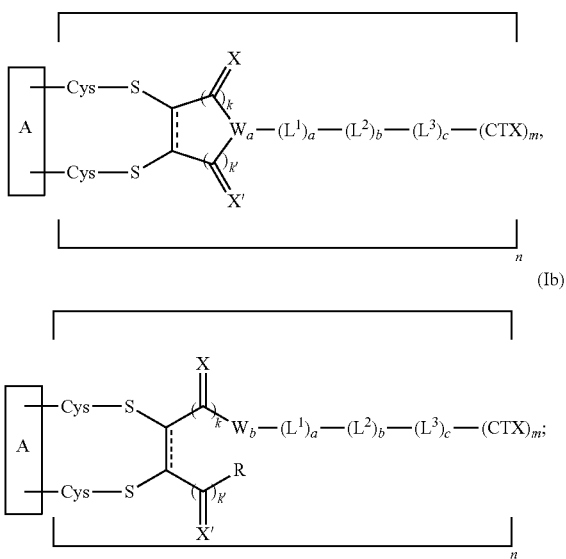

or a pharmaceutically acceptable salt thereof;
wherein:
A is a molecule that have an antigen binding fragment;
the two depicted cysteine residues are from an opened cysteine-cysteine disulfide bond in A;
each X and X' is independently O, S, NH, or NR$^1$ wherein R$^1$ is C$_{1-6}$ alkyl;
W$_a$ is =N—, =CH—, =CHCH$_2$—, =C(R$^2$)—, or =CHCH(R$^2$)—; W$_b$ —NH—, —N(R')—, —CH$_2$—, —CH$_2$—NH—, —CH$_2$—N(R')—, —CH$_2$CH$_2$—, —CH (R$^2$)—, or —CH$_2$CH(R$^2$)—; wherein R$^1$ and R$^2$ are independently C$_{1-6}$ alkyl;
CTX is a cytotoxin;
R is any chemical group; or R is absent;
each L$^1$, L$^2$ and L$^3$ is independently a linker selected from the group consisting of —O—, —C(O)—, —S—, —S(O)—, —S(O)$_2$—, —NH—, —NCH$_3$—, —(CH$_2$)$_q$—, —NH(CH$_2$)$_2$NH—, —OC(O)—, —CO$_2$—, —NHCH$_2$CH$_2$C(O)—, —C(O)NHCH$_2$CH$_2$NH—, —NHCH$_2$C(O)—, —NHC(O)—, —C(O)NH—, —NCH$_3$C(O)—, —C(O)NCH$_3$—, —(CH$_2$CH$_2$O)$_p$—, —(CH$_2$CH$_2$O)$_p$CH$_2$CH$_2$—, —CH$_2$CH$_2$—(CH$_2$CH$_2$O)$_p$—, —OCH(CH$_2$O—)$_2$, -(AA)$_r$-, cyclopentanyl, cyclohexanyl, unsubstituted phenylenyl, and phenylenyl substituted by 1 or 2 substituents selected from the group consisting of halo, CF$_3$—, CF$_3$O—, CH$_3$O—, —C(O)OH, —C(O)OC$_{1-3}$ alkyl, —C(O)CH$_3$, —CN, —NH—, —NH$_2$, —O—, —OH, —NHCH$_3$, —N(CH$_3$)$_2$, and C$_{1-3}$ alkyl;
a, b and c are each independently an integer of 0, 1, 2 or 3, provided that at least one of a, b or c is 1;
each k and k' is independently an integer of 0 or 1;
each p is independently an integer of 1 to 14;
each q is independently an integer from 1 to 12;
each AA is independently an amino acid;
each r is 1 to 12;
m is an integer of 1 to 4;
n is an integer of 1 to 4; and
the ----- bond represents a single or a double bond.

In certain embodiments of the antibody-drug conjugate (ADC) of formula (Ib), R is selected from the group consisting of W, (L$^1$)$_a$, (L$^2$)$_b$, (L$^3$)$_c$, Z, W-(L$^1$)$_a$-(L$^2$)$_b$-(L$^3$)$_c$, (L$^1$)$_a$-(L$^2$)$_b$-(L$^3$)$_c$-Z, and W-(L$^1$)$_a$-(L$^2$)$_b$-(L$^3$)$_c$-Z, as defined herein. In certain embodiments, R is selected from the group consisting of W, (L')$_a$, (L$^2$)$_b$, (L$^3$)$_c$, and W-(L$^1$)$_a$-(L$^2$)$_b$-(L$^3$)$_c$. In certain embodiments, R is selected from the group consisting of Z, (L$^1$)$_a$-(L$^2$)$_b$-(L$^3$)$_c$-Z, and W-(L$^1$)$_a$-(L$^2$)$_b$-(L$^3$)$_c$-Z.

In certain embodiments of the antibody-drug conjugate (ADC) of formula (Ib), R is a detectable probe. In certain embodiments, R is a fluorophore, chromophore, radiolabel, enzyme, ligand, antibody or antibody fragment. In certain embodiments, R is a ligand (e.g., a ligand specific for a receptor on a tumor cell, such as a prostate specific membrane antigen, or a virally infected cell, such as an HIV infected cell).

In certain embodiments of the antibody-drug conjugate (ADC) of formula (Ib), R is bonded to the rest of the linker molecule via an amide, an N—(C$_{1-6}$ alkyl)amide, a carbamate, an N—(C$_{1-6}$ alkyl)carbamate, an amine, an N—(C$_{1-6}$ alkyl)amine, an ether, a thioether, an urea, an N—(C$_{1-6}$ alkyl)urea, or an N,N-di(C$_{1-6}$ alkyl)urea bond.

In certain embodiments of the antibody-drug conjugate (ADC) of formula (Ia) or (Ib), each L$^1$, L$^2$ and L$^3$ is independently selected from the group consisting of —NHC (O)—, —C(O)NH—, —(CH$_2$CH$_2$O)$_p$—, —(CH$_2$CH$_2$O)$_p$CH$_2$CH$_2$—, —CH$_2$CH$_2$—(CH$_2$CH$_2$O)$_p$—, —OCH (CH$_2$O—)$_2$, -(AA)$_r$-, unsubstituted phenylenyl, and phenylenyl substituted by 1 or 2 substituents selected from the group consisting of halo, CF$_3$—, CF$_3$O—, CH$_3$O—, —C(O) OH, —C(O)OC$_{1-3}$ alkyl, —C(O)CH$_3$, —CN, —NH—, —NH$_2$, —O—, —OH, —NHCH$_3$, —N(CH$_3$)$_2$, and C$_{1-3}$ alkyl; where a, b and c are each independently 0 or 1; and each p and r is independently 1, 2 or 3. In certain embodiments, one or more of the L$^1$, L$^2$ and L$^3$ is -(AA)$_r$-, wherein -(AA)$_r$- is ValCit (e.g., the first amino acid is Valine, the second amino acid is Citrulline, and r is 1). In certain embodiments, one or more of the L$^1$, L$^2$ and L$^3$ is -(AA)$_r$-, wherein -(AA)$_r$- is ValAla (e.g., the first amino acid is Valine, the second amino acid is Alanine, and r is 1). In certain embodiments, one or more of the L$^1$, L$^2$ and L$^3$ is phenylenyl substituted by —C(O)OH and —NH$_2$. In certain embodiments, one or more of the L$^1$, L$^2$ and L$^3$ is phenylenyl substituted by —C(O)O— and —NH—. In certain embodiments, one or more of the L$^1$, L$^2$ and L$^3$ is phenylenyl substituted by —OC(O)— and —NH—. In certain embodiments, one or more of the L$^1$, L$^2$ and L$^3$ is phenylenyl substituted by —O— and —NH—. In certain embodiments, one or more of the L$^1$, L$^2$ and L$^3$ is para aminobenzyl (PAB), which is optionally substituted with —C(O)O—, —OC (O)— or —O—. In certain embodiments, L$^1$ is —(CH$_2$)$_q$—, L$^2$ is absent, L$^3$ is absent, and the CTX is bonded to (L$^1$)$_a$-(L$^2$)$_b$-(L$^3$)$_c$ via an amide bond. In certain embodiments, L$^1$ is —(CH$_2$)$_q$—, L$^2$ is —(OCH$_2$CH$_2$)$_p$—, L$^3$ is absent, and the CTX is bonded to (L$^1$)$_a$-(L$^2$)$_b$-(L$^3$)$_c$ via an amide bond. In certain embodiments, L$^1$ is —(CH$_2$CH$_2$O)$_p$—, L$^2$ is —(CH$_2$)$_q$—, L$^3$ is absent, and the CTX is bonded to (L$^1$)$_a$-(L$^2$)$_b$-(L$^3$)$_c$ via an amide bond. In certain embodiments, each L$^1$ is independently selected from the group consisting of —(CH$_2$CH$_2$O)$_p$CH$_2$CH$_2$— and —CH$_2$CH$_2$—(CH$_2$CH$_2$O)$_p$—, L$^2$ is absent, L$^3$ is absent, and the CTX is bonded to (L$^1$)$_a$-(L$^2$)$_b$-(L$^3$)$_c$ via an amide bond. In certain embodiments, each L$^1$ is independently selected from the group consisting of —(CH$_2$)$_q$—, —(CH$_2$CH$_2$O)$_p$, —(CH$_2$CH$_2$O)$_p$CH$_2$CH$_2$—, —CH$_2$CH$_2$—(CH$_2$CH$_2$O)$_p$—, and —C(O)—, L$^2$ is Val-Cit, L$^3$ is PAB, and the CTX is bonded to (L$^1$)$_a$-(L$^2$)$_b$-(L$^3$)$_c$ via an amide bond. In certain embodiments, each L$^1$ is independently selected from the group consisting of —(CH$_2$)$_q$—, —(CH$_2$CH$_2$O)$_p$, —(CH$_2$CH$_2$O)$_p$CH$_2$CH$_2$—, —CH$_2$CH$_2$—(CH$_2$CH$_2$O)$_p$—, and —C(O)—, L$^2$ is Val-Cit, L$^3$ is PAB, and the CTX is bonded to (L$^1$)$_a$-(L$^2$)$_b$-(L$^3$)$_c$ via an amide bond. In certain embodiments, each L$^1$ is independently selected from the group consisting of —(CH$_2$)$_q$—, —(CH$_2$CH$_2$O)$_p$—, —(CH$_2$CH$_2$O)$_p$CH$_2$CH$_2$—, —CH$_2$CH$_2$—(CH$_2$CH$_2$O)$_p$—, and —C(O)—, L$^2$ is Val-Ala, L$^3$ is PAB, and the CTX is bonded to (L$^1$)$_a$-(L$^2$)$_b$-(L$^3$)$_c$ via an amide bond.

In certain embodiments of the antibody-drug conjugate (ADC) of formula (Ia) or (Ib), CTX is selected from a from the group consisting of a tubulin stabilizer, a tubulin destabilizer, a DNA alkylator, a DNA minor groove binder, a DNA intercalator, a topoisomerase I inhibitor, a topoisomerase II inhibitor, a gyrase inhibitor, a protein synthesis inhibitor, a proteosome inhibitor, and an anti-metabolite.

In certain embodiments of the antibody-drug conjugate (ADC) of formula (Ia) or (Ib), the CTX is a chemotherapeutic agent. Those of ordinary skill in the art will be aware of appropriate chemotherapeutic agents as disclosed, for example, in Chu, E., DeVite, V. T., 2012, Physicians' Cancer Chemotherapy Drug Manual 2012 (Jones & Bartlett Learning Oncology), and similar documents.

In certain embodiments, the CTX may be any FDA-approved chemotherapeutic agent. In certain embodiments, the CTX may be any FDA-approved chemotherapeutic agent available for cancer treatment.

In certain embodiments, the CTX is selected from the group consisting of an alkylating agents, an anthracyclines, a cytoskeletal disruptors (taxanes), an epothilones, an histone deacetylase Inhibitor (HDAC), an inhibitor of Topoisomerase I, an Inhibitor of Topoisomerase II, a kinase inhibitor, a monoclonal antibodies, a nucleotide analog, a peptide antibiotic, a platinum-based agent, a retinoids, a Vinca alkaloid or a derivative thereof, and radioisotope.

In certain embodiments, the CTX is selected from the group consisting of Actinomycin, all-trans retinoic acid, Azacitidine, Azathioprine, Bleomycin, Bortezomib, Carboplatin, Capecitabine, Cisplatin, Chlorambucil, Cyclophosphamide, Cytarabine, Daunorubicin, Docetaxel, Doxifluridine, Doxorubicin, Epirubicin, Epothilone, Etoposide, Fluorouracil, Gemcitabine, Hydroxyurea, Idarubicin, Imatinib, Irinotecan, Mechlorethamine, Mercaptopurine, Methotrexate, Mitoxantrone, Oxaliplatin, Paclitaxel, Pemetrexed, Teniposide, Tioguanine, Topotecan, Valrubicin, Vinblastine, Vincristine, Vindesine, and Vinorelbine.

In certain embodiments, the CTX is selected from the group consisting of a tubulin stabilizer, a tubulin destabilizer, a DNA alkylator, a DNA minor groove binder, a DNA intercalator, a topoisomerase I inhibitor, a topoisomerase II inhibitor, a gyrase inhibitor, a protein synthesis inhibitor, a proteosome inhibitor, and an anti-metabolite.

In certain embodiments, the CTX is selected from the group consisting of Actinomycin D, Amonafide, an auristatin, benzophenone, benzothiazole, a calicheamicin, Camptothecin, CC-1065 (NSC 298223), Cemadotin, Colchicine, Combretastatin A4, Dolastatin, Doxorubicin, Elinafide, Emtansine (DM1), Etoposide, KF-12347 (Leinamycin), a maytansinoid, Methotrexate, Mitoxantrone, Nocodazole, Proteosome Inhibitor 1 (PSI 1), Roridin A, T-2 Toxin (trichothecene analog), Taxol, a tubulysin, Velcade®, and Vincristine. In certain embodiments, the CTX is an auristatin, a calicheamicin, a maytansinoid, or a tubulysin.

In certain embodiments, the CTX is monomethylauristatin E (MMAE), monomethylauristatin F (MMAF), a pyrrolobenzodiazepine (PDB), calicheamicin γ, mertansine, or tubulysin T2. In certain embodiments, the CTX is MMAE or MMAF. In certain embodiments, the CTX is a PDB. In certain embodiments, the CTX is tubulysin T2. In certain embodiments, the CTX is tubulysin T3, or tubulysin T4, the structures for which are provided below:

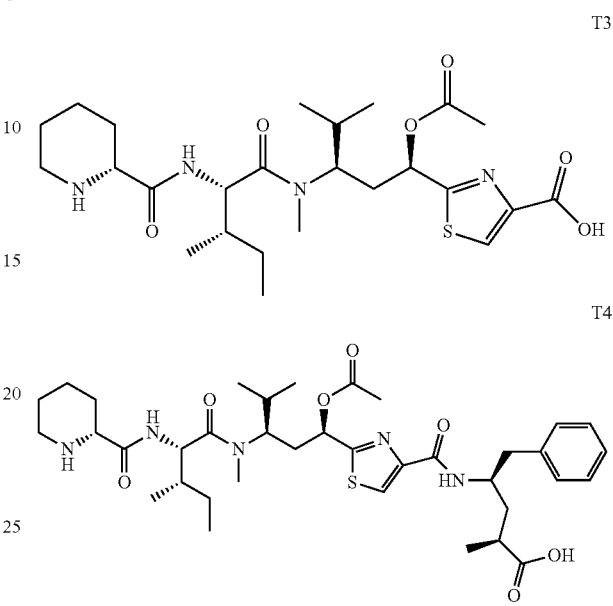

5.3 Other Molecules Binding to BTN1A1 or a BTN1A1 Ligand

In another aspect, provided herein are molecules that selectively bind to BTN1A1 or a BTN1A1 ligand, such GAL-1, GAL-9, NRP-2, or BTLA, whereby the molecule can inhibit the binding of the BTN1A1 ligand to BTN1A1. In some embodiments, the molecule is not an antibody and does not include an antigen binding domain. In some embodiments, the molecule is a decoy receptor, e.g., a GAL-1, GAL-9, NRP-2, BTLA, or BTN1A1 decoy receptor or soluble receptor. In some embodiments, the molecule can inhibit formation of a BTN1A1-BTN1A1 ligand complex (e.g., a complex including GAL-1, GAL-9, NRP-2, or BTLA, and BTN1A1). In some embodiments, the molecule can disrupt a formed BTN1A1-BTN1A1 ligand complex (e.g., a complex including GAL-1, GAL-9, NRP-2, or BTLA, and BTN1A1). In some embodiments, the molecules provided herein that selectively binds to BTN1A1 or a BTN1A1 ligand, such GAL-1, GAL-9, NRP-2, or BTLA, whereby the molecule can inhibit the binding of the BTN1A1 ligand to BTN1A1 can inhibit the immune suppressive function of BTN1A1 or a BTN1A1-BTN1A1 ligand complex.

In another aspect, provided herein is a molecule that selectively binds to BTN1A1 or a BTN1A1 ligand, such GAL-1, GAL-9, NRP-2, or BTLA, whereby the molecule can inhibit the binding of the BTN1A1 ligand to BTN1A1. In some embodiments, the molecule is not an antibody and does not have an antigen binding fragment. In some embodiments, the molecule can inhibit binding of BTN1A1 to GAL-1. In some embodiments, the molecule can inhibit binding of BTN1A1 to GAL-9. In some embodiments, the molecule can inhibit binding of BTN11A1 to NRP-2. In some embodiments, the molecule can inhibit binding of BTN1A1 to BTLA. In some embodiments, the molecule can inhibit binding of a BTN1A1 ligand, such as GAL-1, GAL-9, NRP-2, or BTLA to BTN1A1 completely. In some embodiments, the molecule can inhibit binding of a BTN1A1 ligand, such as GAL-1, GAL-9, NRP-2, or BTLA, to BTN1A1 at least partially. In some embodiments, the molecule can inhibit at least 1%, at least 3%, at least 5%, at least 10%, at least 15%, at least 20%, at least 25%, at least 30%, at least 40%, at least 50%, at least 60%, at least 70%, at least 80%, at least 90%, at least 95%, or at least 99% of binding of a BTN1A1 ligand, such as GAL-1, GAL-9, NPR-2, or BTLA to BTN1A1. In some embodiments, binding of BTN1A1 to a BTN1A1 ligand, such as GAL-1, GAL-9, NRP-2, or BTLA, or inhibition thereof, is determined using surface plasmon resonance, biolayer interferometry, or co-immunoprecipitation. In some embodiments, the molecule can inhibit binding of a BTN1A1 ligand, such as GAL-1, GAL-9, NRP-2, or BTLA, to BTN1A1 with an IC50 value of less than 1 µM, less than 900 nM, less than 800 nM, less than 700 nM, less than 600 nM, less than 500 nM, less than 400 nM, less than 300 nM, less than 200 nM, less than 100 nM, less than 90 nM, less than 80 nM, less than 70 nM, less than 60 nM, less than 50 nM, less than 40 nM, less than 30 nM, less than 20 nM, less than 10 nM, less than 9 nM, less than 8 nM, less than 8 nM, less than 7 nM, less than 6 nM, less than 5 nM, less than 4 nM, less than 3 nM, less than 2 nM, or less than 1 nM. In some embodiments, the neutralization assay is a surface plasmon resonance, biolayer interferometry, co-immunoprecipitation, FRET, or TR-FRET assay, or an ELISA.

In some embodiments, the molecule selectively binds to BTN1A1, whereby the molecule can inhibit binding of two or more BN1A1 ligands, such as GAL-1, GAL-9, NRP-2, or BTLA, to BTN1A1. In some embodiments, the molecule can inhibit binding of GAL-1 and GAL-9 to BTN1A1. In some embodiments, the molecule can inhibit binding of GAL-1 and NRP-2 to BTN1A1. In some embodiments, the molecule can inhibits binding of GAL-1 and BTLA to BTN1A1. In some embodiments, the molecule can inhibit binding of GAL-9 and NRP-2 to BTN1A1. In some embodiments, the molecule can inhibit binding of GAL-9 and BTLA to BTN1A1. In some embodiments, the molecule can inhibit binding of NRP-2 and BTLA to BTN1A1. In some embodiment, the molecule can inhibit binding of GAL-1, GAL-9, and NRP-2 to BTN1A1. In some embodiments, the molecule can inhibit binding of GAL-1, GAL-9, and BTLA to BTN1A1. In some embodiments, the molecule can inhibit binding of GAL-1, NRP-2, and BTLA to BTN1A1. In some embodiments, the molecule can inhibit binding of GAL-9, NRP-2 and BTLA to BTN1A1. In some embodiments, the molecule can inhibit binding of GAL-1, GAL-9, NRP-2, and BTLA to BTN1A1.

In some embodiments, the molecule selectively binds to the extracellular domain (ECD) of BTN1A1.

In some embodiments the molecule provided herein can bind a BTN1A1 ligand, such as GAL-1, GAL-9, NRP-2, or BTLA, with a dissociation constant of 1 µM or less, 900 nM or less, 800 nM or less, 700 nM or less, 600 nM or less, 500 nM or less, 400 nM or less, 300 nM or less, 200 nM or less, 100 nM or less, 90 nM or less, 80 nM or less, 70 nM or less, 60 nM or less, 50 nM or less, 40 nM or less, 30 nM or less, 20 nM or less, 10 nM or less, 5 nM or less, 3 nM or less, or 1 nM or less. In some embodiments, the molecule can bind to GAL-1 with a dissociation constant of 1 µM or less, 900 nM or less, 800 nM or less, 700 nM or less, 600 nM or less, 500 nM or less, 400 nM or less, 300 nM or less, 200 nM or less, 100 nM or less, 90 nM or less, 80 nM or less, 70 nM or less, 60 nM or less, 50 nM or less, 40 nM or less, 30 nM or less, 20 nM or less, 10 nM or less, 5 nM or less, 3 nM or less, or 1 nM or less. In some embodiments, the molecule can bind to GAL-9 with a dissociation constant of 1 µM or less, 900 nM or less, 800 nM or less, 700 nM or less, 600 nM or less, 500 nM or less, 400 nM or less, 300 nM or less, 200 nM or less, 100 nM or less, 90 nM or less, 80 nM or less, 70 nM or less, 60 nM or less, 50 nM or less, 40 nM or less, 30 nM or less, 20 nM or less, 10 nM or less, 5 nM or less, 3 nM or less, or 1 nM or less. In some embodiments, the molecule can bind NRP-2 with a dissociation constant of 1 µM or less, 900 nM or less, 800 nM or less, 700 nM or less, 600 nM or less, 500 nM or less, 400 nM or less, 300 nM or less, 200 nM or less, 100 nM or less, 90 nM or less, 80 nM or less, 70 nM or less, 60 nM or less, 50 nM or less, 40 nM or less, 30 nM or less, 20 nM or less, 10 nM or less, 5 nM or less, 3 nM or less, or 1 nM or less. In some embodiments, the molecule can bind BTLA with a dissociation constant of 1 µM or less, 900 nM or less, 800 nM or less, 700 nM or less, 600 nM or less, 500 nM or less, 400 nM or less, 300 nM or less, 200 nM or less, 100 nM or less, 90 nM or less, 80 nM or less, 70 nM or less, 60 nM or less, 50 nM or less, 40 nM or less, 30 nM or less, 20 nM or less, 10 nM or less, 5 nM or less, 3 nM or less, or 1 nM or less.

In some embodiments, the molecule can modulate an activity or signaling of BTN1A1 or an activity or signaling of a complex of BTN1A1 and a BTN1A1 ligand, such as GAL-1, GAL-9, NRP-2, or BTLA.

In some embodiments, the molecule can modulate T-cell activity. In some embodiment, the T-cell is a CD8+ cell. In some embodiments, the molecule can increase T-cell activation or T-cell proliferation. In some embodiments, the molecule can inhibit T-cell apoptosis In some embodiments, the molecule is a GAL-1 decoy. In some embodiments, the molecule is a GAL-1 decoy as described in International Application No. PCT/US2002/031273 (published, e.g., as WO2003026494 A3), which is hereby incorporated by reference herein. In some embodiments, the molecule is a GAL-9 decoy. In some embodiments, the molecule is a NRP-2 decoy. In some embodiments, the molecule is a BTLA decoy receptor. In some embodiments, the molecule is a soluble BTLA receptor (e.g., a BTLA extracellular domain construct, such as a BTLA-ECD-Fc construct). In some embodiments, the molecule is a membrane-bound BTLA decoy receptor (e.g., a truncated BTLA lacking the cytoplasmic domain). In some embodiments, the molecule is a BTN1A1 decoy or soluble receptor. In some embodiments, the molecule is a BTN1A1 binding agent as described in International Application No. PCT/US2014/071853 (published, e.g., as WO2015100219 A1).

5.4 Compositions

Provided herein are also compositions having molecules that selectively bind to BTN1A1 or a BTN1A1 ligand, such GAL-1, GAL-9, NRP-2, or BTLA, whereby the molecule can inhibit the binding of the BTN1A1 ligand to BTN1A1. In some embodiments, the molecule is not an antibody and does not include an antigen binding fragment. In some embodiments, the molecule is a decoy receptor, e.g., a GAL-1, GAL-9, NRP-2, BTLA, or BTN1A1 decoy receptor or soluble receptor.

In another aspect, provided herein are also compositions having molecules that have an antigen binding fragment, which immunospecifically binds to BTN1A1 or to a BTN1A1 ligand, whereby the molecule can inhibit the binding of a BTN1A1 ligand, such a GAL-1, GAL-9, NRP-2 or BTLA, to BTN1A1. In some embodiments, the antigen binding fragment immunospecifically binds to BTN1A1

(e.g., glycosylated BTN1A1 or a BTN1A1 dimer). In some embodiments, the antigen binding fragment immunospecifically binds to a BTN1A1 ligand (e.g., GAL-1, GAL-9, NRP-2, or BTLA). In some embodiments, the antigen binding fragment immunospecifically binds to GAL-1. In some embodiments, the antigen binding fragment immunospecifically binds to GAL-9. In some embodiments, the antigen binding fragment immunospecifically binds to NRP-2. In some embodiments, the antigen binding fragment immunospecifically binds to BTLA. In some embodiment, the antigen binding fragment immunospecifically binds to BTN1A1. In some embodiments, the antigen binding fragment immunospecifically binds to BTN1A1 glycosylated at positions N55, N215, and/or N449. In some embodiments, the antigen binding fragment immunospecifically binds to BTN1A1 glycosylated at position N55. In some embodiments, the antigen binding fragment immunospecifically binds to BTN1A1 glycosylated at position N215. In some embodiments, the antigen binding fragment immunospecifically binds to BTN1A1 glycosylated at position N449. In some embodiments, the antigen binding fragment immunospecifically binds to one or more glycosylation motifs. In some embodiments, the antigen binding fragment immunospecifically binds to BTN1A1 glycosylated at positions N55 and N215. In some embodiments, the antigen binding fragment immunospecifically binds to BTN1A1 glycosylated at positions N215 and N449. In some embodiments, the antigen binding fragment immunospecifically binds to BTN1A1 glycosylated at positions N55 and N449. In some embodiments, the antigen binding fragment immunospecifically binds to BTN1A1 glycosylated at positions N55, N215 and N449. In some embodiments, the antigen binding fragment immunospecifically binds to a BTN1A1 dimer, e.g., a BTN1A1 dimer glycosylated at one or more of positions N55, N215 and N449 of one or more of the BTN1A1 monomers in the BTN1A1 dimer.

In some embodiments, the compositions have molecules that have an antigen binding fragment that immunospecifically binds to BTN1A1, whereby the molecule can inhibit binding of a BTN1A1 ligand, such as GAL-1, GAL-9, NRP-2, or B- and BTLA, to BTN1A1. In some embodiments, the molecule can inhibit binding of BTN1A1 to GAL-1. In some embodiments, the molecule can inhibit binding of BTN1A1 to GAL-9. In some embodiments, the molecule can inhibit binding of BTN11A1 to NRP-2. In some embodiments, the molecule can inhibit binding of BTN1A1 to BTLA. In some embodiments, the molecule can inhibit binding of a BTN1A1 ligand, such as GAL-1, GAL-9, NRP-2, or BTLA to BTN1A1 completely. In some embodiments, the molecule can inhibit binding of a BTN1A1 ligand, such as GAL-1, GAL-9, NRP-2, or BTLA, to BTN1A1 at least partially. In some embodiments, the molecule can inhibit at least 1%, at least 3%, at least 5%, at least 10%, at least 15%, at least 20%, at least 25%, at least 30%, at least 40%, at least 50%, at least 60%, at least 70%, at least 80%, at least 90%, at least 95%, or at least 99% of binding of a BTN1A1 ligand, such as GAL-1, GAL-9, NPR-2, or BTLA to BTN1A1. In some embodiments, binding of BTN1A1 to a BTN1A1 ligand, such as GAL-1, GAL-9, NRP-2, or BTLA, or inhibition thereof, is determined using surface plasmon resonance, biolayer interferometry, or co-immunoprecipitation. In some embodiments, the molecule can inhibit binding of a BTN1A1 ligand, such as GAL-1, GAL-9, NRP-2, or BTLA, to BTN1A1 with an IC50 value of less than 1 µM, less than 900 nM, less than 800 nM, less than 700 nM, less than 600 nM, less than 500 nM, less than 400 nM, less than 300 nM, less than 200 nM, less than 100 nM, less than 90 nM, less than 80 nM, less than 70 nM, less than 60 nM, less than 50 nM, less than 40 nM, less than 30 nM, less than 20 nM, less than 10 nM, less than 9 nM, less than 8 nM, less than 8 nM, less than 7 nM, less than 6 nM, less than 5 nM, less than 4 nM, less than 3 nM, less than 2 nM, or less than 1 nM. In some embodiments, the neutralization assay is a surface plasmon resonance, biolayer interferometry, co-immunoprecipitation, FRET, or TR-FRET assay, or an ELISA.

In some embodiments, the compositions have molecules that have an antigen binding fragment that immunospecifically binds to BTN1A1, whereby the molecule can inhibit binding of two or more BN1A1 ligands, such as GAL-1, GAL-9, NRP-2, or BTLA, to BTN1A1. In some embodiments, the molecule can inhibit binding of GAL-1 and GAL-9 to BTN1A1. In some embodiments, the molecule can inhibit binding of GAL-1 and NRP-2 to BTN1A1. In some embodiments, the molecule can inhibits binding of GAL-1 and BTLA to BTN1A1. In some embodiments, the molecule can inhibit binding of GAL-9 and NRP-2 to BTN1A1. In some embodiments, the molecule can inhibit binding of GAL-9 and BTLA to BTN1A1. In some embodiments, the molecule can inhibit binding of NRP-2 and BTLA to BTN1A1. In some embodiment, the molecule can inhibit binding of GAL-1, GAL-9, and NRP-2 to BTN1A1. In some embodiments, the molecule can inhibit binding of GAL-1, GAL-9, and BTLA to BTN1A1. In some embodiments, the molecule can inhibit binding of GAL-1, NRP-2, and BTLA to BTN1A1. In some embodiments, the molecule can inhibit binding of GAL-9, NRP-2 and BTLA to BTN1A1. In some embodiments, the molecule can inhibit binding of GAL-1, GAL-9, NRP-2, and BTLA to BTN1A1.

In some embodiments, the compositions have molecules that have an antigen binding fragment that immunospecifically binds to a BTN1A1 ligand, such as GAL-1, GAL-9, NRP-2 or BTLA, whereby the molecule can inhibit binding of the BTN1A1 ligand to BTN1A1. In some embodiments, the antigen binding fragment immunospecifically binds to GAL-1 and the molecule can inhibit binding of GAL-1 to BTN1A1. In some embodiments, the antigen binding fragment immunospecifically binds to GAL-9 and the molecule can inhibit binding of GAL-9 to BTN1A1. In some embodiments, the antigen binding fragment immunospecifically binds NRP-2 and the molecule can inhibit binding of NRP-2 to BTN1A1. In some embodiments, the antigen binding fragment immunospecifically binds to BTLA and the molecule can inhibit binding of BTLA to BTN1A1. In some embodiments, the molecule can inhibit binding of a BTN1A1 ligand, such as GAL-1, GAL-9, NRP-2, or BTLA to BTN1A1 completely. In some embodiments, the molecule can inhibit binding of a BTN1A1 ligand, such as GAL-1, GAL-9, NRP-2, or BTLA, to BTN1A1 at least partially. In some embodiments, the molecule can inhibit at least 1%, at least 3%, at least 5%, at least 10%, at least 15%, at least 20%, at least 25%, at least 30%, at least 40%, at least 50%, at least 60%, at least 70%, at least 80%, at least 90%, at least 95%, or at least 99% of binding of a BTN1A1 ligand, such as GAL-1, GAL-9, NPR-2, or BTLA to BTN1A1. In some embodiments, binding of BTN1A1 to a BTN1A1 ligand, such as GAL-1, GAL-9, NRP-2, or BTLA, or inhibition thereof, is determined using surface plasmon resonance, biolayer interferometry, or co-immunoprecipitation. In some embodiments, the molecule can inhibit binding of a BTN1A1 ligand, such as GAL-1, GAL-9, NRP-2, or BTLA, to BTN1A1 with an IC50 value of less than 1 µM, less than 900 nM, less than 800 nM, less than 700 nM, less than 600 nM, less than 500 nM, less than 400 nM, less than 300 nM, less than 200 nM, less than 100 nM, less than 90 nM, less than 80 nM, less than 70 nM, less than 60 nM, less than 50 nM, less than 40 nM, less than 30 nM, less than 20 nM, less than 10 nM, less than 9 nM, less than 8 nM, less than 8 nM, less than 7 nM, less than 6 nM, less than 5 nM, less than 4 nM, less than 3 nM, less than 2 nM, or less than 1 nM. In some embodiments, the neutralization assay is a surface plasmon resonance, biolayer interferometry, co-immunoprecipitation, FRET, or TR-FRET assay, or an ELISA.

In some embodiments, provided herein are compositions having molecules that have an antigen binding fragment that can bind a BTN1A1 ligand, such as GAL-1, GAL-9, NRP-2, or BTLA, with a dissociation constant of 1 μM or less, 900 nM or less, 800 nM or less, 700 nM or less, 600 nM or less, 500 nM or less, 400 nM or less, 300 nM or less, 200 nM or less, 100 nM or less, 90 nM or less, 80 nM or less, 70 nM or less, 60 nM or less, 50 nM or less, 40 nM or less, 30 nM or less, 20 nM or less, 10 nM or less, 5 nM or less, 3 nM or less, or 1 nM or less, whereby the molecules can inhibit the binding of the BTN1A1 ligand to BTN1A1. In some embodiments, the antigen binding fragment can bind to GAL-1 with a dissociation constant of 1 μM or less, 900 nM or less, 800 nM or less, 700 nM or less, 600 nM or less, 500 nM or less, 400 nM or less, 300 nM or less, 200 nM or less, 100 nM or less, 90 nM or less, 80 nM or less, 70 nM or less, 60 nM or less, 50 nM or less, 40 nM or less, 30 nM or less, 20 nM or less, 10 nM or less, 5 nM or less, 3 nM or less, or 1 nM or less. In some embodiments, the antigen binding fragment can bind to GAL-9 with a dissociation constant of 1 μM or less, 900 nM or less, 800 nM or less, 700 nM or less, 600 nM or less, 500 nM or less, 400 nM or less, 300 nM or less, 200 nM or less, 100 nM or less, 90 nM or less, 80 nM or less, 70 nM or less, 60 nM or less, 50 nM or less, 40 nM or less, 30 nM or less, 20 nM or less, 10 nM or less, 5 nM or less, 3 nM or less, or 1 nM or less. In some embodiments, the antigen binding fragment can bind NRP-2 with a dissociation constant of 1 μM or less, 900 nM or less, 800 nM or less, 700 nM or less, 600 nM or less, 500 nM or less, 400 nM or less, 300 nM or less, 200 nM or less, 100 nM or less, 90 nM or less, 80 nM or less, 70 nM or less, 60 nM or less, 50 nM or less, 40 nM or less, 30 nM or less, 20 nM or less, 10 nM or less, 5 nM or less, 3 nM or less, or 1 nM or less. In some embodiments, the antigen binding fragment can bind BTLA with a dissociation constant of 1 μM or less, 900 nM or less, 800 nM or less, 700 nM or less, 600 nM or less, 500 nM or less, 400 nM or less, 300 nM or less, 200 nM or less, 100 nM or less, 90 nM or less, 80 nM or less, 70 nM or less, 60 nM or less, 50 nM or less, 40 nM or less, 30 nM or less, 20 nM or less, 10 nM or less, 5 nM or less, 3 nM or less, or 1 nM or less.

In some embodiments, the molecules in the compositions provided herein have an antigen binding fragment that immunospecifically binds to BTN1A1, wherein the antigen binding fragment preferentially binds glycosylated BTN1A1 over non-glycosylated BTN1A1. In some embodiments, the glycosylated BTN1A1 is a BTN1A1 dimer. In some embodiments, the antigen binding fragments preferentially bind to BTN1A1 glycosylated at positions N55, N215, and/or N449 over non-glycosylated BTN1A1. In some embodiments, the antigen binding fragments preferentially bind to BTN1A1 glycosylated at position N55 over non-glycosylated BTN1A1. In some embodiments, the antigen binding fragments preferentially bind to BTN1A1 glycosylated at position N215 over non-glycosylated BTN1A1. In some embodiments, the antigen binding fragments preferentially bind to BTN1A1 glycosylated at position N449 over non-glycosylated BTN1A1. In some embodiments, the antigen binding fragments preferentially bind to one or more glycosylation motifs. In some embodiments, the antigen binding fragments preferentially binds BTN1A1 glycosylated at positions N55 and N215 over non-glycosylated BTN1A1. In some embodiments, the antigen binding fragments preferentially bind to BTN1A1 glycosylated at positions N215 and N449 over non-glycosylated BTN1A1. In some embodiments, the antigen binding fragments preferentially bind to BTN1A1 glycosylated at positions N55 and N449 over non-glycosylated BTN1A1. In some embodiments, the antigen binding fragments preferentially bind to BTN1A1 glycosylated at positions N55, N215 and N449 over non-glycosylated BTN1A1.

In some embodiments, the molecules in the compositions provided herein have an antigen binding fragment that immunospecifically binds to BTN1A1, whereby the antigen binding fragment preferentially binds a BTN1A1 dimer over a BTN1A1 monomer. In some embodiments, the BTN1A1 dimer is glycosylated at one or more of positions N55, N215 and N449 of one or more of the BTN1A1 monomers in the BTN1A1 dimer.

In some embodiments, the molecules in the compositions provided herein have an antigen binding fragment that binds to glycosylated BTN1A1 with $K_D$ less than half of the $K_D$ exhibited relative to unglycosylated BTN1A1. In some embodiments, the antigen binding fragment binds to glycosylated BTN1A1 with $K_D$ at least 2 times less than the $K_D$ exhibited relative to unglycosylated BTN1A1. In some embodiments, the antigen binding fragment binds to glycosylated BTN1A1 with $K_D$ at least 5 times less than the $K_D$ exhibited relative to unglycosylated BTN1A1. In some embodiments, the antigen binding fragment binds to glycosylated BTN1A1 with $K_D$ at least 10 times less than the $K_D$ exhibited relative to unglycosylated BTN1A1. In some embodiments, the antigen binding fragment binds to glycosylated BTN1A1 with $K_D$ at least 15 times less than the $K_D$ exhibited relative to unglycosylated BTN1A1. In some embodiments, the antigen binding fragment binds to glycosylated BTN1A1 with $K_D$ at least 20 times less than the $K_D$ exhibited relative to unglycosylated BTN1A1. In some embodiments, the antigen binding fragment binds to glycosylated BTN1A1 with $K_D$ at least 25 times less than the $K_D$ exhibited relative to unglycosylated BTN1A1. In some embodiments, the antigen binding fragment binds to glycosylated BTN1A1 with $K_D$ at least 30 times less than the $K_D$ exhibited relative to unglycosylated BTN1A1. In some embodiments, the antigen binding fragment binds to glycosylated BTN1A1 with $K_D$ at least 40 times less than the $K_D$ exhibited relative to unglycosylated BTN1A1. In some embodiments, the antigen binding fragment binds to glycosylated BTN1A1 with $K_D$ at least 50 times less than the $K_D$ exhibited relative to unglycosylated BTN1A1.

In some embodiments, the antigen binding fragment binds to a BTN1A1 dimer (e.g., a glycosylated BTN1A1 dimer) with $K_D$ less than half of the $K_D$ exhibited relative to a BTN1A1 monomer (e.g., a glycosylated BTN1A1 monomer). In some embodiments, the antigen binding fragment binds to a BTN1A1 dimer (e.g., a glycosylated BTN1A1 dimer) with $K_D$ at least 2 times less than the $K_D$ exhibited relative to a BTN1A1 monomer (e.g., a glycosylated BTN1A1 monomer). In some embodiments, the antigen binding fragment binds to a BTN1A1 dimer (e.g., a glycosylated BTN1A1 dimer) with $K_D$ at least 5 times less than the $K_D$ exhibited relative to a BTN1A1 monomer (e.g., a glycosylated BTN1A1 monomer). In some embodiments, the antigen binding fragment binds to a BTN1A1 dimer (e.g., a glycosylated BTN1A1 dimer) with $K_D$ at least 10 times less than the $K_D$ exhibited relative to a BTN1A1 monomer (e.g., a glycosylated BTN1A1 monomer). In some embodiments, the antigen binding fragment binds to a BTN1A1 dimer (e.g., a glycosylated BTN1A1 dimer) with $K_D$ at least 15 times less than the $K_D$ exhibited relative to a BTN1A1 monomer (e.g., a glycosylated BTN1A1 monomer). In some embodiments, the antigen binding fragment binds to a BTN1A1 dimer (e.g., a glycosylated BTN1A1 dimer) with $K_D$ at least 20 times less than the $K_D$ exhibited relative to a BTN1A1 monomer (e.g., a glycosylated BTN1A1 monomer). In some embodiments, the antigen binding fragment binds to a BTN1A1 dimer (e.g., a glycosylated BTN1A1 dimer) with $K_D$ at least 25 times less than the $K_D$ exhibited relative to a BTN1A1 monomer (e.g., a glycosylated BTN1A1 monomer). In some embodiments, the antigen binding fragment binds to a BTN1A1 dimer (e.g., a glycosylated BTN1A1 dimer) with $K_D$ at least 30 times less than the $K_D$ exhibited relative to a BTN1A1 monomer (e.g., a glycosylated BTN1A1 monomer). In some embodiments, the antigen binding fragment binds to a BTN1A1 dimer (e.g., a glycosylated BTN1A1 dimer) with $K_D$ at least 40 times less than the $K_D$ exhibited relative to a BTN1A1 monomer (e.g., a glycosylated BTN1A1 monomer). In some embodiments, the antigen binding fragment binds to a BTN1A1 dimer (e.g., a glycosylated BTN1A1 dimer) with $K_D$ at least 50 times less than the $K_D$ exhibited relative to a BTN1A1 monomer (e.g., a glycosylated BTN1A1 monomer).

In some embodiments, the antigen binding fragment binds to glycosylated BTN1A1 with an MFI that is at least twice as high as the MFI as exhibited relative to unglycosylated BTN1A1. In some embodiments, the antigen binding fragment binds to glycosylated BTN1A1 with an MFI that is at least five times as high as the MFI as exhibited relative to unglycosylated BTN1A1. In some embodiments, the antigen binding fragment binds to glycosylated BTN1A1 with an MFI that is at least 10 times as high as the MFI as exhibited relative to unglycosylated BTN1A1. In some embodiments, the antigen binding fragment binds to glycosylated BTN1A1 with an MFI that is at least 15 times as high as the MFI as exhibited relative to unglycosylated BTN1A1. In some embodiments, the antigen binding fragment binds to glycosylated BTN1A1 with an MFI that is at least 20 times as high as the MFI as exhibited relative to unglycosylated BTN1A1. In some embodiments, the antigen binding fragment binds to glycosylated BTN1A1 with an MFI that is at least 25 times as high as the MFI as exhibited relative to unglycosylated BTN1A1. In some embodiments, the antigen binding fragment binds to glycosylated BTN1A1 with an MFI that is at least 30 times as high as the MFI as exhibited relative to unglycosylated BTN1A1. In some embodiments, the antigen binding fragment binds to glycosylated BTN1A1 with an MFI that is at least 40 times as high as the MFI as exhibited relative to unglycosylated BTN1A1. In some embodiments, the antigen binding fragment binds to glycosylated BTN1A1 with an MFI that is at least 50 times as high as the MFI as exhibited relative to unglycosylated BTN1A1.

In some embodiments, the antigen binding fragment binds to a BTN1A1 dimer (e.g., a glycosylated BTN1A1 dimer) with an MFI that is at least twice as high as the MFI as exhibited relative to a BTN1A1 monomer (e.g., a glycosylated BTN1A1 monomer). In some embodiments, the antigen binding fragment binds to a BTN1A1 dimer (e.g., a glycosylated BTN1A1 dimer) with an MFI that is at least five times as high as the MFI as exhibited relative to a BTN1A1 monomer (e.g., a glycosylated BTN1A1 monomer). In some embodiments, the antigen binding fragment binds to a BTN1A1 dimer (e.g., a glycosylated BTN1A1 dimer) with an MFI that is at least 10 times as high as the MFI as exhibited relative to a BTN1A1 monomer (e.g., a glycosylated BTN1A1 monomer). In some embodiments, the antigen binding fragment binds to a BTN1A1 dimer (e.g., a glycosylated BTN1A1 dimer) with an MFI that is at least 15 times as high as the MFI as exhibited relative to a BTN1A1 monomer (e.g., a glycosylated BTN1A1 monomer). In some embodiments, the antigen binding fragment binds to a BTN1A1 dimer (e.g., a glycosylated BTN1A1 dimer) with an MFI that is at least 20 times as high as the MFI as exhibited relative to a BTN1A1 monomer (e.g., a glycosylated BTN1A1 monomer). In some embodiments, the antigen binding fragment binds to a BTN1A1 dimer (e.g., a glycosylated BTN1A1 dimer) with an MFI that is at least 25 times as high as the MFI as exhibited relative to a BTN1A1 monomer (e.g., a glycosylated BTN1A1 monomer). In some embodiments, the antigen binding fragment binds to a BTN1A1 dimer (e.g., a glycosylated BTN1A1 dimer) with an MFI that is at least 30 times as high as the MFI as exhibited relative to a BTN1A1 monomer (e.g., a glycosylated BTN1A1 monomer). In some embodiments, the antigen binding fragment binds to a BTN1A1 dimer (e.g., a glycosylated BTN1A1 dimer) with an MFI that is at least 35 times as high as the MFI as exhibited relative to a BTN1A1 monomer (e.g., a glycosylated BTN1A1 monomer). In some embodiments, the antigen binding fragment binds to a BTN1A1 dimer (e.g., a glycosylated BTN1A1 dimer) with an MFI that is at least 40 times as high as the MFI as exhibited relative to a BTN1A1 monomer (e.g., a glycosylated BTN1A1 monomer). In some embodiments, the antigen binding fragment binds to a BTN1A1 dimer (e.g., a glycosylated BTN1A1 dimer) with an MFI that is at least 50 times as high as the MFI as exhibited relative to a BTN1A1 monomer (e.g., a glycosylated BTN1A1 monomer).

In some embodiments, the molecules in the compositions provided herein have an antigen binding fragment that immunospecifically masks BTN1A1 glycosylation at positions N55, N215, and/or N449. In some embodiments, the antigen binding fragments immunospecifically mask BTN1A1 glycosylation at position N55. In some embodiments, the antigen binding fragments immunospecifically mask BTN1A1 glycosylation at position N215. In some embodiments, the antigen binding fragments immunospecifically mask BTN1A1 glycosylation at position N449. In some embodiments, the antigen binding fragments immunospecifically mask one or more glycosylation motifs of BTN1A1. In some embodiments, the antigen binding fragments immunospecifically mask BTN1A1 glycosylation at positions N55 and N215. In some embodiments, the antigen binding fragments immunospecifically mask BTN1A1 glycosylation at positions N215 and N449. In some embodiments, the antigen binding fragments immunospecifically mask BTN1A1 glycosylation at positions N55 and N449. In some embodiments, the antigen binding fragments immunospecifically mask BTN1A1 glycosylation at positions N55, N215 and N449.

In some embodiments, the composition can have at least 0.1% by weight the antibodies or other molecules as described herein. In some embodiments, the composition can have at least 0.5%, 1%, 2%, 3%, 4%, 5%, 6%, 7% 8%, 9%, 10%, 15%, 20%, 25%, 30%, 35%, 40%, 45%, 50%, 55%, 60%, 65%, 70%, 75%, 80%, 85%, 90%, or more by weight of the anti-BTN1A1 antibodies, anti-BTN1A1 ligand (e.g., GAL-1, GAL-9, NRP-2, or BTLA) antibodies or other molecules having an antigen binding fragment that immunospecifically binds to BTN1A1 of a BTN1A1 ligand. In other embodiments, for example, the anti-BTN1A1 antibodies, anti-BTN1A1 ligand (e.g., GAL-1, GAL-9, NRP-, or BTLA) antibodies or other molecules having an antigen binding fragment that immunospecifically binds to BTN1A1 can constitute between about 2% to about 75% of the weight of the composition, between about 25% to about 60%, between about 30% to about 50%, or any range therein.

The composition can be a pharmaceutical composition having anti-BTN1A1 antibodies, anti-BTN1A1 ligand (e.g., GAL-1, GAL-9, NRP-, or BTLA) antibodies or other molecules having an antigen binding fragment that immunospecifically binds to BTN1A1 or a BTN1A1 ligand as the active ingredient as well as a pharmaceutically acceptable carrier. The pharmaceutical composition can further include one or more additional active ingredient. A pharmaceutically acceptable carrier can be a carrier approved by a regulatory agency of the Federal or a state government, or listed in the U.S. Pharmacopeia, European Pharmacopeia or other generally recognized Pharmacopeia for use in animals, and more particularly in humans.

The preparation of a pharmaceutical composition having the antibodies or other molecules as described herein as active ingredient are known to those of skill in the art in light of the present disclosure, as exemplified by Remington's Pharmaceutical Sciences, 18th Ed., 1990, incorporated herein by reference. Moreover, for animal (including human) administration, it is understood that preparations should meet sterility, pyrogenicity, general safety, and purity standards as required by FDA Office of Biological Standards.

The pharmaceutically acceptable carriers include liquid, semi-solid, i.e., pastes, or solid carriers. Examples of carriers or diluents include fats, oils, water, saline solutions, lipids, liposomes, resins, binders, fillers, and the like, or combinations thereof. The pharmaceutically acceptable carrier can include aqueous solvents (e.g., water, alcoholic/aqueous solutions, ethanol, saline solutions, parenteral vehicles, such as sodium chloride, Ringer's dextrose, etc.), non-aqueous solvents (e.g., propylene glycol, polyethylene glycol, vegetable oil, and injectable organic esters, such as ethyloleate), dispersion media, coatings (e.g., lecithin), surfactants, antioxidants, preservatives (e.g., antibacterial or antifungal agents, anti-oxidants, chelating agents, inert gases, parabens (e.g., methylparabens, propylparabens), chlorobutanol, phenol, sorbic acid, thimerosal), isotonic agents (e.g., sugars, sodium chloride), absorption delaying agents (e.g., aluminum monostearate, gelatin), salts, drugs, drug stabilizers (e.g., buffers, amino acids, such as glycine and lysine, carbohydrates, such as dextrose, mannose, galactose, fructose, lactose, sucrose, maltose, sorbitol, mannitol, etc), gels, binders, excipients, disintegration agents, lubricants, sweetening agents, flavoring agents, dyes, fluid and nutrient replenishers, such like materials and combinations thereof, as would be known to one of ordinary skill in the art. Except insofar as any conventional media, agent, diluent, or carrier is detrimental to the recipient or to the therapeutic effectiveness of the composition contained therein, its use in administrable composition for use in practicing the methods is appropriate. The pH and exact concentration of the various components in a pharmaceutical composition are adjusted according to well-known parameters. In accordance with certain aspects of the present disclosure, the composition can be combined with the carrier in any convenient and practical manner, i.e., by solution, suspension, emulsification, admixture, encapsulation, absorption, grinding, and the like. Such procedures are routine for those skilled in the art.

In some embodiments, a pharmaceutically acceptable carrier can be an aqueous pH buffered solution. Examples include buffers such as phosphate, citrate, and other organic acids; antioxidants including ascorbic acid; low molecular weight ((e.g., less than about 10 amino acid residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

In some embodiments, pharmaceutically acceptable carriers can be sterile liquids, such as water and oils, including those of petroleum, animal, vegetable or synthetic origin, such as peanut oil, soybean oil, mineral oil, sesame oil and the like. Water can be a carrier, particularly when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, polysorbate-80 and the like. The composition can also contain minor amounts of wetting or emulsifying agents, or pH buffering agents. These compositions can take the form of solutions, suspensions, emulsion, tablets, pills, capsules, powders, sustained-release formulations and the like.

Certain embodiments of the present disclosure can have different types of carriers depending on whether it is to be administered in solid, liquid, or aerosol form, and whether it needs to be sterile for the route of administration, such as injection. The compositions can be formulated for administration intravenously, intradermally, transdermally, intrathecally, intraarterially, intraperitoneally, intranasally, intravaginally, intrarectally, intramuscularly, subcutaneously, mucosally, orally, topically, locally, by inhalation (e.g., aerosol inhalation), by injection, by infusion, by continuous infusion, by localized perfusion bathing target cells directly, via a catheter, via a lavage, in lipid compositions (e.g., liposomes), or by other methods or any combination of the forgoing as would be known to one of ordinary skill in the art (see, for example, Remington's Pharmaceutical Sciences, 18th Ed., 1990, incorporated herein by reference). Typically, such compositions can be prepared as either liquid solutions or suspensions; solid forms suitable for use to prepare solutions or suspensions upon the addition of a liquid prior to injection can also be prepared; and, the preparations can also be emulsified.

The anti-BTN1A1 antibodies, anti-BTN1A1 ligand (e.g., GAL-1, GAL-9, NRP-, or BTLA) antibodies or other molecules having an antigen binding fragment that immunospecifically binds to BTN1A1 or a BTN1A1 ligand can be formulated into a composition in a free base, neutral, or salt form. Pharmaceutically acceptable salts include the acid addition salts, e.g., those formed with the free amino groups of a proteinaceous composition, or which are formed with inorganic acids, such as, for example, hydrochloric or phosphoric acids, or such organic acids as acetic, oxalic, tartaric, or mandelic acid. Salts formed with the free carboxyl groups can also be derived from inorganic bases, such as, for example, sodium, potassium, ammonium, calcium, or ferric hydroxides; or such organic bases as isopropylamine, trimethylamine, 2-ethylamino ethanol, histidine, or procaine.

In further embodiments, provided herein are pharmaceutical compositions having a lipid. A lipid can broadly include a class of substances that are characteristically insoluble in water and extractable with an organic solvent. Examples include compounds that contain long-chain aliphatic hydrocarbons and their derivatives. A lipid can be naturally occurring or synthetic (i.e., designed or produced by man). A lipid can be a biological substance. Biological lipids are well known in the art, and include for example, neutral fats, phospholipids, phosphoglycerides, steroids, terpenes, lysolipids, glycosphingolipids, glycolipids, sulphatides, lipids with ether- and ester-linked fatty acids, polymerizable lipids, and combinations thereof. Compounds other than those specifically described herein that are understood by one of skill in the art as lipids can also be used.

One of ordinary skill in the art would be familiar with the range of techniques that can be employed for dispersing a composition in a lipid vehicle. For example, antibodies can be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

Generally, the ingredients of compositions are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The amount of active ingredient in each therapeutically useful composition can be prepared in such a way that a suitable dosage will be obtained in any given unit dose of the compound. Factors, such as solubility, bioavailability, biological half-life, route of administration, product shelf life, as well as other pharmacological considerations, can be contemplated by one skilled in the art of preparing such pharmaceutical formulations, and as such, a variety of dosages and treatment regimens may be desirable.

A unit dose or dosage refers to physically discrete units suitable for use in a subject, each unit containing a predetermined quantity of the pharmaceutical composition calculated to produce the desired responses discussed above in association with its administration, i.e., the appropriate route and treatment regimen. The quantity to be administered, both according to number of treatments and unit dose, depends on the effect desired. The actual dosage amount of a composition of the present embodiments administered to a patient or subject can be determined by physical and physiological factors, such as body weight, the age, health, and sex of the subject, the type of disease being treated, the extent of disease penetration, previous or concurrent therapeutic interventions, idiopathy of the patient, the route of administration, and the potency, stability, and toxicity of the particular therapeutic substance. In other non-limiting examples, a dose can have from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 milligram/kg/body weight or more per administration, and any range derivable therein. In non-limiting examples of a derivable range from the numbers listed herein, a range of about 5 milligram/kg/body weight to about 100 milligram/kg/body weight, about 5 microgram/kg/body weight to about 500 milligram/kg/body weight, etc., can be administered, based on the numbers described above. The practitioner responsible for administration will, in any event, determine the concentration of active ingredient(s) in a composition and appropriate dose(s) for the individual subject.

As a person of ordinary skill in the art would understand, the compositions described herein are not limited by the particular nature of the therapeutic preparation. For example, such compositions can be provided in formulations together with physiologically tolerable liquid, gel, or solid carriers, diluents, and excipients. These therapeutic preparations can be administered to mammals for veterinary use, such as with domestic animals, and clinical use in humans in a manner similar to other therapeutic agents. In general, the dosage required for therapeutic efficacy varies according to the type of use and mode of administration, as well as the particularized requirements of individual subjects. The actual dosage amount of a composition administered to an animal patient, including a human patient, can be determined by physical and physiological factors, such as body weight, severity of condition, the type of disease being treated, previous or concurrent therapeutic interventions, idiopathy of the patient, and on the route of administration. Depending upon the dosage and the route of administration, the number of administrations of a preferred dosage and/or an effective amount can vary according to the response of the subject. The practitioner responsible for administration will, in any event, determine the concentration of active ingredient(s) in a composition and appropriate dose(s) for the individual subject.

5.5 Therapeutic Uses and Methods of Treatments

BTN1A1 is specifically and highly expressed in cancer cells.

In another aspect, provided herein are therapeutic uses in cancer treatments for molecules that selectively bind to BTN1A1 or a BTN1A1 ligand, such GAL-1, GAL-9, NRP-2, or BTLA, whereby the molecule can inhibit the binding of the BTN1A1 ligand to BTN1A1. In some embodiments, the molecule is not an antibody and does not include an antigen binding fragment. In some embodiments, the molecule is a decoy receptor, e.g., a GAL-1, GAL-9, NRP-2, BTLA, or BTN1A1 decoy receptor or soluble receptor.

In another aspect, provided herein are therapeutic uses in cancer treatments for molecules that have an antigen binding fragment, which immunospecifically binds to BTN1A1 or to a BTN1A1 ligand (e.g., GAL-1, GAL-9, NRP-2 or BTLA), whereby the molecule can inhibit the binding of a BTN1A1 ligand to BTN1A1. In some embodiments, these molecules bind to BTN1A1-expressing cancer cells and induce an immune response resulting in destruction these cancer cells. In some embodiments, the molecules inhibit BTN1A1-

BTN1A1 ligand (e.g., GAL-1, GAL-2, NRP-2, BTLA) complexes. For example, in some embodiments, the molecules can prevent formation of BTN1A1-BTN1A1 ligand complexes or disrupt already formed BTN1A1-BTN1A1 ligand complexes. The molecules provided herein can enhance T-cell dependent apoptisis of cancer cells and inhibit proliferation of cancer cells.

In another aspect, provided herein is a method of treating cancer in a subject, including administering to the subject a therapeutically effective amount of a molecule that selectively binds to BTN1A1 or a BTN1A1 ligand, such GAL-1, GAL-9, NRP-2, or BTLA, whereby the molecule can inhibit the binding of the BTN1A1 ligand to BTN1A1. In some embodiments, the molecule is not an antibody and does not include an antigen binding fragment. In some embodiments, the molecule is a decoy receptor, e.g., a GAL-1, GAL-9, NRP-2, BTLA, or BTN1A1 decoy receptor or soluble receptor.

In another aspect, provided herein is a method of treating cancer in a subject, including administering to the subject a therapeutically effective amount of a molecule that has an antigen binding fragment, which immunospecifically binds to BTN1A1 or to a BTN1A1 ligand, such as GAL-1, GAL-9, NRP-2 or BTLA, whereby the molecule can inhibit the binding of the BTN1A1 ligand BTN1A1.

In some embodiments, the molecules have an antigen binding fragment that immunospecifically binds to BTN1A1, whereby the molecule can inhibit binding of a BTN1A1 ligand, such as GAL-1, GAL-9, NRP-2, or B- and BTLA, to BTN1A1. In some embodiments, the molecule can inhibit binding of BTN1A1 to GAL-1. In some embodiments, the molecule can inhibit binding of BTN1A1 to GAL-9. In some embodiments, the molecule can inhibit binding of BTN11A1 to NRP-2. In some embodiments, the molecule can inhibit binding of BTN1A1 to BTLA. In some embodiments, the molecule can inhibit binding of a BTN1A1 ligand, such as GAL-1, GAL-9, NRP-2, or BTLA to BTN1A1 completely. In some embodiments, the molecule can inhibit binding of a BTN1A1 ligand, such as GAL-1, GAL-9, NRP-2, or BTLA, to BTN1A1 at least partially. In some embodiments, the molecule can inhibit at least 1%, at least 3%, at least 5%, at least 10%, at least 15%, at least 20%, at least 25%, at least 30%, at least 40%, at least 50%, at least 60%, at least 70%, at least 80%, at least 90%, at least 95%, or at least 99% of binding of a BTN1A1 ligand, such as GAL-1, GAL-9, NPR-2, or BTLA to BTN1A1. In some embodiments, binding of BTN1A1 to a BTN1A1 ligand, such as GAL-1, GAL-9, NRP-2, or BTLA, or inhibition thereof, is determined using surface plasmon resonance, biolayer interferometry, or co-immunoprecipitation. In some embodiments, the molecule can inhibit binding of a BTN1A1 ligand, such as GAL-1, GAL-9, NRP-2, or BTLA, to BTN1A1 with an IC50 value of less than 1 µM, less than 900 nM, less than 800 nM, less than 700 nM, less than 600 nM, less than 500 nM, less than 400 nM, less than 300 nM, less than 200 nM, less than 100 nM, less than 90 nM, less than 80 nM, less than 70 nM, less than 60 nM, less than 50 nM, less than 40 nM, less than 30 nM, less than 20 nM, less than 10 nM, less than 9 nM, less than 8 nM, less than 8 nM, less than 7 nM, less than 6 nM, less than 5 nM, less than 4 nM, less than 3 nM, less than 2 nM, or less than 1 nM. In some embodiments, the neutralization assay is a surface plasmon resonance, biolayer interferometry, co-immunoprecipitation, FRET, or TR-FRET assay, or an ELISA.

In some embodiments, the molecules have an antigen binding fragment that immunospecifically binds to BTN1A1, whereby the molecule can inhibit binding of two or more BN1A1 ligands, such as GAL-1, GAL-9, NRP-2, or BTLA, to BTN1A1. In some embodiments, the molecule can inhibit binding of GAL-1 and GAL-9 to BTN1A1. In some embodiments, the molecule can inhibit binding of GAL-1 and NRP-2 to BTN1A1. In some embodiments, the molecule can inhibits binding of GAL-1 and BTLA to BTN1A1. In some embodiments, the molecule can inhibit binding of GAL-9 and NRP-2 to BTN1A1. In some embodiments, the molecule can inhibit binding of GAL-9 and BTLA to BTN1A1. In some embodiments, the molecule can inhibit binding of NRP-2 and BTLA to BTN1A1. In some embodiment, the molecule can inhibit binding of GAL-1, GAL-9, and NRP-2 to BTN1A1. In some embodiments, the molecule can inhibit binding of GAL-1, GAL-9, and BTLA to BTN1A1. In some embodiments, the molecule can inhibit binding of GAL-1, NRP-2, and BTLA to BTN1A1. In some embodiments, the molecule can inhibit binding of GAL-9, NRP-2 and BTLA to BTN1A1. In some embodiments, the molecule can inhibit binding of GAL-1, GAL-9, NRP-2, and BTLA to BTN1A1.

In some embodiments, the molecules have an antigen binding fragment that immunospecifically binds to a BTN1A1 ligand, such as GAL-1, GAL-9, NRP-2 or BTLA, whereby the molecule can inhibit binding of the BTN1A1 ligand to BTN1A1. In some embodiments, the antigen binding fragment immunospecifically binds to GAL-1 and the molecule can inhibit binding of GAL-1 to BTN1A1. In some embodiments, the antigen binding fragment immunospecifically binds to GAL-9 and the molecule can inhibit binding of GAL-9 to BTN1A1. In some embodiments, the antigen binding fragment immunospecifically binds NRP-2 and the molecule can inhibit binding of NRP-2 to BTN1A1. In some embodiments, the antigen binding fragment immunospecifically binds to BTLA and the molecule can inhibit binding of BTLA to BTN1A1. In some embodiments, the molecule can inhibit binding of a BTN1A1 ligand, such as GAL-1, GAL-9, NRP-2, or BTLA to BTN1A1 completely. In some embodiments, the molecule can inhibit binding of a BTN1A1 ligand, such as GAL-1, GAL-9, NRP-2, or BTLA, to BTN1A1 at least partially. In some embodiments, the molecule can inhibit at least 1%, at least 3%, at least 5%, at least 10%, at least 15%, at least 20%, at least 25%, at least 30%, at least 40%, at least 50%, at least 60%, at least 70%, at least 80%, at least 90%, at least 95%, or at least 99% of binding of a BTN1A1 ligand, such as GAL-1, GAL-9, NPR-2, or BTLA to BTN1A1. In some embodiments, binding of BTN1A1 to a BTN1A1 ligand, such as GAL-1, GAL-9, NRP-2, or BTLA, or inhibition thereof, is determined using surface plasmon resonance, biolayer interferometry, or co-immunoprecipitation. In some embodiments, the molecule can inhibit binding of a BTN1A1 ligand, such as GAL-1, GAL-9, NRP-2, or BTLA, to BTN1A1 with an IC50 value of less than 1 µM, less than 900 nM, less than 800 nM, less than 700 nM, less than 600 nM, less than 500 nM, less than 400 nM, less than 300 nM, less than 200 nM, less than 100 nM, less than 90 nM, less than 80 nM, less than 70 nM, less than 60 nM, less than 50 nM, less than 40 nM, less than 30 nM, less than 20 nM, less than 10 nM, less than 9 nM, less than 8 nM, less than 8 nM, less than 7 nM, less than 6 nM, less than 5 nM, less than 4 nM, less than 3 nM, less than 2 nM, or less than 1 nM. In some embodiments, the neutralization assay is a surface plasmon resonance, biolayer interferometry, co-immunoprecipitation, FRET, or TR-FRET assay, or an ELISA.

In some embodiments, the molecules have an antigen binding fragment that can bind a BTN1A1 ligand, such as GAL-1, GAL-9, NRP-2, or BTLA, with a dissociation constant of 1 µM or less, 900 nM or less, 800 nM or less, 700 nM or less, 600 nM or less, 500 nM or less, 400 nM or less, 300 nM or less, 200 nM or less, 100 nM or less, 90 nM or less, 80 nM or less, 70 nM or less, 60 nM or less, 50 nM or less, 40 nM or less, 30 nM or less, 20 nM or less, 10 nM or less, 5 nM or less, 3 nM or less, or 1 nM or less, whereby the molecules can inhibit the binding of the BTN1A1 ligand to BTN1A1. In some embodiments, the antigen binding fragment can bind to GAL-1 with a dissociation constant of 1 µM or less, 900 nM or less, 800 nM or less, 700 nM or less, 600 nM or less, 500 nM or less, 400 nM or less, 300 nM or less, 200 nM or less, 100 nM or less, 90 nM or less, 80 nM or less, 70 nM or less, 60 nM or less, 50 nM or less, 40 nM or less, 30 nM or less, 20 nM or less, 10 nM or less, 5 nM or less, 3 nM or less, or 1 nM or less. In some embodiments, the antigen binding fragment can bind to GAL-9 with a dissociation constant of 1 µM or less, 900 nM or less, 800 nM or less, 700 nM or less, 600 nM or less, 500 nM or less, 400 nM or less, 300 nM or less, 200 nM or less, 100 nM or less, 90 nM or less, 80 nM or less, 70 nM or less, 60 nM or less, 50 nM or less, 40 nM or less, 30 nM or less, 20 nM or less, 10 nM or less, 5 nM or less, 3 nM or less, or 1 nM or less. In some embodiments, the antigen binding fragment can bind NRP-2 with a dissociation constant of 1 µM or less, 900 nM or less, 800 nM or less, 700 nM or less, 600 nM or less, 500 nM or less, 400 nM or less, 300 nM or less, 200 nM or less, 100 nM or less, 90 nM or less, 80 nM or less, 70 nM or less, 60 nM or less, 50 nM or less, 40 nM or less, 30 nM or less, 20 nM or less, 10 nM or less, 5 nM or less, 3 nM or less, or 1 nM or less. In some embodiments, the antigen binding fragment can bind BTLA with a dissociation constant of 1 µM or less, 900 nM or less, 800 nM or less, 700 nM or less, 600 nM or less, 500 nM or less, 400 nM or less, 300 nM or less, 200 nM or less, 100 nM or less, 90 nM or less, 80 nM or less, 70 nM or less, 60 nM or less, 50 nM or less, 40 nM or less, 30 nM or less, 20 nM or less, 10 nM or less, 5 nM or less, 3 nM or less, or 1 nM or less.

In some embodiments, the molecules provided herein having an antigen binding fragment that immunospecifically binds to BTN1A1, including anti-BTN1A1 antibodies that can cause the internalization of BTN1A1 into lysosomes. Thus, also provided herein are methods of using molecules provided herein to deliver a compound to a cell expressing BTN1A1 by contacting the cell with molecules provided herein conjugated with the compound. The compound can be an imaging agent, a therapeutic agent, a toxin or a radionuclide as described herein. The compound can be conjugated with anti-BTN1A1 antibody. The conjugate can be any conjugate as described herein, such as an ADC. The cell can be a cancer cell. The cell can also be a population of cells that include both cancer cells and normal cells. Because cancer cells specifically and highly express BTN1A1, the molecules described herein can be used to achieve specific drug delivery to cancer cells but not normal cells.

In some embodiments, the molecules provided herein, including anti-BTN1A1 antibodies and anti-BTN1A1-ligand (GAL-1, GAL-9, NRP-2, BTLA) antibodies, can modulate an immune response in a subject. In some embodiments, the molecules can promote T-cell activation. In some embodiments, the molecules can promote T-cell proliferation. In some embodiments, the molecules can increase cytokine production. In some embodiments, the molecules provided herein can also enhance T-cell dependent apoptosis of a cell expressing BTN1A1 or inhibit the proliferation of cells expressing BTN1A1.

Accordingly, provided herein are methods of modulating an immune response in a subject by administering an effective amount of the molecules provided herein that have an antigen binding fragment that immunospecifically binds to BTN1A1 or a BTN1A1 ligand (e.g., GAL-1, GAL-9, NRP-2, BTLA), whereby the molecules can inhibit binding of the BTN1A1 ligand to BTN1A1, including anti-BTN1A1 antibodies and anti-BTN1A1 ligand antibodies. Modulating an immune response can include (a) increasing T-cell activation (e.g., $CD8^+$ T-cell activation); (b) increasing T-cell proliferation; and/or (c) increasing cytokine production. In some embodiments, the methods further include administering an anti-PD1 therapy or an anti-PD-L1 therapy.

Also provided herein are methods of enhancing T-cell dependent apoptosis of a cell expressing BTN1A1 by contacting the cell with an effective amount of molecules described herein that have an antigen binding fragment that immunospecifically binds to BTN1A1 or a BTN1A1 ligand (e.g., GAL-1, GAL-9, NRP-2, BTLA), including anti-BTN1A1 antibodies or anti-BTN1A1 ligand antibodies, whereby the molecules can inhibit binding of the BTN1A1 ligand to BTN1A1. Provided herein are also methods of inhibiting the proliferation of cells expressing BTN1A1 by contacting the cell with an effective amount of molecules described herein that have an antigen binding fragment that immunospecifically binds to BTN1A1 or a BTN1A1 ligand (e.g., GAL-1, GAL-9, NRP-2, BTLA), including anti-BTN1A1 antibodies, whereby the molecule can inhibit binding of the BTN1A1 ligand to BTN1A1. The cells can be cancer cells. In some embodiments, the methods further include administering an anti-PD1 therapy or an anti-PD-L1 therapy.

In some embodiments, these molecules can be used to treat cancer by inhibiting the suppressive activity of BTN1A1 in T-cell activation or proliferation. Accordingly, provided herein are uses of these molecules in up-modulating the immune system of a subject by inhibiting or blocking the BTN1A1 signaling. In some embodiments, provided herein are uses of these molecules to block BTN1A1 from binding T cells.

In some embodiments, these molecules result in the destruction of cancer cells through ADCC or CDC mechanism. In some embodiments, these molecules are engineered to have enhanced ADCC activity. In some embodiments, these molecules are engineered to have enhanced CDC activity. For example, these molecules can be engineered to have enhanced interaction with killer cells bearing Fc receptors. Methods to produce such engineered molecules, including engineered antibodies or Fc-fusion proteins, are described herein and also known in the art.

In another aspect, provided herein is a method of killing or inhibiting the proliferation of a cancer cell resistant to an anti-PD-1 therapy or an anti-PD-L1 therapy, including contacting the cell with an effective amount of a molecule including an antigen binding fragment that immunospecifically binds to BTN1A1 or a BTN1A1 ligand (e.g., GAL-1, GAL-9, NRP-2, or BTLA), whereby the molecule can inhibit binding of the BTN1A1 ligand to BTN1A1.

In some embodiments, provided herein are uses of molecules having an antigen binding fragment that immunospecifically binds to BTN1A1 or a BTN1A1 ligand (e.g., GAL-1, GAL-9, NRP-2, BTLA), whereby the molecule can inhibit binding of the BTN1A1 ligand to BTN1A1, including anti-BTN1A1 antibodies and anti-BTN1A1 ligand antibodies to treat a disease or disorder in a subject who overexpresses BTN1A1. In some embodiments, the expression level of BTN1A1 in the subject is higher than a reference level. The reference level can be the average or medium expression level of BTN1A1 in a population of healthy individuals. The reference level can also be determined by statistic analysis of the expression level of a sample population.

In another aspect, provided herein is a method of treating an anti-PD-1 therapy or anti-PD-L1 therapy resistant or refractory cancer in a subject, including administering to the subject a therapeutically effective amount of a molecule including an antigen binding fragment that immunospecifically binds to BTN1A1 or a BTN1A1 ligand (e.g., GAL-1, GAL-9, NRP-2, BTLA), whereby the molecule can inhibit binding of the BTN1A1 ligand to BTN1A1.

In some embodiments, the subject has an anti-PD-1 therapy or anti-PD-L1 therapy resistant cancer. In some embodiments, the subject has an anti-PD-1 therapy resistant cancer. In some embodiments, the subject has an anti-PD-L1 therapy resistant cancer.

In some embodiments, the subject has an anti-PD-1 therapy or anti-PD-L1 therapy refractory cancer. In some embodiments, the subject has an anti-PD-1 therapy refractory cancer. In some embodiment, the subject has an anti-PD-L1 therapy refractory cancer.

In some embodiments, the anti-PD-1 therapy or the anti-PD-L1 therapy includes an anti-PD-1 or anti-PD-L1 antibody or antibody fragment, or a soluble PD-1 or PD-L1 ligand, or Fc-fusion protein thereof (e.g., AMP-224, a PD-L2 Fc fusion soluble receptor).

In some embodiments, the anti-PD-1 therapy includes nivolumab (Opdivo), pembrolizumab (Keytruda®), pidilizumab, AMP-514, or AMP-224.

In some embodiments, the anti-PD-1 therapy includes an anti-PD-1 antibody provided in International Application No. PCT/US2016/64394.

In some embodiments, the anti-PD-L1 therapy includes YW243.55.S70, MPDL3280A, MEDI-4736, MSB-0010718C, or MDX-1105.

In some embodiments, the anti-PD-L1 therapy includes an antibody provided in International Application No. PCT/US2016/024691, published as WO 2016/160792 A1, and International Application No. PCT/US2017/024027.

In some embodiments, the subject is treatment naïve (e.g., the subject has not received any anti-cancer treatment) prior to treatment with the molecule including an antigen binding fragment that immunospecifically binds to BTN1A1 or a BTN1A1 ligand (e.g., GAL-1, GAL-9, NRP-2, BTLA). In some embodiments, the subject has received one or more anti-cancer treatments other than an anti-PD-1 therapy or anti-PD-L1 therapy (e.g., a chemotherapy, radiation therapy, surgery, or treatment with another targeted anticancer drug, such as Herceptin® (trastuzumab)) prior to treatment with the molecule including an antigen binding fragment that immunospecifically binds to BTN1A1 or a BTN1A1 ligand (e.g., GAL-1, GAL-9, NRP-2, BTLA). In some embodiments, the subject has received one or more anti-PD1 therapies or anti-PD-L1 therapies prior to treatment with the molecule including an antigen binding fragment that immunospecifically binds to BTN1A1 or to a BTN1A1 ligand (e.g., GAL-1, GAL-9, NRP-2, or BTLA).

In some embodiments, the anti-PD-1 therapy or anti-PD-L1 therapy resistant or refractory cancer is a lung cancer or a breast cancer. In some embodiments, the anti-PD-1 therapy or anti-PD-L1 therapy resistant or refractory cancer is a lung cancer. In some embodiments, the anti-PD-1 therapy or anti-PD-L1 therapy resistant or refractory cancer is a breast cancer. In some embodiments, the lung cancer is a Lewis lung carcinoma. In some embodiments, the breast cancer is a mammary carcinoma.

In some embodiments, the molecule including an antigen binding fragment that immunospecifically binds to BTN1A1 or to a BTN1A1 ligand (e.g., GAL-1, GAL-9, NRP-2, BTLA) is administered parenterally. In some embodiments, the molecule includes an anti-BTN1A1 dimer antibody or antigen binding fragment thereof.

In some embodiment the treatment produces at least one therapeutic effect, such as a reduction in size of a tumor, a reduction in number of metastatic lesions over time, a complete response, a partial response, or a stable disease.

In another aspect, provided herein is a method of treating cancer, including (i) obtaining a sample including cancer cells from the subject having the cancer; (ii) determining the level of BTN1A1 or of a BTN1A1 ligand (e.g., GAL-1, GAL-9, NRP-2, BTLA) in the sample; (iii) diagnosing the subject as being likely to be responsive to a molecule including an antigen binding fragment that immunospecifically binds to BTN1A1 or to a BTN1A1 ligand (e.g., GAL-1, GAL-9, NRP-2, BTLA), if the level of BTN1A1 or of the BTN1A1 ligand (e.g., GAL-1, GAL-9, NRP-2, BTLA) in the sample is higher than or equal to a BTN1A1 or BTN1A1 ligand reference level, and (iv) administering to the subject a therapeutically effective amount of the molecule including an antigen binding fragment that immunospecifically binds to BTN1A1 or to a BTN1A1 ligand (e.g., GAL-1, GAL-9, NRP-2, BTLA), whereby the molecule can inhibit binding of the BTN1A1 ligand to BTN1A1.

In another aspect, provided herein is a method of treating cancer, including (i) obtaining a sample including cancer cells from the subject having the cancer; (ii) determining the level of PD-L1 in the sample; (iii) diagnosing the subject as being likely to be responsive to a molecule including an antigen binding fragment that immunospecifically binds to BTN1A1 or a BTN1A1 ligand (e.g., GAL-1, GAL-9, NRP-2, BTLA), whereby the molecule can inhibit binding of the BTN1A1 ligand to BTN1A1, if the level of PD-L1 in the sample is lower than or equal to a PD-L1 reference level, and (iv) administering to the subject a therapeutically effective amount of the molecule including an antigen binding fragment that immunospecifically binds to BTN1A1 or the BTN1A1 ligand.

In another aspect, provided herein is a method of treating an anti-PD1 therapy or anti-PD-L1 therapy resistant or refractory cancer, including (i) obtaining a sample including cancer cells from the subject having the anti-PD1 therapy or anti-PD-L1 therapy resistant or refractory cancer; (ii) determining the level of BTN1A1 or a BTN1A1 ligand (GAL-1, GAL-9, NRP-2, BTLA) in the sample; (iii) diagnosing the subject as being likely to be responsive to a molecule including an antigen binding fragment that immunospecifically binds to BTN1A1 or a BTN1A1 ligand (e.g., GAL-1, GAL-9, NRP-2, BTLA), whereby the molecule can inhibit binding of the BTN1A1 ligand to BTN1A1, if the level of BTN1A1 or the BTN1A1 ligand in the sample is higher than or equal to a BTN1A1 reference level, and (iv) administering to the subject a therapeutically effective amount of the molecule including an antigen binding fragment that immunospecifically binds to BTN1A1 or a BTN1A1 ligand.

In another aspect, provided herein is a method of treating an anti-PD1 therapy or anti-PD-L1 therapy resistant or refractory cancer, including (i) obtaining a sample including cancer cells from the subject having the anti-PD1 therapy or anti-PD-L1 therapy resistant or refractory cancer; (ii) determining the level of BTN1A1 or a BTN1A1 ligand (e.g., GAL-1, GAL-9, NRP-2, BTLA) and/or PD-L1 in the sample; (iii) diagnosing the subject as being likely to be responsive to a molecule including an antigen binding fragment that immunospecifically binds to BTN1A1 or a BTN1A1 ligand (e.g., GAL-1, GAL-9, NRP-2, BTLA), whereby the molecule can inhibit binding of the BTN1A1 ligand to BTN1A1, if the level of BTN1A1 or BTN1A1 ligand in the sample is higher than or equal to a BTN1A1 or BTN1A1 reference level and/or if the level of PD-L1 in the sample is equal to or lower than a PD-L1 reference level, and (iv) administering to the subject a therapeutically effective amount of the molecule including an antigen binding fragment that immunospecifically binds to BTN1A1 or BTN1A1 ligand.

In another aspect, provided herein is a method of treating cancer, including (i) obtaining a sample including cancer cells from the subject having the cancer; (ii) determining the level of BTN1A1 or a BTN1A1 ligand (e.g., GAL-1, GAL-9, NRP-2, BTLA) and/or PD-L1 in the sample; (iii) diagnosing the subject as being likely to be responsive to a molecule including an antigen binding fragment that immunospecifically binds to BTN1A1 or a BTN1A1 ligand, whereby the molecule can inhibit binding of the BTN1A1 ligand to BTN1A1, if the level of BTN1A1 or BTN1A1 ligand in the sample is higher than or equal to a BTN1A1 reference level and/or if the level of PD-L1 in the sample is equal to or lower than a PD-L1 reference level, and (iv) administering to the subject a therapeutically effective amount of the molecule including an antigen binding fragment that immunospecifically binds to BTN1A1 or BTN1A1 ligand.

In some embodiments, the subject has an anti-PD-1 therapy or anti-PD-L1 therapy resistant or refractory cancer. In some embodiments, the subject has an anti-PD-1 therapy or anti-PD-L1 therapy resistant cancer. In some embodiments, the subject has an anti-PD-1 therapy resistant cancer. In some embodiments, the subject has an anti-PD-L1 therapy resistant cancer. In some embodiments, the subject has an anti-PD-1 therapy or anti-PD-L1 therapy refractory cancer. In some embodiments, the subject has an anti-PD-1 therapy refractory cancer. In some embodiment, the subject has an anti-PD-L1 therapy refractory cancer.

In some embodiments, the anti-PD-1 therapy or anti-PD-L1 therapy resistant or refractory cancer is a lung cancer or a breast cancer. In some embodiments, the anti-PD-1 therapy or anti-PD-L1 therapy resistant or refractory cancer is a lung cancer. In some embodiments, the anti-PD-1 therapy or anti-PD-L1 therapy resistant or refractory cancer is a a breast cancer. In some embodiments, the lung cancer is a Lewis lung carcinoma. In some embodiments, the breast cancer is a mammary carcinoma.

In some embodiments, the subject has a cancer that is, at least partially, responsive to an anti-PD-1 therapy or anti-PD-L1 therapy.

In some embodiment, the BTN1A1 is expressed in the cancer, In some embodiments, the BTN1A1 expressing cancer includes, e.g., breast cancer, neuroendocrine prostate cancer (NEPC), diffuse large B-cell lymphoma, melanoma, a cancer from the National Cancer Institute cancer panel (NCI 60), uveal melanoma, pancreas cancer, ovarian cancer, uterine cancer, lung adenocarcinoma, desmoplastic small-round-cell tumor, bladder cancer, colorectal cancer, lung squamous cell carcinoma, liver cancer, lung cancer, stomach cancer, cholangiocarcinoma, esophagus squamous cell carcinoma, head and neck cancer, sarcoma, prostate cancer, liver cancer, pancreas cancer, pheochromocytoma or paraganglioma (PCPG), cervical cancer, glioma, or acute myeloid leukemia (AML).

In some embodiments, the method includes determining the level of BTN1A1 or BTN1A1 in the sample. In some embodiment, the method includes determining the level of PD-L1 in the sample. In some embodiments, the method includes determining the level of BTN1A1 or BTN1A1 ligand and PD-L1 in the sample.

In some embodiments, the subject is diagnosed as being likely to be responsive to a molecule including an antigen binding fragment that immunospecifically binds to BTN1A1 or BTN1A1 ligand (e.g., GAL-1, GAL-9, NRP-2, BTLA), whereby the molecule can inhibit binding of the BTN1A1 ligand to BTN1A1, if the level of BTN1A1 or BTN1A1 ligand (e.g., GAL-1, GAL-9, NRP-2, BTLA) in the sample is higher than or equal to a BTN1A1 or BTN1A1 ligand reference level. In some embodiments, the subject is diagnosed as being likely to be responsive to a molecule including an antigen binding fragment that immunospecifically binds to BTN1A1 or BTN1A1 ligand, if the level of BTN1A1 or BTN1A1 ligand in the sample is higher than a BTN1A1 or BTN1A1 ligand reference level.

In some embodiments, the subject is diagnosed as being likely to be responsive to a molecule including an antigen binding fragment that immunospecifically binds to BTN1A1 or BTN1A1 ligand (e.g., GAL-1, GAL-9, NRP-2, BTLA), whereby the molecule can inhibit binding of the BTN1A1 ligand to BTN1A1, if the level of PD-L1 in the sample is lower than or equal to a PD-L1 reference level. In some embodiments, the subject is diagnosed as being likely to be responsive to a molecule including an antigen binding fragment that immunospecifically binds to BTN1A1 or a BTN1A1 ligand, if the level of PD-L1 in the sample is lower than a PD-L1 reference level.

In some embodiments, the subject is diagnosed as being likely to be responsive to a molecule including an antigen binding fragment that immunospecifically binds to BTN1A1 or a BTN1A1 ligand (e.g., GAL-1, GAL-9, NRP-2, BTLA), whereby the molecule can inhibit binding of the BTN1A1 ligand to BTN1A1, if the level of BTN1A1 or BTN1A1 ligand is equal to or higher than a BTN1A1 reference level and if the level of PD-L1 is lower than or equal to a PD-L1 reference level. In some embodiments, the subject is diagnosed as being likely to be responsive to a molecule including an antigen binding fragment that immunospecifically binds to BTN1A1 or a BTN1A1 ligand (e.g., GAL-1, GAL-9, NRP-2, BTLA), whereby the molecule can inhibit binding of the BTN1A1 ligand to BTN1A1, if the level of BTN1A1 or BTN1A1 ligand (e.g., GAL-1, GAL-9, NRP-2, BTLA) is higher than or equal to a BTN1A1 reference level and if the level of PD-L1 is lower than a PD-L1 reference level. In some embodiments, the subject is diagnosed as being likely to be responsive to a molecule including an antigen binding fragment that immunospecifically binds to BTN1A1 or a BTN1A1 ligand (e.g., GAL-1, GAL-9, NRP-2, BTLA), whereby the molecule can inhibit binding of the BTN1A1 ligand to BTN1A1, if the level of BTN1A1 or BTN1A1 ligand is higher than a BTN1A1 or BTN1A1 reference level and if the level of PD-L1 is lower than a PD-L1 reference level.

The sample can be any solid or liquid sample from the subject.

In some embodiments, the sample is a liquid biopsy sample. In some embodiments, the sample used in the methods provided herein includes body fluids from a subject. Non-limiting examples of body fluids include blood (e.g., whole blood), blood plasma, amniotic fluid, aqueous humor, bile, cerumen, cowper's fluid, pre-ejaculatory fluid, chyle, chyme, female ejaculate, interstitial fluid, lymph, menses, breast milk, mucus, pleural fluid, pus, saliva, sebum, semen, serum, sweat, tears, urine, vaginal lubrication, vomit, water, feces, internal body fluids (including cerebrospinal fluid surrounding the brain and the spinal cord), synovial fluid, intracellular fluid (the fluid inside cells), and vitreous humour (the fluid in the eyeball). In some embodiments, the sample is a blood sample. The blood sample can be obtained using conventional techniques as described in, e.g., Innis et al, eds., PCR Protocols (Academic Press, 1990). White blood cells can be separated from blood samples using conventional techniques or commercially available kits, e.g., RosetteSep kit (Stein Cell Technologies, Vancouver, Canada). Sub-populations of white blood cells, e.g., mononuclear cells, B cells, T cells, monocytes, granulocytes, or lymphocytes, can be further isolated using conventional techniques, e.g., magnetically activated cell sorting (MACS) (Miltenyi Biotec, Auburn, Calif.) or fluorescently activated cell sorting (FACS) (Becton Dickinson, San Jose, Calif.).

In some embodiments, the sample is a solid biopsy sample. In some embodiments, the sample used in the present methods includes a biopsy (e.g., a tumor biopsy). The biopsy can be from any organ or tissue, for example, skin, liver, lung, heart, colon, kidney, bone marrow, teeth, lymph node, hair, spleen, brain, breast, or other organs. Any biopsy technique known by those skilled in the art can be used for isolating a sample from a subject, for instance, open biopsy, close biopsy, core biopsy, incisional biopsy, excisional biopsy, or fine needle aspiration biopsy.

In some embodiments, the sample is a paraffin embedded formaldehyde fixed tissue sample. In some embodiments, the sample is a tissue slice. In some embodiments, the sample is provided on a tissue array.

In some embodiments the level of the biomarkers is measured by determining the protein level of the biomarker.

The level of BTN1A1, BTN1A1 ligand (e.g., GAL-1, GAL-9, NRP-2, BTLA) or PD-L1 in the sample can be analyzed using any method known in the art. See, e.g., Section 5.7 (Companion Diagnostics). In some embodiments, determining the level of BTN1A1, BTN1A1 ligand (e.g., GAL-1, GAL-9, NRP-2, BTLA) or PD-L1 in the sample can include analyzing the level of a BTN1A1, BTN1A1 ligand or PD-L1 nucleic acid or a BTN1A1, BTN1A1 ligand or PD-L1 protein. BTN1A1, BTN1A1 ligand or PD-L1 nucleic acid levels can, e.g., be analyzed using a polymerase chain reaction (PCR) method (e.g., RT-PCR or Q-PCR), a nucleic acid array based method (e.g., a genchip), or a nucleic acid sequencing method, such as a next-generation sequencing method. BTN1A1, BTN1A1 ligand, or PD-L1 protein levels can be determined using, e.g., a western-blot, ELISA, FACS, immunohistochemistry method. BTN1A1, BTN1A1 ligand or PD-L1 levels can be determined in absolute quantitative terms (e.g., weight BTN1A1, BTN1A1 ligand or PD-L1 per weight of tissue, or molar amounts per tissue volume or per liquid sample volume). In some embodiments, BTN1A1, BTN1A1 ligand or PD-L1 levels are determined in relative or semi-quantitative terms (e.g., relative intensities of BTN1A1 or PD-L1 specific staining in different regions of a tissue sample). BTN1A1, BTN1A1 ligand or PD-L1 levels can be determined independently using the same method or different methods. In some embodiments, relative BTN1A1, BTN1A1 ligand or PD-L1 levels are determined in a tissue slice of a solid tumor sample using immunohistochemistry combined with fluorescence microscopy or bright field microscopy.

In some embodiments, determining the level of BTN1A1, BTN1A1 ligand (e.g., GAL-1, GAL-9, NRP-2, BTLA) and/or PD-L1 in the sample includes analyzing the cell surface expression of BTN1A1, BTN1A1 ligand and/or PD-L1, e.g., using a FACS assay or immunocytochemistry.

In some embodiment the treatment produces at least one therapeutic effect, such as a reduction in size of a tumor, a reduction in number of metastatic lesions over time, a complete response, a partial response, or a stable disease.

In some embodiments the reference is prepared by using a control sample obtained from the subject prior to administering the molecule including an antigen binding fragment that immunospecifically binds to BTN1A1 or a BTN1A1 ligand (e.g., GAL-1, GAL-9, NRP-2, BTLA) to the subject, and the control sample is from the same source as the sample. In some embodiments the reference is prepared by using a control sample obtained from a healthy subject not having cancer, and the control sample is from the same source as the sample. In some embodiments the reference is prepared by using a control sample obtained from a group of healthy subjects not having cancer, and the control sample is from the same source as the sample. In some embodiments the reference is prepared by using a control sample obtained from a second subject having cancer, and the control sample is from the same source as the sample. In some embodiments the reference is prepared by using a control sample obtained from a group of subjects having cancer, and the control sample is from the same source as the sample.

5.4.1. Diseases and Disorders

In some embodiments, provided herein are uses of the antibodies or other molecules to mediate increased production of cytokines, such as IFN-γ. Thus, provided herein are uses of such antibodies or other molecules in the treatment of diseases and conditions that can be treated with cytokines, such as ovarian and other forms of cancer. In some embodiments, provided herein are uses of the antibodies and other molecules in mediating increased T-cell (e.g., CD8$^+$ T-cell) activity or proliferation. Thus, provided in some embodiments are the use of such antibodies and other molecules in the treatment of diseases and conditions that are treatable by increasing T-cell activity or proliferation, such as cancer. In some embodiments, provided herein are uses of the antibodies or other molecules as described herein to mediate both increased T-cell activity and increased T-cell proliferation.

Up-modulation of the immune system is particularly desirable in the treatment of cancers. Additionally, BTN1A1 is specifically and highly expressed in cancer cells. Molecules described herein can also bind to cancer cells and cause their destruction by either direct cytotoxicity, or through ADCC or CDC mechanism. Thus, provided herein are methods of cancer treatment. A cancer refers to a neoplasm or tumor resulting from abnormal uncontrolled growth of cells. A cancer can be a primary cancer or a metastatic cancer.

In some embodiments, provided herein are methods to treat a cancer in a subject by administering a molecule having an antigen binding fragment that immunospecifically binds to BTN1A1 or a BTN1A1 ligand (e.g., GAL-1, GAL-9, NRP-2, BTLA), whereby the molecule inhibits binding of the BTN1A1 ligand to BTN1A1. Cancers for which the treatment methods can be useful include any malignant cell type, such as those found in a solid tumor or a hematological cancer. Exemplary solid tumors include, but are not limited to, a tumor of an organ selected from the group consisting of pancreas, colon, cecum, esophagus, stomach, brain, head, neck, thyroid, thymus, ovary, kidney, larynx, sarcoma, lung, bladder, melanoma, prostate, and breast. Exemplary hematological cancers include, but not limited to, tumors of the bone marrow, T or B cell malignancies, leukemias, lymphomas, blastomas, myelomas, and the like. In some embodiments, the methods further include administering an anti-PD1 therapy or an anti-PD-L1 therapy.

In some embodiments, provided herein are methods to treat a cancer in a subject by administering the molecule described herein having an antigen binding fragment that immunospecifically binds to BTN1A1 or a BTN1A1 ligand (e.g., GAL-1, GAL-9, NRP-2, BTLA), whereby the molecule can inhibit binding of the BTN1A1 ligand to BTN1A1, whereby the cancer can be breast cancer, neuroendocrine prostate cancer (NEPC), diffuse large B-cell lymphoma, melanoma, cancer from the National Cancer Institute cancer panel (NCI 60), uveal melanoma, pancreas cancer, ovarian cancer, uterine cancer, lung adenocarcinoma, desmoplastic small-round-cell tumor, bladder cancer, colorectal cancer, lung squamous cell carcinoma, liver cancer, lung cancer, stomach cancer, cholangiocarcinoma, esophagus squamous cell carcinoma, head and neck cancer, sarcoma, prostate cancer, liver cancer, pancreas cancer, pheochromocytoma or paraganglioma (PCPG), cervical cancer, glioma, or acute myeloid leukemia (AML). The molecules used for treating the cancer can be any molecules described herein having an antigen binding fragment that immunospecifically binds to BTN1A1 or a BTN1A1 ligand (e.g., GAL-1, GAL-9, NRP-2, BTLA), whereby the molecule can inhibit binding of the BTN1A1 ligand to BTN1A1. In some embodiments, the antigen binding fragment preferentially binds glycosylated BTN1A1 over non-glycosylated BTN1A1. In some embodiments, the antigen binding fragment preferentially binds a BTN1A1 dimer (e.g., a glycosylated BTN1A1 dimer) over a BTN1A1 monomer (e.g., a glycosylated BTN1A1 monomer). In some embodiments, the antigen binding fragments immunospecifically mask BTN1A1 glycosylation at positions N55, N215, N449, or any combination thereof.

In some embodiments, provided herein are methods to treat a cancer in a subject by administering the molecule described herein having an antigen binding fragment that immunospecifically binds to BTN1A1 or a BTN1A1 ligand (e.g., GAL-1, GAL-9, NRP-2, BTLA), whereby the molecule can inhibit binding of the BTN1A1 ligand to BTN1A1, whereby the cancer can be lung squamous carcinoma, prostate adenocarcinoma, pancreatic adenocarcinoma, or hepatocellular carcinoma. The molecules used for treating lung squamous carcinoma, prostate adenocarcinoma, pancreatic adenocarcinoma, or hepatocellular carcinoma can be any molecules described herein having an antigen binding fragment that immunospecifically binds to BTN1A1 or a BTN1A1 ligand, whereby the molecule inhibits binding of the BTN1A1 ligand to BTN1A1. In some embodiments, the antigen binding fragment preferentially binds glycosylated BTN1A1 over non-glycosylated BTN1A1. In some embodiments, the antigen binding fragment preferentially binds a BTN1A1 dimer (e.g., a glycosylated BTN1A1 dimer) over a BTN1A1 monomer (e.g., a glycosylated BTN1A1 monomer). In some embodiments, the antigen binding fragments immunospecifically mask BTN1A1 glycosylation at positions N55, N215, N449, or any combination thereof.

In some embodiments, provided herein are methods to treat a cancer in a subject by administering the molecule described herein having an antigen binding fragment that immunospecifically binds to BTN1A1 or a BTN1A1 ligand (e.g., GAL-1, GAL-9, NRP-2, BTLA), wereby the molecule can inhibit binding of the BTN1A1 ligand to BTN1A1, whereby the cancer is an anti-PD-1 therapy or an anti-PD-L1 therapy resistant or refractory cancer. The molecules used for treating is an anti-PD-1 therapy or an anti-PD-L1 therapy resistant or refractory cancer can be any molecules described herein having an antigen binding fragment that immunospecifically binds to BTN1A1 or a BTN1A1 ligand (e.g., GAL-1, GAL-9, NRP-2, BTLA), whereby the molecule inhibits binding of the BTN1A1 ligand to BTN1A1. In some embodiments, the antigen binding fragment preferentially binds glycosylated BTN1A1 over non-glycosylated BTN1A1. In some embodiments, the antigen binding fragment preferentially binds a BTN1A1 dimer (e.g., a glycosylated BTN1A1 dimer) over a BTN1A1 monomer (e.g., a glycosylated BTN1A1 monomer). In some embodiments, the antigen binding fragments immunospecifically mask BTN1A1 glycosylation at positions N55, N215, N449, or any combination thereof. In some embodiments, the cancer is an anti-PD-1 therapy resistant or refractory cancer. In some embodiments, the cancer is an anti-PD-L1 therapy resistant or refractory cancer. In some embodiments, the anti-PD-1 therapy resistant or refractory cancer is a breast cancer or a lung cancer. In some embodiments, the anti-PD-1 therapy resistant or refractory cancer is a mammary carcinoma or a Lewis lung carcinoma. In some embodiments, the anti-PD-1 therapy resistant or refractory cancer is a mammary carcinoma. In some embodiments, the anti-PD-1 therapy resistant or refractory cancer is a Lewis lung carcinoma.

Further examples of cancers that can be treated using the methods provided herein include, but are not limited to, carcinoma, lymphoma, blastoma, sarcoma, leukemia, squamous cell cancer, lung cancer (including small-cell lung cancer, non-small cell lung cancer, adenocarcinoma of the lung, and squamous carcinoma of the lung, mesothelioma), cancer of the peritoneum, hepatocellular cancer, gastric or stomach cancer (including gastrointestinal cancer and gastrointestinal stromal cancer), esophageal cancer, pancreatic cancer, glioblastoma, cervical cancer, ovarian cancer, liver cancer, bladder cancer, breast cancer, colon cancer, colorectal cancer, endometrial or uterine carcinoma, salivary gland carcinoma, kidney or renal cancer, prostate cancer, vulvar cancer, thyroid cancer, various types of head and neck cancer, melanoma, superficial spreading melanoma, lentigo malignant melanoma, acral lentiginous melanomas, nodular melanomas, uveal melanomas, germ cell tumors (yolk sac tumors, testicular cancer, choriocarcinoma), as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's macroglobulinemia), chronic lymphocytic leukemia (CLL), acute lymphoblastic leukemia (ALL), Hairy cell leukemia, multiple myeloma, acute myeloid leukemia (AML) and chronic myeloblastic leukemia.

The cancer can also be of any of the following histological types: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

In some embodiments, provided herein are methods to treat a cancer in a subject by administering the molecule described herein having an antigen binding fragment that immunospecifically binds to BTN1A1 or BTN1A1 ligand (e.g., GAL-1, GAL-9, NRP-2, BTLA), whereby the molecule can inhibit binding of the BTN1A1 ligand to BTN1A1, whereby the cancer is lung cancer, prostate cancer, pancreas cancer, ovarian cancer, liver cancer, head & neck cancer, breast cancer, or stomach cancer. In some embodiments, provided herein are methods to treat a cancer in a subject by administering the molecule described herein having an antigen binding fragment that immunospecifically binds to BTN1A1 or a BTN1A1 ligand (e.g., GAL-1, GAL-9, NRP-2, BTLA), whereby the molecule can inhibit binding of the BTN1A1 ligand to BTN1A1, whereby the cancer can be lung cancer. The lung cancer can be non-small cell lung cancer (NSCLC). The lung cancer can be small cell lung cancer (SCLC). The NSCLC can be squamous NSCLC. The molecules used for treating lung cancer can be any molecules described herein having an antigen binding fragment that immunospecifically binds to BTN1A1 or glycosylated BTN1A1. In some embodiments, the antigen binding fragment preferentially binds glycosylated BTN1A1 over non-glycosylated BTN1A1. In some embodiments, the antigen binding fragments immunospecifically mask BTN1A1 glycosylation at positions N55, N215, N449, or any combination thereof. In some embodiments, the methods further include administering an anti-PD1 therapy or an anti-PD-L1 therapy.

In some embodiments, provided herein are methods to treat a cancer in a subject by administering the molecule described herein having an antigen binding fragment that immunospecifically binds to BTN1A1 or a BTN1A1 ligand (e.g., GAL-1, GAL-9, NRP-2, BTLA), whereby the molecule can inhibit binding of the BTN1A1 ligand to BTN1A1, whereby the cancer can be prostate cancer. The molecules used for treating prostate cancer can be any molecules described herein having an antigen binding fragment that immunospecifically binds to BTN1A1 or a BTN1A1 ligand (e.g., GAL-1, GAL-9, NRP-2, BTLA), whereby the molecule can inhibit binding of the BTN1A1 ligand to BTN1A1. In some embodiments, the antigen binding fragment preferentially binds glycosylated BTN1A1 over non-glycosylated BTN1A1. In some embodiments, the antigen binding fragment preferentially binds a BTN1A1 dimer (e.g., a glycosylated BTN1A1 dimer) over a BTN1A1 monomer (e.g., a glycosylated BTN1A1 monomer). In some embodiments, the antigen binding fragments immunospecifically mask BTN1A1 glycosylation at positions N55, N215, N449, or any combination thereof. In some embodiments, the methods further include administering an anti-PD1 therapy or an anti-PD-L1 therapy.

In some embodiments, provided herein are methods to treat a cancer in a subject by administering the molecule described herein having an antigen binding fragment that immunospecifically binds to BTN1A1 or a BTN1A1 ligand (e.g., GAL-1, GAL-9, NRP-2, BTLA), whereby the molecule can inhibit binding of the BTN1A1 ligand to BTN1A1, whereby the cancer can be pancreas cancer. The molecules used for treating pancreas cancer can be any molecules described herein having an antigen binding fragment that immunospecifically binds to BTN1A1 or a BTN1A1 ligand (e.g., GAL-1, GAL-9, NRP-2, BTLA), whereby the molecule can inhibit binding of the BTN1A1 ligand to BTN1A1. In some embodiments, the antigen binding fragment preferentially binds glycosylated BTN1A1 over non-glycosylated BTN1A1. In some embodiments, the antigen binding fragment preferentially binds a BTN1A1 dimer (e.g., a glycosylated BTN1A1 dimer) over a BTN1A1 monomer (e.g., a glycosylated BTN1A1 monomer). In some embodiments, the methods further include administering an anti-PD1 therapy or an anti-PD-L1 therapy.

In some embodiments, provided herein are methods to treat a cancer in a subject by administering the molecule described herein having an antigen binding fragment that immunospecifically binds to BTN1A1 or a BTN1A1 ligand (e.g., GAL-1, GAL-9, NRP-2, BTLA), whereby the molecule can inhibit binding of the BTN1A1 ligand to BTN1A1, whereby the cancer can be ovarian cancer. The molecules used for treating ovarian cancer can be any molecules described herein having an antigen binding fragment that immunospecifically binds to BTN1A1 or a BTN1A1 ligand (e.g., GAL-1, GAL-9, NRP-2, BTLA), whereby the molecule can inhibit binding of the BTN1A1 ligand to BTN1A1. In some embodiments, the antigen binding fragment preferentially binds glycosylated BTN1A1 over non-glycosylated BTN1A1. In some embodiments, the antigen binding fragment preferentially binds a BTN1A1 dimer (e.g., a glycosylated BTN1A1 dimer) over a BTN1A1 monomer (e.g., a glycosylated BTN1A1 monomer). In some embodiments, the antigen binding fragments immunospecifically mask BTN1A1 glycosylation at positions N55, N215, N449, or any combination thereof. In some embodiments, the methods further include administering an anti-PD1 therapy or an anti-PD-L1 therapy.

In some embodiments, provided herein are methods to treat a cancer in a subject by administering the molecule described herein having an antigen binding fragment that immunospecifically binds to BTN1A1 or a BTN1A1 ligand (e.g., GAL-1, GAL-9, NRP-2, BTLA), whereby the molecule inhibits binding of the BTN1A1 ligand to BTN1A1, whereby the cancer can be liver cancer. The molecules used for treating liver cancer can be any molecules described herein having an antigen binding fragment that immunospecifically binds to BTN1A1 or a BTN1A1 ligand (e.g., GAL-1, GAL-9, NRP-2, BTLA). In some embodiments, the antigen binding fragment preferentially binds glycosylated BTN1A1 over non-glycosylated BTN1A1. In some embodiments, the antigen binding fragment preferentially binds a BTN1A1 dimer (e.g., a glycosylated BTN1A1 dimer) over a BTN1A1 monomer (e.g., a glycosylated BTN1A1 monomer). In some embodiments, the antigen binding fragments immunospecifically mask BTN1A1 glycosylation at positions N55, N215, N449, or any combination thereof. In some embodiments, the methods further include administering an anti-PD1 therapy or an anti-PD-L1 therapy.

In some embodiments, provided herein are methods to treat a cancer in a subject by administering the molecule described herein having an antigen binding fragment that immunospecifically binds to BTN1A1 or a BTN1A1 ligand (e.g., GAL-1, GAL-9, NRP-2, BTLA), whereby the molecule inhibits binding of the BTN1A1 ligand to BTN1A1, whereby the cancer can be head & neck cancer. The molecules used for treating head & neck cancer can be any molecules described herein having an antigen binding fragment that immunospecifically binds to BTN1A1 or a BTN1A1 ligand (e.g., GAL-1, GAL-9, NRP-2, BTLA). In some embodiments, the antigen binding fragment preferentially binds glycosylated BTN1A1 over non-glycosylated BTN1A1. In some embodiments, the antigen binding fragment preferentially binds a BTN1A1 dimer (e.g., a glycosylated BTN1A1 dimer) over a BTN1A1 monomer (e.g., a glycosylated BTN1A1 monomer). In some embodiments, the antigen binding fragments immunospecifically mask BTN1A1 glycosylation at positions N55, N215, N449, or any combination thereof. In some embodiments, the methods further include administering an anti-PD1 therapy or an anti-PD-L1 therapy.

In some embodiments, provided herein are methods to treat a cancer in a subject by administering the molecule described herein having an antigen binding fragment that immunospecifically binds to BTN1A1 or a BTN1A1 ligand (e.g., GAL-1, GAL-9, NRP-2, BTLA), whereby the molecule inhibits binding of the BTN1A1 ligand to BTN1A1, whereby the cancer can be breast cancer. The molecules used for treating breast cancer can be any molecules described herein having an antigen binding fragment that immunospecifically binds to BTN1A1 or a BTN1A1 ligand (e.g., GAL-1, GAL-9, NRP-2, BTLA). In some embodiments, the antigen binding fragment preferentially binds glycosylated BTN1A1 over non-glycosylated BTN1A1. In some embodiments, the antigen binding fragment preferentially binds a BTN1A1 dimer (e.g., a glycosylated BTN1A1 dimer) over a BTN1A1 monomer (e.g., a glycosylated BTN1A1 monomer). In some embodiments, the antigen binding fragments immunospecifically mask BTN1A1 glycosylation at positions N55, N215, N449, or any combination thereof. In some embodiments, the methods further include administering an anti-PD1 therapy or an anti-PD-L1 therapy.

In some embodiments, provided herein are methods to treat a cancer in a subject by administering the molecule described herein having an antigen binding fragment that immunospecifically binds to BTN1A1 or a BTN1A1 ligand (e.g., GAL-1, GAL-9, NRP-2, BTLA), whereby the molecule inhibits binding of the BTN1A1 ligand to BTN1A1, whereby the cancer can be stomach cancer. The molecules used for treating stomach cancer can be any molecules described herein having an antigen binding fragment that immunospecifically binds to BTN1A1 or a BTN1A1 ligand (e.g., GAL-1, GAL-9, NRP-2, BTLA). In some embodiments, the antigen binding fragment preferentially binds glycosylated BTN1A1 over non-glycosylated BTN1A1. In some embodiments, the antigen binding fragment preferentially binds a BTN1A1 dimer (e.g., a glycosylated BTN1A1 dimer) over a BTN1A1 monomer (e.g., a glycosylated BTN1A1 monomer). In some embodiments, the antigen binding fragments immunospecifically mask BTN1A1 glycosylation at positions N55, N215, N449, or any combination thereof. In some embodiments, the methods further include administering an anti-PD1 therapy or an anti-PD-L1 therapy.

5.4.2. Methods of Administration

Provided herein are also methods of using the anti-BTN1A1 antibodies, anti-BTN1A1 ligand (e.g., GAL-1, GAL-9, NRP-2, BTLA) antibodies or other molecules having an antigen binding fragment that immunospecifically binds to BTN1A1 or a BTN1A1 ligand as an antitumor agent by administering a therapeutically effective amount of the antibodies or molecules provided herein to a patient in need thereof. In some embodiments, the patient is a cancer patient.

Various delivery systems are also known and can be used to administer the anti-BTN1A1 antibodies, anti-BTN1A1 ligand (e.g., GAL-1, GAL-9, NRP-2, BTLA) antibodies or other molecules having an antigen binding fragment that immunospecifically binds to BTN1A1 or a BTN1A1 ligand, or related pharmaceutical compositions, such as encapsulation in liposomes, microparticles, microcapsules, recombinant cells capable of expressing the antibody or fusion protein, receptor-mediated endocytosis (see, e.g., Wu and Wu, 1987, 1 *Biol. Chem.* 262:4429-4432), construction of a nucleic acid as part of a retroviral or other vector, etc.

The methods of administration as provided herein include, but are not limited to, injection, as by parenteral administration (e.g., intradermal, intramuscular, intraperitoneal, intravenous and subcutaneous), epidural, and mucosal (e.g., intranasal and oral routes). In some embodiments, the antibodies, other molecules, or pharmaceutical compositions provided herein are administered intramuscularly, intravenously, subcutaneously, intravenously, intraperitoneally, orally, intramuscularly, subcutaneously, intracavity, transdermally, or dermally. The compositions can be administered by any convenient route, for example, by infusion or bolus injection, by absorption through epithelial or mucocutaneous linings (e.g., oral mucosa, rectal and intestinal mucosa, etc.) and can be administered together with other biologically active agents. Administration can be systemic or local. In addition, pulmonary administration can also be employed, e.g., by use of an inhaler or nebulizer, and formulation with an aerosolizing agent. See, e.g., U.S. Pat. Nos. 6,019,968; 5,985,20; 5,985,309; 5,934,272; 5,874,064; 5,855,913; 5,290,540; and 4,880,078; and PCT Publication Nos. WO 92/19244; WO 97/32572; WO 97/44013; WO 98/31346; and WO 99/66903; all of which are hereby incorporated by reference in their entireties. In some embodiments, the antibodies, other molecules, or pharmaceutical compositions provided herein are administered locally to the area in need of treatment, which can be achieved by, for example, local infusion, by injection, or by means of an implant, said implant being of a porous, non-porous, or gelatinous material, including membranes, such as sialastic membranes, or fibers. In some embodiments, when administering antibodies or other molecules as described herein, care is taken to use materials to which the antibodies or other molecules do not absorb.

In some embodiments, the humanized or chimeric antibodies provided herein are formulated in liposomes for targeted delivery. Liposomes are vesicles comprised of concentrically ordered phopsholipid bilayers which encapsulate an aqueous phase. Liposomes typically have various types of lipids, phospholipids, and/or surfactants. The components of liposomes are arranged in a bilayer configuration, similar to the lipid arrangement of biological membranes. Liposomes can be useful delivery vehicles due, in part, to their biocompatibility, low immunogenicity, and low toxicity. Methods for preparation of liposomes are known in the art and are provided herein, see, e.g., Epstein et al., 1985, *Proc. Natl. Acad. Sci. USA,* 82: 3688; Hwang et al., 1980 *Proc. Natl. Acad. Sci. USA,* 77: 4030-4; U.S. Pat. Nos. 4,485,045 and 4,544,545; all of which are hereby incorporated by reference in their entireties.

Provided herein are also methods of preparing liposomes with a prolonged serum half-life, i.e., enhanced circulation time, such as those disclosed in U.S. Pat. No. 5,013,556. In some embodiments, liposomes used in the methods provided herein are not rapidly cleared from circulation, i.e., are not taken up into the mononuclear phagocyte system (MPS). Provided herein are also sterically stabilized liposomes which are prepared using common methods known to one skilled in the art. Sterically stabilized liposomes can contain lipid components with bulky and highly flexible hydrophilic moieties, which reduces the unwanted reaction of liposomes with serum proteins, reduces oposonization with serum components and reduces recognition by MPS. Sterically stabilized liposomes can be prepared using polyethylene glycol. For preparation of liposomes and sterically stabilized liposome, see, e.g., Bendas et al., 2001 *BioDrugs,* 15(4): 215-224; Allen et al., 1987 *FEBS Lett.* 223: 42-6; Klibanov et al., 1990 *FEBS Lett.,* 268: 235-7; Blum et al., 1990, *Biochim. Biophys. Acta.,* 1029: 91-7; Torchilin et al., 1996, *J. Liposome Res.* 6: 99-116; Litzinger et al., 1994, *Biochim. Biophys. Acta,* 1190: 99-107; Maruyama et al., 1991, *Chem. Pharm. Bull.,* 39: 1620-2; Klibanov et al., 1991, *Biochim Biophys Acta,* 1062; 142-8; Allen et al., 1994, *Adv. Drug Deliv. Rev,* 13: 285-309, which are hereby incorporated by reference in their entireties.

Provided herein are also liposomes that are adapted for specific organ targeting, see, e.g., U.S. Pat. No. 4,544,545, or specific cell targeting, see, e.g., U.S. Patent Application Publication No. 2005/0074403, which are hereby incorporated by reference in their entireties. Particularly useful liposomes for use in the compositions and methods provided herein can be generated by reverse phase evaporation method with a lipid composition including phosphatidylcholine, cholesterol, and PEG derivatized phosphatidylethanolamine (PEG-PE). Liposomes can be extruded through filters of defined pore size to yield liposomes with the desired diameter. In some embodiments, a molecule having an antigen binding fragment, e.g., F(ab'), can be conjugated to the liposomes using previously described methods, see, e.g., Martin et al., 1982, *J. Biol. Chem.* 257: 286-288, which is hereby incorporated by reference in its entirety.

The humanized or chimeric antibodies as described herein can also be formulated as immunoliposomes. Immunoliposomes refer to a liposomal composition, whereby an antibody or a fragment thereof is linked, covalently or non-covalently to the liposomal surface. The chemistry of linking an antibody to the liposomal surface is known in the art, see, e.g., U.S. Pat. No. 6,787,153; Allen et al., 1995, *Stealth Liposomes,* Boca Rotan: CRC Press, 233-44; Hansen et al., 1995, *Biochim. Biophys. Acta,* 1239: 133-144, which are hereby incorporated by reference in their entireties. In some embodiments, immunoliposomes for use in the methods and compositions provided herein are further sterically stabilized. In some embodiments, the humanized antibodies as described herein are linked covalently or non-covalently to a hydrophobic anchor, which is stably rooted in the lipid bilayer of the liposome. Examples of hydrophobic anchors include, but are not limited to, phospholipids, e.g., phosoatidylethanolamine (PE), phospahtidylinositol (PI). To achieve a covalent linkage between an antibody and a hydrophobic anchor, any of the known biochemical strategies in the art can be used, see, e.g., J. Thomas August ed., 1997, *Gene Therapy: Advances in Pharmacology,* Volume 40, Academic Press, San Diego, Calif., p. 399-435, which are hereby incorporated by reference in their entireties. For example, a functional group on an antibody molecule can react with an active group on a liposome associated hydrophobic anchor, e.g., an amino group of a lysine side chain on an antibody may be coupled to liposome associated N-glutaryl-phosphatidylethanolamine activated with water-soluble carbodiimide; or a thiol group of a reduced antibody can be coupled to liposomes via thiol reactive anchors, such as pyridylthiopropionylphosphatidylethanolamine. See, e.g., Dietrich et al., 1996, *Biochemistry,* 35: 1100-1105; Loughrey et al., 1987, *Biochim. Biophys. Acta,* 901: 157-160; Martin et al., 1982, *J. Biol. Chem.* 257: 286-288; Martin et al., 1981, *Biochemistry,* 20: 4429-38, which are hereby incorporated by reference in their entireties. The immunoliposomal formulations having the anti-BTN1A1 antibodies or other molecules having an antigen binding fragment that immunospecifically binds to BTN1A1 or glycosylated BTN1A1 can be particularly effective as therapeutic agents, since they deliver the active ingredient to the cytoplasm of the target cell, i.e., the cell including the receptor to which the antibody binds. In some embodiments, the immunoliposomes can have an increased half-life in blood, specifically target cells, and can be internalized into the cytoplasm of the target cells thereby avoiding loss of the therapeutic agent or degradation by the endolysosomal pathway.

The immunoliposomal compositions provided herein can have one or more vesicle forming lipids, an antibody or other molecule of the invention or a fragment or derivative thereof, and, optionally, a hydrophilic polymer. A vesicle forming lipid can be a lipid with two hydrocarbon chains, such as acyl chains and a polar head group. Examples of vesicle forming lipids include phospholipids, e.g., phosphatidylcholine, phosphatidylethanolamine, phosphatidic acid, phosphatidylinositol, sphingomyelin, and glycolipids, e.g., cerebrosides, gangliosides. Additional lipids useful in the formulations provided herein are known to one skilled in the art and encompassed within the description. In some embodiments, the immunoliposomal compositions further include a hydrophilic polymer, e.g., polyethylene glycol, and ganglioside GM1, which increases the serum half-life of the liposome. Methods of conjugating hydrophilic polymers to liposomes are well known in the art and encompassed within the description. Additional exemplary immunoliposomes and methods of preparing them can be find in, e.g., U.S. Patent Application Publication No. 2003/0044407; PCT International Publication No. WO 97/38731, Vingerhoeads et al., 1994, *Immunomethods*, 4: 259-72; Maruyama, 2000, *Biol. Pharm. Bull.* 23(7): 791-799; Abra et al., 2002, *Journal of Liposome Research*, 12(1&2): 1-3; Park, 2002, *Bioscience Reports*, 22(2): 267-281; Bendas et al., 2001 *BioDrugs*, 14(4): 215-224, J. Thomas August ed., 1997, *Gene Therapy: Advances in Pharmacology*, Volume 40, Academic Press, San Diego, Calif., p. 399-435; all of which are hereby incorporated by reference in their entireties.

Provided herein are also methods of treating a cancer patient by administering a unit dose to the patient the anti-BTN1A1 antibodies, anti-BTN1A1 antibodies or other molecules having an antigen binding fragment that immunospecifically binds to BTN1A or a BTN1A1 ligand (e.g., GAL-1, GAL-9, NRP-2, BTLA). A unit dose refers to physically discrete units suitable as unitary dosage for the subject, each unit containing a predetermined quantity of active material calculated to produce the desired therapeutic effect in association with the required diluent, i.e., carrier, or vehicle.

The antibodies, molecules, or compositions are administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient required to be administered depend on the judgment of the practitioner and are peculiar to each individual subject. However, suitable dosage ranges for systemic application are disclosed herein and depend on the route of administration. Suitable regimes for initial and booster administration are also contemplated and typically include by an initial administration followed by repeated doses at one or more hour intervals by a subsequent injection or other administration. Exemplary multiple administrations are described herein and are useful to maintain continuously high serum and tissue levels of polypeptide or antibody. Alternatively, continuous intravenous infusion sufficient to maintain concentrations in the blood in the ranges specified for in vivo therapies are contemplated.

A therapeutically effective amount is a predetermined amount calculated to achieve the desired effect. Generally, the dosage will vary with age of, condition of, sex of, and extent of the disease in the patient and can be determined by one of skill in the art. The dosage can be adjusted by the individual physician in the event of any complication.

In some embodiments, the antibodies, molecules, or pharmaceutical compositions provided herein are packaged in a hermetically sealed container, such as an ampoule or sachette. In one embodiment, the antibodies, molecules, or pharmaceutical compositions provided herein are supplied as a dry sterilized lyophilized powder or water free concentrate in a hermetically sealed container and can be reconstituted, e.g., with water or saline to the appropriate concentration for administration to a subject. In some embodiments, the antibodies, molecules, or pharmaceutical compositions provided herein are supplied as a dry sterile lyophilized powder in a hermetically sealed container at a unit dosage of at least 5 mg, more preferably at least 10 mg, at least 15 mg, at least 25 mg, at least 35 mg, at least 45 mg, at least 50 mg, or at least 75 mg. The lyophilized antibodies, molecules, or pharmaceutical compositions provided herein should be stored at between 2 and 8° C. in their original container and should be administered within 12 hours, preferably within 6 hours, within 5 hours, within 3 hours, or within 1 hour after being reconstituted. In an alternative embodiment, the antibodies, molecules, or pharmaceutical compositions provided herein are supplied in liquid form in a hermetically sealed container indicating the quantity and concentration of the antibodies, molecules, or pharmaceutical compositions. In some embodiments, the liquid form of the antibodies, molecules, or pharmaceutical compositions provided herein are supplied in a hermetically sealed container at least 1 mg/ml, more preferably at least 2.5 mg/ml, at least 5 mg/ml, at least 8 mg/ml, at least 10 mg/ml, at least 15 mg/ml, at least 25 mg/ml, at least 50 mg/ml, at least 100 mg/ml, at least 150 mg/ml, at least 200 mg/ml.

The precise dose to be employed in the formulation will also depend on the route of administration, and the seriousness of the condition, and should be decided according to the judgment of the practitioner and each patient's circumstances. Effective doses can be extrapolated from dose-response curves derived from in vitro or animal model test systems. For the anti-BTN1A1 antibodies, anti-BTN1A1 ligand (e.g., GAL-1, GAL-9, NRP-2, or BTLA) antibodies or other molecules having an antigen binding fragment that immunospecifically binds to BTN1A1 or a BTN1A1 ligand, the dosage administered to a patient is typically 0.01 mg/kg to 100 mg/kg of the patient's body weight. In some embodiments, the dosage administered to a patient is between 0.01 mg/kg and 20 mg/kg, 0.01 mg/kg and 10 mg/kg, 0.01 mg/kg and 5 mg/kg, 0.01 and 2 mg/kg, 0.01 and 1 mg/kg, 0.01 mg/kg and 0.75 mg/kg, 0.01 mg/kg and 0.5 mg/kg, 0.01 mg/kg to 0.25 mg/kg, 0.01 to 0.15 mg/kg, 0.01 to 0.10 mg/kg, 0.01 to 0.05 mg/kg, or 0.01 to 0.025 mg/kg of the patient's body weight. In particular, the dosage administered to a patient can be 0.2 mg/kg, 0.3 mg/kg, 1 mg/kg, 3 mg/kg, 6 mg/kg or 10 mg/kg. A dose as low as 0.01 mg/kg is predicted to show appreciable pharmacodynamic effects. Dose levels of 0.10-1 mg/kg are predicted to be most appropriate. Higher doses (e.g., 1-30 mg/kg) can also be expected to be active. Generally, human antibodies have a longer half-life within the human body than antibodies from other species due to the immune response to the foreign polypeptides. Thus, lower dosages of human antibodies and less frequent administration can be practiced. Further, the dosage and frequency of administration of antibodies or other molecules provided herein can be reduced by enhancing uptake and tissue penetration of the antibodies by modifications such as, for example, lipidation.

In yet another embodiment, the compositions can be delivered in a controlled release or sustained release system. Any technique known to one of skill in the art can be used to produce sustained release formulations having one or more antibodies, molecules, or pharmaceutical compositions provided herein. See, e.g., U.S. Pat. No. 4,526,938; PCT publication WO 91/05548; PCT publication WO 96/20698; Ning et al., Radiotherapy & Oncology 39:179-189 (1996), Song et al., PDA Journal of Pharmaceutical Science & Technology 50:372-397 (1995); Cleek et al., Pro. Int'l. Symp. Control. Rel. Bioact. Mater. 24:853-854 (1997); and Lam et al., Proc. Int'l. Symp. Control Rel. Bioact. Mater. 24:759-760(1997); all of which are hereby incorporated by reference in their entireties. In one embodiment, a pump can be used in a controlled release system (See Langer, supra; Sefton, 1987, CRC Crit. Ref Biomed. Eng. 14:20; Buchwald et al., 1980, Surgery 88:507; and Saudek et al., 1989, N. Engl. J. Med. 321:574). In another embodiment, polymeric materials can be used to achieve controlled release of antibodies (see e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J., Macromol. Sci. Rev. Macromol. Chem. 23:61; see also Levy et al., 1985, Science 228:190; During et al., 1989, Ann. Neurol. 25:351; Howard et al., 1989, J. Neurosurg. 7 1:105); U.S. Pat. Nos. 5,679,377; 5,916,597; 5,912,015; 5,989,463; 5,128,326; PCT Publication No. WO 99/15154; and PCT Publication No. WO 99/20253); all of which are hereby incorporated by references in their entireties.

Examples of polymers that can be used in sustained release formulations include, but are not limited to, poly(-hydroxy ethyl methacrylate), poly(methyl methacrylate), poly(acrylic acid), poly(ethylene-co-vinyl acetate), poly (methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In yet another embodiment, a controlled release system can be placed in proximity of the therapeutic target (e.g., the lungs), thus requiring only a fraction of the systemic dose (see, e.g., Goodson, in Medical Applications of Controlled Release, supra, vol. 2, pp. 115-138 (1984)). In another embodiment, polymeric compositions useful as controlled release implants are used according to Dunn et al. (see U.S. Pat. No. 5,945,155), which is hereby incorporated by references in its entirety. Based upon the therapeutic effect of the in situ controlled release of the bioactive material from the polymer system, the implantation can generally occur anywhere within the body of the patient in need of therapeutic treatment.

In another embodiment, a non-polymeric sustained delivery system is used, whereby a non-polymeric implant in the body of the subject is used as a drug delivery system. Upon implantation in the body, the organic solvent of the implant will dissipate, disperse, or leach from the composition into surrounding tissue fluid, and the non-polymeric material will gradually coagulate or precipitate to form a solid, microporous matrix (see U.S. Pat. No. 5,888,533). Controlled release systems are also discussed in the review by Langer (1990, Science 249:1527-1533). Any technique known to one of skill in the art can be used to produce sustained release formulations including one or more therapeutic agents provided herein. See, e.g., U.S. Pat. No. 4,526,938; International Publication Nos. WO 91/05548 and WO 96/20698; Ning et al., 1996, Radiotherapy & Oncology 39:179-189; Song et al., 1995, PDA Journal of Pharmaceutical Science & Technology 50:372-397; Cleek et al., 1997, Pro. Int'l. Symp. Control. Rel. Bioact. Mater. 24:853-854; and Lam et al., 1997, Proc. Int'l. Symp. Control Rel. Bioact. Mater. 24:759-760; all of which are hereby incorporated by references in their entireties.

Provided herein are also embodiment whereby the composition has nucleic acids encoding antibodies or other molecules as provided herein, whereby the nucleic acid can be administered in vivo to promote expression of its encoded antibody or other molecule, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (See e.g., Joliot et al., 1991, Proc. Natl. Acad. Sci. USA 88:1864-1868). Alternatively, a nucleic acid can be introduced intracellularly and incorporated within host cell DNA for expression by homologous recombination.

Treatment of a subject with a therapeutically effective amount of antibodies, other molecules or pharmaceutical composition provided herein can include a single treatment or a series of treatments. It is contemplated that the antibodies, molecules, or pharmaceutical compositions provided herein can be administered systemically or locally to treat disease, such as to inhibit tumor cell growth or to kill cancer cells in cancer patients with locally advanced or metastatic cancers. They can be administered intravenously, intrathecally, and/or intraperitoneally. They can be administered alone or in combination with anti-proliferative drugs. In one embodiment, they are administered to reduce the cancer load in the patient prior to surgery or other procedures. Alternatively, they can be administered after surgery to ensure that any remaining cancer (e.g., cancer that the surgery failed to eliminate) does not survive. In some embodiments, they can be administered after the regression of primary cancer to prevent metastasis.

5.6 Combination Therapies

Also provided herein are compositions and methods that include administration of the anti-BTN1A1 antibodies, anti-BTN1A1 ligand (e.g., GAL-1, GAL-9, NRP-2, BTLA) antibodies or other molecules having an antigen binding fragment that immunospecifically binds to BTN1A1 or a BTN1A1 ligand to a subject in need thereof, in combination with a second therapy. In some embodiments, the subject is a cancer patient and the second therapy is an anti-cancer or anti-hyperproliferative therapy.

In some embodiments, the compositions and methods that include administration of the antibodies or other molecules provided herein, when used in combination with another anti-cancer or anti-hyperproliferative therapy, can enhance the therapeutic potency of the other anti-cancer or anti-hyperproliferative therapy. Accordingly, methods and compositions described herein can be provided in combination with a second therapy to achieve the desired effect, such as killing of a cancer cell, inhibition of cellular hyperproliferation, and/or inhibition of cancer metastasis.

In some embodiments, the second therapy has a direct cytotoxic effect, such as a chemotherapy, a targeted therapy, a cryotherapy, a hyperthermia therapy, a photodynamic therapy, a high intensity focused ultrasound (HIFU) therapy, a radiotherapy, or a surgical therapy. The targeted therapy can be a biological targeted therapy or a small molecule targeted therapy. In other embodiments, the second therapy does not have a direct cytotoxic effect. For example, the second therapy may be an agent that upregulates the immune system without having a direct cytotoxic effect.

The second therapy can be an anti-PD1 therapy or an anti-PD-L1 therapy.

Accordingly, in another aspect, provided herein is a method of treating cancer in a subject, including administering to the subject a therapeutically effective amount of a molecule including an antigen binding fragment that immunospecifically binds to BTN1A1 and a therapeutically effective amount of an anti-PD-1 therapy and/or an anti-PD-L1 therapy.

In some embodiments, the method includes administering an anti-PD-1 therapy. In some embodiments, the method includes administering an anti-PD-L1 therapy. In some embodiments, the method includes administering an anti-PD-1 therapy and an anti-PD-L1 therapy.

In some embodiments, the anti-PD-1 therapy or the anti-PD-L1 therapy includes an anti-PD-1 or anti-PD-L1 antibody or antibody fragment, or a soluble PD-1 or PD-L1 ligand, or Fc-fusion protein thereof.

In some embodiments, the anti-PD-1 therapy includes nivolumab (Opdivo), pembrolizumab (Keytruda), pidilizumab, AMP-514, AMP-224, or a combination thereof.

In some embodiments, the anti-PD-1 therapy includes an anti-PD-1 antibody provided in International Application No. PCT/US2016/64394.

In some embodiments, the anti-PD-L1 therapy includes YW243.55.S70, MPDL3280A, MEDI-4736, MSB-0010718C, MDX-1105 or a combination thereof.

In some embodiments, the anti-PD-L1 therapy includes an antibody provided in International Application No. PCT/US2016/024691, published as WO 2016/160792 A1, and International Application No. PCT/US2017/024027.

In some embodiments, the molecule including the antigen binding fragment that immunospecifically binds to BTN1A1 and the anti-PD-1 therapy and/or an anti-PD-L1 therapy are formulated together.

In some embodiments, the molecule including the antigen binding fragment that immunospecifically binds to BTN1A1 and the anti-PD-1 therapy and/or an anti-PD-L1 therapy are formulated separately.

In some embodiments, the molecule including the antigen binding fragment that immunospecifically binds to BTN1A1 and the anti-PD-1 therapy or an anti-PD-L1 therapy are administered independently at the same time or separately within time intervals, optionally followed by one or more cycles of repeat dosing.

In some embodiments, the treatment produces at least one therapeutic effect selected from a group consisting of a reduction in size of a tumor, a reduction in number of metastatic lesions over time, a complete response, a partial response, and a stable disease.

Provided herein are methods that include administration of the anti-BTN1A1 antibodies, anti-BTN1A1 ligand antibodies or other molecules having an antigen binding fragment that immunospecifically binds to BTN1A1 or a BTN1A1 ligand (e.g., GAL-1, GAL-9, NRP-2, BTLA) to a subject in need thereof, in combination with a second or additional therapy (e.g., an anti-PD-1 therapy or an anti-PD-L1 therapy). The antibodies, other molecules, or pharmaceutical compositions provided herein can be administered before, during, after, or in various combinations relative to the second anti-cancer therapy. The administrations can be in intervals ranging from concurrently to minutes to days to weeks. In some embodiments where the antibodies or other molecules described herein are provided to a patient separately from a second anti-cancer agent, one would generally ensure that a significant period of time did not expire between the time of each delivery, such that the two compounds would still be able to exert an advantageously combined effect on the patient. In such instances, it is contemplated that one can provide a patient with the antibodies or other molecules provided herein, and the second anti-cancer therapy within about 12 to 24 or 72 h of each other and, more particularly, within about 6-12 h of each other. In some situations the time period for treatment can be extended significantly where several days (2, 3, 4, 5, 6, or 7) to several weeks (1, 2, 3, 4, 5, 6, 7, or 8) lapse between respective administrations.

In some embodiments, a course of treatment will last 1-90 days or more (this such range includes intervening days). It is contemplated that one agent can be given on any day of day 1 to day 90 (this such range includes intervening days) or any combination thereof, and another agent is given on any day of day 1 to day 90 (this such range includes intervening days) or any combination thereof. Within a single day (24-hour period), the patient can be given one or multiple administrations of the agent(s). Moreover, after a course of treatment, it is contemplated that there is a period of time at which no anti-cancer treatment is administered. This time period can last 1-7 days, and/or 1-5 weeks, and/or 1-12 months or more (this such range includes intervening days), depending on the condition of the patient, such as their prognosis, strength, health, etc. The treatment cycles can be repeated as necessary.

Various combinations can be employed. Listed below are some examples with the treatment with the anti-BTN1A1 antibody, anti-BTN1A1 ligand antibody or other molecules described herein as "A" and a second anti-cancer therapy (e.g., an anti-PD-1 therapy or an anti-PD-L1 therapy) as "B":

A/B/A B/A/B B/B/A A/A/B A/B/B B/A/A A/B/B/B B/A/B/B B/B/B/A B/B/A/B
A/A/B/B A/B/A/B A/B/B/A B/B/A/A B/A/B/A B/A/A/B A/A/A/B B/A/A/A
A/B/A/A A/A/B/A

Administration of any antibodies, molecules, or pharmaceutical compositions provided herein, in combination of a second therapy (e.g., an anti-PD-1 therapy or an anti-PD-L1 therapy) to a patient will follow general protocols for the administration of such second therapy, taking into account the toxicity, if any, of the second therapy. Therefore, in some embodiments there is a step of monitoring toxicity that is attributable to combination therapy.

Chemotherapy

A wide variety of chemotherapeutic agents can be used in accordance with the present embodiments as the second therapy. A chemotherapeutic can be a compound or composition that is administered in the treatment of cancer. These agents or drugs can be categorized by their mode of activity within a cell, for example, whether and at what stage they affect the cell cycle. Alternatively, an agent can be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammaI1 and calicheamicin omegaI1); dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; antimetabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid; capecitabine; carboplatin, procarbazine, plicomycin, gemcitabien, navelbine, farnesyl-protein transferase inhibitors, transplatinum, and pharmaceutically acceptable salts, acids, or derivatives of any of the above.

Radiotherapy

Another conventional anticancer therapy that can be used in combination with the methods and compositions described herein is radiotherapy, or radiation therapy. Radiotherapy include using γ-rays, X-rays, and/or the directed delivery of radioisotopes to tumor cells. Other forms of DNA damaging factors are also contemplated, such as microwaves, proton beam irradiation (U.S. Pat. Nos. 5,760, 395 and 4,870,287; all of which are hereby incorporated by references in their entireties), and UV-irradiation. It is most likely that all of these factors affect a broad range of damage on DNA, on the precursors of DNA, on the replication and repair of DNA, and on the assembly and maintenance of chromosomes.

Tumor microenvironment is intrinsically inhibitory due to the presence of myeloid-derived suppressor cells and regulatory T cells that infiltrate the tumor and function to suppress immune responses. In addition, the expression of certain inhibitory molecules on T cells and antigen presenting cells (APCs) can limit effective immune responses. Radiation mediates anti-tumor effects through the induction of tumor cell apoptosis, senescence, autophagy, and in some situations, can stimulate more effective immune responses.

Radiation can be a means to place tumor cells under a stressed condition so that the tumor cells can activate mechanisms to survive the stress. Molecules activated under such stressed conditions can be served as targets for therapies used in combination of radiation. BTN1A1 was identified as a potential target that overexpresses under such conditions.

The molecules as described herein that have an antigen binding fragment that immunospecifically binds BTN1A1 or a BTN1A1 ligand (e.g., GAL-1, GAL-9, NRP-2, BTLA) can stimulate local and systemic immune response. In some embodiments, a therapeutically effective amount of the antibodies, other molecules, or pharmaceutical compositions as described herein are administered before, at the same time with, or after a radiotherapy to achieve a synergistic effect.

In some embodiments, a therapeutically effective amount of the antibodies, other molecules, or pharmaceutical compositions described herein are administered that effectively sensitizes a tumor in a host to irradiation. Irradiation can be ionizing radiation and in particular gamma radiation. In some embodiments, the gamma radiation is emitted by linear accelerators or by radionuclides. The irradiation of the tumor by radionuclides can be external or internal.

In some embodiments, the administration of the antibodies, other molecules, or pharmaceutical compositions described herein commences up to one month, in particular up to 10 days or a week, before the irradiation of the tumor.

Additionally, irradiation of the tumor is fractionated the administration of the antibodies, other molecules, or pharmaceutical compositions described herein is maintained in the interval between the first and the last irradiation session.

Irradiation can also be X-ray radiation, gamma ray radiation, or charged particle radiation (proton beam, carbon beam, helium beam) (or "radiation" in general). Dosage ranges for radiation range from daily doses of 50 to 600 roentgens for some interval periods of time (2 or more days to several weeks), to single doses of 800 to 6000 roentgens. Radiation can be administered once daily, twice daily, three times daily, or four times daily. Dosage ranges for radioisotopes vary widely, and depend on the half-life of the isotope, the strength and type of radiation emitted, and the uptake by the neoplastic cells.

Targeted Therapy

Targeted cancer therapies are drugs or other substances that block the growth and spread of cancer by interfering with specific molecules ("molecular targets") that are involved in the growth, progression, and spread of cancer. Targeted cancer therapies are also referred to as "molecularly targeted drugs," "molecularly targeted therapies," "precision medicines," or similar names. Differing from standard chemotherapy, targeted therapies act on specific molecular targets that are associated with cancer, whereas standard chemotherapies usually act on all rapidly dividing normal and cancerous cells.

Targeted therapies include both small molecules targeted therapies and biologic targeted therapies, such as monoclonal antibodies. Small-molecule compounds are typically developed for targets that are located inside the cell because such agents are able to enter cells relatively easily. Biologic targeted therapies such as monoclonal antibodies are commonly used for targets that are outside cells or on the cell surface.

A number of different targeted therapies have been approved for use in cancer treatment. These therapies include hormone therapies, signal transduction inhibitors, gene expression modulator, apoptosis inducer, angiogenesis inhibitor, immunotherapies, and toxin delivery molecules.

Hormone therapies slow or stop the growth of hormone-sensitive tumors, which require certain hormones to grow. Hormone therapies act by preventing the body from producing the hormones or by interfering with the action of the hormones. Hormone therapies have been approved for both breast cancer and prostate cancer.

Signal transduction inhibitors block the activities of molecules that participate in signal transduction, the process by which a cell responds to signals from its environment. During this process, once a cell has received a specific signal, the signal is relayed within the cell through a series of biochemical reactions that ultimately produce the appropriate response(s). In some cancers, the malignant cells are stimulated to divide continuously without being prompted to do so by external growth factors. Signal transduction inhibitors interfere with this inappropriate signaling.

Gene expression modulators modify the function of proteins that play a role in controlling gene expression. Apoptosis inducers cause cancer cells to undergo a process of controlled cell death called apoptosis. Apoptosis is one method the body uses to get rid of unneeded or abnormal cells, but cancer cells have strategies to avoid apoptosis. Apoptosis inducers can get around these strategies to cause the death of cancer cells.

Angiogenesis inhibitors block the growth of new blood vessels to tumors (a process called tumor angiogenesis). A blood supply is necessary for tumors to grow beyond a certain size because blood provides the oxygen and nutrients that tumors need for continued growth. Treatments that interfere with angiogenesis can block tumor growth. Some targeted therapies that inhibit angiogenesis interfere with the action of vascular endothelial growth factor (VEGF), a substance that stimulates new blood vessel formation. Other angiogenesis inhibitors target other molecules that stimulate new blood vessel growth.

Immunotherapies trigger the immune system to destroy cancer cells. Some immunotherapies are monoclonal antibodies that recognize specific molecules on the surface of cancer cells. Binding of the monoclonal antibody to the target molecule results in the immune destruction of cells that express that target molecule. Other monoclonal antibodies bind to certain immune cells to help these cells better kill cancer cells.

Monoclonal antibodies that deliver toxic molecules can cause the death of cancer cells specifically. Once the antibody has bound to its target cell, the toxic molecule that is linked to the antibody—such as a radioactive substance or a poisonous chemical—is taken up by the cell, ultimately killing that cell. The toxin will not affect cells that lack the target for the antibody—i.e., the vast majority of cells in the body.

Cancer vaccines and gene therapy are also considered targeted therapies because they interfere with the growth of specific cancer cells.

For illustration, provided below is a list of FDA approved targeted therapies that can be used in accordance with the present embodiments as the second therapy.

Adenocarcinoma of the stomach or gastroesophageal junction: Trastuzumab (Herceptin®), ramucirumab (Cyramza®)

Basal cell carcinoma: Vismodegib (Erivedge™), sonidegib (Odomzo®)

Brain cancer: Bevacizumab (Avastin®), everolimus (Afinitor®)

Breast cancer: Everolimus (Afinitor®), tamoxifen, toremifene (Fareston®), Trastuzumab (Herceptin®), fulvestrant (Faslodex®), anastrozole (Arimidex®), exemestane (Aromasin®), lapatinib (Tykerb®), letrozole (Femara®), pertuzumab (Perjeta®), ado-trastuzumab emtansine (Kadcyla™), palbociclib (Ibrance®)

Cervical cancer: Bevacizumab (Avastin®)

Colorectal cancer: Cetuximab (Erbitux®), panitumumab (Vectibix®), bevacizumab (Avastin®), ziv-aflibercept (Zaltrap®), regorafenib (Stivarga®), ramucirumab (Cyramza®)

Dermatofibrosarcoma protuberans: Imatinib mesylate (Gleevec®)

Endocrine/neuroendocrine tumors: Lanreotide acetate (Somatuline® Depot)

Head and neck cancer: Cetuximab (Erbitux®)

Gastrointestinal stromal tumor: Imatinib mesylate (Gleevec®), sunitinib (Sutent®), regorafenib (Stivarga®)

Giant cell tumor of the bone: Denosumab (Xgeva®)

Kaposi sarcoma: Alitretinoin (Panretin®)

Kidney cancer: Bevacizumab (Avastin®), sorafenib (Nexavar®), sunitinib (Sutent®), pazopanib (Votrient®), temsirolimus (Torisel®), everolimus (Afinitor®), axitinib (Inlyta®)

Leukemia: Tretinoin (Vesanoid®), imatinib mesylate (Gleevec®), dasatinib (Sprycel®), nilotinib (Tasigna®), bosutinib (Bosulif®), rituximab (Rituxan®), alemtuzumab (Campath®), ofatumumab (Arzerra®), obinutuzumab (Gazyva™) ibrutinib (Imbruvica™), idelalisib (Zydelig®), blinatumomab (Blincyto™)

Liver cancer: Sorafenib (Nexavar®)

Lung cancer: Bevacizumab (Avastin®), crizotinib (Xalkori®), erlotinib (Tarceva®), gefitinib (Iressa®), afatinib dimaleate (Gilotrif®), ceritinib (LDK378/Zykadia), ramucirumab (Cyramza®), nivolumab (Opdivo®), pembrolizumab (Keytruda®)

Lymphoma: Ibritumomab tiuxetan (Zevalin®), denileukin diftitox (Ontak®), brentuximab vedotin (Adcetris®), rituximab (Rituxan®), vorinostat (Zolinza®), romidepsin (Istodax®), bexarotene (Targretin®), bortezomib (Velcade®), pralatrexate (Folotyn®), lenaliomide (Revlimid®), ibrutinib (Imbruvica™) siltuximab (Sylvant™), idelalisib (Zydelig®), belinostat (Beleodag™)

Melanoma: Ipilimumab (Yervoy®), vemurafenib (Zelboraf®), trametinib (Mekinist®), dabrafenib (Tafinlar®), pembrolizumab (Keytruda®), nivolumab (Opdivo®)

Multiple myeloma: Bortezomib (Velcade®), carfilzomib (Kyprolis®), lenaliomide (Revlimid®), pomalidomide (Pomalyst®), panobinostat (Farydak®)

Myelodysplastic/myeloproliferative disorders: Imatinib mesylate (Gleevec®), ruxolitinib phosphate (Jakafi™)

Neuroblastoma: Dinutuximab (Unituxin™)

Ovarian epithelial/fallopian tube/primary peritoneal cancers: Bevacizumab (Avastin®), olaparib (Lynparza™)

Pancreatic cancer: Erlotinib (Tarceva®), everolimus (Afinitor®), sunitinib (Sutent®)

Prostate cancer: Cabazitaxel (Jevtana®), enzalutamide (Xtandi®), abiraterone acetate (Zytiga®), radium 223 chloride (Xofigo®)

Soft tissue sarcoma: Pazopanib (Votrient®)

Systemic mastocytosis: Imatinib mesylate (Gleevec®)

Thyroid cancer: Cabozantinib (Cometriq™), vandetanib (Caprelsa®), sorafenib (Nexavar®), lenvatinib mesylate (Lenvima™)

Immunotherapy

The skilled artisan will understand that immunotherapies can be used in combination or in conjunction with methods of the embodiments. In the context of cancer treatment, immunotherapeutics generally rely on the use of immune effector cells and molecules to target and destroy cancer cells. Rituximab (RITUXAN®) is such an example. Checkpoint inhibitors, such as, for example, ipilumimab, are another such example. The immune effector can be, for example, an antibody specific for some marker on the surface of a tumor cell. The antibody alone can serve as an effector of therapy or it can recruit other cells to actually affect cell killing. The antibody also can be conjugated to a drug or toxin (e.g., chemotherapeutic, radionuclide, ricin A chain, cholera toxin, pertussis toxin) and serve merely as a targeting agent. Alternatively, the effector can be a lymphocyte carrying a surface molecule that interacts, either directly or indirectly, with a tumor cell target. Various effector cells include cytotoxic T cells and NK cells.

In some embodiments, the immunotherapy is an anti-PD-1 therapy or an anti-PD-L1 therapy).

An anti-PD-1 therapy can include any inhibitor of PD-1. In some embodiments, an anti-PD-1 therapy can include an anti-PD-1 antibody or antigen binding fragment thereof, an inhibitory nucleic acid, or a soluble PD-1 ligand (e.g., a soluble PD-L1), or a fusion-protein thereof (e.g., an Fc-fusion protein). In some embodiments, the anti-PD-1 therapy includes nivolumab (Opdivo), pembrolizumab (Keytruda), pidilizumab, AMP-514, or AMP-224.

In some embodiments, the anti-PD-1 therapy includes Nivolumab (CAS Registry Number: 946414-94-4). Nivolumab is also known as MDX-1 106, MDX-1 106-04, ONO-4538, or BMS-936558. Nivolumab is a fully human IgG4 monoclonal antibody that specifically blocks PD-1. Nivolumab (clone 5C4) and other human monoclonal antibodies that specifically bind to PD-1 are disclosed in U.S. Pat. No. 8,008,449 and WO2006/121 168.

In some embodiments, the anti-PD-1 therapy includes Pembrolizumab. Pembrolizumab is also known as KEYTRUDA®, lambrolizumab, Merck 3745, MK-3475 or SCH-900475. Pembrolizumab is a humanized IgG4 monoclonal antibody that binds to PD-1. Pembrolizumab is disclosed, e.g., in Hamid, O. et al. (2013) New England Journal of Medicine 369 (2): 134-44, WO2009/1 14335, and U.S. Pat. No. 8,354,509.

In some embodiments, the anti-PD-1 therapy is Pidilizumab. Pidilizumab, also known as CT-011 (CureTech), is a humanized IgG1 monoclonal antibody that binds to PD-1. Pidilizumab and other humanized anti-PD-1 monoclonal antibodies are disclosed in WO2009/101611.

In some embodiments, the anti-PD-1 therapy includes an anti-PD-1 antibody provided in International Application No. PCT/US2016/64394.

Additional anti-PD 1 antibodies that can be useful as anti-PD1 therapies are disclosed in U.S. Pat. No. 8,609,089, US 2010028330, and/or US 201201 14649.

In some embodiments, the anti-PD-1 therapy includes the fusion protein AMP 514 (Amplimmune). AMP-224, also known as B7-DCIg is, e.g., disclosed in WO2010/027827 and WO201 1/066342. AMP-224 is a PD-L2 Fc fusion soluble receptor that blocks the interaction between PD1 and B7-H1.

In some embodiments, the anti-PD-1 therapy includes an immunoadhesin (e.g., an immunoadhesin including an extracellular or PD-1 binding portion of PD-L1 or PD-L2 fused to a constant region (e.g., an Fc region of an immunoglobulin sequence)). In some embodiments, the anti-PD-1 therapy includes the fusion protein AMP-224 (Fc-fusion of PD-L2).

An anti-PD-L1 therapy can include any inhibitor of PD-L1. In some embodiments, an anti-PD-1 therapy can include an anti-PD-L1 antibody or antigen binding fragment thereof, an inhibitory nucleic acid, or a soluble PD-L1 ligand (e.g., a soluble PD-1), or a fusion-protein thereof (e.g., an Fc-fusion protein). In some embodiments, the anti-PD-L1 therapy includes YW243.55.S70, MPDL3280A, MEDI-4736, MSB-0010718C, or MDX-1105.

In some embodiments, the anti-PD-L1 therapy includes MDX-1105. MDX-1105, is also known as BMS-936559. See, e.g., WO2007/005874.

In some embodiments, the PD-L1 therapy includes the antibody YW243.55.S70, as described, e.g., in WO 2010/077634 (heavy and light chain variable region sequences shown in SEQ ID NOS: 20 and 21, respectively).

In some embodiments, the PD-L1 therapy includes MDPL3280A (Genentech/Roche). MDPL3280A is a human Fc optimized IgG1 monoclonal antibody that binds to PD-L1. MDPL3280A and other human monoclonal antibodies to PD-L1 are disclosed, e.g., in U.S. Pat. No. 7,943,743 and U.S. Publication No.: 20120039906.

In some embodiments, the anti-PD-L1 therapy includes the antibody MSB0010718C (Merck Serono). MSB0010718C is also known as A09-246-2.

In some embodiments, the anti-PD-L1 therapy includes MDPL3280A (Genentech/Roche), a human Fc optimized IgG1 monoclonal antibody that binds to PD-L1. MDPL3280A and other human monoclonal antibodies to PD-L1 are disclosed in U.S. Pat. No. 7,943,743 and U.S Publication No.: 20120039906.

In some embodiments, the anti-PD-L1 therapy includes an antibody provided in International Application No. PCT/US2016/024691, published as WO 2016/160792 A1, and International Application No. PCT/US2017/024027.

In one aspect of immunotherapy, the tumor cell bear some marker that is amenable to targeting, i.e., is not present on the majority of other cells. Many tumor markers exist and any of these can be suitable for targeting in the context of the present embodiments. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies currently under investigation or in use are immune adjuvants, e.g., *Mycobacterium bovis, Plasmodium falciparum*, dinitrochlorobenzene, and aromatic compounds (U.S. Pat. Nos. 5,801,005 and 5,739,169; Hui and Hashimoto, *Infect Immun.*, 66(11):5329-36 (1998); Christodoulides et al., *Microbiology*, 66(11):5329-36(1998)); cytokine therapy, e.g., interferons α, β, and γ, IL-1, GM-CSF, and TNF (Bukowski et al., *Clin Cancer Res.*, 4(10):2337-47 (1998); Davidson et al., *J Immunother.*, 21(5):389-98(1998); Hellstrand et al., *Acta Oncol.* 37(4): 347-53(1998)); gene therapy, e.g., TNF, IL-1, IL-2, and p53 (Qin et al., *Proc Natl Acad Sci USA*, 95(24):14411-6(1998); Austin-Ward and Villaseca, *Rev Med Chil*, 126(7):838-45 (1998); U.S. Pat. Nos. 5,830,880 and 5,846,945); and monoclonal antibodies, e.g., anti-PD1, anti-PDL1, anti-CD20, anti-ganglioside GM2, and anti-p185 (Topalian et al., *The New England journal of medicine*, 366:2443-2454 (2012); Brahmer et al., *The New England journal of medicine* 366:2455-2465 (2012); Hollander, *Front Immunol* (2012): 3:3. doi: 10.3389/fimmu.2012.00003; Hanibuchi et al., *Int J Cancer*, 78(4):480-5(1998); U.S. Pat. No. 5,824,311); all of which are hereby incorporated by reference in their entireties. It is contemplated that one or more anti-cancer therapies can be employed with the therapies described herein that involve the use the molecules having an antigen binding fragment that immunospecifically binds to BTN1A1 or a BTN1A1 ligand (e.g., GAL-1, GAL-9, NRP-2, BTLA), whereby the molecule can inhibit binding of the BTN1A1 ligand to BTN1A1.

Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment can be accomplished by perfusion, direct injection, or local application of the area with an additional anti-cancer therapy. Such treatment can be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments can be of varying dosages as well.

Additional Types of Therapies

Additional types of cancer therapies known in the art can be used in combination or in conjunction with methods and compositions provided herein, including but not limited to a cryotherapy, a hyperthermia therapy, a photodynamic therapy, and a high intensity focused ultrasound (HIFU) therapy.

Cryotherapy (also called cryosurgery) is the use of extreme cold produced by liquid nitrogen (or argon gas) to destroy abnormal tissue. Cryosurgery is used to treat external tumors, such as those on the skin. For external tumors, liquid nitrogen is applied directly to the cancer cells with a cotton swab or spraying device. Cryosurgery can also be used to treat tumors inside the body (internal tumors and tumors in the bone). For internal tumors, liquid nitrogen or argon gas is circulated through a hollow instrument called a cryoprobe, which is placed in contact with the tumor. The probes can be put into the tumor during surgery or through the skin (percutaneously). After cryosurgery, the frozen tissue thaws and is either naturally absorbed by the body (for internal tumors), or it dissolves and forms a scab (for external tumors).

A hyperthermia therapy (also called thermal therapy or thermotherapy) is a type of cancer treatment in which body tissue is exposed to high temperatures (up to 113° F.). There are several methods of hyperthermia, including local, regional, and whole-body hyperthermia.

In local hyperthermia, heat is applied to a small area, such as a tumor, using various techniques that deliver energy to heat the tumor. Different types of energy can be used to apply heat, including microwave, radiofrequency, and ultrasound. Depending on the tumor location, there are several approaches to local hyperthermia, including external approaches, intraluminal or endocavitary methods, and interstitial techniques.

In regional hyperthermia, various approaches can be used to heat large areas of tissue, such as a body cavity, organ, or limb, including deep tissue approaches, regional perfusion techniques, and continuous hyperthermic peritoneal perfusion (CHPP).

Whole-body hyperthermia can be used to treat metastatic cancer that has spread throughout the body, which can be accomplished by several techniques that raise the body temperature to 107-108° F., including the use of thermal chambers (similar to large incubators) or hot water blankets.

A photodynamic therapy (PDT) is a treatment that uses a drug, called a photosensitizer or photosensitizing agent, and a particular type of light. When photosensitizers are exposed to a specific wavelength of light, they produce a form of oxygen that kills nearby cells. In the first step of PDT for cancer treatment, a photosensitizing agent is injected into the bloodstream. The agent is absorbed by cells all over the body but stays in cancer cells longer than it does in normal cells. Approximately 24 to 72 hours after injection, when most of the agent has left normal cells but remains in cancer cells, the tumor is exposed to light. The photosensitizer in the tumor absorbs the light and produces an active form of oxygen that destroys nearby cancer cells.

The light used for PDT can come from a laser or other sources. Laser light can be directed through fiber optic cables (thin fibers that transmit light) to deliver light to areas inside the body. Other light sources include light-emitting diodes (LEDs), which can be used for surface tumors, such as skin cancer. Extracorporeal photopheresis (ECP) is a type of PDT in which a machine is used to collect the patient's blood cells, treat them outside the body with a photosensitizing agent, expose them to light, and then return them to the patient.

A high intensity focused ultrasound therapy (or HIFU) is a type of cancer treatment. Doctors give the HIFU treatment using a machine that gives off high frequency sound waves that deliver a strong beam to a specific part of a cancer and kill the cancer cells.

Other Agents

It is contemplated that other agents can be used in combination with certain aspects of the present embodiments to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions can increase the anti-hyperproliferative effects on the neighboring hyperproliferative cell population. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, can be used in combination with certain aspects of the present embodiments to improve the treatment efficacy.

5.7 Companion Diagnostics

This disclosure is based, at least in part, on the recognition that the expression of BTN1A1 and PD-L1 is mutually exclusive in certain cancers. Accordingly, provided herein are methods using BTN1A1, BTN1A1 lignads (e.g., GAL-1, GAL-9, NRP-2, BTLA) and PD-L1 as biomarkers and companion diagnostics for cancer.

BTN1A1 is highly and specifically expressed in cancer cells. Provided herein are also methods for detecting expression of BTN1A1 or a BTN1A1 ligand (e.g., GAL-1, GALS, NRP-2, BTLA) in a sample from a subject using molecules described herein that have an antigen binding fragment that immunospecifically binds to BTN1A1 or a BTN1A1 ligand. Accordingly, provided herein are also uses of the molecules described herein as a cancer diagnostic. In some embodiments, provided herein are methods to detect BTN1A1 or a BTN1A1 ligand (e.g., GAL-1, GAL-9, NRP-2, BTLA) in a sample from a subject by contacting the sample with molecules described herein to form a complex between the molecule and BTN1A1 or a BTN1A1 ligand, and detecting the complex in the sample. In some embodiments, provided herein are methods to provide or aid cancer diagnosis of a subject, including contacting a sample from the subject with molecules described herein to form a complex between the molecule and BTN1A1 or a BTN1A1 ligand, detecting the complex, and diagnosing the subject as likely having cancer if the complex is detected in the sample. In some embodiments, the methods include detecting the presence of glycosylated BTN1A1 in the sample using an molecules described herein having an antigen binding fragment that immunospecifically binds to glycosylated BTN1A1.

In some embodiments, the methods further include detecting the presence of PD-L1. Methods for detecting PD-L1 expression in a sample are known in the art, including, e.g., antibody-based detection methods (e.g., ELISA, FACS, immunocytochemistry) or nucleic acid-based detection methods (e.g., PCR, microarrays, DNA sequencing).

Also provided herein are methods for detecting expression of BTN1A1 or a BTN1A1 ligand (e.g., GAL-1, GAL-9, NRP-2, BTLA) in a sample from a subject using molecules described herein that have an antigen binding fragment that competitively blocks (e.g., in a dose-dependent manner) a BTN1A1 epitope or a BTN1L1 ligand epitope described herein. In some embodiments, the methods further include detecting expression of PD-L1.

Also provided herein are methods for detecting expression of BTN1A1 or a BTN1A1 ligand (e.g., GAL-1, GAL-9, NRP-2, BTLA) in a sample from a subject using molecules described herein that have an antigen binding fragment that immunospecifically binds to an epitope of BTN1A1 or of a BTN1A1 ligand as described herein. In some embodiments, the methods further include detecting expression of PD-L1.

In some embodiments, detecting BTN1A1 or a BTN1A1 ligand (e.g., GAL-1, GAL-9, NRP-2, BTLA) in a sample includes measuring the expression level of BTN1A1 or a BTN1A1 ligand in the sample using molecules described herein. In some embodiments, detecting BTN1A1 or a BTN1A1 ligand further includes comparing the expression level of BTN1A1 or a BTN1A1 ligand in the sample from the subject to a reference level. In some embodiments, the methods include measuring the expression level of the BTN1A1 or BTN1A1 lignad in a sample using the molecules described herein, comparing the expression level of the BTN1A1 or BTN1A1 ligand in the sample with a reference level, and diagnosing the subject as likely having cancer, or as likely to be responsive to a molecule including an antigen binding fragment that immunospecifically binds to BTN1A1 or a BTN1A1 ligand, if the expression level of BTN1A1 or BTN1A1 ligand in the sample is higher than the reference level.

In some embodiments, detecting PD-L1 in a sample includes measuring the expression level of PD-L1 in the sample using molecules described herein. In some embodiments, detecting PD-L1 further includes comparing the expression level of PD-L1 in the sample from the subject to a reference level. In some embodiments, the methods include measuring the expression level of the PD-L1 in a sample using the molecules described herein, comparing the expression level of the PD-L1 in the sample with a reference level, and diagnosing the subject as likely to be responsive to a molecule including an antigen binding fragment that immunospecifically binds to BTN1A1 or a BTN1A1 ligand (e.g., GAL-1, GAL-9, NRP-2, BTLA) if the expression level of PD-L1 in the sample is lower than the reference level.

In some embodiments, measuring the BTN1A1 level or BTN1A1 ligand level includes measuring the level of glycosylated BTN1A1 using molecules having an antigen binding fragment that immunospecifically binds to glycosylated BTN1A1, such as anti-glycosylated BTN1A1 antibodies. In some embodiments, measuring the level of glycosylated BTN1A1 in a sample further includes comparing the level of glycosylated BTN1A1 in the sample with a reference level, and diagnosing the subject as likely having cancer or as likely to be responsive to a molecule including an antigen binding fragment that immunospecifically binds to glycosylated-BTN1A1 if the level of glycosylated BTN1A1 in the sample is higher than the reference level.

In some embodiments, measuring the BTN1A1 level includes measuring the level of BTN1A1 dimers using molecules having an antigen binding fragment that immunospecifically binds to BTN1A1 dimers, such as anti-BTN1A1 dimer antibodies. In some embodiments, measuring the level of BTN1A1 dimers in a sample further includes comparing the level of glycosylated BTN1A1 in the sample with a reference level, and diagnosing the subject as likely having cancer or as likely to be responsive to a molecule including an antigen binding fragment that immunospecifically binds to a BTN1A1 dimer if the level of BTN1A1 dimers in the sample is higher than the reference level.

In some embodiments, the reference level can be the expression level of BTN1A1, a BTN1A1 ligand (e.g., GAL-1, GAL-9, NRP-2, BTLA) or PD-L1 in a sample from a healthy individual. In some embodiments, the reference level can be the average or medium expression level of BTN1A1, a BTN1A1 ligand or PD-L1 in samples from a population of healthy individuals. The reference level can also be a cutoff value determined by statistic analysis of the expression levels of BTN1A1, a BTN1A1 ligand or PD-L1 from samples of a population. Statistic methods that can be used to determine such cutoff value are well known in the art. For example, Receiver Operator Characteristic (ROC) analysis can be utilized to determine the reference expression ratio. A review of the ROC analysis can be found in Soreide, *J Clin Pathol,* 10:1136 (2008), which is herby incorporated by reference in its entirety.

In some embodiments, the subject can be a healthy subject undergoing a routine medical checkup. In some embodiments, the healthy subject is at risk of having cancer, as determined by the presence of certain risk factors that are well known in the art. Such risk factors include, without limitation, a genetic predisposition, a personal disease history, a familial disease history, a lifestyle factor, an environmental factor, a diagnostic indicator, and the like. In some embodiments, the subject is asymptomatic. An asymptomatic subject further includes a cancer patient who display mild early diagnostic indicators of cancer, but is otherwise symptom or complaint free. In some embodiments, the subject has cancer.

In some embodiments, the subject is suspected of having cancer. In some embodiments, the subject has a genetic predisposition for developing cancer or a family history of cancer. In some embodiments, the subject is exposed to certain lifestyle factors promoting the development of cancer or the subject shows clinical disease manifestations of cancer. In some embodiments, the subject is a patient who is receiving a clinical workup to diagnose cancer or to assess the risk of developing cancer.

The cancer can be a metastatic cancer. The cancer can be a hematological cancer or a solid tumor. In some embodiments, the cancer is a hematological cancer selected from the group consisting of leukemia, lymphoma, and myeloma. In some embodiments, the cancer is a solid tumor selected from the group consisting of breast cancer, lung cancer, thymic cancer, thyroid cancer, head & neck cancer, prostate cancer, esophageal cancer, tracheal cancer, brain cancer, liver cancer, bladder cancer, kidney cancer, stomach cancer, pancreatic cancer, ovarian cancer, uterine cancer, cervical cancer, testicular cancer, colon cancer, rectal cancer or skin cancer, both melanomatous and non-melanomatous skin cancers. The cancer can also be any other type of cancer as described herein.

In some embodiments, the cancer is an anti-PD1 therapy or an anti-PD-L1 therapy resistant or refractory cancer. In some embodiments, the cancer is an anti-PD1 therapy resistant or refractory cancer. In some embodiments, the cancer is an anti-PD-L1 therapy resistant or refractory cancer. In some embodiments, the cancer is a breast cancer or a lung cancer. In some embodiments, the cancer is a mammary carcinoma. In some embodiments, the cancer is a Lewis lung carcinoma.

In some embodiments, the subject is treatment naïve. In some embodiments, the subject is undergoing treatments for cancer (e.g., chemotherapy). In some embodiments, the subject is in remission. In some embodiments, the remission is drug-induced. In some embodiments, the remission is drug-free.

In some embodiments, the methods of detecting BTN1A1 or a BTN1A1 ligand (e.g., GAL-1, GAL-9, NRP-2, BTLA) or PD-L1 include obtaining a sample from a subject. The subject can be a human. The subject can be a cancer patient. The sample can be a whole blood sample, a bone marrow sample, a partially purified blood sample, PBMCs, tissue biopsy, circulating tumor cells, circulating elements such as protein complexes or exosomes. In some embodiments, the sample is a blood sample. In some embodiments, the sample is tissue biopsy.

In some embodiments, the methods provided herein include detecting BTN1A1, a BTN1A1 ligand or PD-L1 in a sample using a variety of immunohistochemistry (IHC) approaches or other immunoassay methods using molecules described herein, including anti-BTN1A1 antibodies, anti-BTN1A1 ligand antibodies, and anti-PD-L1 antibodies.

IHC staining of tissue sections has been shown to be a reliable method of assessing or detecting presence of proteins in a sample. Immunohistochemistry techniques utilize an antibody to probe and visualize cellular antigens in situ, generally by chromogenic or fluorescent methods. Thus, antibodies or antisera, preferably polyclonal antisera, and most preferably monoclonal antibodies specific for BTN1A1, a BTN1A1 ligand (e.g., GAL-1, GAL-9, NRP-2, BTLA) or PD-L1 can be used. As discussed in greater detail below, the antibodies can be detected by direct labeling of the antibodies themselves, for example, with radioactive labels, fluorescent labels, hapten labels such as, biotin, or an enzyme such as horse radish peroxidase or alkaline phosphatase. Alternatively, unlabeled primary antibody is used in conjunction with a labeled secondary antibody, including antisera, polyclonal antisera or a monoclonal antibody specific for the primary antibody. Immunohistochemistry protocols and kits are well known in the art and are commercially available. Automated systems for slide preparation and IHC processing are available commercially. The Ventana® BenchMark XT system is an example of such an automated system.

Standard immunological and immunoassay procedures can be found in *Basic and Clinical Immunology* (Stites & Terr eds., 7th ed. 1991). Moreover, the immunoassays can be performed in any of several configurations, which are reviewed extensively in *Enzyme Immunoassay* (Maggio, ed., 1980); and Harlow & Lane, supra. For a review of the general immunoassays, see also *Methods in Cell Biology: Antibodies in Cell Biology,* volume 37 (Asai, ed. 1993); *Basic and Clinical Immunology* (Stites & Ten, eds., 7th ed. 1991).

Commonly used assays to detect BTN1A1, a BTN1A1 ligand or PD-L1 include an enzyme-linked immunosorbent assay (ELISA), a fluorescent immunosorbent assay (FIA), a chemiluminescent immunosorbent assay (CLIA), a radioimmunoassay (RIA), an enzyme multiplied immunoassay (EMI), a solid phase radioimmunoassay (SPROA), a fluorescence polarization (FP) assay, a fluorescence resonance energy transfer (FRET) assay, a time-resolved fluorescence resonance energy transfer (TR-FRET) assay and a surface plasmon resonance (SPR) assay.

In some embodiments, the ELISA is a sandwich ELISA. In some embodiments, the ELISA is a direct ELISA. In some embodiments, the ELISA includes the initial step of immobilizing the molecules described herein on a solid support (e.g., on the wall of a microtiter plate well or of a cuvette).

The assays to detect BTN1A1, a BTN1A1 ligand or PD-L1 include noncompetitive assays, e.g., sandwich assays, and competitive assays. Typically, an assay such as an ELISA assay can be used. ELISA assays are known in the art, e.g., for assaying a wide variety of tissues and samples, including blood, plasma, serum or bone marrow.

A wide range of immunoassay techniques using such an assay format are available, see, e.g., U.S. Pat. Nos. 4,016,043, 4,424,279, and 4,018,653, which are hereby incorporated by reference in their entireties. These include both single-site and two-site or "sandwich" assays of the noncompetitive types, as well as in the traditional competitive binding assays. These assays also include direct binding of a labeled antibody to a target antigen. Sandwich assays are commonly used assays. A number of variations of the sandwich assay technique exist. For example, in a typical forward assay, an unlabelled anti-BTN1A1 antibody is immobilized on a solid substrate, and the sample to be tested brought into contact with the bound antibody. After a suitable period of incubation, for a period of time sufficient to allow formation of an antibody-antigen complex, a second anti-BTN1A1 antibody, labeled with a reporter molecule capable of producing a detectable signal is then added and incubated, allowing time sufficient for the formation of another complex of antibody-antigen-labeled antibody. Any unreacted material is washed away, and the presence of the antigen is determined by observation of a signal produced by the reporter molecule. The results may either be qualitative by simple observation of the visible signal, or can be quantitated by comparing with a control sample containing standard amounts of the antigen.

Variations on the forward assay include a simultaneous assay, in which both sample and labeled antibody are added simultaneously to the bound antibody. These techniques are well known to those skilled in the art, including any minor variations as will be readily apparent. In a typical forward sandwich assay, for example, a first anti-BTN1A1, anti-BTN1A1 ligand antibody or a first anti-PD-L1 antibody is either covalently or passively bound to a solid surface. The solid surface can be glass or a polymer, the most commonly used polymers being cellulose, polyacrylamide, nylon, polystyrene, polyvinyl chloride, or polypropylene. The solid supports can be in the form of tubes, beads, discs of microplates, or any other surface suitable for conducting an immunoassay. The binding processes are well-known in the art and generally consist of cross-linking covalently binding or physically adsorbing, the polymer-antibody complex is washed in preparation for the test sample. An aliquot of the sample to be tested is then added to the solid phase complex and incubated for a period of time sufficient (e.g. 2-40 minutes or overnight if more convenient) and under suitable conditions (e.g., from room temperature to 40° C. such as between 25° C. and 32° C. inclusive) to allow binding of any subunit present in the antibody. Following the incubation period, the antibody subunit solid phase is washed and dried and incubated with a second antibody specific for a portion of the antigen. The second anti-BTN1A1 antibody or second anti-PD-L1 antibody is linked to a reporter molecule which is used to indicate the binding of the second antibody to the molecular marker.

In some embodiments, flow cytometry (FACS) can be used to detect the level of BTN1A1, a BTN1A1 ligand, or PD-L1 in a sample. The flow cytometer detects and reports the intensity of the fluorichrome-tagged antibody, which indicates the level of BTN1A1, a BTN1A1 ligand or PD-L1. Non-fluorescent cytoplasmic proteins can also be observed by staining permeablized cells. The stain can either be a fluorescence compound able to bind to certain molecules, or a fluorichrome-tagged antibody to bind the molecule of choice.

In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, beta-galactosidase, and alkaline phosphatase, and other are discussed herein. The substrates to be used with the specific enzymes are generally chosen for the production, upon hydrolysis by the corresponding enzyme, of a detectable color change. Examples of suitable enzymes include alkaline phosphatase and peroxidase. It is also possible to employ fluorogenic substrates, which yield a fluorescent product rather than the chromogenic substrates noted above. In all cases, the enzyme-labeled antibody is added to the first antibody-molecular marker complex, allowed to bind, and then the excess reagent is washed away. A solution containing the appropriate substrate is then added to the complex of antibody-antigen-antibody. The substrate will react with the enzyme linked to the second antibody, giving a qualitative visual signal, which can be further quantitated, usually spectrophotometrically, to give an indication of the amount of BTN1A1, a BTN1A1 ligand or PD-L1 present in the sample. Alternately, fluorescent compounds, such as fluorescein and rhodamine, can be chemically coupled to antibodies without altering their binding capacity. When activated by illumination with light of a particular wavelength, the fluorochrome-labeled antibody adsorbs the light energy, inducing a state to excitability in the molecule, followed by emission of the light at a characteristic color visually detectable with a light microscope. As in the EIA, the fluorescent labeled antibody is allowed to bind to the first antibody-molecular marker complex. After washing off the unbound reagent, the remaining tertiary complex is then exposed to the light of the appropriate wavelength, the fluorescence observed indicates the presence of BTN1A1 or a BTN1A1 ligand or PD-L 1. Immunofluorescence and EIA techniques are both well established in the art and are discussed herein.

As such, provided herein are methods of cancer diagnosis include detecting the presence or expression levels of BTN1A1 or a BTN1A1 ligand in a sample from a subject using the molecules described therein having an antigen binding fragment that immunospecifically binds to BTN1A1 or a BTN1A1 ligand. In some embodiments, the methods further include administering a cancer treatment to the subject diagnosed to have cancer. The cancer treatment can be any cancer therapy as described herein or otherwise known in the art. In some embodiments, the cancer treatment includes administering a therapeutically effective amount of anti-BTN1A1 antibodies or anti-BTN1A1 ligand antibodies to the subject. In some embodiments, the cancer treatment includes administering a therapeutically effective amount of an anti-PD1 therapy or an anti-PD-L1 therapy.

5.8 Evaluating Efficacy of Treatment

The expression level of BTN1A1 in a subject can correlate with cancer development. An increase in BTN1A1 level can indicate cancer progression, and a decrease in BTN1A1 level can indicate cancer regression. Accordingly, provided herein are also methods to evaluate the efficacy of a particular cancer treatment in a subject by monitoring the BTN1A1 level or BTN1A1 ligand (e.g., GAL-1, GAL-9, NRP-2, BTLA) level in samples of the subject over a course of the treatment using molecules described herein having an antigen binding fragment that immunospecifically binds to BTN1A1 or a BTN1A1 ligand. In some embodiments, the methods include detecting the expression levels of BTN1A1 or a BTN1A1 ligand. In some embodiments, the methods include detecting the levels of glycosylated BTN1A1. In some embodiments, the methods include detecting the levels of BTN1A1 dimers.

In some embodiments, the molecules have an antigen binding fragment that immunospecifically binds to GAL-1, GAL-9, NRP-2, or BTLA. In some embodiments, the molecules have an antigen binding fragment that immunospecifically binds to GAL-1. In some embodiments, the molecules have an antigen binding fragment that immunospecifically binds to GAL-9. In some embodiments, the molecules have an antigen binding fragment that immunospecifically binds to NRP-2. In some embodiments, the molecules have an antigen binding fragment that immunospecifically binds to BTLA.

In some embodiments, provided herein are also methods to evaluate the efficacy of a particular cancer treatment in a subject by monitoring the BTN1A1 level or BTN1A1 ligand (e.g., GAL-1, GAL-9, NRP-2, BTLA) level in samples of the subject over a course of the treatment using molecules described herein having an antigen binding fragment. In some embodiments, the molecules can have an antigen binding fragment that competitively blocks (e.g., in a dose-dependent manner) a BTN1A1 epitope or a BTN1A1 ligand epitope described herein.

In some embodiment, provided herein are methods of evaluating the efficacy of a particular cancer treatment in a patient, including: a) contacting two or more samples obtained from the patient at a first and at least one subsequent time point throughout the course of the treatment with a molecule described herein; b) measuring the levels of BTN1A1 or a BTN1A1 ligand (e.g., GAL-1, GAL-9, NRP-2, BTLA) in the two or more samples, and c) comparing the levels of BTN1A1 or a BTN1A1 ligand in the two or more samples, where a decreased level of BTN1A1 or a BTN1A1 ligand in a sample obtained at a subsequent time point relative to the level of BTN1A1 or a BTN1A1 ligand in the sample obtained at the first time point indicate that the cancer treatment is efficacious. The molecule can be an anti-BTN1A1 antibody or anti-BTN1A1 ligand antibody. In some embodiments, the BTN1A1 level can be the level of glycosylated BTN1A1. In some embodiments, the BTN1A1 level can be the level of a BTN1A1 dimer (e.g., a glycosylated BTN1A1 dimer).

In some embodiments, the methods include contacting two or more samples obtained from the patient at a first and at least one subsequent time point throughout the course of the treatment with a molecule described herein to form complexes between the molecule and BTN1A1 or BTN1A1 ligand in the samples and measuring the levels of BTN1A1 or a BTN1A1 ligand in the two or more samples by measuring the complexes in the sample.

In some embodiments, the levels of BTN1A1 or a BTN1A1 ligand from two or more samples are measured in one assay. In other embodiments, the levels the levels of BTN1A1 or a BTN1A1 ligand from two or more samples are measured in multiple assays. In some embodiments, the level of BTN1A1 or a BTN1A1 ligand is measured the same day as the sample is obtained from the subject. In some embodiments, the level of BTN1A1 or a BTN1A1 ligand is measured without storage of the sample obtained from the subject.

The sample from a cancer patient can be a whole blood sample, a bone marrow sample, a partially purified blood sample, PBMCs, tissue biopsy, circulating tumor cells, circulating elements such as protein complexes or exosomes. In some embodiments, the sample is a blood sample. In some embodiments, the sample is tissue biopsy. As a person of ordinary skill in the art would understand, any methods of determining the expression level of a protein in a sample as described herein or otherwise known in the art can be used to determine the level of BTN1A1 or a BTN1A1 ligand in a sample from a cancer patient. In some embodiments, the methods include an immunoassay. The immunoassay can be an immunohistochemistry approach, including using molecules described herein to probe and visualize BTN1A1 or a BTN1A1 ligand. The immunoassay can include FIA, CLIA, RIA, EMI, SPROA, FP assay, FRET assay, TR-FRET assay or SPR assay.

The cancer treatment or cancer therapy can be any therapy described herein or otherwise known in the art, including but not limited to: a surgical therapy, chemotherapy, biological targeted therapy, small molecular targeted therapy, radiation therapy, cryotherapy, hormonal therapy, immunotherapy and cytokine therapy. In some embodiments, the cancer treatment include a FDA-approved cancer treatment, including an experimental cancer treatment in clinical development. In some embodiments, the cancer treatment includes treatments with a combination of two or more drugs, or two or more types of therapies.

In some embodiments, the cancer treatment includes administering an anti-BTN1A1 antibody or a BTN1A1 ligand antibody to the cancer patient.

In some embodiments, one or more samples were obtained at the beginning of the course of the cancer treatment and one or more samples were obtained at later time points throughout the course of the treatment. In some embodiments, the subsequent time points are 2 or more, 3 or more, 4 or more, 5 or more, 6 or more, 7 or more, 8 or more, 9 or more, 10 or more, 15 or more, 20 or more, 25 or more or 30 or more time points.

In some embodiments, the method further includes adjusting the treatment if the treatment is determined to be not efficacious. Adjusting the treatment can include, for example, adjusting the dose of a drug treatment, increasing the frequency of a drug treatment, treating with a different drug or combination of drugs, or ending the treatment.

In some embodiments, the method further includes repeating a treatment if the treatment is determined to be efficacious.

In some embodiments, the level of BTN1A1 or BTN1A1 ligand in the samples obtained at the first time point is decreased by more than 10%, more than 20%, more than 30%, more than 40%, more than 50%, more than 60%, more than 70%, more than 80%, more than 90%, more than 95%, or more than 99% at a subsequent time point.

5.9 Patient Selection

Provided herein are uses of molecules having an antigen binding fragment that immunospecifically binds to BTN1A1 or a BTN1A1 ligand (e.g., GAL-1, GAL-2, NRP-2, BTLA) to predict responsiveness of a cancer patient to a cancer treatment by determining the presence or expression level of BTN1A1 or a BTN1A1 ligand in a sample from the patient. In some embodiments, the methods include detecting BTN1A1 or a BTN1A1 ligand in a sample from a cancer patient by contacting the sample with a molecule described herein to form a complex between the molecule and BTN1A1 or a BTN1A1 ligand, and predicting that the subject will likely be responsive to a cancer treatment if the complex is detected. In some embodiments, the methods include detecting the presence of glycosylated BTN1A1 in the sample using molecules having an antigen-binding fragment that immunospecifically binds to glycosylated BTN1A1. In some embodiments, the methods include detecting the presence of a BTN1A1 dimer (e.g., a glycosylated BTN1A1 dimer) in the sample using molecules having an antigen binding fragment that immunospecifically binds to a BTN1A1 dimer (e.g., a glycosylated BTN1A1 dimer). In some embodiments, the method further includes determining the presence or expression level of PD-L1. In some embodiments, the methods include detecting the presence of a BTN1A1 ligand, such as GAL-1, GAL-9, NRP-2, or BTLA, in the sample using molecules having an antigen-binding fragment that immunospecifically binds to GAL-1, GAL-9, NRP-2, or BTLA. In some embodiments, the methods include detecting the presence of a BTN1A1 ligand, such as GAL-1 in the sample using molecules having an antigen-binding fragment that immunospecifically binds to GAL-1. In some embodiments, the methods include detecting the presence of a BTN1A1 ligand, such as GAL-9 in the sample using molecules having an antigen-binding fragment that immunospecifically binds to GAL-9. In some embodiments, the methods include detecting the presence of a BTN1A1 ligand, such as NRP-2 in the sample using molecules having an antigen-binding fragment that immunospecifically binds to NRP-2. In some embodiments, the methods include detecting the presence of a BTN1A1 ligand, such as BTLA, in the sample using molecules having an antigen-binding fragment that immunospecifically binds to BTLA.

In other embodiments, detecting BTN1A1 or a BTN1A1 ligand (e.g., GAL-1, GAL-9, NRP-2, BTLA), e.g., alone or in combination with PD-L1, in a sample includes measuring the expression level of BTN1A1 or a BTN1A1 ligand, e.g., alone or in combination with PD-L1, in the sample using molecules described herein. In some embodiments, detecting BTN1A1 or a BTN1A1 ligand, e.g., alone or in combination with PD-L1, further includes comparing the expression level of BTN1A1 or a BTN1A1 ligand, e.g., alone or in combination with PD-L1, in the sample from the subject to a reference level. In some embodiments, the methods include measuring the expression level of the BTN1A1 or a BTN1A1 ligand, e.g., alone or in combination with PD-L1, in a sample using an anti-BTN1A1 antibody or an anti-BTN1A1 ligand antibody, comparing the expression level of BTN1A1 or a BTN1A1 ligand, e.g., alone or in combination with PD-L1, in the sample with a reference level, and predicting that the subject will likely be responsive to a cancer treatment if the expression level of BTN1A1 or a BTN1A1 ligand in the sample is higher than the BTN1A1 or BTN1A1 ligand reference level, and, optionally, if the expression level of PD-L1 is lower than the PD-L1 reference level.

In some embodiments, measuring the BTN1A1 level or BTN1A1 ligand level, e.g., alone or in combination with PD-L1, includes measuring the level of GAL-1, GAL-9, NRP-2, or BTLA, e.g., alone or in combination with PD-L1, using an anti-GAL-1 antibody, anti-GAL-9 antibody, anti-NRP-2 antibody, or anti-BTLA antibody. In some embodiments, measuring the BTN1A1 level or BTN1A1 ligand level, e.g., alone or in combination with PD-L1, includes measuring the level of GAL-1, e.g., alone or in combination with PD-L1, using an anti-GAL-1 antibody. In some embodiments, measuring the BTN1A1 level or BTN1A1 ligand level, e.g., alone or in combination with PD-L1, includes measuring the level of GAL-9, e.g., alone or in combination with PD-L1, using an anti-GAL-9 antibody. In some embodiments, measuring the BTN1A1 level or BTN1A1 ligand level, e.g., alone or in combination with PD-L1, includes measuring the level of NRP-2, e.g., alone or in combination with PD-L1, using an anti-NRP-2 antibody. In some embodiments, measuring the BTN1A1 level or BTN1A1 ligand level, e.g., alone or in combination with PD-L1, includes measuring the level of BTLA, e.g., alone or in combination with PD-L1, using an anti-BTLA antibody.

The sample from a cancer patient can be a whole blood sample, a bone marrow sample, a partially purified blood sample, PBMCs, tissue biopsy, circulating tumor cells, circulating elements such as protein complexes or exosomes. In some embodiments, the sample is a blood sample. Methods to detect the presence of BTN1A1, a BTN1A1 ligand (e.g., GAL-1, GAL-9, NRP-2, BTLA) or PD-L1 or measure the expression level of BTN1A1, a BTN1A1 ligand or PD-L1 are described herein or otherwise known in the art.

The cancer treatment or cancer therapy can be any therapy described herein or otherwise known in the art, including but not limited to: a surgical therapy, chemotherapy, biological targeted therapy, small molecular targeted therapy, radiation therapy, cryotherapy, hormonal therapy, immunotherapy and cytokine therapy. In some embodiments, the cancer treatment include a FDA-approved cancer treatment, including an experimental cancer treatment in clinical development. In some embodiments, the cancer treatment includes treatments with a combination of two or more drugs, or two or more types of therapies.

In some embodiments, the cancer treatment includes administering an anti-BTN1A1 antibody to the cancer patient. In some embodiments, the cancer treatment further includes administering an anti-PD-1 therapy or an anti-PD-L1 therapy.

5.10 Kit

Provided herein are kits containing a molecule described herein and one or more ancillary agents. In some embodiments, provided herein is a kit for preparing and/or administering a therapy provided herein. The kit can have one or more sealed vials containing any of the pharmaceutical compositions described herein. The kit can include, for example, a molecule having an antigen binding fragment that immunospecifically binds to BTN1A1 or a BTN1A1 ligand (e.g., GAL-1, GAL-9, NRP-2, BTLA) as well as reagents to prepare, formulate, and/or administer the molecule or perform one or more steps of the methods disclosed herein.

In some embodiments, the antigen binding fragment immunospecifically binds to a BTN1A1 ligand, such as GAL-1, GAL-9, NRP-2, or BTLA. In some embodiments, the antigen binding fragment immunospecifically binds to GAL-1. In some embodiments, the antigen binding fragment immunospecifically binds to a GAL-9. In some embodiments, the antigen binding fragment immunospecifically binds to NRP-2. In some embodiments, the antigen binding fragment immunospecifically binds to BTLA.

In some embodiments, the molecule is an anti-BTN1A1 antibody or anti-BTN1A1 ligand antibody. In some embodiments, the anti-BTN1A1 antibody or anti-BTN1A1 ligand antibody is humanized antibody or human antibody.

In some embodiments, the kit further includes a second anticancer agent. The second anticancer agent can be a chemotherapeutic agent, a immunotherapeutic agent, a hormonal therapeutic agent, or a cytokine.

In some embodiments, the second anticancer agent is an anti-PD1-therapy or an anti-PD-L1 therapy. In some embodiments, the second anticancer agent is an anti-PD1-therapy. In some embodiments, the second anticancer agent is an anti-PD-L1 therapy. In some embodiments, the second anticancer agent is an anti-PD1 therapy and an anti-PD-L1 therapy. In some embodiments, the anti-PD-1 therapy or the anti-PD-L1 therapy includes an anti-PD-1 or anti-PD-L1 antibody or antibody fragment, or a soluble PD-1 or PD-L1 ligand, or Fc-fusion protein thereof. In some embodiments, the anti-PD-1 therapy includes nivolumab (Opdivo), pembrolizumab (Keytruda), pidilizumab, AMP-514, or AMP-224. In some embodiments, the anti-PD-1 therapy includes an anti-PD-1 antibody provided in International Application No. PCT/US2016/64394. In some embodiments, the anti-PD-L1 therapy includes YW243.55.S70, MPDL3280A, MEDI-4736, MSB-0010718C, or MDX-1105. In some embodiments, the anti-PD-L1 therapy includes an antibody provided in International Application No. PCT/US2016/024691, published as WO 2016/160792 A1, and International Application No. PCT/US2017/024027.

Provided herein are also kits that can be used as a companion diagnostic for cancer. In some embodiments, the kits can be used to provide or aid cancer diagnosis. In some embodiments, the kits can be used to evaluate the efficacy of a cancer treatment. In some embodiments, the kits can be used to predict the responsiveness of a patient to a cancer treatment. In some embodiments, the kits can be used to select patients for a particular cancer treatment. The kit can include, for example, reagents for detecting BTN1A1 or a BTN1A1 ligand in a sample. In some embodiments, the kit includes a reagent for detecting PD-L1 (e.g., an anti-PD-L1 antibody).

The reagent can be a molecule having an antigen binding fragment that immunospecifically binds to BTN1A1 or a BTN1A1 ligand (e.g., GAL-1, GAL-9, NRP-2, BTLA). In some embodiments, the antigen binding fragment binds to GAL-1. In some embodiments, the antigen binding fragment binds to GAL-9. In some embodiments, the antigen binding fragment binds to NRP-2. In some embodiments, the antigen binding fragment binds to BTLA.

The cancer therapies can be any therapy described herein or otherwise known in the art, including but not limited to: a surgical therapy, chemotherapy, biological targeted therapy, small molecular targeted therapy, radiation therapy, cryotherapy, hormonal therapy, immunotherapy and cytokine therapy. In some embodiments, the cancer therapy includes administering to a cancer patient molecules described herein that have an antigen binding fragment that immunospecifically binds to BTN1A1 or a BTN1A1 ligand, such as anti-BTN1A1 antibodies or anti-BTN1A1 ligand antibodies, including anti-GAL-1 antibodies, anti-GAL-9 antibodies, anti-NRP-2 antibodies, and anti-BTLA antibodies.

In some embodiments, the ancillary reagent for the diagnostic kit can be a secondary antibody, a detection reagent, an immobilization buffer, a blocking buffer, a washing buffer, a detection buffer, or any combination thereof.

Secondary antibodies can include, for example, an anti-human IgA antibody, an anti-human IgD antibody, an anti-human IgE antibody, an anti-human IgG antibody, or an anti-human IgM antibody. In some embodiments, the secondary antibodies are anti-bovine antibodies. Secondary detection antibodies can be monoclonal or polyclonal antibodies. Secondary antibodies can be derived from any mammalian organism, including mice, rats, hamsters, goats, camels, chicken, rabbit, and others. Secondary antibodies can be conjugated to enzymes (e.g., horseradish peroxidase (HRP), alkaline phosphatase (AP), luciferase, and the like) or dyes (e.g., colorimetric dyes, fluorescent dyes, fluorescence resonance energy transfer (FRET)-dyes, time-resolved (TR)-FRET dyes, and the like). In some embodiments, the secondary antibody is a polyclonal rabbit-anti-human IgG antibody, which is HRP-conjugated.

In some embodiments, the detection reagent contains a fluorescent detection reagent or a luminescent detection reagent. In some other embodiments, the luminescent detection reagent contains luminol or luciferin.

A large selection of washing buffers are known in the art, such as tris(hydroxymethyl)aminomethane (Tris)-based buffers (e.g., Tris-buffered saline, TBS) or phosphate buffers (e.g., phosphate-buffered saline, PBS). Washing buffers can include detergents, such as ionic or non-ionic detergents. In some embodiments, the washing buffer is a PBS buffer (e.g., about pH 7.4) including Tween®20 (e.g., about 0.05% Tween®20).

Any dilution buffer known in the art can be included in a kit of this disclosure. Dilution buffers can include a carrier protein (e.g., bovine serum albumin, BSA) and a detergent (e.g., Tween®20). In some embodiments, the dilution buffer is PBS (e.g., about pH 7.4) including BSA (e.g., about 1% BSA) and Tween®20 (e.g., about 0.05% Tween®20).

In some embodiments, the detection reagent is a colorimetric detection reagent, a fluorescent detection reagent, or a chemiluminescent detection reagent. In some embodiments, the colorimetric detection reagent includes PNPP (p-nitrophenyl phosphate), ABTS (2,2'-azino-bis(3-ethylbenzothiazoline-6-sulphonic acid)) or OPD (o-phenylenediamine). In some embodiments, the fluorescent detection reagent includes QuantaBlu™ or QuantaRed™ (Thermo Scientific, Waltham, Mass.). In some embodiments, the luminescent detection reagent includes luminol or luciferin. In some embodiments, the detection reagent includes a trigger (e.g., $H_2O_2$) and a tracer (e.g., isoluminol-conjugate).

Any detection buffer known in the art can be included in a kit of this disclosure. In some embodiments the detection buffer is a citrate-phosphate buffer (e.g., about pH 4.2).

Any stop solution known in the art can be included in a kit of this disclosure. The stop solutions of this disclosure terminate or delay the further development of the detection reagent and corresponding assay signals. Stop solutions can include, for example, low-pH buffers (e.g., glycine-buffer, pH 2.0), chaotrophic agents (e.g., guanidinium chloride, sodium-dodecylsulfate (SDS)) or reducing agents (e.g., dithiothreitol, mecaptoethanol), or the like.

In some embodiments, the kits provided herein include a cleaning reagent for an automated assay system. An automated assay system can include systems by any manufacturer. In some embodiments, the automated assay systems include, for example, the BIO-FLASH™, the BEST 2000™, the DS2™, the EL×50 WASHER, the EL×800 WASHER, the EL×800 READER, and the Autoblot S20™. A cleaning reagent can include any cleaning reagent known in the art. In some embodiments, the cleaning reagent is the cleaning reagent recommended by the manufacturer of the automated assay system.

In some embodiments, the kits can also include a suitable container means, which is a container that does not react with components of the kit, such as an eppendorf tube, an assay plate, a syringe, a bottle, or a tube. The container can be made from sterilizable materials, such as plastic or glass.

In some embodiments, the kits further include a solid support. The solid support can include any support known in the art on which a protein of this disclosure can be immobilized. In some embodiments, solid the solid substrates are microtiter well plates, slides (e.g., glass slides), chips (e.g., protein chips, biosensor chips, such as Biacore chips), microfluidic cartridges, cuvettes, beads (e.g., magnetic beads) or resins.

In some other embodiments, the kits provided herein include instruction for using the subunits of the kit for detecting BTN1A1 or a BTN1A1 ligand (e.g., GAL-1, GAL-9, NRP-2, BLTA) in the sample from the subject.

The kits provided herein can be tailored to specific assay technologies. In some embodiments, the kit is an ELISA kit, Dot Blot kit, chemiluminescence immunoassay (CIA) kit or multiplex kit. In some embodiments, the ELSA kit can include a washing buffer, a sample diluents, a secondary antibody-enzyme conjugate, a detection reagent and a stop solution. In some embodiments, the Dot Blot kit includes a washing buffer, a sample diluents, a secondary antibody-enzyme conjugate, a detection reagent, and a stop solution. In some embodiments, the CIA kit includes a washing buffer, a sample diluent, a tracer (e.g., isoluminol-conjugate) and a trigger (e.g., $H_2O_2$). In some embodiments, the multiplex kit includes a washing buffer, a sample diluents and a secondary antibody-enzyme conjugate.

In some embodiments, the kit of the present invention has a packaging that includes a label indicating the kit is used for diagnosis, prognosis or monitoring of a cancer. In some embodiments, the kit is used as companion diagnostics for cancer treatments. In some other embodiments, the packaging has a label indicates that the kit is used with a cancer drug. In some embodiments, the kit is used to select a patient for a specific cancer treatment.

In some embodiments, the packaging of the kit includes an FDA-approved label. FDA approved labels can include notification of an FDA-approved use and instructions. In some embodiments, the kit is labeled for Research Use Only (RUO) or for Investigational Use Only (IUO). In some embodiments, the kit is labeled for In Vitro Diagnostic Use (IVD). In some embodiments, the kit is labeled in accordance with Title 21, Code of Federal Regulations, Section 809, Subpart B (21 CFR 89, Subpart B).

6. EXAMPLES

It is understood that modifications which do not substantially change the nature and spirit of the various embodiments described herein are also contemplated. Accordingly, the following examples are intended to illustrate but not in any way limiting.

6.1 Example 1: Identification of Galectin-1, Galectin-9 and Neuropilin-2 as BTN1A1 Ligands To identify BTN1A1 ligands a plasma membrane protein array was screened using Retrogenix™ cell microarray technology (Whaley Bridge, United Kingdom).

In brief, expression vectors encoding plasma membrane proteins were arrayed on slides and reverse transfected into HEK293 cells to create microarrays of cells expressing candidate BTN1A1 ligands. Binding of BTN1A1-Fc to candidate BTN1A1 ligands was detected by fluorescence imaging. Identified BTN1A1 ligands were confirmed using the same cell microarray technology and secondary assays, including co-immunoprecipitation and surface-plasmon resonance assays (Biacore™).

Primary Screen and Reconfirmation 4550 expression vectors, each encoding a full-length human plasma membrane protein, were arrayed in duplicate across 13 microarray slides ("slide sets"). More than 3500 of the arrayed expression vectors encoded unique genes. One expression vector control (pIRES-hEGFR-IRES-ZsGreen1) was spotted in quadruplicates on each slide to confirm that a minimal threshold of transfection efficiency was met or exceeded on each slide (mean ZsGreen signal from the pIRES-EGFR-ZsGreen vector over background of 1.5). Human HEK293 cells were used for reverse transfection and protein expression. BTN1A1-ECD-Fc was added to each slide as a test ligand at a final concentration of 20 μg/ml following cell fixation. BTN1A1-Fc binding to HEK293 cell expressing BTN1A1 ligands or negative control cells was detected using an anti-IgG antibody and fluorescence imaging. Two replicate slides were screened for each of the 13 microarray slides of the primary screen slide set. Fluorescent images were analyzed and quantitated (for transfection efficiency) using ImageQuant software (GE). A primary 'hit' was defined as a duplicate spot on a microarray slide showing an increased signal relative to background levels. Primary hits were identified by visual inspection of images gridded by ImageQuant software. Primary hits were classified as 'strong,' 'medium,' 'weak' or 'very weak,' based on the fluorescence intensity of duplicate spots.

Primary hits were reconfirmed in the cell microarray assay. Vectors encoding the primary hits were arrayed on multiple slide sets. Each slide in the confirmation assay also included CD86 positive control and EGFR negative control. Candidate BTN1A1-ligands were expressed in HEK293 cells and the cells were fixed. Different slides were then treated with 20 μg/ml BTN1A1-Fc, 20 μg/ml CTLA4-Fc, or no ligand (detection antibody only) (n=2 slides per treatment).

BTN1A1-Fc generally showed only low background binding to fixed untransfected HEK293 slides when tested at 2 μg/ml, 5 μg/ml, or 20 μg/ml. A total of 40 slides were screened in the primary screen (26 slides) and secondary confirmation assays (14 slides). Transfection efficiencies exceeded the targeted transfection efficiency threshold. In the primary screen, 11 duplicate hits (expression vector clones) were identified. The 11 primary hits covered a range of spot intensities (signal to background) from very weak to strong. Identified vectors were sequenced to confirm the identities of candidate BTN1A1 ligands. Vectors encoding the 11 hits, CD86/ZsGreen1 (positive control) or EGFR/ZsGreen1 (negative control) were tested in secondary confirmation assays.

FIG. 1 shows an image illustrating results of an exemplary reconfirmation assay. Strong binding signals were observed for the positive control interaction of CTLA4-hFc (soluble ligand) with CD86 (cellular membrane protein), which validated the assay conditions. Three primary hits Galectin-1 (Gal-1), Galectin-9 (Gal-9), and Neuropilin-2 (NRP-2) showed specific binding with BTN1A1-Fc, but not with negative controls, in the reconfirmation assays. Thus, Gal-1, Gal-9, and Nrp2 were confirmed as BTN1A1-ligands.

Co-Immunoprecipitation

Gal-1 and Gal-9 were further validated as BTN1A1 ligands by co-immunoprecipitation (co-IP). BTN1A1-Flag was expressed in HEK293T cells alone or in combination with Myc- and Flag-double tagged Gal-1 or Gal-9 (FIG. 2A). Immunoprecipitation (pull-down) was then performed with anti-Myc or anti-BTN1A1 antibodies (FIG. 2B). Immunoprecipitates were analyzed by SDS-PAGE to probe the interaction between BTN1A1 and Gal-1 or Gal-9 (FIG. 2C). Pull-down of Myc-tagged Gal-1 and Gal-9 using an anti-Myc antibody resulted in co-IP of Flag-tagged BTN1A1 (FIG. 2C). To further confirm the specificity of the BTN1A1-Gal-1 and BTN1A1-Gal9 interations, BTN1A1 was pulled-down using the BTN1A1-specific antibody STC810. BTN1A1 pull down with STC810 resulted in co-IP of Gal-1 and Gal-9 (FIG. 2C). These results further validated Gal-1 and Gal-9 as bona fide ligands of BTN1A1.

Surface Plasmon Resonance

The BTN1A1-Gal-1 interaction was further analysed in a surface plasmon resonance (Biacore™) binding assay. BTN1A1-Fc fusion proteins were captured on a protein A-coated CM5 chip, and Gal-1 ligand was injected onto the CM5 chip at five or more different concentrations. FIGS. 3A-D show exemplary BIAcore sensograms illustrating Gal-1-binding to glycosylated BTN1A1 wild type (BTN1A1, FIG. 3A), non-glycosylated BTN1A1 mutant (BTN1A1-2NQ) or other members of the BTN1A1 family (BTN2A1—FIG. 3C; BTN3A2—FIG. 3D) Gal-1 was not found to detectably bind to an unglycosylated BTN1A1-2NQ mutant protein (FIG. 3B), demonstrating that Gal-1 binds to BTN1A1 in a glycospecific manner. In addition, Gal-1 was not found to detectably bind to other members of the BTN1A1 family, such as BTN2A1 (FIG. 3C) or BTN3A2 (FIG. 3D), demonstrating that Gal-1 is a selective ligand of BTN1A1 within the BTN1A1 family.

6.2 Example 2: Identification of BLTA as a BTN1A1 Ligand

β-Galactosidase Complementation Assay

Chimeric proteins composed of proteins of interest fused to complementing β-galactosidase (β-gal) deletion mutants are useful to analyze intracellular protein complexes. β-Gal activity resulting from a forced interaction of nonfunctional weakly complementing β-gal peptides (Δα and Δω) can serve as a measure of the extent of interaction of non-β-gal portions of the chimeras. Using β-gal complementation, cis-acting protein—protein interactions occurring at the plasma membrane can be detected.

FIG. 4A shows a graph illustrating the design of a β-gal complementation assay. β-Galactosidase complementation assays are typically designed using two inactive fragments of β-galactosidase (β-gal), the enzyme donor (ED) and the enzyme acceptor (EA), which combine to create an active β-gal enzyme. An N-terminal 45 amino acid fragment Pro-Linker (designated PK) as an ED was fused to a candidate BTN1A1 ligand protein and the BTN1A1 was fused to EA. Interactions between the two proteins can promote complementation between PK and EA, resulting in formation of an active β-gal enzyme that cleaves a substrate to generate chemiluminescent signal. BTN1A1-EA cell lines were engineered to stably express large β-gal enzyme reporter fragment EA (enzyme acceptor). BTN1A1-ligand candidates fused to PK were transfected into the EA parental cell lines. β-galactosidase activity was measured as an indicater of a direct BTN1A1-BTN1A1-ligand interaction. β-galactosidase complementation of BTN1A1-EA and BTLA-PK or Nrp-2-PK was observed (FIG. 4B). The results of the β-gal complementation assay show that BTLA and Nrp-2 interact with BTN1A1 in a cis-acting manner.

Co-Immunoprecipiation

To validate BTN1A1 ligands identified in the β-Gal complementation screen BTN1A1 was cotransfected with BTLA and Nrp-2 and co-immunoprecipitated. FIG. 5 shows images of western blots with representative results of BTN1A1-BTLA Co-IP experiments. Co-IP was performed with anti-FLAG or anti-Myc antibodies as shown in FIG. 5. Precipitates of HEK293T cells expressing BTN1A1-Flag and BTLA-Myc or Nrp-2-Myc were analyzed by SDS-PAGE (Nrp-2 data not shown in FIG. 5). Co-IP with an anti-FLAG antibody resulted in co-precipitation of BTLA-Myc or Nrp-2-Myc. To confirm the specificity of observed BTN1A1-BTN1A1-ligand interactions, an anti-Myc antibody was used to pull-down BTLA-Myc or Nrp-2-My from cell lysates. BTN1A1-Flag was found to co-precipitate with BTLA-Myc or Nrp-2-My, demonstrating that BTLA and Nrp-2 are bona fide ligands of BTN1A1.

Surface Plasmon Resonance

The interaction between BTN1A1 and BTLA was further analyzed in a Biacore™ assay. BTN1A1-Fc fusion proteins were captured on a protein A-coated CMS chip, and BTLA or Gal-1 were injected onto the chip at 3.2 µM. FIG. 6A shows a sensogram illustrating Gal-1 and BTLA binding to BTN1A1-Fc. Gal-1 binding is indicated by a positive response signal in the sensogram. BTLA binding to immobilized BTN1A1-Fc on the Biacore™ chip resulted in a reduction of the response signal in the sensogram (negative signal). FIG. 6B shows sensograms illustrating the dose-dependent decrease of response signals observed when injecting BTLA onto a Biacore™ chip with immobilized BTN1A1-Fc at 0.4 µM, 0.8 µM, 1.6 µM, 3.2 µM, or 6.4 µM. Without being bound by a particular theory, it is believed that the observed decrease in SPR signals resulting from BTLA binding to BTN1A1 indicates a conformational change, e.g., in BTN1A1 upon BTN1A1-BTLA complex formation.

Biolayer Interferometry

FIG. 7 shows sensograms illustrating the results of a bio-layer interferometry (BLI) experiment analyzing BTLA binding to BTN1A1-Fc on an Octet® system (FortéBio, Menlo Park, Calif.). Anti-hIgG Fc capture (AHC) tips of a FortéBio Octet® RED96 system were coated with BTN1A1-Fc. The coated biosensor tips were dipped into solutions of increasing concentrations of BTLA (0.8 µM, 1.6 µM, or 3.2 µM) and BTLA binding to BTN1A1 was monitored. Table XX shows results for the binding kinetics and dissociation constant of the BTN1A1-BTLA interaction individually determined for each BTN1A1 concentration. An overall $K_D$ value was calculated by steady state analysis using FortéBio Data Analysis 9.0 software. According to this calculation, BTLA was determined to bind BTN1A1 with a $K_D$ of 17 µM±0.81 µM of $K_D$.

| Loading Sample ID | Sample ID | Conc. (µM) | Response | $K_D$ (M) | $k_{on}$ (1/Ms) | $k_{dis}$ (1/s) | RMax |
| --- | --- | --- | --- | --- | --- | --- | --- |
| BTN1A1-Fc | BTLA-His | 6.4 | 0.0840 | 8.43E−07 | 9.23E+02 | 7.78E−04 | 0.0849 |
| BTN1A1-Fc | BTLA-His | 3.2 | 0.0436 | 5.79E−07 | 1.26E+03 | 7.28E−04 | 0.0476 |
| BTN1A1-Fc | BTLA-His | 1.6 | 0.0227 | 7.24E−07 | 1.65E+03 | 1.19E−03 | 0.0336 |
| BTN1A1-Fc | BTLA-His | 0.8 | 0.0067 | 9.53E−06 | 7.98E+01 | 7.61E−04 | 0.2222 |

Throughout this application various publications have been referenced. The disclosures of these publications in their entireties are hereby incorporated by reference in this application in order to more fully describe the state of the art to which this disclosure pertains. While examples of certain particular embodiments are provided herein, it will be apparent to those skilled in the art that various changes and modifications may be made. Such modifications are also intended to fall within the scope of the appended claims.

What is claimed is:

1. A method of activating a T-cell, comprising the steps of
   1) determining interaction between BTN1A1 and a BTN1A1 ligand expressed on a cell surface; and
   2) contacting the T-cell with an effective amount of an antibody that specifically binds to the BTN1A1 ligand, wherein the antibody inhibits binding of the BTN1A1 to the BTN1A1 ligand, thereby activating the T-cell, and wherein the BTN1A1 ligand is GAL-1 or GAL-9.

2. The method of claim 1, wherein the T-cell is a CD8+ cell.

3. The method of claim 1, wherein the T-cell activation comprises an increase in T-cell proliferation.

4. The method of claim 1, wherein the T-cell activation comprises a decrease in T-cell apoptosis.

5. The method of claim 1, wherein the T-cell activation comprises an increase in cytokine production.

6. The method of claim 5, wherein the cytokine is IFNγ or IL-2.

7. The method of claim 1, wherein the T-cell is in a subject.

8. The method of claim 7, wherein the subject has a cancer.

9. The method of claim 8, wherein the cancer is a lung cancer, prostate cancer, pancreas cancer, ovarian cancer, liver cancer, head and neck cancer, breast cancer, or stomach cancer.

10. The method of claim 9, wherein the cancer is a lung cancer.

11. The method of claim 10, wherein the lung cancer is a non-small cell lung cancer (NSCLC).

12. The method of claim 11, wherein the NSCLC is squamous NSCLC.

13. The method of claim 10, wherein the lung cancer is a Lewis lung carcinoma.

14. The method of claim 9, wherein the cancer is a breast cancer.

15. The method of claim 14, wherein the breast cancer is a mammary carcinoma.

16. The method of claim 8, wherein the cancer is a cancer that is resistant or refractory to an anti-PD-1 therapy.

17. The method of claim 8, wherein the cancer is a cancer that is resistant or refractory to an anti-PD-L1 therapy.

18. The method of claim 8, wherein the subject is further administered a high-dose radiation therapy.

* * * * *